US011459315B2

(12) United States Patent
Brenneman et al.

(10) Patent No.: US 11,459,315 B2
(45) Date of Patent: Oct. 4, 2022

(54) MODULATORS OF METHYL MODIFYING ENZYMES, COMPOSITIONS AND USES THEREOF

(71) Applicant: Constellation Pharmaceuticals, Inc., Boston, MA (US)

(72) Inventors: Jehrod B. Brenneman, Marblehead, MA (US); Alexandre Côté, Cambridge, MA (US); Victor S. Gehling, Somerville, MA (US); Avinash Khanna, Cambridge, MA (US); Julian R. Levell, Arlington, MA (US); Ludivine Moine, Cambridge, MA (US)

(73) Assignee: Constellation Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 16/762,600

(22) PCT Filed: Nov. 8, 2018

(86) PCT No.: PCT/US2018/059763
§ 371 (c)(1),
(2) Date: May 8, 2020

(87) PCT Pub. No.: WO2019/094552
PCT Pub. Date: May 16, 2019

(65) Prior Publication Data
US 2021/0230148 A1    Jul. 29, 2021

Related U.S. Application Data

(60) Provisional application No. 62/583,737, filed on Nov. 9, 2017.

(51) Int. Cl.
| C07D 405/14 | (2006.01) |
| C07D 401/12 | (2006.01) |
| C07D 401/14 | (2006.01) |
| C07D 471/04 | (2006.01) |

(52) U.S. Cl.
CPC ......... C07D 405/14 (2013.01); C07D 401/12 (2013.01); C07D 401/14 (2013.01); C07D 471/04 (2013.01)

(58) Field of Classification Search
CPC combination set(s) only.
See application file for complete search history.

(56) References Cited

U.S. PATENT DOCUMENTS 9,469,646 B2 * 10/2016 Albrecht ............... A61P 25/00
2017/0217941 A1   8/2017 Campbell

FOREIGN PATENT DOCUMENTS

| WO | 2013/120104 A2 | 8/2013 |
| WO | 2014/124418 A1 | 8/2014 |
| WO | 2015/023915 A1 | 2/2015 |
| WO | 2016/130396 A1 | 8/2016 |

OTHER PUBLICATIONS

Silverman, R. "The Organic Chemistry of Drug Design and Drug Action," 2004, Elsevier, pp. 20-32.*

* cited by examiner

*Primary Examiner* — Heidi Reese
(74) *Attorney, Agent, or Firm* — McCarter & English, LLP; Steven G. Davis; Michael J. DeGrazia

(57) ABSTRACT

Provided are compounds of Formula (I): and pharmaceutically acceptable salts and compostions thereof, which are useful for treating a variety of conditions associated with methyl modifying enzymes.

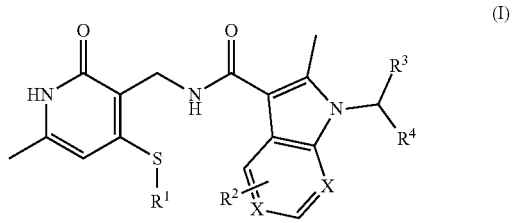

11 Claims, No Drawings
Specification includes a Sequence Listing.

MODULATORS OF METHYL MODIFYING ENZYMES, COMPOSITIONS AND USES THEREOF

RELATED APPLICATIONS

This application is a U.S. national stage filing under 35 U.S.C. § 371 based on International Application No. PCT/US2018/059763 filed Nov. 8, 2018, which claims priority to U.S. Provisional Application No. 62/583,737, filed Nov. 9, 2017, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created on Feb. 11, 2019, is named 124033-01920_SL.txt and is 79,104 bytes in size.

BACKGROUND

Eukaryotic chromatin is composed of macromolecular complexes called nucleosomes. A nucleosome has 147 base pairs of DNA wrapped around a protein octamer having two subunits of each of histone protein H2A, H2B, H3, and H4. Histone proteins are subject to post-translational modifications which in turn affect chromatin structure and gene expression. One type of post-translational modification found on histones is methylation of lysine and arginine residues. Histone methylation plays a critical role in the regulation of gene expression in eukaryotes. Methylation affects chromatin structure and has been linked to both activation and repression of transcription (Zhang and Reinberg, Genes Dev. 15:2343-2360, 2001). Enzymes that catalyze attachment and removal of methyl groups from histones are implicated in gene silencing, embryonic development, cell proliferation, and other processes.

One class of histone methylases is characterized by the presence of a SET domain, comprising about 130 amino acids. EZH2 is an example of a human SET-domain containing methylase. EZH2 associates with EED (Embryonic Ectoderm Development) and SUZ12 (suppressor of zeste 12 homolog) to form a complex known as PRC2 (Polycomb Group Repressive Complex 2) having the ability to trimethylate histone H3 at lysine 27 (Cao and Zhang, Mol. Cell 15:57-67, 2004). PRC2 complexes can also include RBAP46 and RBAP48 subunits. Another example is the related methylase EZH1.

The oncogenic activities of EZH2 have been shown by a number of studies in various different cancer types. ~15-20% GCB-DLBCLs harbor a gain-of-function mutation in EZH2 (Y641 residue) and these cells are hypersensitive to EZH2 inhibition both in vitro and in vivo (McCabe et al, 2012; Bradley et al, 2014). In cell line experiments, overexpression of EZH2 induces cell invasion, growth in soft agar, and motility, while knockdown of EZH2 inhibits cell proliferation and cell invasion (Kleer et al., 2003, Proc. Nat. Acad. Sci. USA 100:11606-11611; Varambally et al., (2002), "The polycomb group protein EZH2 is involved in progression of prostate cancer," Nature 419, 624-629). It has been shown that EZH2 represses the expression of several tumor suppressors, including E-cadherin, DAB2IP and RUNX3 among others. In xenograft models, EZH2 knockdown inhibits tumor growth and metastasis. It has been shown that down modulation of EZH2 in murine models blocks prostate cancer metastasis (Min et al., "An oncogene-tumor suppressor cascade drives metastatic prostate cancer by coordinately activating Ras and nuclear factor-kappaB," Nat Med. 2010 March; 16(3):286-94). Recently, it was demonstrated that EZH2 is over-expressed in neuroendocrine tumors and inhibition of EZH2 in mouse tumors restore androgen dependence (Ku et al, Science, 355, 2017). EZH2 overexpression is associated with aggressiveness of certain cancers such as breast cancer (Kleer et al., Proc. Nat. Acad. Sci. USA 100:11606-11611, 2003). Recent studies also suggest that prostate cancer specific oncogenic fusion gene TMPRSS2-ERG induces repressive epigenetic programs via direct activation of EZH2 (Yu et al., "An Integrated Network of Androgen Receptor, Polycomb, and TMPRSS2-ERG Gene Fusions in Prostate Cancer Progression," Cancer Cell. 2010 May 18; 17(5):443-454).

Given their role in the regulation of diverse biological processes, methyl modifying enzymes, in particular EZH2 and mutant forms thereof, are attractive targets for modulation.

SUMMARY

Disclosed herein are compounds and pharmaceutically acceptable compositions thereof that are modulators of EZH2 (See e.g., Table 1). Such compounds include those of structural formula I:

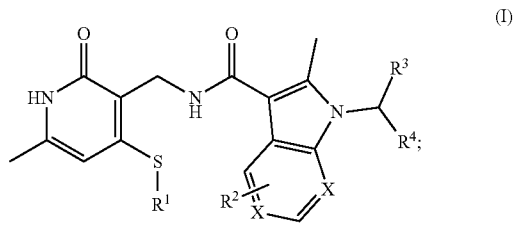

or a pharmaceutically acceptable salt thereof, wherein each of $R^1$, $R^2$, $R^3$, and $R^4$ are defined and described herein.

In one aspect, introducing a thiol group (—$SR^1$) on the methyl pyridinone of the disclosed compounds was found to have a profound effect on the residence time. See e.g., Table 3, where replacement of a methoxy, methyl or chlorine for —$SCH_3$ resulted in over a 17 fold increase in residence time, and afforded compounds with improved cellular activity.

The disclosed compounds, pharmaceutically acceptable salts, and pharmaceutically acceptable compositions, are useful for treating a variety of conditions associated with methyl modifying enzymes. These conditions include e.g., one or more cancers.

DETAILED DESCRIPTION

1. General Description of Compounds

In certain embodiments, the present disclosure provides a compound of Formula I:

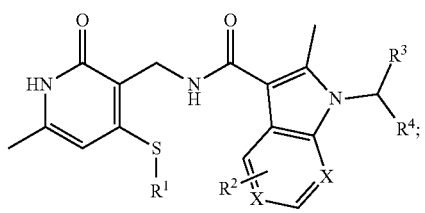

or a pharmaceutically acceptable salt thereof, wherein
each X is independently CH or N;
$R^1$ is $(C_1-C_4)$alkyl, $-(C_3-C_5)$cycloalkyl, or $(C_1-C_4)$haloalkyl;
$R^2$ is hydrogen, halo, $(C_1-C_4)$alkyl, halo$(C_1-C_4)$alkyl, $(C_1-C_4)$alkoxy, halo$(C_1-C_4)$alkoxy, or —CN;
$R^3$ is $(C_1-C_4)$alkyl or halo$(C_1-C_4)$alkyl;
$R^4$ is $(C_1-C_4)$alkyl, halo$(C_1-C_4)$alkyl, halo$(C_1-C_4)$alkoxy, $-(C_1-C_4)$alkylOH, $-(C_1-C_4)$alkylO$(C_1-C_4)$alkyl, phenyl, 5-6 membered heteroaryl, monocyclic $(C_3-C_7)$cycloalkyl, bridged bicyclic $(C_5-C_8)$cycloalkyl, or 4-7 membered monocyclic heterocyclyl, wherein said phenyl, heteroaryl, monocyclic cycloalkyl, bridged bicyclic cycloalkyl, and heterocyclyl are each optionally substituted with 1 to 3 groups selected from $R^5$;
$R^5$ is selected from $(C_1-C_6)$alkyl, $(C_3-C_6)$cycloalkyl, halo$(C_3-C_6)$cycloalkyl, $-(C_1-C_4)$alkylOH, halo$(C_1-C_4)$alkyl, $(C_1-C_4)$alkoxy, halo$(C_1-C_4)$alkoxy, halo, nitrile, amide, urea, carbamate, sulfonamide, hydroxyl, oxo, $OR^6$, —OC(O)$(C_1-C_4)$alkyl, —C(O)$(C_1-C_4)$alkyl, —C(O)$(C_1-C_4)$alkylOH, —C(O)$(C_1-C_4)$alkylNH$(C_1-C_4)$alkyl, —C(O)$(C_1-C_4)$alkylN(($C_1-C_4)$alkyl)$_2$, —C(O)$(C_1-C_4)$alkylNH$_2$, —SO$_2$$(C_1-C_4)$alkyl, $(C_1-C_4)$alkyl-O—$(C_1-C_4)$alkyl, substituted phenyl, 5-6 membered heteroaryl, 4-7 membered heterocyclyl, and $NR^AR^B$, wherein said cycloalkyl for $R^5$ is optionally substituted with —O$(C_1-C_4)$alkyl;
$R^A$ is hydrogen, $(C_1-C_4)$alkyl, halo$(C_1-C_4)$alkyl, $(C_3-C_6)$cycloalkyl, 4-7 membered heterocyclyl, or $(C_1-C_4)$alkyl-O—$(C_1-C_4)$alkyl;
$R^B$ is hydrogen, $(C_1-C_4)$alkyl, $-(C_3-C_5)$cycloalkyl, or 4-7 membered heterocyclyl, wherein said $(C_1-C_4)$alkyl for $R^B$ is optionally substituted with 1 to 3 groups selected from halo, phenyl, $(C_1-C_4)$alkyl, $(C_1-C_4)$alkoxy, and OH and wherein said heterocyclyl, $-(C_3-C_5)$cycloalkyl for $R^B$ is optionally substituted with 1 to 3 groups selected from $(C_1-C_4)$alkyl, halo$(C_1-C_4)$alkyl, hydroxy$(C_1-C_4)$alkyl, —O$(C_1-C_4)$alkyl, and —C(=O)O$(C_1-C_4)$alkyl; or
$R^A$ and $R^B$ taken together with the nitrogen atom to which they are attached form a 3-7 membered heterocyclyl optionally substituted with 1 to 3 groups selected from halo$(C_1-C_4)$alkyl, halo$(C_1-C_4)$alkyl, $(C_1-C_4)$alkoxy, oxo, halo$(C_1-C_4)$alkoxy, 5-6 membered heteroaryl, $(C_3-C_6)$cycloalkyl, —SO$_2$$(C_1-C_4)$alkyl, NMe$_2$, hydroxy, cyano, spirooxetanyl and $(C_1-C_4)$cycloalkoxy optionally substituted with $(C_1-C_4)$alkyl, halo$(C_1-C_4)$alkyl, or $(C_1-C_4)$alkoxy; and
$R^6$ is $(C_3-C_6)$cycloalkyl, 4-7 membered heterocyclyl, or 5-6 membered heteroaryl, —O$(C_1-C_4)$alkyl, wherein said 4-7 membered heterocyclyl for $R^6$ is optionally substituted with 1 or 2 $(C_1-C_4)$alkyl groups.

2. Definitions

The terms "halo" and "halogen" as used herein refer to an atom selected from fluorine (fluoro, —F), chlorine (chloro, —Cl), bromine (bromo, —Br), and iodine (iodo, —I).

The term "alkyl," as used herein, refers to a monovalent saturated, straight- or branched-chain hydrocarbon radical, having unless otherwise specified, 1-8 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

The term "alkoxy," as used herein, refers to an alkyl group which is attached to another moiety via an oxygen atom (—O(alkyl)). Non-limiting examples include e.g., methoxy, ethoxy, propoxy, and butoxy.

The term "haloalkyl" includes mono, poly, and perhaloalkyl groups where the halogens are independently selected from fluorine, chlorine, bromine, and iodine.

"Haloalkoxy" is a haloalkyl group which is attached to another moiety via an oxygen atom such as, e.g., but are not limited to —OCHCF$_2$ or —OCF$_3$.

The term "aryl" refers to an aromatic carbocyclic ring system having, unless otherwise specified, a total of 6 to 14 ring members, e.g., phenyl, naphthyl, and the like. The term "aryl" may be used interchangeably with the term "aryl ring", "aryl group", "aryl moiety," or "aryl radical". It will be understood that when specified, optional substituents on an aryl group (e.g., in the case of an optionally substituted aryl or aryl which is optionally substituted) may be present on any substitutable position, i.e., any ring carbon substituted with hydrogen. In one aspect, substituents for a substituted phenyl group include halo, $(C_1-C_4)$alkyl, halo$(C_1-C_4)$alkyl, $(C_1-C_4)$alkoxy, halo$(C_1-C_4)$alkoxy. In other aspect, include halo, $(C_1-C_4)$alkyl, and halo$(C_1-C_4)$alkyl.

The term "carbocyclyl" (also referred to herein as "carbocycle" or "cycloaliphatic", as used herein, means a monocyclic, bicyclic (e.g., a bridged or spiro bicyclic ring), polycyclic (e.g., tricyclic), or fused hydrocarbon ring system that is completely saturated or that contains one or more units of unsaturation, but where there is no aromatic ring. Cycloalkyl is a completely saturated carbocycle. Monocyclic cycloalkyl groups include, without limitation, cyclopropyl, cyclobutyl, cyclopentyl, cyclohexyl, cycloheptyl, and cyclooctyl. Bridged bicyclic cycloalkyl groups include, without limitation, bicyclo[3.2.1]octane, bicyclo[2.2.1]heptane, bicyclo[3.1.0]hexane, bicyclo[1.1.1]pentane, and the like. Spiro bicyclic cycloalkyl groups include, e.g., spiro[3.6]decane, spiro[4.5]decane, and the like. Fused cycloalkyl rings include, e.g., decahydronaphthalene, octahydropentalene, and the like. It will be understood that when specified, optional substituents on a carbocyclyl (e.g., in the case of an optionally substituted carbocyclyl or carbocyclyl which is optionally substituted) may be present on any substitutable position and, include, e.g., the position at which the carbocyclyl group is attached.

The term "oxo" means the group "=O".

The term "amide" means the group —C(O)NR$^x$R$^y$, where R$^x$ and R$^y$ are each independently hydrogen or $(C_1-C_4)$alkyl.

The term "urea" means the group —NRC(O)NR$^x$R$^y$, where R$^x$ and R$^y$ are each independently hydrogen or $(C_1-C_4)$alkyl.

The term "carbamate" means the group —OC(O)NR$^x$R$^y$, where R$^x$ and R$^y$ are each independently hydrogen or (C$_1$-C$_4$)alkyl.

The term "sulfonamide" means the group —S(O)$_2$NR$^x$R$^y$, where R$^x$ and R$^y$ are each independently hydrogen or (C$_1$-C$_4$)alkyl.

The term "heteroaryl" used alone or as part of a larger moiety as in "heteroarylalkyl", "heteroarylalkoxy", or "heteroarylaminoalkyl", refers to a 5-10-membered aromatic radical containing 1-4 heteroatoms selected from N, O, and S, and includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl" may be used interchangeably with the terms "heteroaryl ring", "heteroaryl group", or "heteroaromatic". The terms "heteroaryl" also include groups in which a heteroaromatic ring is fused to one or more aromatic rings, where the radical or point of attachment is on the heteroaromatic ring. Nonlimiting examples include indolyl, indazolyl, benzimidazolyl, benzthiazolyl, quinolyl, quinazolinyl, and quinoxalinyl. It will be understood that when specified, optional substituents on a heteroaryl group may be present on any substitutable position (carbon and nitrogen).

The term "heterocyclyl" means a 3-12 membered (e.g., a 4-, 5-, 6- and 7-membered) saturated or partially unsaturated heterocyclic ring containing 1 to 4 heteroatoms independently selected from N, O, and S. It can be mononcyclic, bicyclic (e.g., a bridged, fused, or spiro bicyclic ring), or tricyclic. The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, oxetanyl, azetidinyl and tetrahydropyrimidinyl. A heterocyclyl group may be mono- or bicyclic. The term "heterocyclyl" also includes, e.g., unsaturated heterocyclic radicals fused to another unsaturated heterocyclic radical or aryl or heteroaryl ring, such as for example, tetrahydronaphthyridine, indolinone, dihydropyrrolotriazole, imidazopyrimidine, quinolinone, dioxaspirodecane. It will also be understood that when specified, optional substituents on a heterocyclyl group may be present on any substitutable position and, include, e.g., the position at which the heterocyclyl is attached (e.g., in the case of an optionally substituted heterocyclyl or heterocyclyl which is optionally substituted).

The term "spiro" refers to two rings that shares one ring atom (e.g., carbon).

The term "fused" refers to two rings that share two adjacent ring ring atoms with one another.

The term "bridged" refers to two rings that share three ring atoms with one another.

Structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers, if present. Therefore, single stereochemical isomers as well as enantiomeric, diastereomeric, and geometric (or conformational) mixtures of the present compounds are within the scope of the present disclosure. Tautomeric forms of the compounds are also included.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. When a disclosed compound is named or depicted by structure without indicating a particular geometric isomer form, it is to be understood that the name or structure encompasses one geometric isomer free of other geometric isomers, mixtures of geometric isomers, or mixtures of all geometric isomers.

Unless otherwise specified, when the stereochemistry of a disclosed compound is named or depicted by structure, the named or depicted stereoisomer is at least 60%, 70%, 80%, 90%, 99% or 99.9% by weight pure relative to all of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer. Enantiomers may be resolved by methods known to those skilled in the art, for example by formation of diastereoisomeric salts which may be separated, for example, by crystallization; formation of diastereoisomeric derivatives or complexes which may be separated, for example, by crystallization, supercritical fluid or liquid chromatography; selective reaction of one enantiomer with an enantiomer-specific reagent, for example enzymatic esterification; or supercritical fluid or liquid chromatography in a chiral environment, for example on a chiral support for example silica with a bound chiral ligand or in the presence of a chiral solvent. Specific enantiomers may also be synthesized by asymmetric synthesis using optically active reagents, substrates, catalysts or solvents, or by converting one enantiomer into the other by asymmetric transformation.

Unless otherwise specified, when a disclosed compound is named or depicted by structure without indicating the stereochemistry, and the compound has at least one chiral center, the name or structure encompasses one enantiomer of compound free from the corresponding optical isomer, a racemic mixture of the compound and mixtures enriched in one enantiomer relative to its corresponding optical isomer.

Unless otherwise specified, when a disclosed compound is named or depicted by structure without indicating the stereochemistry and has at least two chiral centers, the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s), for example, by a molar excess of at least 60%, 70%, 80%, 90%, 99% or 99.9%. Diastereoisomeric pairs may be separated by methods known to those skilled in the art, for example chromatography or crystallization and the individual enantiomers within each pair may be separated.

Unless otherwise specified, when only some of the stereochemical centers in a disclosed compound are depicted or named by structure, the named or depicted configuration is enriched relative to the remaining configurations, for example, by a molar excess of at least 60%, 70%, 80%, 90%, 99% or 99.9%. For example, the substructure:

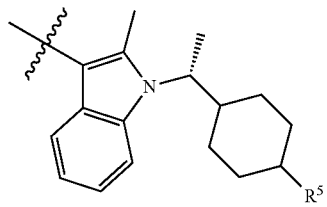

means that that the configuration about the chiral carbon is stereochemically enriched as R (e.g., by a molar excess of at least 60%, 70%, 80%, 90%, 99% or 99.9%) and that the geometry about the cyclohexyl may be cis or trans, or a mixture thereof.

Unless otherwise specified, when referred to as part of the structure or name, isomer 1 and isomer 2 refer to cis and trans isomers of the 1,4-disubstituted cyclohexane or a 1,3-disubstituted cyclobutene. Isomer 1 is either the product eluting with the shortest retention time when isolated from a chiral column chromatography purification or regular phase chromatography purification or it is the product with the higher Rf when isolated via prep-TLC. In some cases, only one of the cis or trans isomers is isolated during the synthesis. These products have been referred to as single isomers rather than isomer 1 or isomer 2 because their counterpart was not synthesized as a relative reference.

The term "patient," as used herein, means an animal, such as a mammal, and such as a human. The terms "subject" and "patient" may be used interchangeably.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The terms "treatment," "treat," and "treating" refer to reversing, alleviating, or inhibiting the progress of a disease or disorder, or one or more symptoms thereof, as described herein. Treatment may also be continued after symptoms have resolved, for example to delay recurrence.

The term "effective amount" or "therapeutically effective amount" refers to an amount of a compound described herein that will elicit a biological or medical response of a subject e.g., a dosage of between 0.01-100 mg/kg body weight/day.

3. Compounds

In a first embodiment, provided herein is a compound of Formula I, wherein $R^5$ is selected from $(C_1-C_6)$alkyl, $(C_3-C_6)$cycloalkyl, halo$(C_3-C_6)$cycloalkyl, —$(C_1-C_4)$alkylOH, halo$(C_1-C_4)$alkyl, $(C_1-C_4)$alkoxy, halo$(C_1-C_4)$alkoxy, halo, nitrile, amide, urea, carbamate, sulfonamide, hydroxyl, oxo, $(C_1-C_4)$alkyl-O—$(C_1-C_4)$alkyl, substituted phenyl, 5-6 membered heteroaryl and $NR^AR^B$;

$R^B$ is hydrogen, $(C_1-C_4)$alkyl or 4-7 membered heterocyclyl, wherein said $(C_1-C_4)$alkyl for $R^B$ is optionally substituted with 1 to 3 groups selected from halo, phenyl, $(C_1-C_4)$alkoxy, and OH and wherein said heterocyclyl for $R^B$ is optionally substituted with 1 to 3 groups selected from $(C_1-C_4)$alkyl, —O$(C_1-C_4)$alkyl, and —C(=O)O$(C_1-C_4)$alkyl; or $R^A$ and $R^B$ taken together with the nitrogen atom to which they are attached form a 4-7 membered heterocyclyl optionally substituted with 1 to 3 groups selected from halo, $(C_1-C_4)$alkyl, halo$(C_1-C_4)$alkyl, $(C_1-C_4)$alkoxy, oxo, halo $(C_1-C_4)$alkoxy, and $(C_1-C_4)$cycloalkoxy optionally substituted with $(C_1-C_4)$alkyl, halo$(C_1-C_4)$alkyl, or $(C_1-C_4)$ alkoxy; and the remaining variables are as described above.

In a second embodiment, the compound of Formula I is of the Formula Ia:

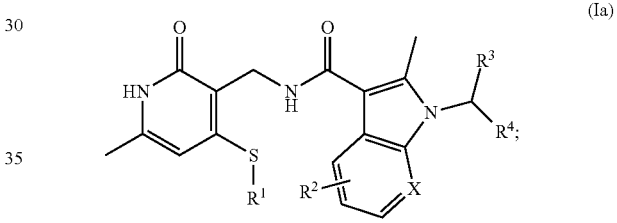

or a pharmaceutically acceptable salt thereof, wherein the variables are as described above for Formula I or the first embodiment.

In a third embodiment, the compound of Formula I is of the Formula Ia':

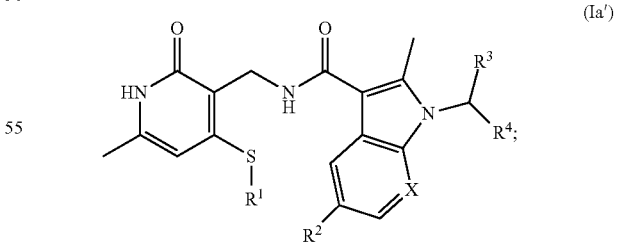

or a pharmaceutically acceptable salt thereof, wherein the variables are as described above for Formula I or the first embodiment.

In a fourth embodiment, $R^2$ in the compound of Formula I, Ia, or Ia' is hydrogen or fluorine, wherein the variables are as described above for Formula I or the first embodiment.

In a fifth embodiment, the compound of Formula I is of the Formula II or IIa:

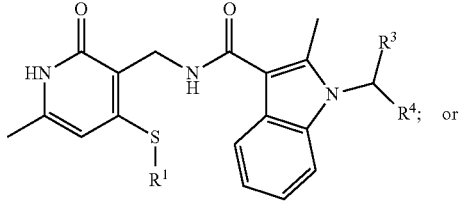
(II)

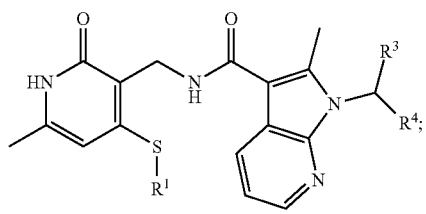
(IIa)

or a pharmaceutically acceptable salt thereof, wherein the variables are as described above for Formula I or the first embodiment.

In a sixth embodiment, $R^3$ in the compound of Formula I, Ia, Ia', II, or IIa is $(C_1$-$C_4)$alkyl; $R^4$ is —$(C_1$-$C_4)$alkylOH, —$(C_1$-$C_4)$alkylO$(C_1$-$C_4)$alkyl, monocyclic $(C_3$-$C_6)$cycloalkyl, bridged bicyclic $(C_5$-$C_8)$cycloalkyl, or 4-7 membered heterocyclyl, wherein said cycloalkyl and heterocyclyl are each optionally substituted with 1 to 2 groups selected from $R^5$; $R^5$ is selected from $(C_1$-$C_4)$alkyl, $(C_3$-$C_6)$cycloalkyl, hydroxyl, $(C_1$-$C_4)$alkoxy, halo, —$(C_1$-$C_4)$alkylOH, halo$(C_1$-$C_4)$alkyl, and $NR^A R^B$; and $R^B$ is hydrogen, $(C_1$-$C_4)$alkyl or 4-7 membered heterocyclyl, wherein said $(C_1$-$C_4)$alkyl for $R^B$ is optionally substituted with 1 to 3 groups selected from halo, phenyl, and OH and wherein said heterocyclyl for $R^B$ is optionally substituted with 1 to 3 groups selected from $(C_1$-$C_4)$alkyl, —O$(C_1$-$C_4)$alkyl, and —C(=O)O$(C_1$-$C_4)$alkyl; or $R^A$ and $R^B$ taken together with the nitrogen atom to which they are attached form a 4-7 membered heterocyclyl optionally substituted with 1 or 2 groups selected from $(C_1$-$C_4)$alkyl, halo$(C_1$-$C_4)$alkoxy, halo, and $(C_1$-$C_4)$alkoxy, wherein the variables are as described above for Formula I or the first embodiment.

In a seventh embodiment, the compound of Formula I, Ia, Ia', II, or IIa is of the Formula III or IIIa:

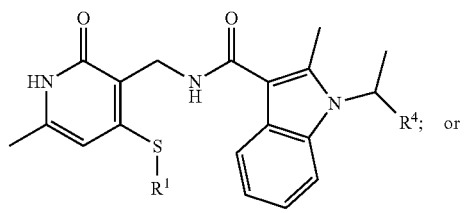
(III)

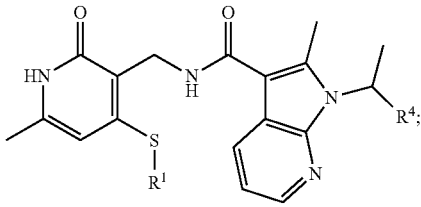
(IIIa)

or a pharmaceutically acceptable salt thereof, wherein the remaining variables are as described for Formula I or the first or sixth embodiment.

In an eighth embodiment, the compound of any one of Formulae I to IIIa is of the Formula IV or IVa:

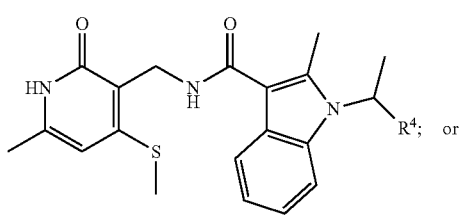
(IV)

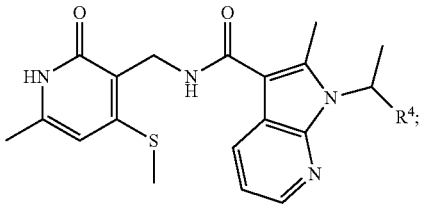
(IVa)

or a pharmaceutically acceptable salt thereof, wherein the remaining variables are as described for Formula I or the first or sixth embodiment.

In a ninth embodiment, the compound of any one of Formulae I to IVa is of the Formula V or Va:

(V)

(Va)

or a pharmaceutically acceptable salt thereof, wherein $X_1$ and $X_2$ are each independently absent, O, or $CH_2$; $X_3$ is O, NH, —$NR^7$, $CH_2$, or $CHR^5$; $R^6$ is hydrogen or $R^6$ and $X_3$ taken together with their intervening ring atoms form a bridged bicyclic $(C_5-C_8)$cycloalkyl; and $R^7$ is $(C_1-C_4)$alkyl, $(C_3-C_6)$cycloalkyl, —$(C_1-C_4)$alkylOH, or halo$(C_1-C_4)$alkyl; provided that $X_3$ is not O, NH, or $NR^7$ when $X_1$ and $X_2$ are each O, wherein the remaining variables are as described for Formula I or the first or sixth embodiment.

In a tenth embodiment, the compound of any one of Formulae I to V is of the Formula VI, VII, VIII, IX, X, or XI:

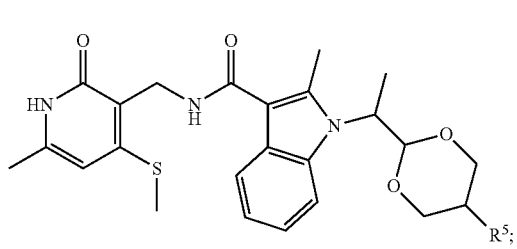
(VI)

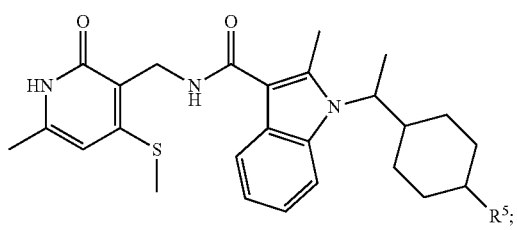
(VII)

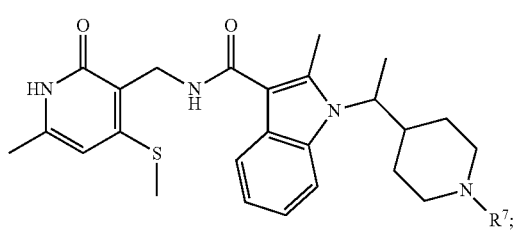
(VIII)

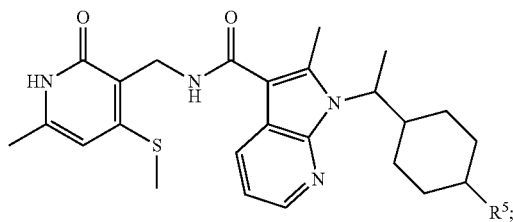
(IX)

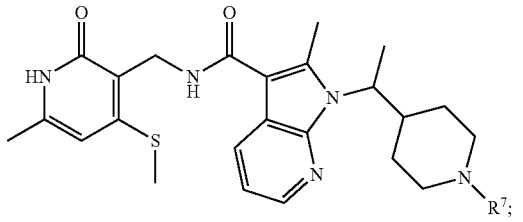
(X)

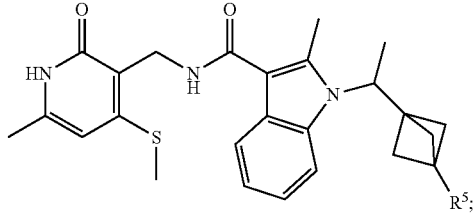
(XI)

or a pharmaceutically acceptable salt thereof, wherein the remaining variables are as described for Formula I or the first, sixth, or ninth embodiment. Alternatively, the compound of any one of Formulae I to V is of the Formula XII, XIII, XIV, XV, XVI, or XVII:

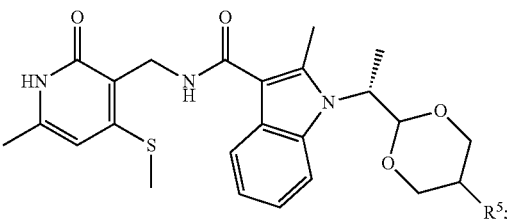
(XII)

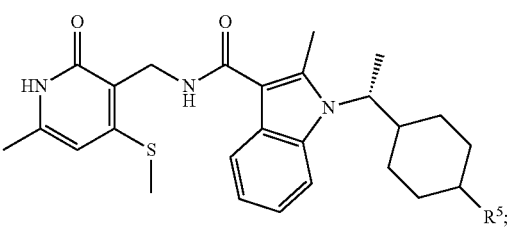
(XIII)

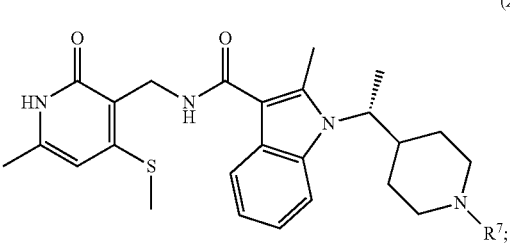
(XIV)

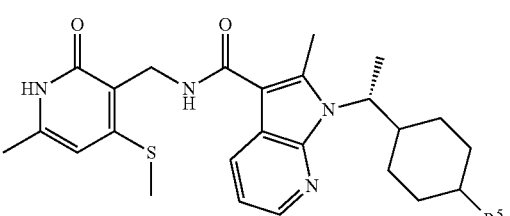
(XV)

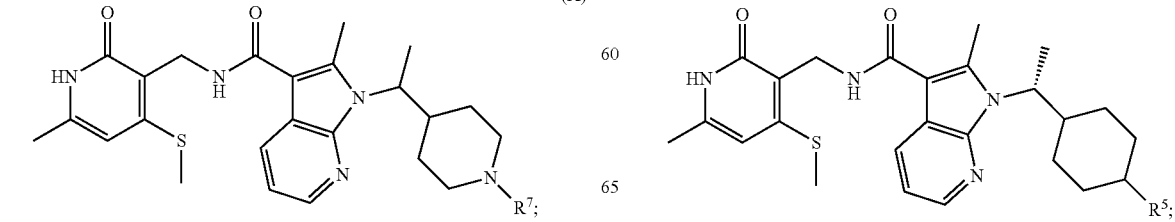

-continued

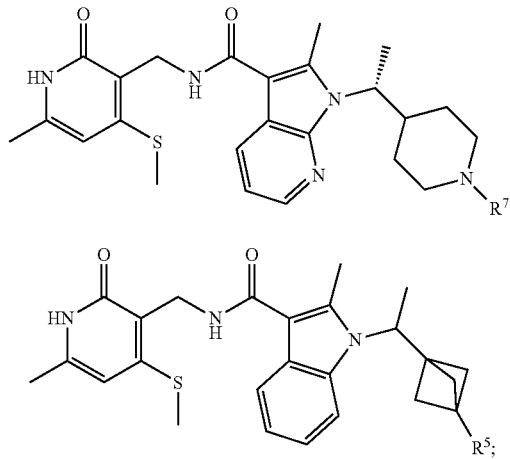

(XVI)

(XVII)

or a pharmaceutically acceptable salt thereof, wherein the remaining variables are as described for Formula I or the first, sixth, or ninth embodiment. In another alternative, the compound of any one of Formulae I to V is of the Formula XVIII, XIX, or XX:

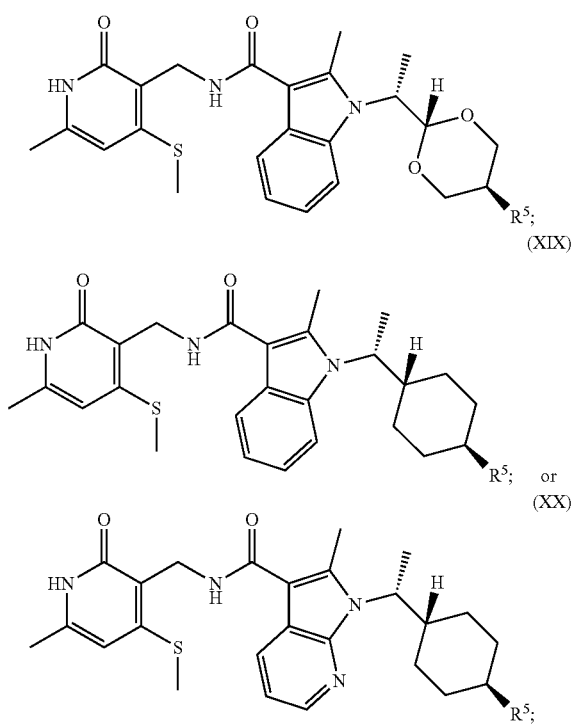

(XVIII)

(XIX)

(XX)

or a pharmaceutically acceptable salt thereof, wherein the remaining variables are as described for Formula I or the first, sixth, or ninth embodiment. In an eleventh embodiment, $R^5$ in the compound of any one of Formulae I to VII, IX, XI, XII, XIII, XV, XVII, XVIII, XIX, and XX is halo($C_1$-$C_4$)alkyl, hydroxyl, ($C_1$-$C_4$)alkoxy, or $NR^AR^B$, wherein the remaining variables are as described for Formula I or the first, sixth, or ninth embodiment. In another alternative, the compound of any one of Formulae I to V is of the Formula XVIII', XIX', or XX':

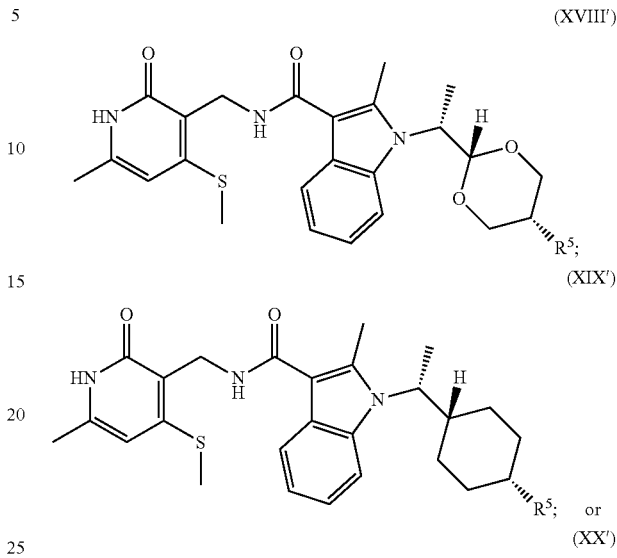

(XVIII')

(XIX')

(XX')

or a pharmaceutically acceptable salt thereof, wherein the remaining variables are as described for Formula I or the first, sixth, or ninth embodiment.

In a twelfth embodiment, $R^7$ in the compound of Formula VIII, X, XIV, or XVI is halo($C_1$-$C_4$)alkyl, —($C_1$-$C_4$)alkylOH, or ($C_3$-$C_6$)cycloalkyl, wherein the remaining variables are as described for Formula I or the first, sixth, or ninth embodiment.

In a thirteenth embodiment, $R^B$ in the compound of any one of Formulae I to VII, IX, XI, XII, XIII, XV, XVII, XVIII, XVIII', XIX, XIX', XX and XX' is ($C_1$-$C_4$)alkyl or a monocyclic 4- to 6-membered heterocyclyl, wherein said ($C_1$-$C_4$)alkyl for $R^B$ is optionally substituted with 1 to 3 groups selected from halo and O($C_1$-$C_4$)alkyl and wherein said heterocyclyl for $R^B$ is optionally substituted with 1 to 2 ($C_1$-$C_4$)alkyl; or $R^A$ and $R^B$ taken together with the nitrogen atom to which they are attached form a monocyclic 4- to 6-membered heterocyclyl optionally substituted with 1 or 2 groups selected from ($C_1$-$C_4$)alkyl, halo, halo($C_1$-$C_4$)alkoxy, and ($C_1$-$C_4$)alkoxy, wherein the remaining variables are as described for Formula I or the first, fourth, sixth, ninth, or twelfth embodiment.

In a fourteenth embodiment, $R^B$ in the compound of any one of Formulae I to VII, IX, XI, XII, XIII, XV, XVII, XVIII, XVIII', XIX, XIX', XX and XX' is ($C_1$-$C_4$)alkyl or oxetanyl, wherein said ($C_1$-$C_4$)alkyl for $R^B$ is optionally substituted with 1 to 3 groups selected from halo and —O($C_1$-$C_4$)alkyl and wherein said oxetanyl for $R^B$ is optionally substituted with 1 to 2 ($C_1$-$C_4$)alkyl; or $R^A$ and $R^B$ taken together with the nitrogen atom to which they are attached form an azetidinyl or oxetanyl, each of which are optionally substituted with 1 or 2 groups selected from $(C_1-C_4)$alkyl, halo, halo$(C_1-C_4)$alkoxy, and $(C_1-C_4)$alkoxy, wherein the remaining variables are as described for Formula I or the first, fourth, sixth, ninth, twelfth, or thirteenth embodiment.

In a fifteenth embodiment, $R^A$ in the compound of any one of Formulae I to VII, IX, XI, XII, XIII, XV, XVII, XVIII, XVIII', XIX, XIX', XX and XX' is hydrogen, halo$(C_1-C_4)$alkyl, or $(C_1-C_4)$alkyl, wherein the remaining variables are as described for Formula I or the first, fourth, sixth, ninth, twelfth, or thirteenth embodiment.

In a sixteenth embodiment, $R^A$ in the compound of any one of Formulae I to VII, IX, XI, XII, XIII, XV, XVII, XVIII, XVIII', XIX, XIX', XX and XX' is hydrogen, halo $(C_1-C_4)$alkyl, or $(C_1-C_4)$alkyl; $R^B$ is $(C_1-C_4)$alkyl, halo$(C_1-C_4)$alkyl, or oxetanyl, wherein said oxetanyl is optionally substituted with $(C_1-C_4)$alkyl; or $R^A$ and $R^B$ taken together with the nitrogen atom to which they are attached form an azetidinyl optionally substituted with 1 or 2 groups selected from $(C_1-C_4)$alkoxy, halo, and halo$(C_1-C_4)$alkoxy, wherein the remaining variables are as described for Formula I or the first, fourth, sixth, ninth, twelfth, thirteenth, or fourteenth embodiment.

In a seventeenth embodiment, $R^A$ in the compound of any one of Formulae I to VII, IX, XI, XII, XIII, XV, XVII, XVIII, XVIII', XIX, XIX', XX and XX' is hydrogen or methyl; $R^B$ is $(C_1-C_4)$alkyl, halo$(C_1-C_4)$alkyl, or oxetanyl, wherein said oxetanyl is optionally substituted with methyl; or $R^A$ and $R^B$ taken together with the nitrogen atom to which they are attached form an azetidinyl optionally substituted with methoxy, trifluoromethoxy, difluoromethoxy, difluoromethyl, or one or two fluoro wherein the remaining variables are as described for Formula I, wherein the remaining variables are as described for Formula I or the first, fourth, sixth, ninth, twelfth, thirteenth, fourteenth, or fifteenth embodiment.

In an eighteenth embodiment, the compound of Formula I is of the Formula XXI, XXII, XXIII, or XXIV:

(XXI)

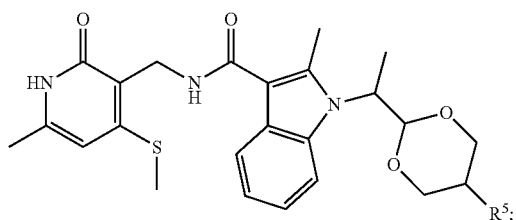

(XXII)

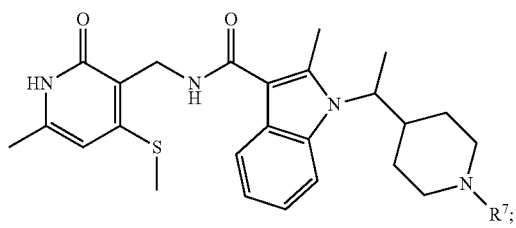

(XXIII)

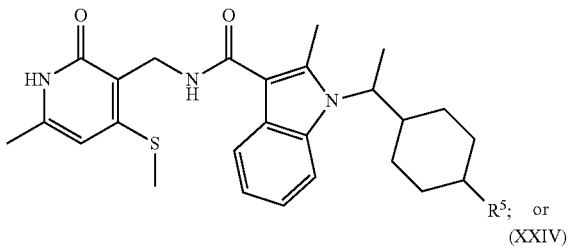

(XXIV)

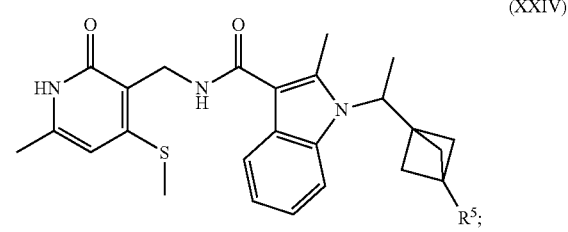

or a pharmaceutically acceptable salt thereof, wherein $R^5$ is hydroxyl, $(C_1-C_4)$alkoxy, or $NR^A R^B$;

$R^A$ is hydrogen, $(C_1-C_4)$alkyl, or halo$(C_1-C_4)$alkyl;

$R^B$ is $(C_1-C_4)$alkyl or monocyclic 4- to 6-membered heterocyclyl optionally substituted with 1 or 2 $(C_1-C_4)$alkyl; or $R^A$ and $R^B$ taken together with the nitrogen atom to which they are attached form a monocyclic 4- to 6-membered heterocyclyl optionally substituted with halo, $(C_1-C_4)$alkoxy or halo$(C_1-C_4)$alkoxy.

In a nineteenth embodiment, the compound of Formula I is of the Formula XXV, XXVI, XXVII, or XXVIII:

(XXV)

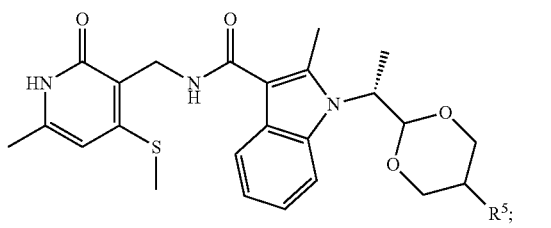

(XXVI)

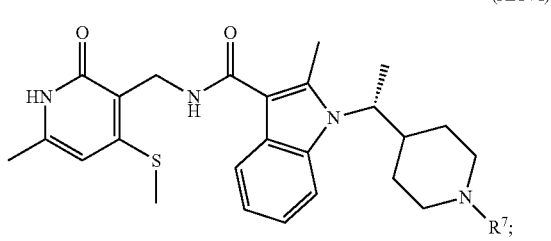

(XXVII)

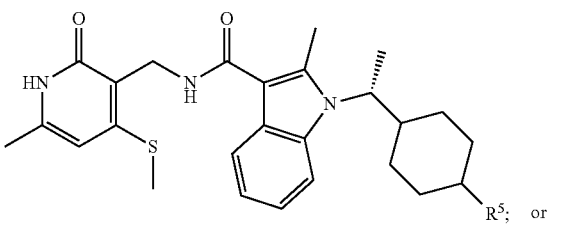

-continued

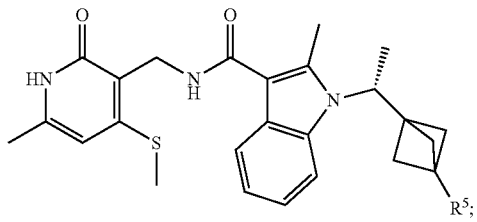
(XXVIII)

or a pharmaceutically acceptable salt thereof, wherein the variables are as described above in the eighteenth embodiment.

In a twentieth embodiment, the compound of Formula I is of the Formula XXIX or XXX:

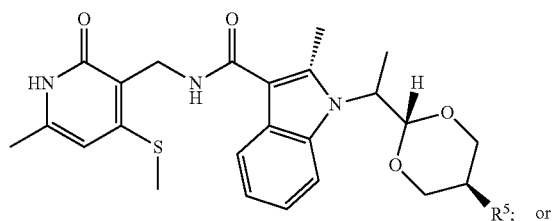
(XXIX)

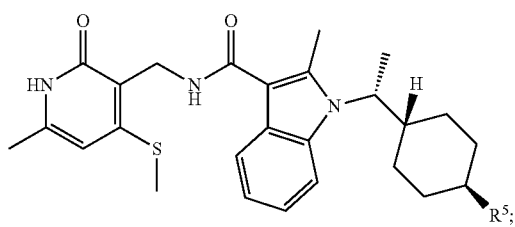
(XXX)

or a pharmaceutically acceptable salt thereof, wherein the variables are as described above in the eighteenth embodiment.

In a twenty-first embodiment, the compound of Formula I is of the Formula XXXI or XXXII:

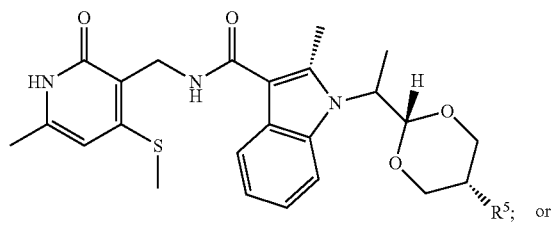
(XXXI)

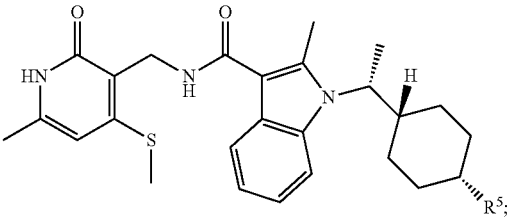
(XXXII)

or a pharmaceutically acceptable salt thereof, wherein the variables are as described above in the eighteenth embodiment.

In a twenty-second embodiment, $R^A$ in the compound of the Formula XXI, XXIII, XXIV, XXV, XXVII, XXVIII, XXIX, XXX, XXXI, and XXXII is hydrogen, $(C_1-C_4)$alkyl, or halo$(C_1-C_4)$alkyl; $R^B$ is $(C_1-C_4)$alkyl or oxetanyl optionally substituted with $(C_1-C_4)$alkyl; or $R^A$ and $R^B$ taken together with the nitrogen atom to which they are attached form an azetidinyl optionally substituted with halo, $(C_1-C_4)$alkoxy or halo$(C_1-C_4)$alkoxy. Alternatively, $R^A$ is hydrogen, methyl, or 2,2,2-trifluoroethyl; $R^B$ is methyl or oxetanyl optionally substituted with methyl; or $R^A$ and $R^B$ taken together with the nitrogen atom to which they are attached form an azetidinyl optionally substituted with methoxy, difluoromethoxy, or fluoro.

In a twenty-third embodiment, $R^7$ in the compound of the Formula XXII or XXVI is halo$(C_1-C_4)$alkyl or —$(C_1-C_4)$alkylOH.

In a twenty-fourth embodiment, the compound of Formula I is of the Formula XXXIII:

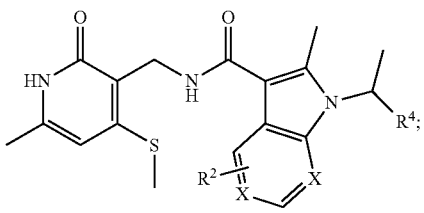
(XXXIII)

or a pharmaceutically acceptable salt thereof, wherein
$R^2$ is hydrogen or halo;
$R^4$ is cyclohexyl, piperidinyl or dioxanyl, each of which being optionally and independently substituted with 1 to 3 groups selected from $R^5$;
$R^5$ is selected from halo, $(C_3-C_6)$cycloalkyl, $OR^6$, —OC(O)$(C_1-C_4)$alkyl, —C(O)$(C_1-C_4)$alkylOH, —C(O)$(C_1-C_4)$alkylN($(C_1-C_4)$alkyl$)_2$, —SO$_2$$(C_1-C_4)$alkyl, 4-7 membered heterocyclyl, and NR$^A$R$^B$, wherein said cycloalkyl for $R^5$ is optionally substituted with —O$(C_1-C_4)$alkyl;
$R^A$ is hydrogen;
$R^B$ is $(C_3-C_5)$cycloalkyl or 4-7 membered heterocyclyl, wherein said heterocyclyl or cycloalkyl for $R^B$ is optionally substituted with 1 to 3 groups selected from $(C_1-C_4)$alkyl, halo$(C_1-C_4)$alkyl, and hydroxy$(C_1-C_4)$alkyl; or
$R^A$ and $R^B$ taken together with the nitrogen atom to which they are attached form a 3-7 membered heterocyclyl optionally substituted with 1 to 3 groups selected from halo, hydroxyl, cyano, $(C_1-C_4)$alkyl, hydroxy$(C_1-C_4)$alkyl, NMe$_2$, —SO$_2$$(C_1-C_4)$alkyl, 5-6 membered heteroaryl, and $(C_3-C_6)$cycloalkyl; and $R^6$ is $(C_3-C_6)$cycloalkyl, 4-7 membered heterocyclyl, 5-6 membered heteroaryl, or —O($C_1-C_4$)alkyl, wherein said 4-7 membered heterocyclyl and said 5-6 membered heteroaryl for $R^6$ are each optionally and independently substituted with 1 or 2 ($C_1-C_4$)alkyl groups.

In a twenty-fifth embodiment, $R^5$ in the Compound of Formula XXXIII is selected from halo, $(C_3-C_6)$cycloalkyl, $OR^6$, —OC(O)($C_1-C_4$)alkyl, —C(O)($C_1-C_4$)alkylOH, —C(O)($C_1-C_4$)alkylN(($C_1-C_4$)alkyl)$_2$, —SO$_2$($C_1-C_4$)alkyl, 4-7 membered heterocyclyl, and $NR^AR^B$, wherein said cycloalkyl for $R^5$ is optionally substituted with —O($C_1-C_4$)alkyl;

$R^A$ is hydrogen;

$R^B$ is $(C_3-C_5)$cycloalkyl or 4-7 membered heterocyclyl, wherein said heterocyclyl or cycloalkyl for $R^B$ are each optionally and independently substituted with 1 to 3 groups selected from ($C_1-C_4$)alkyl, halo($C_1-C_4$)alkyl, and hydroxy($C_1-C_4$)alkyl; or $R^A$ and $R^B$ taken together with the nitrogen atom to which they are attached form a 3-7 membered heterocyclyl optionally substituted with 1 to 3 groups selected from halo, hydroxyl, cyano, ($C_1-C_4$)alkyl, NMe$_2$, hydroxy($C_1-C_4$)alkyl, —SO$_2$($C_1-C_4$)alkyl, 5-6 membered heteroaryl, and ($C_3-C_6$)cycloalkyl; and $R^6$ is $(C_3-C_6)$cycloalkyl, 4-7 membered heterocyclyl, 5-6 membered heteroaryl, or —O($C_1-C_4$)alkyl, wherein said 4-7 membered heterocyclyl and said 5-6 membered heteroaryl for $R^6$ are each optionally and independently substituted with 1 or 2 ($C_1-C_4$)alkyl groups, wherein the remaining variables are as described in the twenty-fourth embodiment.

In a twenty-sixth embodiment, the compound of Formula XXXIII is of the Formula XXXIV:

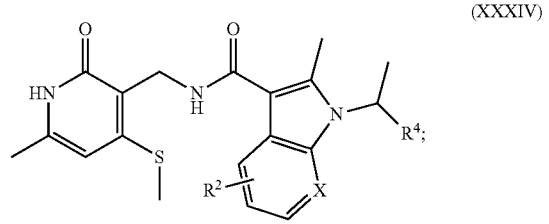

(XXXIV)

or a pharmaceutically acceptable salt thereof, wherein the remaining variables are as described for Formula XXXIII or the twenty-fifth embodiment.

In a twenty-sixth embodiment, the compound of Formula XXXIII is of the Formula XXXV:

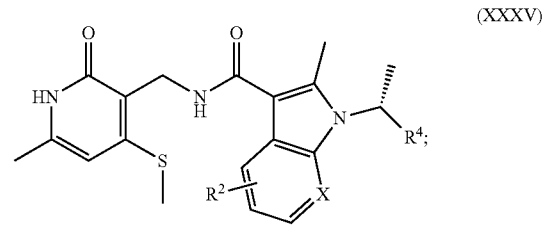

(XXXV)

or a pharmaceutically acceptable salt thereof, wherein the remaining variables are as described for Formula XXXIII or the twenty-fifth embodiment.

In a twenty-seventh embodiment, $R^2$ in the compounds of Formula XXXIII to XXXV is hydrogen or fluorine, wherein the remaining variables are as described for Formula XXXIII or the twenty-fifth embodiment.

In a twenty eighth embodiment, $R^5$ in the compounds of Formula XXXIII to XXXV is selected from halo, $(C_3-C_6)$ cycloalkyl, —OC(O)($C_1-C_4$)alkyl, —C(O)($C_1-C_4$)alkylOH, —C(O)($C_1-C_4$)alkylN(($C_1-C_4$)alkyl)$_2$, —SO$_2$($C_1-C_4$)alkyl, and $NR^AR^B$ wherein said cycloalkyl for $R^5$ is optionally substituted with —O($C_1-C_4$)alkyl;

$R^B$ is $(C_3-C_5)$cycloalkyl or 4-7 membered heterocyclyl each optionally and independently substituted with 1 to 3 groups selected from ($C_1-C_4$)alkyl, halo($C_1-C_4$)alkyl, and hydroxy($C_1-C_4$)alkyl; or $R^A$ and $R^B$ taken together with the nitrogen atom to which they are attached form a 3-7 membered heterocyclyl optionally substituted with 1 to 3 groups selected from halo, hydroxyl, cyano, ($C_1-C_4$)alkyl, NMe$_2$, —SO$_2$($C_1-C_4$)alkyl, 5-6 membered heteroaryl, and ($C_3-C_6$)cycloalkyl; and $R^6$ is 4-7 membered heterocyclyl or 5-6 membered heteroaryl, wherein said 4-7 membered heterocyclyl and said 5-6 membered heteroaryl for $R^6$ are each optionally and independently substituted with ($C_1-C_4$)alkyl, wherein the remaining variables are as described for Formula XXXIII or the twenty-fifth or twenty-seventh embodiment.

In a twenty-ninth embodiment, $R^5$ in the compounds of Formula XXXIII to XXXV is selected from halo, cyclobutyl, —OC(O)($C_1-C_4$)alkyl, —C(O)($C_1-C_4$)alkylOH, —C(O)($C_1-C_4$)alkylN(($C_1-C_4$)alkyl)$_2$, —SO$_2$($C_1-C_4$)alkyl, and $NR^AR^B$ wherein said cyclobutyl for $R^5$ is optionally substituted with —O($C_1-C_4$)alkyl;

$R^B$ is tetrahydrofuranyl, cyclopropyl, or oxatanyl, each optionally and independently substituted with 1 to 3 groups selected from ($C_1-C_4$)alkyl, halo($C_1-C_4$)alkyl, and hydroxy ($C_1-C_4$)alkyl; or $R^A$ and $R^B$ taken together with the nitrogen atom to which they are attached form an azetidinyl, oxaazaspirohexanyl, oxaazaspiroheptanyl, each of which are optionally and independently substituted with 1 to 3 groups selected from halo, hydroxyl, cyano, ($C_1-C_4$)alkyl, NMe$_2$, —SO$_2$($C_1-C_4$)alkyl, triazolyl, and cyclopropyl; and $R^6$ is an oxetanyl, azetidinyl, pyrazolyl, 4-7 membered heterocyclyl or 5-6 membered heteroaryl, wherein said 4-7 membered heterocyclyl and said 5-6 membered heteroaryl for $R^6$ are each optionally and independently substituted with ($C_1-C_4$)alkyl, wherein the remaining variables are as described for Formula XXXIII or the twenty-fifth, twenty-seventh, or twenty-eighth embodiment.

In a thirtieth embodiment, the compound of Formula XXXIII is of the Formula XXXVI:

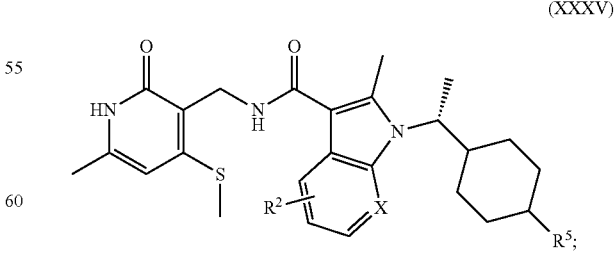

(XXXV)

or a pharmaceutically acceptable salt thereof, wherein the remaining variables are as described for Formula XXXIII or the twenty-fifth, twenty-seventh, or twenty-eighth embodiment.

Specific examples of compounds are provided in the EXEMPLIFICATION section and are included as part of a thirteenth embodiment herein. Pharmaceutically acceptable salts as well as the neutral forms of these compounds are also included.

4. Uses, Formulation and Administration

In some embodiments, the present disclosure provides a composition comprising a compound described herein or a pharmaceutically acceptable derivative thereof and a pharmaceutically acceptable carrier. The amount of compound in a provided composition is such that is effective to measurably modulate a histone methyl modifying enzyme, or a mutant thereof, in a biological sample or in a patient.

In certain embodiments, a composition described herein is formulated for administration to a patient in need of such composition. Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the compositions described herein may be aqueous or oleaginous suspension. These suspensions may be formulated according to techniques known in the art using suitable dispersing or wetting agents and suspending agents.

In some embodiments, the compositions are administered orally.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the composition.

The compounds described herein may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include e.g., ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, benzoates and salts with amino acids such as glutamic acid.

Compounds and compositions described herein are generally useful for the modulating of activity of one or more enzymes involved in epigenetic regulation and in particular EZH1 and EZH2 and, even more specifically EZH2 and mutant forms thereof. In some embodiments, compounds described herein down-regulate or suppress the activity of EZH2. In some embodiments, compounds described herein are antagonists of EZH2 activity. In some embodiments, compounds described herein down-regulate or suppress the activity of EZH1. In some embodiments, compounds described herein are antagonists of EZH1 activity.

In some embodiments, compounds and compositions described herein are useful in treating diseases and/or disorders associated with overexpression of EZH1 or EZH2 and/or expression of a mutant form of EZH2, such as those mutant forms that alter EZH2 substrate activity. The study of EZH2 deletions, missense and frameshift mutations suggest that EZH2 functions as a tumor suppressor in blood disorders such as myelodysplastic syndromes (MDS) and myeloid malignancies (Ernst et al., Nat Genet. 2010 August; 42(8):722-6; Nikoloski et al., Nat Genet. 2010 August; 42(8):665-7). In some embodiments, compounds and compositions described herein are useful in treating diseases and/or disorders associated with the presence of EZH2 having a Y641N, Y641C, Y641F, Y641H, Y641S, A677G, or A687 mutation. In a particular aspect of this embodiment, the EZH2 has a Y641N mutation.

In some embodiments, the present disclosure provides a method of treating a subject suffering from a disease and/or disorder associated with overexpression of EZH1 or EZH2 and/or expression of a mutant form of EZH2 comprising the step of administering a compound described herein, or a pharmaceutically acceptable salt or composition thereof. In some embodiments, the above method additionally comprises the preliminary step of determining if the subject is overexpressing EZH2 or expressing a mutant form of EZH2.

In some embodiments, the disease or disorder associated with the presence of a mutant form of EZH2 is a human B cell lymphoma. In some embodiments, the disease and/or disorder associated with the presence of Y641N EZH2 is follicular lymphoma or diffuse large-B-cell lymphoma. In some embodiments, compounds or compositions described herein are useful in treating blood disorders, such as myelodysplastic syndromes, leukemia, anemia and cytopenia. Sneeringer et al., "Coordinated activities of wild-type plus mutant EZH2 drive tumor-associated hypertrimethylation of lysine 27 on histone H3 (H3K27) in human B-cell lymphomas," Sneeringer et al., Proc. Natl Acad. Sci. 2010 December; 109(48):20980-20985.

In some embodiments, compounds and compositions described herein are useful in treating diseases and/or disorders associated with cellular proliferation. In some embodiments, compounds and compositions described herein are useful in treating diseases and/or disorders associated with misregulation of cell cycle or DNA repair. In some embodiments, compounds and compositions described herein are useful in treating cancer.

In one aspect, cancers that may be treated by the compounds, compositions and methods described herein include, but are not limited to Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, clear cell carcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

In one aspect, the cancer treated by the compounds, compositions, and methods described herein are selected from breast cancer, prostate cancer, colon cancer, renal cell carcinoma, glioblastoma multiforme cancer, bladder cancer, melanoma, bronchial cancer, lymphoma and liver cancer.

EXEMPLIFICATION

The representative examples that follow are intended to help illustrate the present disclosure, and are not intended to, nor should they be construed to, limit the scope of the invention.

Synthesis of Intermediate A6: 3-(aminomethyl)-6-methyl-4-(methylthio)pyridin-2(1H)-one

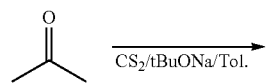

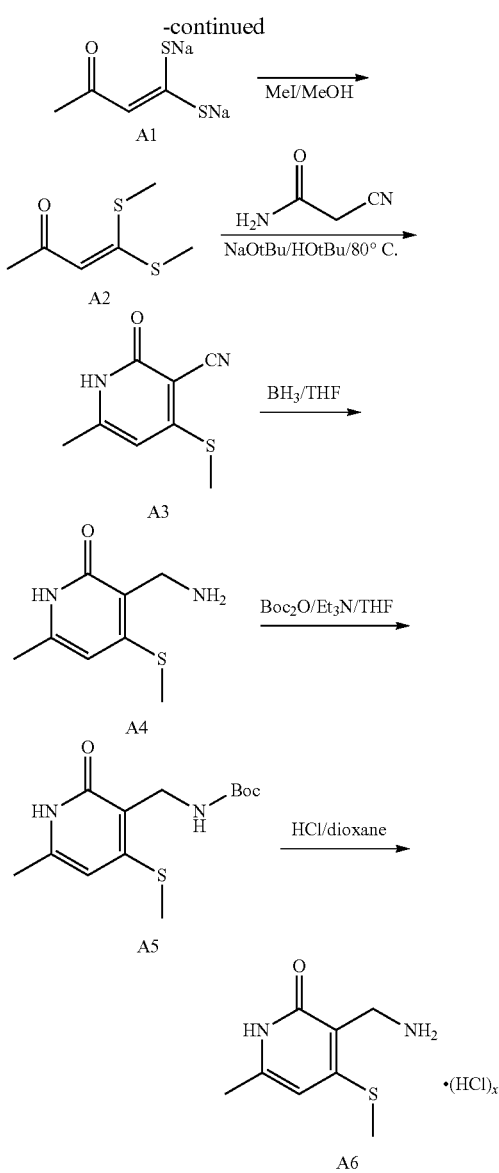

Step 1: Synthesis of Sodium 3-oxobut-1-ene-1,1-bis(thiolate) (A1)

A mixture of t-BuONa (16.6 g, 172 mmol, 2.0 equiv) in toluene (30 mL) was degassed and purged with $N_2$ 3 times, and then acetone (5.0 g, 86 mmol, 1.0 equiv) was added at 0° C. Then $CS_2$ (6.6 g, 86 mmol, 1.0 equiv) was added slowly. The resulting mixture was stirred at 0° C. for 4 h. The reaction mixture was filtered, and the filter cake was dried to give A1, sodium 3-oxobut-1-ene-1,1-bis(thiolate) (15.4 g, crude), as a yellow solid, which was used directly in the next step without further purification.

Step 2: 4,4-bis(methylthio)but-3-en-2-one (A2)

To a solution of A1 (15.4 g, 86.4 mmol, 1.0 equiv) in methanol (90 mL) was added MeI (24.5 g, 173 mmol, 2.0 equiv) slowly. The mixture was stirred at 70° C. for 1 h. The reaction mixture was then concentrated and water (30 mL) was added to the reaction mixture. The mixture was extracted with ethyl acetate (60 mL*3). The organic layer was dried over sodium sulfate and concentrated to give a A2, 4,4-bis(methylthio)but-3-en-2-one (6.8 g, 36 mmol, 42% yield) was obtained as a brown oil. LCMS [M+H]$^+$ m/z: calc'd 163.02; found 163.0. $^1$H NMR (400 MHz, CDCl$_3$) δ 6.02 (s, 1H), 2.45 (s, 3H), 2.43 (s, 3H), 2.15 (s, 3H).

Step 3: Synthesis of 6-methyl-4-(methylthio)-2-oxo-1,2-dihydropyridine-3-carbonitrile (A3)

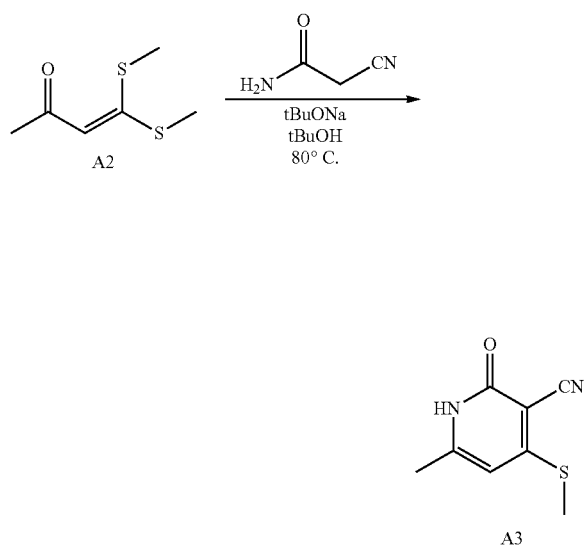

To a solution of 4,4-bis(methylthio)but-3-en-2-one (2.9 g, 18 mmol, 1.0 equiv) and 2-cyanoacetamide (1.5 g, 18 mmol, 1.0 equiv) in 2-methylpropan-2-ol (50 mL) was added t-BuONa (1.9 g, 20 mmol, 1.1 equiv). The mixture was stirred at 80° C. for 12 h. Two batches of the reaction were performed and combined at this stage. Water (20 mL) was added and the pH was adjusted to 5-6 with 10% HCl solution. Then the resulting mixture was filtered, and the filter cake was washed with petroleum ether (petroleum ether) (20 mL*2) to give crude A3, 6-methyl-4-(methylthio)-2-oxo-1,2-dihydropyridine-3-carbonitrile (4.8 g, 27 mmol, 74% yield), as an off-white solid. LCMS [M+H]$^+$ m/z: calc'd 181.04; found 181.0. $^1$H NMR (400 MHz, DMSO-d$_6$) δ 6.27 (s, 1H), 2.56 (s, 3H), 2.25 (s, 3H).

Step 4: Synthesis 3-(aminomethyl)-6-methyl-4-(methylthio)pyridin-2(1H)-one (A4)

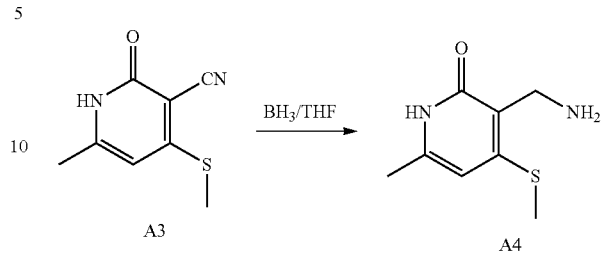

A mixture of 6-methyl-4-(methylthio)-2-oxo-1,2-dihydropyridine-3-carbonitrile (3.6 g, 20 mmol, 1.0 equiv) in tetrahydrofuran (50 mL) was degassed and purged with N$_2$ 3 times at 0° C., and then BH$_3$-Me$_2$S (10 M, 8.0 mL, 4.0 equiv) was added slowly. The reaction mixture was warmed to 70° C. and was stirred for 2 h. Methanol (15 mL) was slowly added at 0° C. to quench the reaction before the mixture was concentrated to give A4, 3-(aminomethyl)-6-methyl-4-(methylthio)pyridin-2(1H)-one (3.8 g, crude), as a light yellow solid and used directly in the next step. LCMS [M+H]$^+$ m/z: calc'd 185.07; found 185.0.

Step 5: Synthesis of tert-butyl ((6-methyl-4-(methylthio)-2-oxo-1,2-dihydropyridin-3-yl)methyl)carbamate (A5)

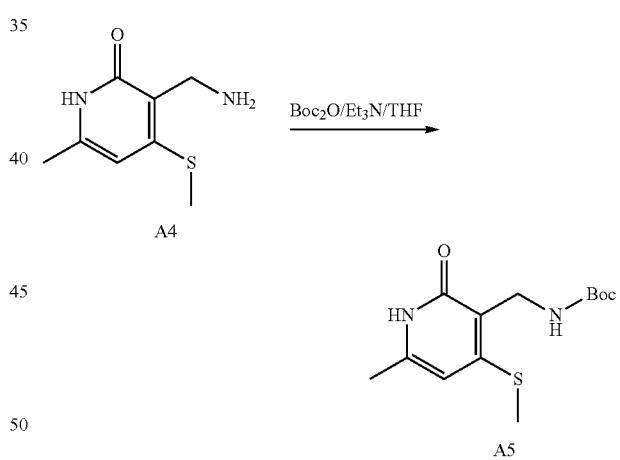

To a solution of 3-(aminomethyl)-6-methyl-4-methylsulfanyl-1H-pyridin-2-one (3.6 g, 20 mmol, 1.0 equiv) in tetrahydrofuran (80 mL) was added triethylamine (5.9 g, 59 mmol, 3.0 equiv). The mixture was stirred at 25° C. for 0.5 h. Then (Boc)$_2$O (6.4 g, 29 mmol, 1.5 equiv) was added and the reaction was stirred at 25° C. for 12 h. The reaction mixture was then concentrated, the residue washed with water (35 mL) and the desired product extracted with a 5:1 mixture of petroleum ether/ethyl acetate (30 mL*3). A5, tert-butyl ((6-methyl-4-(methylthio)-2-oxo-1,2-dihydropyridin-3-yl)methyl)carbamate (5.8 g, crude) was obtained as a white solid. LCMS [M+H]$^+$ m/z: calc'd 285.12; found 284.9. $^1$H NMR (400 MHz, DMSO-d$_6$) δ 6.05 (s, 1H), 4.03-4.00 (m, 2H), 2.42 (s, 3H), 2.15 (s, 3H), 1.39 (s, 9H).

Step 6: 3-(aminomethyl)-6-methyl-4-(methylthio) pyridin-2(1H)-one hydrochloride (A6)

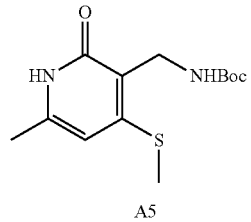

tert-butyl ((6-methyl-4-(methylthio)-2-oxo-1,2-dihydropyridin-3-yl)methyl)carbamate (5.0 g, 17.6 mmol, 1.0 equiv) was added to a HCl solution (100 mL, 4 M in 1,4-dioxane). The reaction mixture was stirred at 25° C. for 2 h then concentrated under reduced pressure. The residue was washed with dichloromethane (30 mL*2) and ethyl acetate (30 mL*1). A6, 3-(aminomethyl)-6-methyl-4-(methylthio)pyridin-2(1H)-one hydrochloride (4.5 g, crude, HCl salt) was obtained as a yellow solid and was used directly in the next step without further purification. LCMS [M+H]$^+$ m/z: calc'd 185.07; found 185.0. $^1$H NMR (400 MHz, D$_2$O) δ 6.31 (s, 1H), 4.03 (s, 2H), 2.41 (s, 3H), 2.18 (s, 3H).

Synthesis of methyl (R)-2-methyl-1-(1-(4-oxocyclohexyl)ethyl)-1H-indole-3-carboxylate (B15)

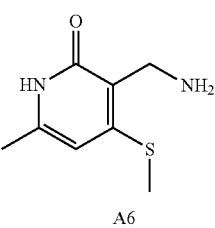

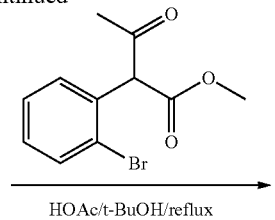

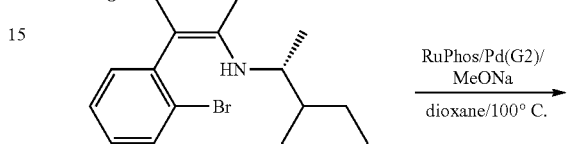

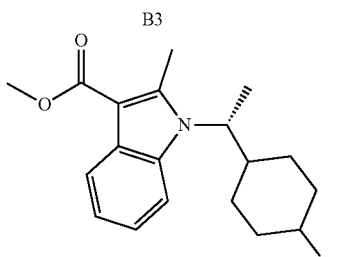

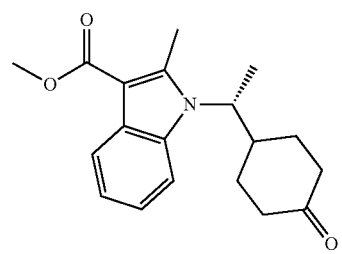

Step 1: Synthesis of 4-[(1R)-1-aminoethyl]phenol;hydrobromide (B1)

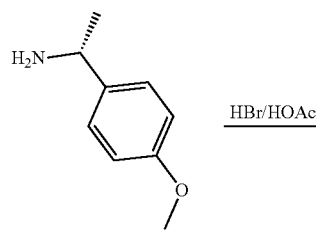

The mixture of (1R)-1-(4-methoxyphenyl)ethanamine (20 g, 132.27 mmol, 1 equiv) in HBr 35% in acetic acid (170 mL, 1.03 mol, 7.81 equiv) was stirred at 0° C. for 1 h then stirred at 20° C. for 47 hours. The reaction was concentrated and acetonitrile (200 mL) was added to the residue. The mixture was stirred at 0° C. for 1 h, then filtered. The filter cake was washed with acetonitrile (50 mL) and ethylacetate (150 mL), then dried under in vacuum. The desired compound, 4-[(1R)-1-aminoethyl]phenol hydrobromide salt (24 g, 110.05 mmol, 83.20% yield) was obtained as a white solid. $^1$H NMR (400 MHz, DMSO-$d_6$) δ 9.57 (br s, 1H), 8.18 (br s, 3H), 7.32-7.26 (m, J=8.5 Hz, 2H), 6.82-6.76 (m, J=8.5 Hz, 2H), 4.30 (td, J=5.8, 11.9 Hz, 1H), 1.46 (d, J=6.8 Hz, 3H).

Step 2: Synthesis of
4-[(1R)-1-aminoethyl]cyclohexanol (B2)

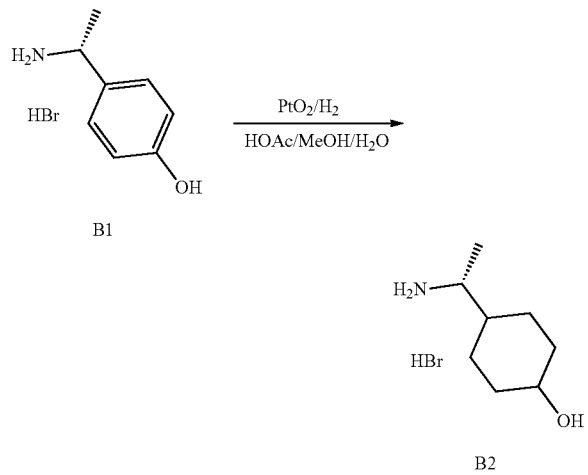

To a solution of 4-[(1R)-1-aminoethyl]phenol hydrobromide salt (20 g, 92 mmol, 1 equiv) in methanol (250 mL) was added acetic acid (12 mL), water (12 mL) and PtO$_2$ (2.0 g, 8.8 mmol, 0.1 equiv) under a nitrogen atmosphere. The suspension was degassed (several under vacuum and hydrogen refill cycles). The reaction was stirred under hydrogen atmosphere (55 psi) at 20° C. for 48 hours (Four batches were run in parallel). The batches were combined, filtered and concentrated under reduced pressure. The residue was dissolved in methanol (200 mL) and potassium carbonate (50 g) was added. The mixture was stirred at 20° C. for 1 h, then filtered and concentrated under reduced pressure. The residue was dissolved in a 10:1 mixture of dichloromethane:methanol (200 mL) and filtered. The filtrate was concentrated under reduced pressure to the desired compound, 4-[(1R)-1-aminoethyl]cyclohexanol (80 g, crude) as a white solid. It was used in the next step without further purification.

Step 3: The Synthesis of methyl 2-(2-bromophenyl)-3-(((1R)-1-(4-hydroxycyclohexyl)ethyl)amino)but-2-enoate (B3)

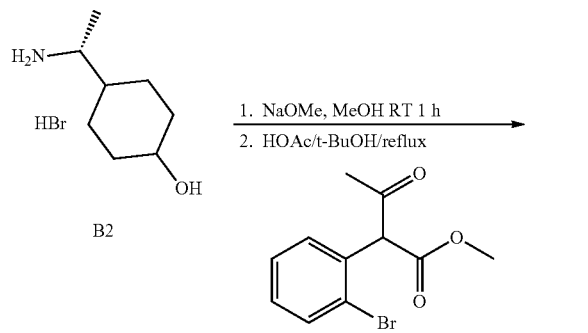

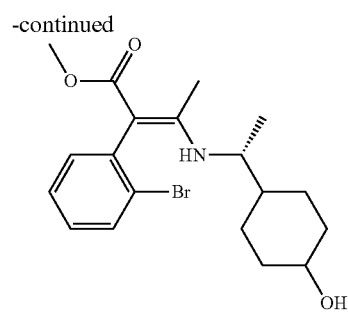

A mixture of crude (R)-4-(1-aminoethyl)cyclohexan-1-ol (10.0 g, 44.6 mmol, 1.0 equiv, HBr salt) and NaOMe (2.65 g, 49.1 mmol, 1.1 equiv) in methanol (20.0 mL) was stirred at 25° C. for 1 h under N$_2$. Then the reaction mixture was filtered, and the filtrate was concentrated to give (R)-4-(1-aminoethyl)cyclohexan-1-ol free base. Then methyl 2-(2-bromophenyl)-3-oxo-butanoate (13.3 g, 49.1 mmol, 1.1 equiv), t-BuOH (100 mL) and acetic acid (3.48 g, 58.0 mmol, 1.3 equiv) were added. The resulting mixture was stirred at 85° C. for 12 h and then concentrated under vacuum and quenched with saturated sodium bicarbonate (80 mL). The mixture was extracted with ethyl acetate (160 mL*3). The organic layer was dried by anhydrous sodium sulfate, filtered and concentrated under vacuum. The crude was purified by flash silica gel chromatography to give B3, methyl 2-(2-bromophenyl)-3-(((1R)-1-(4-hydroxycyclohexyl)ethyl)amino)but-2-enoate (2.0 g, 3.4 mmol, 8% yield), as a brown gum. LCMS [M+Na]$^+$ m/z: calc'd 418.11; found 418.0.

Step 4: The Synthesis of methyl 1-((1R)-1-(4-hydroxycyclohexyl)ethyl)-2-methyl-1H-indole-3-carboxylate (B4)

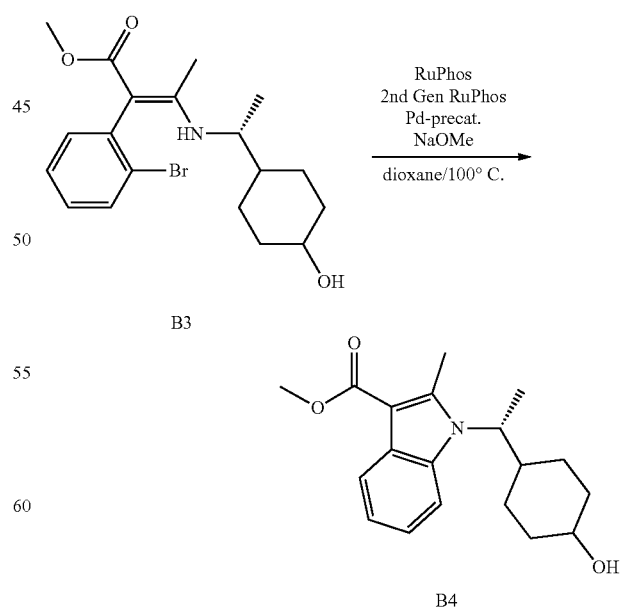

A mixture of methyl 2-(2-bromophenyl)-3-(((1R)-1-(4-hydroxycyclohexyl)ethyl)amino)but-2-enoate (2.5 g, 6.3 mmol, 1.0 equiv), sodium methoxide (510 mg, 9.5 mmol, 1.5 equiv), RuPhos (294 mg, 631 umol, 0.1 equiv) and 2nd Gen RuPhos precatalyst (490 mg, 631 umol, 0.1 equiv) in 1,4-dioxane (100 mL) was degassed and purged with $N_2$ 3 times, and then the mixture was stirred at 100° C. for 13 h under $N_2$. The reaction mixture was concentrated and then water (30 mL) was added. The desired product was extracted with dichloromethane (60 mL*3) and the organic layer was dried over anhydrous sodium sulfate, filtered and concentrated under vacuum. The crude was purified by flash silica gel chromatography to give B4, methyl 1-((1R)-1-(4-hydroxycyclohexyl)ethyl)-2-methyl-indole-3-carboxylate (3.70 g, 11.1 mmol, 88% yield), as a yellow solid. LCMS [M+H]$^+$ m/z: calc'd 316.41; found 315.9.

The following intermediates were synthesized using similar conditions as those described in Steps 3 and 4, above, along with appropriate starting materials.

| Structure | Name | Intermediate | LCMS |
|---|---|---|---|
| 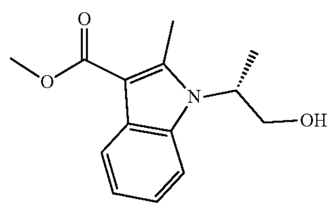 [SMILES: COC(=O)c1c(C)n([C@H](C)CO)c2ccccc12] | methyl (R)-1-(1-hydroxypropan-2-yl)-2-methyl-1H-indole-3-carboxylate | C1 | LCMS [M + H]$^+$ m/z: calc'd 248.12; found 247.9. |
| 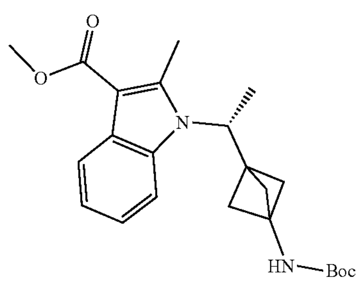 [SMILES: COC(=O)c1c(C)n([C@H](C)C23CC(NC(=O)OC(C)(C)C)(C2)C3)c2ccccc12] | methyl (R)-1-(1-(3-((tert-butoxycarbonyl)amino)bicyclo[1.1.1]pentan-1-yl)ethyl)-2-methyl-1H-indole-3-carboxylate | D8 | LCMS [M + H]$^+$ m/z: calc'd 399.22; found 399.2. |
| 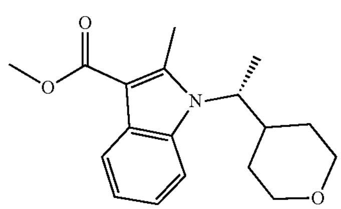 [SMILES: COC(=O)c1c(C)n([C@H](C)C2CCOCC2)c2ccccc12] | methyl (R)-2-methyl-1-(1-(tetrahydro-2H-pyran-4-yl)ethyl)-1H-indole-3-carboxylate | F1 | LCMS [M + H]$^+$ m/z: calc'd 302.17; found 301.9. |
| 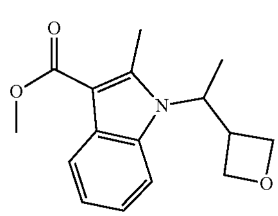 [SMILES: COC(=O)c1c(C)n(C(C)C2COC2)c2ccccc12] | methyl 2-methyl-1-(1-(oxetan-3-yl)ethyl)-1H-indole-3-carboxylate | G1 | LCMS [M + H]$^+$ m/z : calc'd 274.14; found 273.9. |

Step 5: The Synthesis of methyl (R)-2-methyl-1-(1-(4-oxocyclohexyl)ethyl)-1H-indole-3-carboxylate (B5)

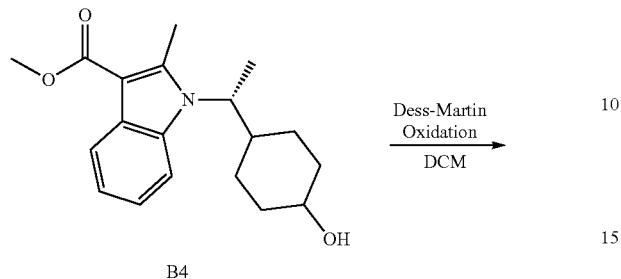

B4

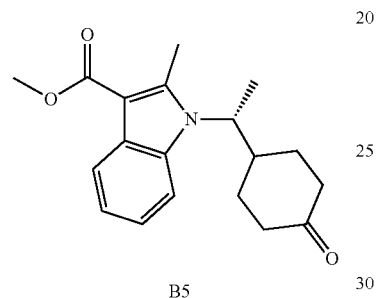

B5

To the solution of methyl 1-((1R)-1-(4-hydroxycyclohexyl)ethyl)-2-methyl-1H-indole-3-carboxylate (180 mg, 571 umol, 1.0 equiv) in dichloromethane (8 mL) was added Dess-Martin periodinane (484 mg, 1.10 mmol, 0.35 mL, 2.0 equiv) in portions at 10° C. The mixture was stirred at 10° C. for 16 h. The reaction was quenched with saturated sodium bicarbonate (30 mL) and the desired product was extracted with dichloromethane (20 mL*3). The organic layers were washed with saturated sodium thiosulfate (50 mL), dried over sodium sulfate and concentrated under vacuum. The crude was purified by silica gel chromatography to give B5, methyl (R)-2-methyl-1-(1-(4-oxocyclohexyl)ethyl)-1H-indole-3-carboxylate (150 mg, 441 umol, 77% yield), as a light yellow oil. LCMS [M+Na]$^+$ m/z: calc'd 336.17; found 336.2.

The following intermediates were synthesized using similar conditions as those described in Step 5, above, along with appropriate starting materials.

| Structure | Name | Intermediate | LCMS |
|---|---|---|---|
| 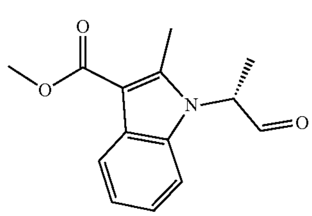 | (R)-methyl 2-methyl-1-(1-oxopropan-2-yl)-1H-indole-3-carboxylate | C2 | LCMS ([M + H$_2$O]$^+$) m/z: calc'd 264.12; found 263.9. |

Synthesis of methyl (R)-2-methyl-1-(1-(5-oxo-1,3-dioxan-2-yl)ethyl)-1H-indole-3-carboxylate (C4)

Step 1: Synthesis of methyl (R)-2-methyl-1-(1-(5-methylene-1,3-dioxan-2-yl)ethyl)-1H-indole-3-carboxylate (C3)

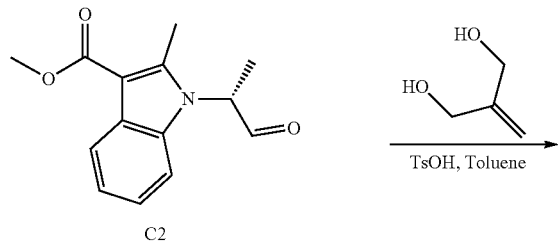

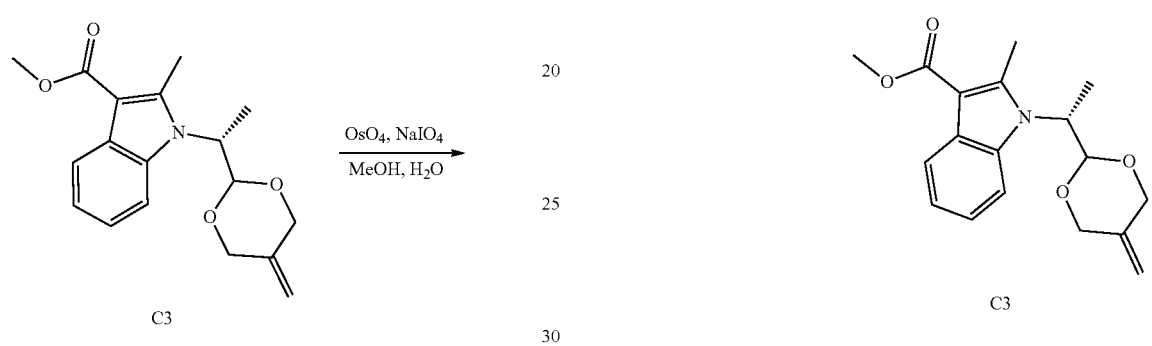

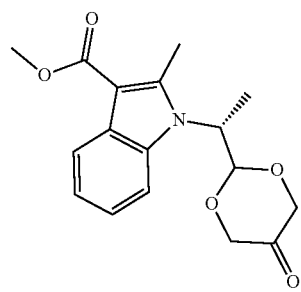

The mixture of (R)-methyl 2-methyl-1-(1-oxopropan-2-yl)-1H-indole-3-carboxylate (4.1 g, 17 mmol, 1 equiv), 2-methylenepropane-1,3-diol (5.9 g, 67 mmol, 5.5 mL, 4 equiv) and TsOH (864 mg, 5.01 mmol, 0.3 equiv) in toluene (50 mL) was stirred at 120° C. for 17 h. The mixture was concentrated and to the residue was added saturated aqueous Na$_2$CO$_3$ (30 mL). The desired product was extracted with ethyl acetate (35 mL*3). The combined organic layer was washed with brine (35 mL*3), dried over sodium sulfate, filtered and concentrated. The crude was purified by silica-gel column chromatography to give C3, methyl (R)-2-methyl-1-(1-(5-methylene-1,3-dioxan-2-yl)ethyl)-1H-indole-3-carboxylate (3.3 g, 10 mmol, 63% yield) as a yellow oil. LCMS [M+H]$^+$ m/z: calc'd 316.15; found 316.0.

The following intermediate(s) were synthesized using similar conditions as those described in Step 1, above, along with appropriate starting materials.

| Structure | Name | Intermediate | LCMS |
|---|---|---|---|
| 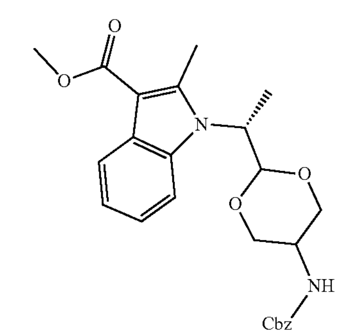 [SMILES: COC(=O)c1c(C)n([C@H](C)C2OCC(NC(=O)OCc3ccccc3)CO2)c2ccccc12] | methyl (R)-1-(1-(5-(((benzyloxy)carbonyl)amino)-1,3-dioxan-2-yl)ethyl)-2-methyl-1H-indole-3-carboxylate | C5 | LCMS [M + Na]$^+$ m/z: calc'd 475.19; found 475.0. |

Step 2: Synthesis of methyl (R)-2-methyl-1-(1-(5-oxo-1,3-dioxan-2-yl)ethyl)-1H-indole-3-carboxylate (C4)

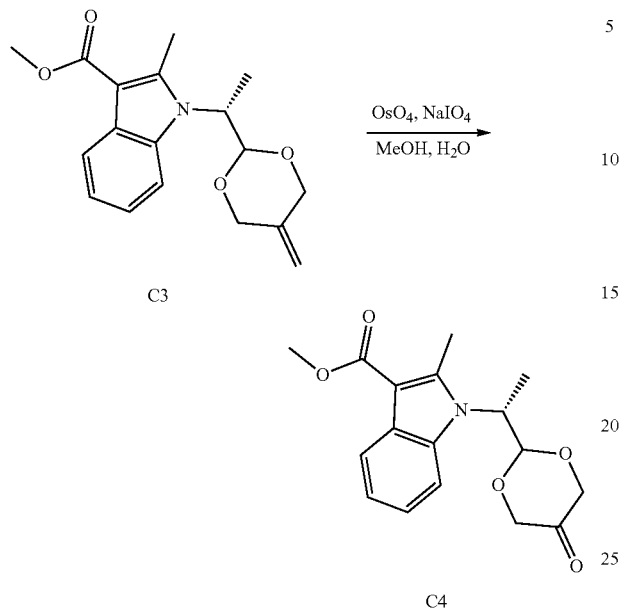

The mixture of methyl (R)-2-methyl-1-(1-(5-methylene-1,3-dioxan-2-yl)ethyl)-1H-indole-3-carboxylate (2.0 g, 6.4 mmol, 1 equiv), NaIO$_4$ (5.4 g, 25 mmol, 1.4 mL, 4 equiv) and OsO$_4$ (8.0 g, 31 mmol, 1.6 mL, 5 equiv) was stirred in methanol (48 mL) and water (32 mL) at 25° C. for 17 h. The mixture was extracted with ethyl acetate (60 mL*4), washed with saturated sodium chloride (50 mL*2), dried with sodium sulfate, concentrated under vacuum. The crude was purified by silica-gel column chromatography to give C5, methyl (R)-2-methyl-1-(1-(5-oxo-1,3-dioxan-2-yl)ethyl)-1H-indole-3-carboxylate (1.3 g, 4.1 mmol, 65% yield), as a yellow oil. LCMS ([M+H$_2$O]$^+$) m/z: calc'd 336.13; found 335.9.

Synthesis of methyl (R)-2-methyl-1-(1-(5-(methylamino)-1,3-dioxan-2-yl)ethyl)-1H-indole-3-carboxylate (C7)

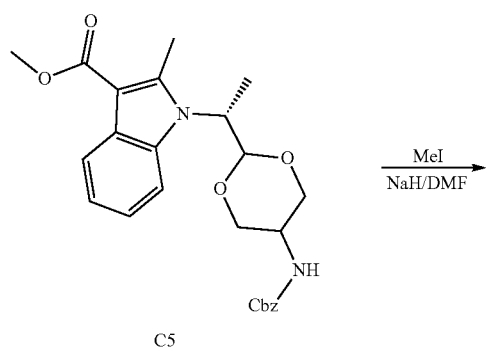

Step 1: Synthesis of methyl (R)-1-(1-(5-(((benzyloxy)carbonyl)(methyl)amino)-1,3-dioxan-2-yl)ethyl)-2-methyl-1H-indole-3-carboxylate (C6)

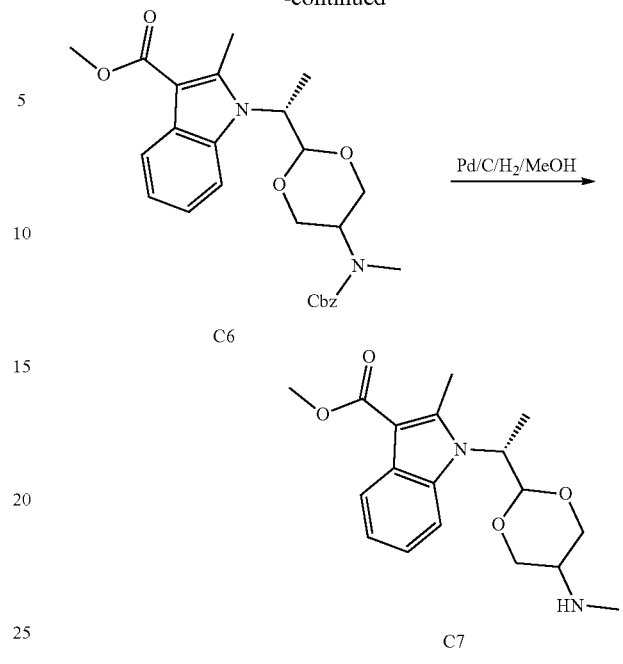

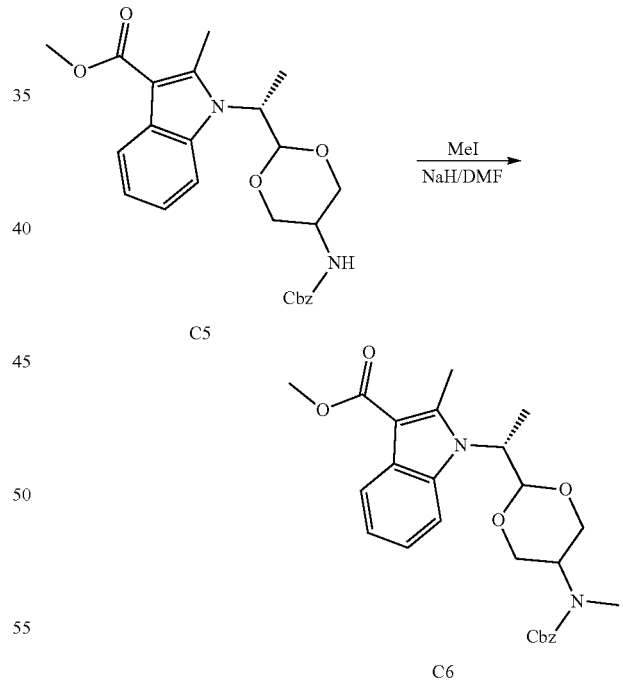

To a mixture of methyl (R)-1-(1-(5-(((benzyloxy)carbonyl)amino)-1,3-dioxan-2-yl)ethyl)-2-methyl-1H-indole-3-carboxylate (400 mg, 884 umol, 1 equiv) in N,N-dimethylformamide (2 mL) was added sodium hydride (42 mg, 1.1 mmol, 60% in mineral oil, 1.2 equiv) at 0° C. under N$_2$ atmosphere. The mixture was stirred at 20° C. for 0.3 h. To the reaction was added methyl iodide (2.15 g, 15.1 mmol, 17.1 equiv). The mixture was stirred at 20° C. for 4 hours. To the mixture was diluted with ethyl acetate (10 mL). The reaction was quenched by addition water (10 mL) at 0° C. The desired product was extracted with ethyl acetate (5 mL*3). The organic phases were combined, dried over sodium sulfate, filtered and concentrated under reduced pressure to give a residue. The residue was purified by silica gel flash chromatography (0 to 20% ethyl acetate in petroleum ether). C6, methyl (R)-1-(1-(5-(((benzyloxy)carbonyl)(methyl)amino)-1,3-dioxan-2-yl)ethyl)-2-methyl-1H-indole-3-carboxylate (396 mg, 603 umol, 68% yield), was obtained as a yellow solid.

The following intermediate(s) were synthesized using similar conditions as those described in Step 1, above, along with appropriate starting materials.

| Structure | Name | Intermediate | LCMS |
|---|---|---|---|
| 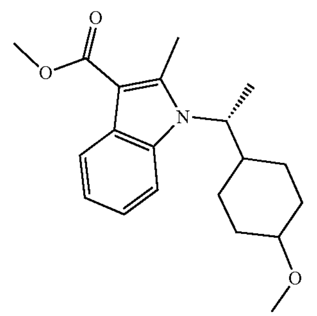 [SMILES: COC(=O)c1c(C)n([C@H](C)C2CCC(OC)CC2)c2ccccc12] | methyl (R)-1-(1-(4-methoxycyclohexyl)ethyl)-2-methyl-1H-indole-3-carboxylate | B6 | LCMS [M + H]$^+$ m/z: calc'd 330.20; found 330.0. |

Step 2: Synthesis of methyl (R)-2-methyl-1-(1-(5-(methylamino)-1,3-dioxan-2-yl)ethyl)-1H-indole-3-carboxylate (C7)

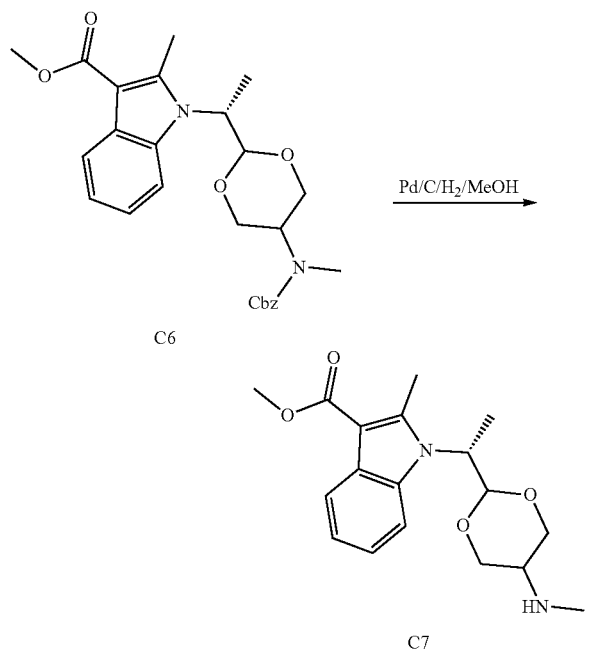

A mixture of methyl (R)-1-(1-(5-(((benzyloxy)carbonyl)(methyl)amino)-1,3-dioxan-2-yl)ethyl)-2-methyl-1H-indole-3-carboxylate (600 mg, 1.3 mmol, 1.0 equiv) and Pd/C (150 mg, 1.3 mmol, 10% w/w, 1 equiv) in methanol (3 mL) (caution: methanol can catch fire in contact with Pd/C) was degassed and purged with H$_2$ 3 times, and then the mixture was stirred at 20° C. for 2 h under H$_2$ atmosphere (15 Psi). The catalyst was removed by filtration through celite and the filtrate concentrated under reduced pressure. C7, methyl (R)-2-methyl-1-(1-(5-(methylamino)-1,3-dioxan-2-yl)ethyl)-1H-indole-3-carboxylate (460 mg, 1.27 mmol, 99% yield), was obtained as a yellow solid. LCMS [M+Na]$^+$ m/z: calc'd 333.17; found 332.9.

Synthesis of ethyl (R)-1-(1-(1-(tert-butoxycarbonyl)piperidin-4-yl)ethyl)-2-methyl-1H-pyrrolo[2,3-b]pyridine-3-carboxylate (H2)

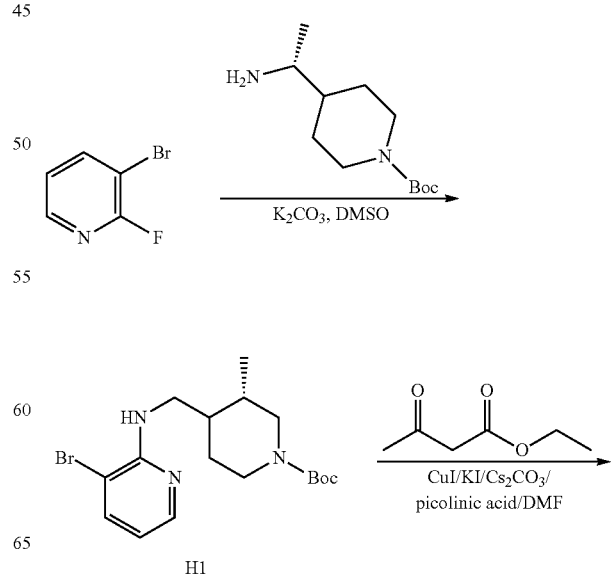

Step 2: Synthesis of ethyl (R)-1-(1-(1-(tert-butoxycarbonyl)piperidin-4-yl)ethyl)-2-methyl-1H-pyrrolo[2,3-b]pyridine-3-carboxylate (H2)

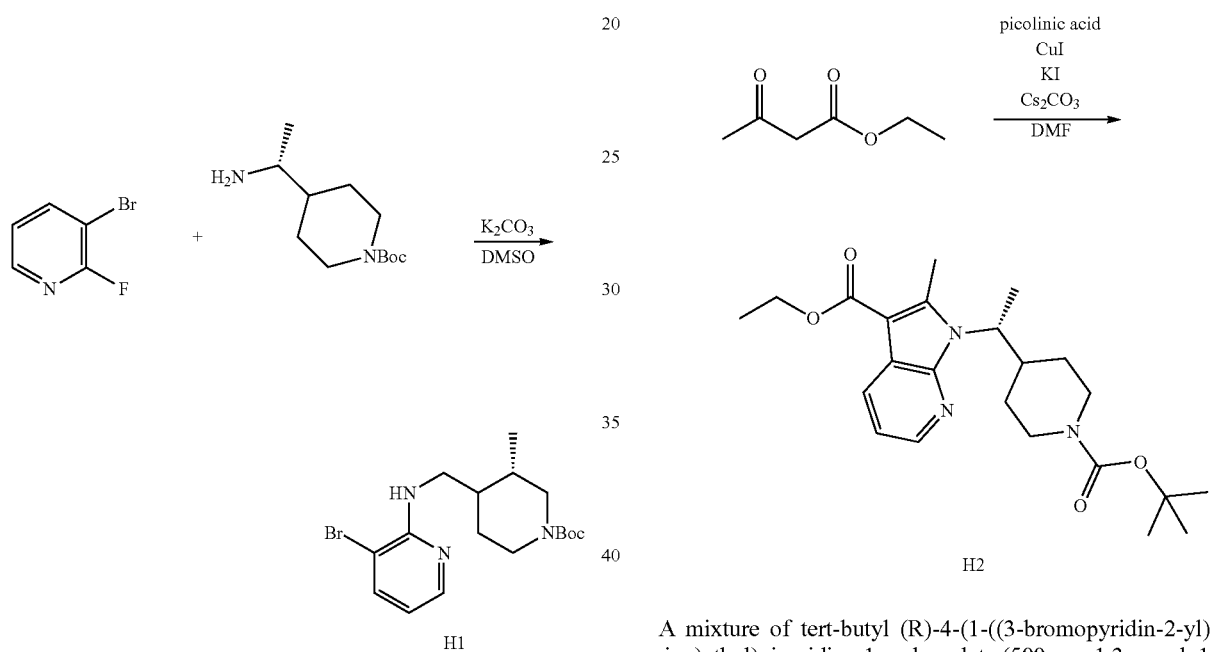

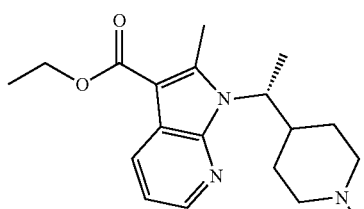

Step 1: Synthesis of tert-butyl (R)-4-(1-((3-bromopyridin-2-yl)amino)ethyl)piperidine-1-carboxylate (H1)

A mixture of tert-butyl 4-[(1R)-1-aminoethyl]piperidine-1-carboxylate (1.0 g, 4.4 mmol, 1 equiv), 3-bromo-2-fluoropyridine (800 mg, 4.6 mmol, 1 equiv), and potassium carbonate (1.8 g, 13 mmol, 3.0 equiv) in dimethyl sulfoxide (15 mL) was degassed and purged with $N_2$ 3 times. The reaction was stirred at 120° C. for 18 hr under $N_2$ atmosphere, then quenched with water (20 mL) after cooling to 25° C. The desired product was extracted with ethyl acetate (20 mL*3) and the combined organic layers were washed with brine (20 mL*2), dried over anhydrous sodium sulfate, filtered and concentrated under reduced pressure. The crude was purified by column chromatography ($SiO_2$, Petroleum ether/Ethyl acetate=20/1 to 5/1). Compound H1, tert-butyl (R)-4-(1-((3-bromopyridin-2-yl)amino)ethyl)piperidine-1-carboxylate (1.0 g, 2.6 mmol, 59% yield) was obtained as a colorless oil. LCMS [M+H]$^+$ m/z: calc'd 384.12; found 384.0. $^1$H NMR (400 MHz, $CDCl_3$) δ 8.02 (dd, J=4.8 Hz, 1.2 Hz, 1H), 7.58 (dd, J=8.0 Hz, 2.0 Hz, 1H), 6.43-6.40 (m, 1H), 4.81 (d, J=8.4 Hz, 1H), 4.19-4.09 (m, 1H), 2.66 (br s, 2H), 1.78-1.76 (m, 2H), 1.69-1.57 (m, 2H), 1.44 (s, 9H), 1.33-1.23 (m, 3H), 1.18 (d, J=6.8 Hz, 3H).

A mixture of tert-butyl (R)-4-(1-((3-bromopyridin-2-yl)amino)ethyl)piperidine-1-carboxylate (500 mg, 1.3 mmol, 1 equiv), ethyl 3-oxobutanoate (680 mg, 5.2 mmol, 4 equiv), picolinic acid (130 mg, 1.1 mmol, 0.8 equiv), CuI (25 mg, 131 umol, 0.1 equiv), KI (325 mg, 2.0 mmol, 1.5 equiv) and cesium carbonate (1.27 g, 3.9 mmol, 3 equiv) in N,N-dimethylformamide (6 mL) was degassed and purged with $N_2$ for 3 times and then the mixture was stirred at 150° C. for 1 h under $N_2$ atmosphere. The reaction mixture was quenched by addition water (15 mL) at 25° C., and then the desired product extracted with ethyl acetate (20 mL*2). The combined organic layers were washed with brine (20 mL*2), dried over anhydrous sodium sulfate, filtered and concentrated under reduced pressure. The residue was purified by column chromatography ($SiO_2$, Petroleum ether/Ethyl acetate=20/1-5/1). Compound H2, ethyl (R)-1-(1-(1-(tert-butoxycarbonyl)piperidin-4-yl)ethyl)-2-methyl-1H-pyrrolo[2,3-b]pyridine-3-carboxylate (200 mg, 399 umol, 31% yield) was obtained as a colorless oil. LCMS [M+H]$^+$ m/z: calc'd 416.25; found 416.1. $^1$H NMR (400 MHz, $CDCl_3$) δ 8.33 (d, J=8.0 Hz, 1H), 8.26 (d, J=8.0 Hz, 1H), 7.15 (dd, J=8.0 Hz, 4.0 Hz, 1H), 4.40 (d, J=8.0 Hz, 2H), 4.26-4.17 (m, 1H), 4.07-3.91 (m, 2H), 2.80 (br s, 3H), 2.02-1.97 (m, 1H), 1.89-1.85 (m, 1H), 1.59 (d, J=6.8 Hz, 3H), 1.45 (t, J=8.0 Hz, 3H), 1.43 (s, 9H), 1.29-1.11 (m, 3H), 0.95-0.84 (m, 2H).

Synthesis of methyl (R)-1-(1-(3-aminobicyclo[1.1.1]pentan-1-yl)ethyl)-2-methyl-1H-indole-3-carboxylate (D9)

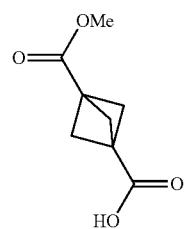

DPPA/Et₃N/Tol•  
t-BuOH

D1

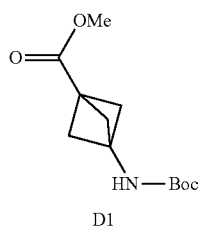

$\underrightarrow{\text{MeNHOMe}}$  
i-PrMgCl/THF

D2

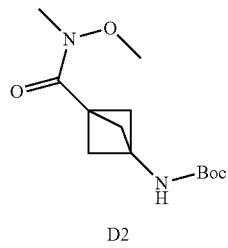

MeMgBr  
THF

D3

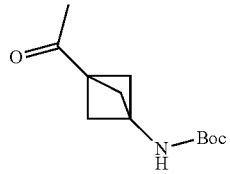

$\underrightarrow{\text{t-Bu-S(O)NH}_2}$  
Ti(OEt)₄/THF

D4

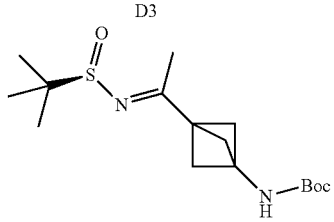

DIBAL—H  
THF/-78° C.

D5

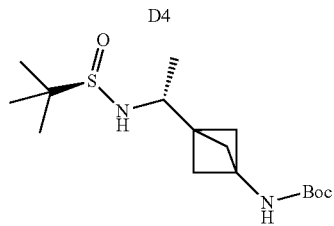

HCl(1M)  
MeOH

-continued

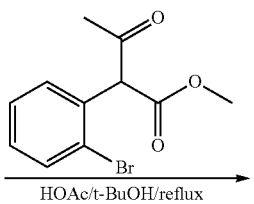

D6

HOAc/t-BuOH/reflux

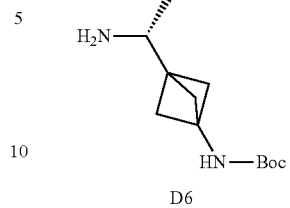

D7

RuPhOS/Pd(G2)  
MeONa/dioxane/100° C.

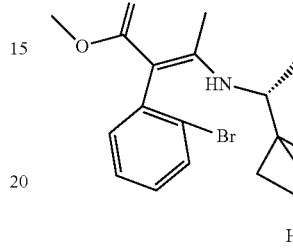

D8

HCl/MeOH

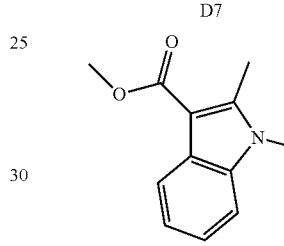

D9

Step 1: Synthesis of methyl 3-((tert-butoxycarbonyl)amino)bicyclo[1.1.1]pentane-1-carboxylate (D1)

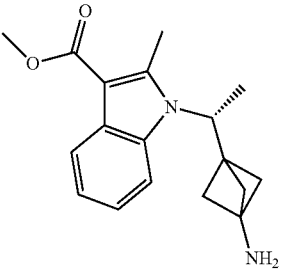

DPPA/Et₃N/Tol•  
t-BuOH

D1

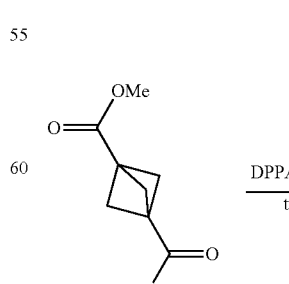

To a mixture of 3-(methoxycarbonyl)bicyclo[1.1.1]pentane-1-carboxylic acid (10 g, 59 mmol, 1.0 equiv), diphenylphosphoryl azide (DPPA) (19.4 g, 70.5 mmol, 15.3 mL, 1.2 equiv) and triethylamine (7.1 g, 71 mmol, 9.8 mL, 1.2 equiv) in toluene (150 mL) was added t-BuOH (8.70 g, 118 mmol, 11.2 mL, 2.0 equiv). The mixture was stirred at 110° C. for 12 h. The reaction was cooled to 25° C. and concentrated. The residue was diluted with water (50 mL) and the desired product extracted with ethyl acetate (100 mL*3). The combined organic layer was washed with brine (50 mL), dried over sodium sulfate, filtered and concentrated. The crude was purified by column chromatography on silica gel to give D1, methyl 3-((tert-butoxycarbonyl)amino)bicyclo[1.1.1]pentane-1-carboxylate (10.5 g, 43.5 mmol, 74% yield) as a white solid. ¹H NMR (400 MHz, CDCl₃) δ 4.96 (br s, 1H), 3.68 (s, 3H), 2.28 (s, 6H), 1.44 (s, 9H).

Step 2: Synthesis of tert-butyl (3-(methoxy(methyl)carbamoyl)bicyclo[1.1.1]pentan-1-yl)carbamate (D2)

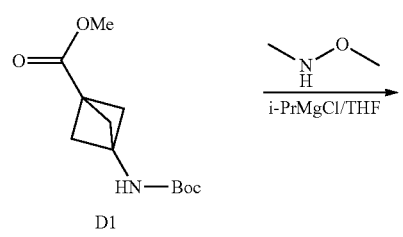

To a solution of methyl 3-((tert-butoxycarbonyl)amino)bicyclo[1.1.1]pentane-1-carboxylate (10.5 g, 43.5 mmol, 1.0 equiv) and N-methoxymethanamine (6.4 g, 65 mmol, 1.5 equiv, HCl salt) in tetrahydrofuran (100 mL) was added i-PrMgCl (2 M in Et₂O, 87 mL, 4 equiv) dropwise at 0° C. The mixture was stirred at 0° C. for 4 h then poured into cooled saturated NH₄Cl (50 mL) and diluted with water (20 mL), and extracted with ethyl acetate (100 mL*3). The combined organic layer was washed with brine (100 mL), dried over sodium sulfate, filtered and concentrated. The crude was purified by column chromatography on silica gel to give D2, tert-butyl (3-(methoxy(methyl)carbamoyl)bicyclo[1.1.1]pentan-1-yl)carbamate (10 g, 37 mmol, 85% yield) as a white solid. LCMS [M+H]⁺ m/z: calc'd 270.16; found 270.9. ¹H NMR (400 MHz, CDCl₃) δ 5.05 (br s, 1H), 3.65 (s, 3H), 3.17 (s, 3H), 2.33 (s, 6H), 1.43 (s, 9H).

Step 3: Synthesis of tert-butyl (3-acetylbicyclo[1.1.1]pentan-1-yl)carbamate (D3)

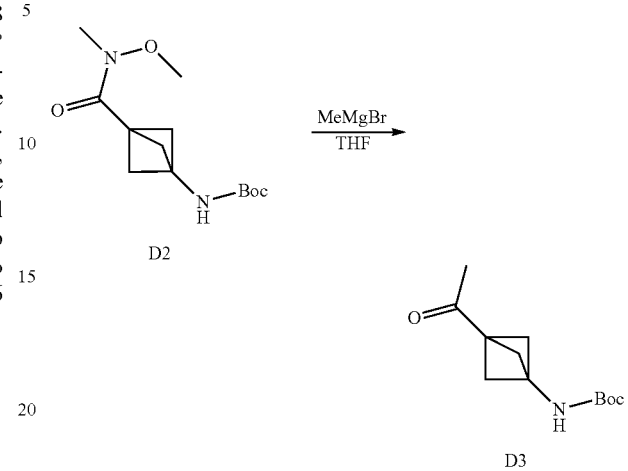

To a solution of tert-butyl (3-(methoxy(methyl)carbamoyl)bicyclo[1.1.1]pentan-1-yl)carbamate (10 g, 37 mmol, 1.0 equiv) in tetrahydrofuran (100 mL) was added MeMgBr (3 M, 99 mL, 8.0 equiv) dropwise at 0° C. The mixture was stirred at 0° C. for 4 h. The mixture was poured into saturated NH₄Cl (30 mL), diluted with water (10 mL), and extracted with ethyl acetate (80 mL*3). The combined organic layer was washed with brine (100 mL), dried over sodium sulfate, filtered and concentrated. The crude was purified by column chromatography on silica to give D3, tert-butyl (3-acetylbicyclo[1.1.1]pentan-1-yl)carbamate (4.50 g, 18.8 mmol, 51% yield), as a white solid. ¹H NMR (400 MHz, CDCl₃) δ 4.99 (br s, 1H), 2.26 (s, 6H), 2.14 (s, 3H), 1.44 (s, 9H).

Step 4: Synthesis of tert-butyl (R,E)-(3-(1-((tert-butylsulfinyl)imino)ethyl)bicyclo[1.1.1]pentan-1-yl)carbamate (D4)

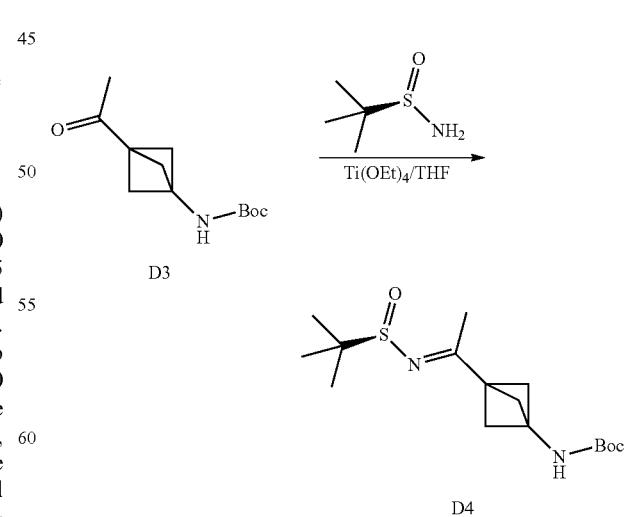

To a solution of tert-butyl (3-acetylbicyclo[1.1.1]pentan-1-yl)carbamate (4.5 g, 20 mmol, 1.0 equiv) and 2-methylpropane-2-sulfinamide (3.6 g, 30 mmol, 1.5 equiv) in tetrahydrofuran (80 mL) was added Ti(OEt)$_4$ (9.1 g, 40 mmol, 2.0 equiv). The mixture was stirred at 85° C. for 12 h. The mixture was cooled to 25° C., and then water (15 mL) was added to the mixture resulting in formation of a white precipitate. The mixture was diluted with dichloromethane (80 mL) and filtered. The filtrate was washed with brine (30 mL). The filter cake was washed with dichloromethane (80 mL*2). The combined filtrate was concentrated. The crude was purified by column chromatography on silica gel to give D4, tert-butyl (R,E)-(3-(1-((tert-butylsulfinyl)imino)ethyl)bicyclo[1.1.1]pentan-1-yl)carbamate (3.60 g, 10.6 mmol, 53% yield) as a white solid.

Step 5: Synthesis of tert-butyl (3-((R)-1-(((R)-tert-butylsulfinyl)amino)ethyl)bicyclo[1.1.1]pentan-1-yl)carbamate (D5)

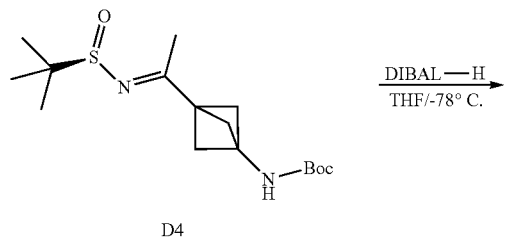

To a solution of tert-butyl (R,E)-(3-(1-((tert-H butylsulfinyl)imino)ethyl)bicyclo[1.1.1]pentan-1-yl)carbamate (7.0 g, 21 mmol, 1.0 equiv) in tetrahydrofuran (80 mL) was added DIBAL-H (1 M in toluene, 43 mL, 2.0 equiv) dropwise at −78° C. The mixture was stirred at −78° C. for 2 h. The reaction was quenched with methanol (20 mL), and then diluted with water (20 mL) and ethyl acetate (50 mL). The mixture was filtered and the filtrate was washed with brine (30 mL). The filter cake was washed with ethyl acetate (50 mL*3). The combined filtrate was dried over sodium sulfate, filtered and concentrated. The crude was purified by column chromatography on silica gel to give D5, tert-butyl (3-((R)-1-(((R)-tert-butylsulfinyl)amino)ethyl)bicyclo[1.1.1]pentan-1-yl)carbamate (5.70 g, 13.5 mmol, 63% yield), as a white solid. $^1$H NMR (400 MHz, CDCl$_3$) δ 4.96 (br s, 1H), 3.55-3.49 (m, 1H), 3.02 (s, 1H), 2.04-1.87 (m, 6H), 1.44 (s, 9H), 1.18 (s, 9H), 1.12 (d, J=6.8 Hz, 3H).

Step 6: Synthesis of tert-butyl (R)-(3-(1-aminoethyl)bicyclo[1.1.1]pentan-1-yl)carbamate (D6)

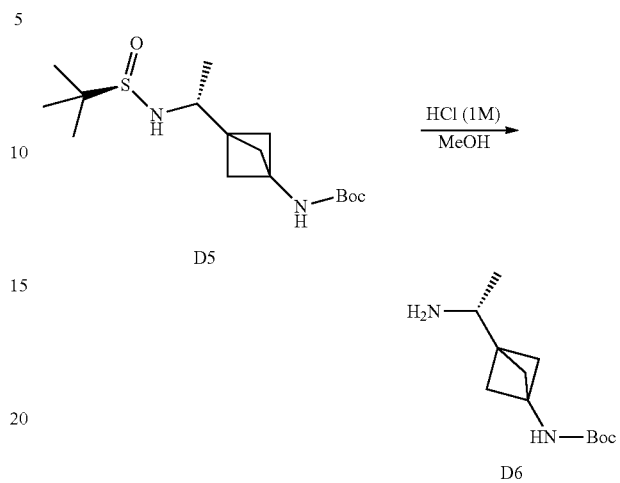

To a solution of tert-butyl (3-((R)-1-(((R)-tert-butylsulfinyl)amino)ethyl)bicyclo[1.1.1]pentan-1-yl)carbamate (3.3 g, 10 mmol, 1.0 equiv) in methanol (15 mL) was added HCl (1 M in methanol, 10 mL, 1.0 equiv) at 15° C. The mixture was stirred at 15° C. for 30 min after which the pH was adjusted to 78 with saturated sodium bicarbonate solution and concentrated to dryness. The residue was washed with dichloromethane (100 mL) and filtered. The filter cake was washed with dichloromethane (100 mL*2). The combined filtrate was concentrated to give D6, tert-butyl (R)-(3-(1-aminoethyl)bicyclo[1.1.1]pentan-1-yl)carbamate (2.0 g, crude) as a white solid. LCMS [M+H]$^+$ m/z: calc'd 227.17; found 227.0. $^1$H NMR (400 MHz, CDCl$_3$) δ 5.30 (br s, 1H), 3.21-3.16 (m, 1H), 1.96-1.92 (m, 6H), 1.44 (s, 9H), 1.13 (d, J=6.4 Hz, 3H).

Steps 7 and 8: Synthesis of Intermediate D8 from Intermediate D6 was Performed Using the Procedures Described Previously Step 9: Synthesis of methyl (R)-1-(1-(3-aminobicyclo[1.1.1]pentan-1-yl)ethyl)-2-methyl-1H-indole-3-carboxylate (D9)

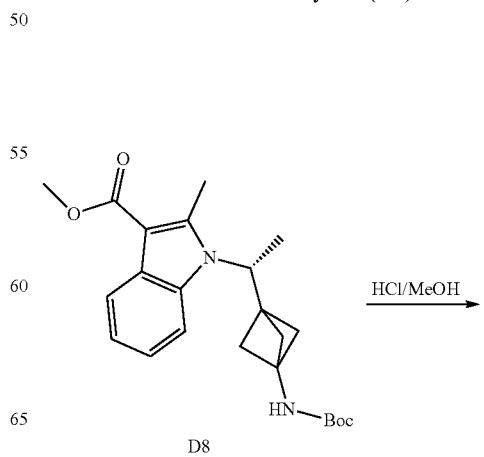

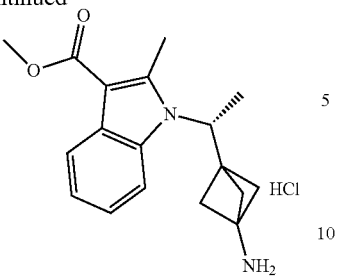

D9

A mixture of methyl (R)-1-(1-(3-((tert-butoxycarbonyl)amino)bicyclo[1.1.1]pentan-1-yl)ethyl)-2-methyl-1H-indole-3-carboxylate (200 mg, 0.502 mmol, 1.0 equiv) in a solution of HCl (4 M in methanol, 5.0 mL, 40 equiv) was stirred at 15° C. for 30 min. The mixture pH was adjusted to 7-8 with saturated sodium bicarbonate and concentrated. The solid was washed with dichloromethane (20 mL*3) and filtered. The filtrate was concentrated to give D9, methyl (R)-1-(1-(3-aminobicyclo[1.1.1]pentan-1-yl)ethyl)-2-methyl-1H-indole-3-carboxylate (0.14 g, crude), as white solid. LCMS [M+H]$^+$ m/z: calc'd 299.17; found 299.0.

The following intermediate(s) were synthesized using similar conditions as those described in Step 9, above, along with appropriate starting materials.

| Structure | Name | Intermediate | LCMS |
|---|---|---|---|
| 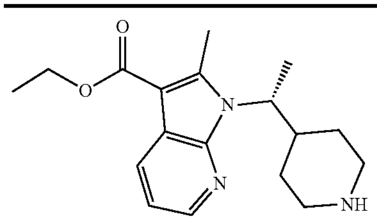 | ethyl (R)-2-methyl-1-(1-(piperidin-4-yl)ethyl)-1H-pyrrolo[2,3-b]pyridine-3-carboxylate | H3 | LCMS [M + H]$^+$ m/z: calc'd 316.19; found 315.9. |

Synthesis methyl (R)-2-methyl-1-(1-(3-((2,2,2-trifluoroethyl)amino)bicyclo[1.1.1]pentan-1-yl)ethyl)-1H-indole-3-carboxylate (D14)

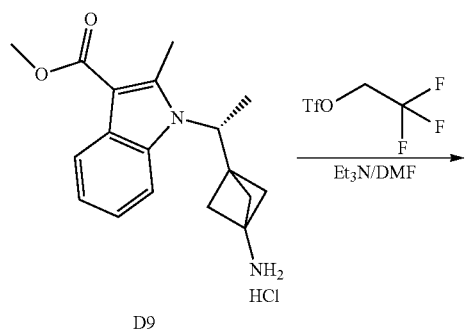

D9

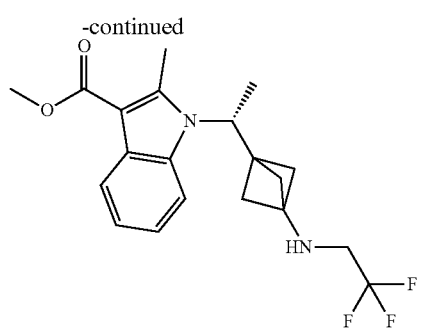

D14

To a mixture of methyl (R)-1-(1-(3-aminobicyclo[1.1.1]pentan-1-yl)ethyl)-2-methyl-1H-indole-3-carboxylate (180 mg, 537 umol, 1 equiv, HCl salt) and triethylamine (218 mg, 2.20 mmol, 299 uL, 4 equiv) in N,N-dimethylformamide (8 mL) was added 2,2,2-trifluoroethyltriflate (211 mg, 1.1 mmol, 144 uL, 2 equiv). The mixture was stirred at 100° C. for 16 h. The mixture was cooled to 15° C. and concentrated. The residue was diluted with water (15 mL) and the desired product extracted with ethyl acetate (40 mL*3). The combined organic layer was dried over sodium sulfate, filtered and concentrated. The crude was purified by flash silica gel chromatography to give D14, methyl (R)-2-methyl-1-(1-(3-

((2,2,2-trifluoroethyl)amino)bicyclo[1.1.1]pentan-1-yl) ethyl)-1H-indole-3-carboxylate (120 mg, 300 umol, 56% yield) as a yellow oil. LCMS [M+H]$^+$ m/z: calc'd 381.17; found 381.1.

The following intermediate(s) were synthesized using similar conditions as those described in the step above, along with appropriate starting materials.

| Structure | Name | Intermediate | LCMS |
|---|---|---|---|
| 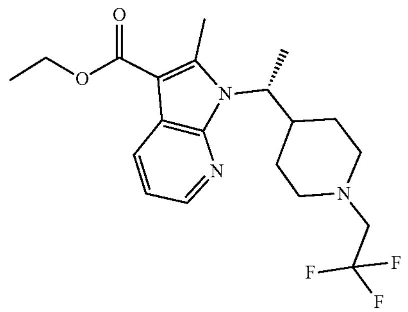 [SMILES: CCOC(=O)c1c(C)n([C@H](C)C2CCN(CC(F)(F)F)CC2)c2ncccc12] | ethyl (R)-2-methyl-1-(1-(1-(2,2,2-trifluoroethyl)piperidin-4-yl)ethyl)-1H-pyrrolo[2,3-b]pyridine-3-carboxylate | H4 | LCMS [M + H]$^+$ m/z: calc'd 398.20; found 398.0. |

Synthesis of 1-[(1R)-1-(1-cyclopropyl-4-piperidyl)ethyl]-2-methyl-pyrrolo[2,3-b]pyridine-3-carboxylate (H6)

A solution of ethyl 2-methyl-1-[(1R)-1-(4-piperidyl)ethyl]pyrrolo[2,3-b]pyridine-3-carboxylate dihydrochloride salt (250 mg, 0.64 mmol, 1 equiv) in saturated aqueous NaHCO$_3$ (10 mL) was extracted with ethyl acetate (10 mL×3) and the combined organic layers were dried over anhydrous Na$_2$SO$_4$, filtered, and concentrated to dryness to give the free amine. To a solution of the free amine and (1-ethoxycyclopropoxy)-trimethyl-silane (230 mg, 1.3 mmol, 265 uL, 2 equiv) in THF (3 mL) and MeOH (0.2 mL) were added AcOH (79 mg, 1.3 mmol, 75 uL, 2 equiv) and NaBH$_3$CN (60 mg, 0.96 mmol, 1.5 equiv). The reaction was stirred at 60° C. for 16 hours then quenched with saturated aqueous NH$_4$Cl (5 mL). The desired product was extracted with ethyl acetate (10 mL×3) and the combined organic layers were dried over anhydrous Na$_2$SO$_4$, filtered and concentrated under vacuum to dryness. The residue was purified by prep-TLC (SiO$_2$, petroleum ether:ethyl acetate, 1:1). The title compound, ethyl 1-[(1R)-1-(1-cyclopropyl-4-piperidyl)ethyl]-2-methyl-pyrrolo[2,3-b]pyridine-3-carboxylate (105 mg, 0.274 mmol, 43% yield, 93% purity), was obtained as yellow oil. LCMS [M+H]$^+$ m/z: calc'd 356.2; found 356.1.

Synthesis of (R)-2-methyl-N-((6-methyl-4-(methylthio)-2-oxo-1,2-dihydropyridin-3-yl)methyl)-1-(1-(4-((3-methyloxetan-3-yl)amino)cyclohexyl)ethyl)-1H-indole-3-carboxamide (Example 1, Isomer 1 and Isomer 2)

53

-continued

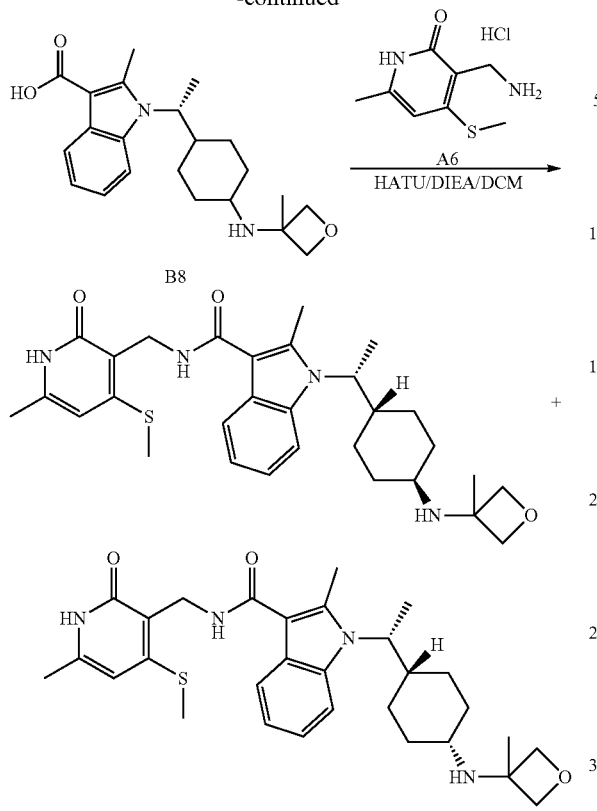

Example 1

Step 1: Synthesis of methyl (R)-2-methyl-1-(1-(4-((3-methyloxetan-3-yl)amino)cyclohexyl)ethyl)-1H-indole-3-carboxylate (B6)

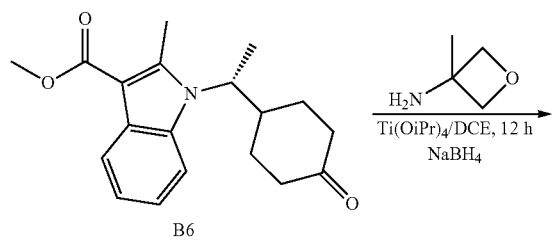

54

-continued

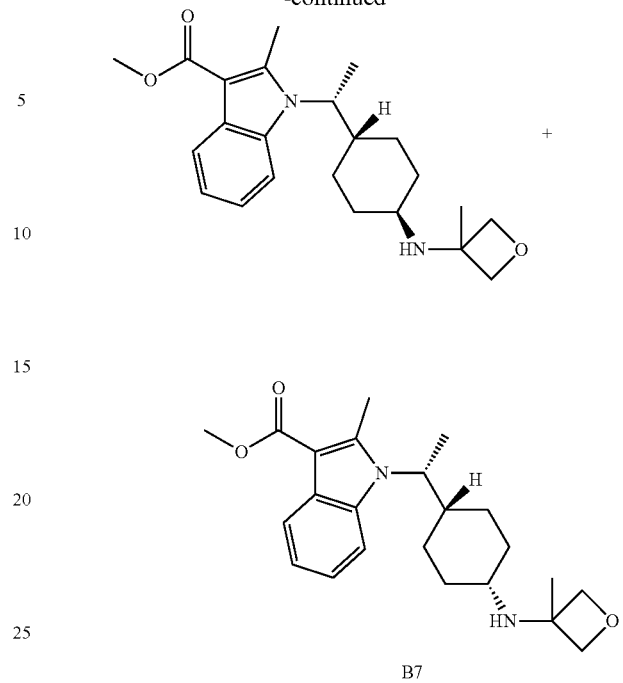

To a solution of methyl (R)-2-methyl-1-(1-(4-oxocyclohexyl)ethyl)-1H-indole-3-carboxylate (300 mg, 957 umol, 1 equiv) and 3-methyloxetan-3-amine (250 mg, 2.9 mmol, 3 equiv) in dichloroethane (10 mL) was added Ti(Oi-Pr)$_4$ (816 mg, 2.9 mmol, 847 uL, 3 equiv). The mixture was stirred at 15° C. for 13 h. Sodium borohydride (217 mg, 5.7 mmol, 6 equiv) was then added to the mixture and stirred at 15° C. for 2 h. The mixture was then diluted with saturated sodium bicarbonate (15 mL) and water (10 mL), extracted with dichloromethane (40 mL*3). The combined organic layer was washed with brine (30 mL), dried over sodium sulfate, filtered and concentrated. The crude was purified by column chromatography on silica gel to give B7 as a mixture of cis/trans isomers, methyl (R)-2-methyl-1-(1-(4-((3-methyloxetan-3-yl)amino)cyclohexyl)ethyl)-1H-indole-3-carboxylate (300 mg, 749 μmol, 78% yield) as a white solid. LCMS [M+H]$^+$ m/z: calc'd 385.24; found 385.1.

The following intermediates were synthesized using similar conditions as those described in Step 1, above, along with appropriate starting materials and reagents.

| Structure and Name | Intermediate | Cis/trans Isomer Separation Method and Retention Time (if any) | LCMS |
|---|---|---|---|
|  | B9 |  | LCMS [M + H]$^+$ m/z: calc'd 371.23; found 371.1. |

| Structure and Name | Intermediate | Cis/trans Isomer Separation Method and Retention Time (if any) | LCMS |
|---|---|---|---|
| methyl 2-methyl-1-((1R)-1-(4-(oxetan-3-ylamino)cyclohexyl)ethyl)-1H-indole-3-carboxylate 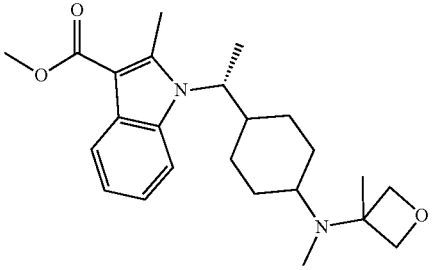 [SMILES: COC(=O)c1c(C)n([C@H](C)C2CCC(N(C)C3(C)COC3)CC2)c2ccccc12] | B10 | | LCMS [M + H]$^+$ m/z: calc'd 399.26; found 399.1. |
| methyl (R)-2-methyl-1-(1-(4-(methyl(3-methyloxetan-3-yl)amino)cyclohexyl)ethyl)-1H-indole-3-carboxylate 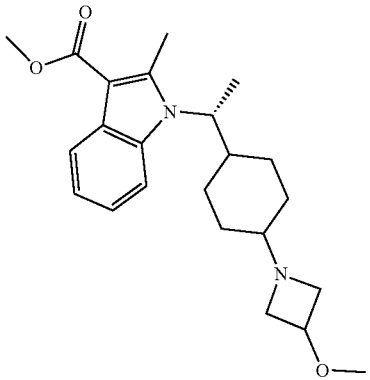 | B11 | | LCMS [M + H]$^+$ m/z: calc'd 385.24; found 385.1. $^1$H NMR (400 MHz, CDCl$_3$) δ 8.15 (d, J = 7.6 Hz, 1H), 7.48 (d, J = 8.0 Hz, 1H), 7.21-7.15 (m, 2H), 4.28-4.04 (m, 2H), 3.93 (s, 3H), 3.66-3.58 (m, 2H), 3.25 (s, 3H), 2.95-2.77 (m, 5H), 2.29-2.05 (m, 3H), 1.72-1.41 (m, 6H), 1.17-0.79 (m, 4H). |
| methyl 1-((1R)-1-(4-(3-methoxyazetidin-1-yl)cyclohexyl)ethyl)-2-methyl-1H-indole-3-carboxylate 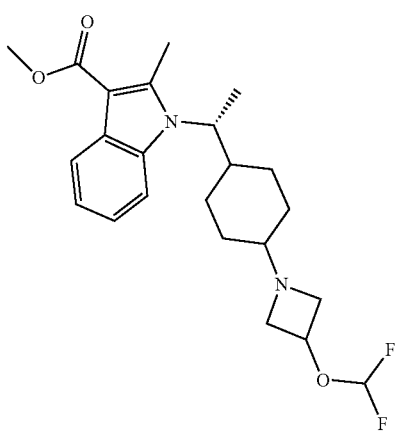 [SMILES: COC(=O)c1c(C)n([C@H](C)C2CCC(N3CC(OC(F)F)C3)CC2)c2ccccc12] | B12 Isomer 1 (1$^{st}$ eluting isomer) | Cis-trans isomers separated by silica-gel column chromatography Eluent of 0~60% Ethyl acetate/Petroleum ether gradient @ 30 mL/min | LCMS [M + H]$^+$ m/z: calc'd 421.22; found 421.1. |

-continued

| Structure and Name | Intermediate | Cis/trans Isomer Separation Method and Retention Time (if any) | LCMS |
|---|---|---|---|
| methyl (R)-1-(1-(4-(3-(difluoromethoxy)azetidin-1-yl)cyclohexyl)ethyl)-2-methyl-1H-indole-3-carboxylate 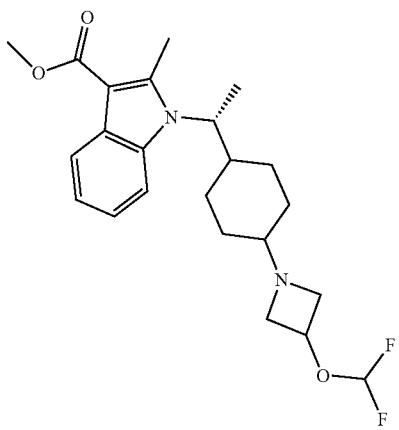 [SMILES: COC(=O)c1c(C)n([C@H](C)C2CCC(N3CC(OC(F)F)C3)CC2)c2ccccc12] methyl (R)-1-(1-(4-(3-(difluoromethoxy)azetidin-1-yl)cyclohexyl)ethyl)-2-methyl-1H-indole-3-carboxylate | B12 Isomer 2 (2$^{nd}$ eluting isomer) | Cis-trans isomers separated by silica-gel column chromatography Eluent of 0~60% Ethyl acetate/Petroleum ether gradient @ 30 mL/min | LCMS [M + H]$^+$ m/z: calc'd 421.22; found 421.1. |
| 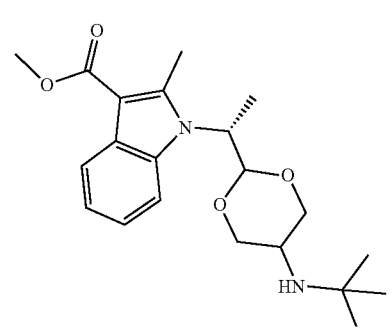 [SMILES: COC(=O)c1c(C)n([C@H](C)C2OCC(NC(C)(C)C)CO2)c2ccccc12] methyl (R)-1-(1-(5-(tert-butylamino)-1,3-dioxan-2-yl)ethyl)-2-methyl-1H-indole-3-carboxylate | C8 | | LCMS [M + H]$^+$ m/z: calc'd 375.22; found 375.1. |
| 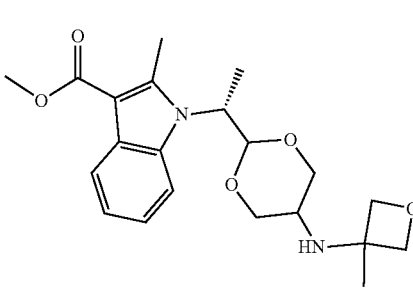 methyl (R)-2-methyl-1-(1-(5-((3-methyloxetan-3-yl)amino)-1,3-dioxan-2-yl)ethyl)-1H-indole-3-carboxylate | C9 Isomer 1 (1$^{st}$ eluting isomer) | Cis-trans isomers separated by silica-gel column chromatography (Petroleum ether/Ethyl acetate = 10/1-1/2). | LCMS [M + Na]$^+$ m/z: calc'd: 411.20.; found 411.1. $^1$H NMR (400 MHz, CDCl$_3$) δ 8.15 (br d, J = 7.2 Hz, 1H), 7.50 (br d, J = 7.2 Hz, 1H), 7.24-7.16 (m, 2H), 4.94 (br d, J = 5.0 Hz, 1H), 4.64-4.53 (m, 1H), 4.37 (s, 2H), 4.35 (s, 2H), 4.14 (br d, J = 12.4 Hz, 1H), 3.93 (s, 3H), 3.92-3.84 (m, 2H), 3.30 (br t, J = 9.6 Hz, 1H), 3.04 (br d, J = 4.8 Hz, 2H), 2.80 (br s, 3H), 1.66 (br d, J = 7.2 Hz, 3H), 1.47 (s, 3H) |

| Structure and Name | Intermediate | Cis/trans Isomer Separation Method and Retention Time (if any) | LCMS |
|---|---|---|---|
| 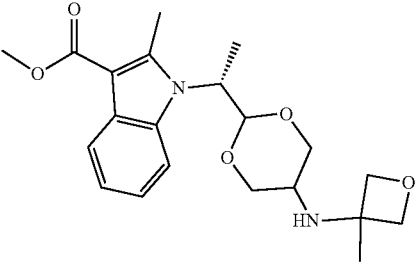 [SMILES: COC(=O)c1c(C)n([C@H](C)C2OCC(NC3(C)COC3)CO2)c2ccccc12]<br>methyl (R)-2-methyl-1-(1-(5-((3-methyloxetan-3-yl)amino)-1,3-dioxan-2-yl)ethyl)-1H-indole-3-carboxylate | C9 Isomer 2 (2$^{nd}$ eluting isomer) | Cis-trans isomers separated by silica-gel column chromatography (Petroleum ether/Ethyl acetate = 10/1-1/2). | LCMS ([M + Na]$^+$) m/z: calc'd: 411.20; found 411.1. $^1$H NMR (400 MHz, CDCl$_3$) δ 8.16 (br d, J = 7.6 Hz, 1H), 7.55 (br d, J = 7.2 Hz, 1H), 7.24-7.15 (m, 2H), 5.07 (br d, J = 5.2 Hz, 1H), 4.71-4.59 (m, 1H), 4.47 (br d, J = 6.0 Hz, 2H), 4.41-4.36 (m, 2H), 3.93 (s, 3H), 3.91-3.80 (m, 2H), 3.73-3.59 (m, 2H), 2.83 (s, 3H), 2.67 (br s, 1H), 1.70 (d, J = 7.2 Hz, 3H), 1.46 (s, 3H) |
| 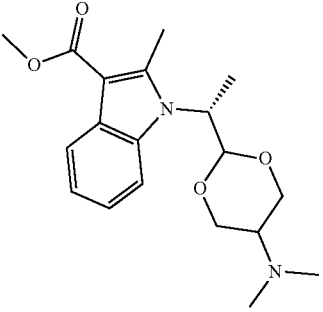<br>methyl (R)-1-(1-(5-(dimethylamino)-1,3-dioxan-2-yl)ethyl)-2-methyl-1H-indole-3-carboxylate | C10 | | LCMS [M + H]$^+$ m/z: calc'd 347.19; found 346.9 |
| 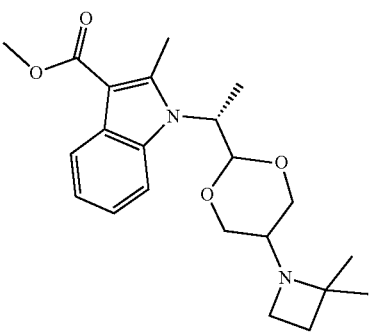<br>methyl (R)-1-(1-(5-(2,2-dimethylazetidin-1-yl)-1,3-dioxan-2-yl)ethyl)-2-methyl-1H-indole-3-carboxylate | C11 | | LCMS [M + H]$^+$ m/z: calc'd 387.22; found 387.0 |

-continued

| Structure and Name | Intermediate | Cis/trans Isomer Separation Method and Retention Time (if any) | LCMS |
|---|---|---|---|
| 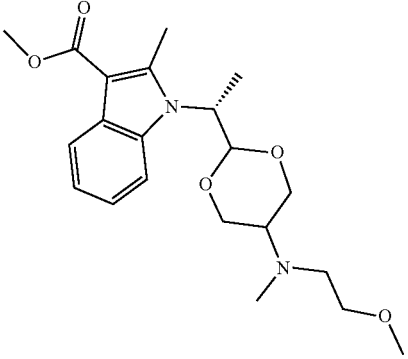<br>methyl (R)-1-(1-(5-((2-methoxyethyl)(methyl)amino)-1,3-dioxan-2-yl)ethyl)-2-methyl-1H-indole-3-carboxylate | C12 | | LCMS [M + H]+ m/z: calc'd 391.22; found 391.0 |
| 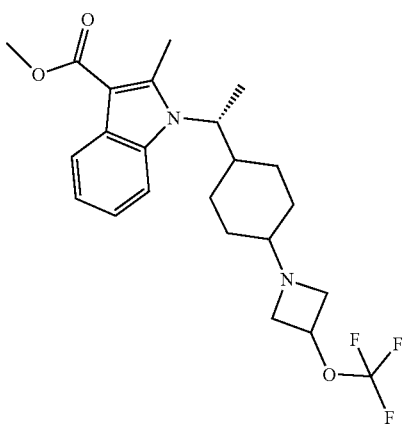 [SMILES: COC(=O)c1c(C)n([C@H](C)C2CCC(N3CC(OC(F)(F)F)C3)CC2)c2ccccc12]<br>methyl (R)-2-methyl-1-(1-(4-(3-(trifluoromethoxy)azetidin-1-yl)cyclohexyl)ethyl)-1H-indole-3-carboxylate | B13 Isomer 1 (1st eluting isomer) | Cis-trans isomers separated by silica-gel preparative thin-layer chromatography (Petroleum ehter/Ethyl acetate = 3/1). | LCMS [M + H]+ calc'd. 439.21; found 439.0. |
| 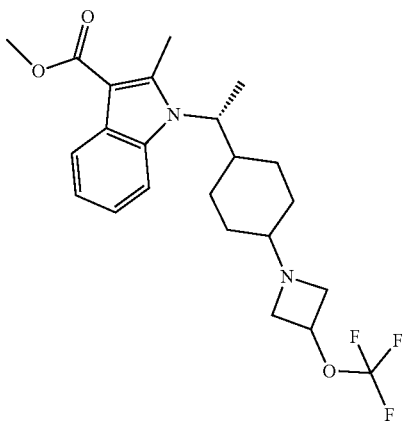 [SMILES: COC(=O)c1c(C)n([C@H](C)C2CCC(N3CC(OC(F)(F)F)C3)CC2)c2ccccc12] | B13 Isomer 2 (2nd eluting isomer) | Cis-trans isomers separated by silica-gel preparative thin-layer chromatography (Petroleum ether/Ethyl acetate = 3/1). | LCMS [M + H]+ calc'd. 439.21; found 439.0. |

-continued

| Structure and Name | Intermediate | Cis/trans Isomer Separation Method and Retention Time (if any) | LCMS |
|---|---|---|---|
| methyl (R)-2-methyl-1-(1-(4-(3-(trifluoromethoxy)azetidin-1-yl)cyclohexyl)ethyl)-1H-indole-3-carboxylate 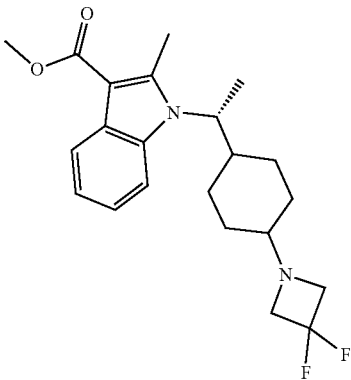 [SMILES: COC(=O)c1c(C)n([C@H](C)C2CCC(N3CC(F)(F)C3)CC2)c2ccccc12] | B14 Isomer 1 (1st eluting isomer) | Cis-trans isomers separated by silica-gel preparative thin-layer chromatography (Petroleum ether/Ethyl acetate = 5/0-5/2). | LCMS [M + H]+ m/z: calc'd 391.21; found 391.0 |
| methyl (R)-1-(1-(4-(3,3-difluoroazetidin-1-yl)cyclohexyl)ethyl)-2-methyl-1H-indole-3-carboxylate 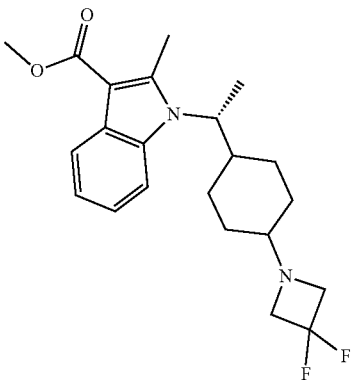 [SMILES: COC(=O)c1c(C)n([C@H](C)C2CCC(N3CC(F)(F)C3)CC2)c2ccccc12] | B14 Isomer 2 (2nd eluting isomer) | Cis-trans isomers separated by silica-gel preparative thin-layer chromatography (Petroleum ether/Ethyl acetate = 5/0-5/2). | LCMS [M + H]+ m/z: calc'd 391.21; found 391.0 |
| methyl (R)-1-(1-(4-(3,3-difluoroazetidin-1-yl)cyclohexyl)ethyl)-2-methyl-1H-indole-3-carboxylate 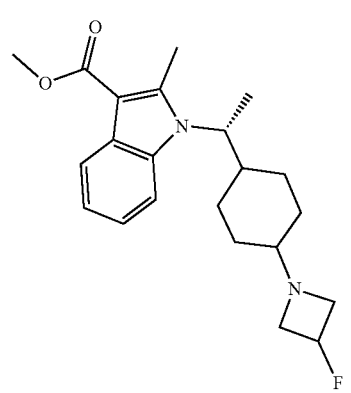 [SMILES: COC(=O)c1c(C)n([C@H](C)C2CCC(N3CC(F)C3)CC2)c2ccccc12] | B15 Isomer 1 (1st eluting isomer) | Cis-trans isomers separated by silica-gel preparative thin-layer chromatography (Petroleum ether/Ethyl acetate = 5/0-5/5). | LCMS [M + H]+ m/z: calc'd 373.22; found 373.1. |

| Structure and Name | Intermediate | Cis/trans Isomer Separation Method and Retention Time (if any) | LCMS |
|---|---|---|---|
| methyl (R)-1-(1-(4-(3-fluoroazetidin-1-yl)cyclohexyl)ethyl)-2-methyl-1H-indole-3-carboxylate<br><br>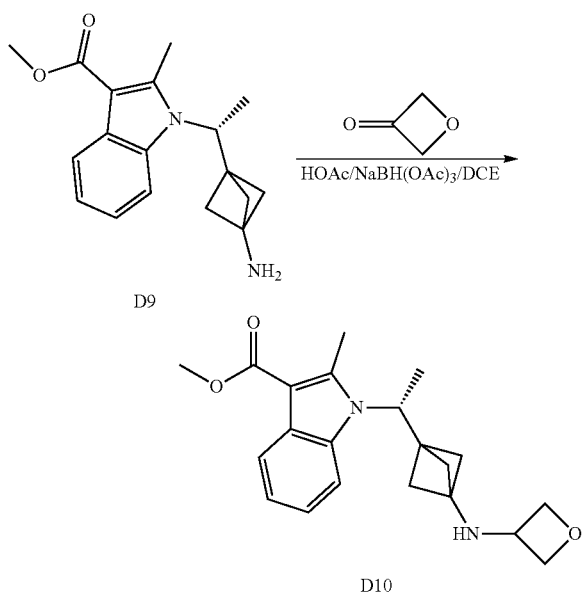<br><br>methyl (R)-1-(1-(4-(3-fluoroazetidin-1-yl)cyclohexyl)ethyl)-2-methyl-1H-indole-3-carboxylate | B15 Isomer 2 (2$^{nd}$ eluting isomer) | Cis-trans isomers separated by silica-gel preparative thin-layer chromatography (Petroleum ether/Ethyl acetate = 5/0-5/5). | LCMS [M + H]$^+$ m/z: calc'd 373.22; found 373.1. |

Step 10: Synthesis methyl (R)-2-methyl-1-(1-(3-(oxetan-3-ylamino)bicyclo[1.1.1]pentan-1-yl)ethyl)-1H-indole-3-carboxylate (D10)

To a solution of D9, methyl (R)-1-(1-(3-aminobicyclo[1.1.1]pentan-1-yl)ethyl)-2-methyl-1H-indole-3-carboxylate (170 mg, 570 umol, 1.0 equiv) and oxetan-3-one (123 mg, 1.7 mmol, 3.0 equiv) in dichloroethane (3.0 mL) was added AcOH (34 mg, 570 umol, 33 uL, 1.0 equiv). The mixture was stirred at 15° C. for 12 h. NaBH(OAc)$_3$ (604 mg, 2.90 mmol, 5.0 equiv) was added into the flask. The mixture was stirred at 15° C. for 2 h. TLC (ethyl acetate) showed new spots formed. The mixture was diluted with saturated sodium bicarbonate (3 mL) and water (10 mL), extracted with dichloromethane (20 mL*3). The combined organic layer was washed with brine (20 mL), dried over sodium sulfate, filtered and concentrated. The residue was purified by preparative-TLC (ethyl acetate). methyl (R)-2-methyl-1-(1-(3-(oxetan-3-ylamino)bicyclo[1.1.1]pentan-1-yl)ethyl)-1H-indole-3-carboxylate (60 mg, 168 umol, 29% yield) was obtained as white solid. $^1$H NMR (400 MHz, CDCl$_3$) δ 8.13 (d, J=7.6 Hz, 1H), 7.45 (d, J=8.0 Hz, 1H), 7.21-7.13 (in, 2H), 4.79-4.70 (n, 3H), 4.36-4.33 (n, 2H), 3.95-3.92 (in, 4H), 2.84-2.76 (in, 3H), 1.72-1.65 (in, 9H).

The following intermediates were synthesized using similar reductive mination conditions as those described above, along with appropriate starting materials and reagents.

| Structure and Name | Intermediate | Isomer Separation Method and Retention Time (if any) | LCMS |
|---|---|---|---|
| 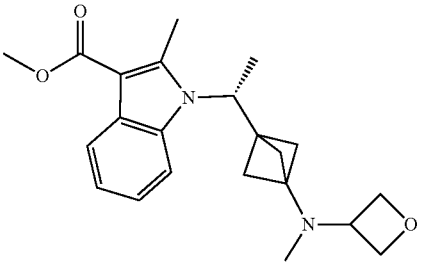 [SMILES: COC(=O)c1c(C)n([C@H](C)C23CC(N(C)C4COC4)(C2)C3)c2ccccc12]<br>methyl (R)-2-methyl-1-(1-(3-(methyl(oxetan-3-yl)amino)bicyclo[1.1.1]pentan-1-yl)ethyl)-1H-indole-3-carboxylate | D11 | | LCMS [M + H]$^+$ m/z: calc'd 369.21; found 369.1 |
| 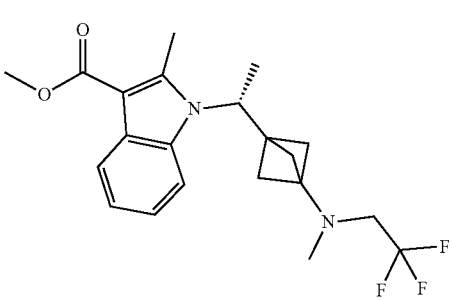 [SMILES: COC(=O)c1c(C)n([C@H](C)C23CC(N(C)CC(F)(F)F)(C2)C3)c2ccccc12]<br>methyl (R)-2-methyl-1-(1-(3-(methyl(2,2,2-trifluoroethyl)amino)bicyclo[1.1.1]pentan-1-yl)ethyl)-1H-indole-3-carboxylate | D12 | | LCMS [M + H]$^+$ m/z: calc'd 395.19; found 395.0. |

Synthesis of methyl (R)-1-(1-(1-(2-hydroxy-2-methylpropyl)piperidin-4-yl)ethyl)-2-methyl-1H-indole-3-carboxylate (E1)

Synthesis of methyl (R)-2-methyl-1-(1-(1-(2,2,2-trifluoroethyl)piperidin-4-yl)ethyl)-1H-indole-3-carboxylate (E2)

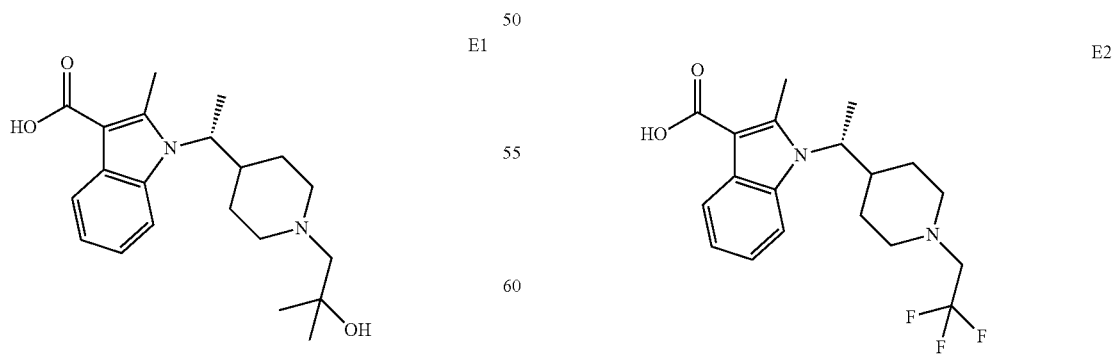

E1, methyl (R)-1-(1-(1-(2-hydroxy-2-methylpropyl)piperidin-4-yl)ethyl)-2-methyl-1H-indole-3-carboxylate was prepared according to the procedure reported in WO2015/023915. LCMS [M+H]$^+$ m/z: calc'd 372.24, found 373.1.

E2, methyl (R)-2-methyl-1-(1-(1-(2,2,2-trifluoroethyl)piperidin-4-yl)ethyl)-1H-indole-3-carboxylate was prepared according to the procedure reported in WO2015/023915.

Synthesis of methyl (R)-1-(1-(4-hydroxy-4-methyl-cyclohexyl)ethyl)-2-methyl-1H-indole-3-carboxylate (B16)

Step 2: (R)-2-methyl-1-(1-(4-((3-methyloxetan-3-yl)amino)cyclohexyl)ethyl)-1H-indole-3-carboxylic Acid (B8)

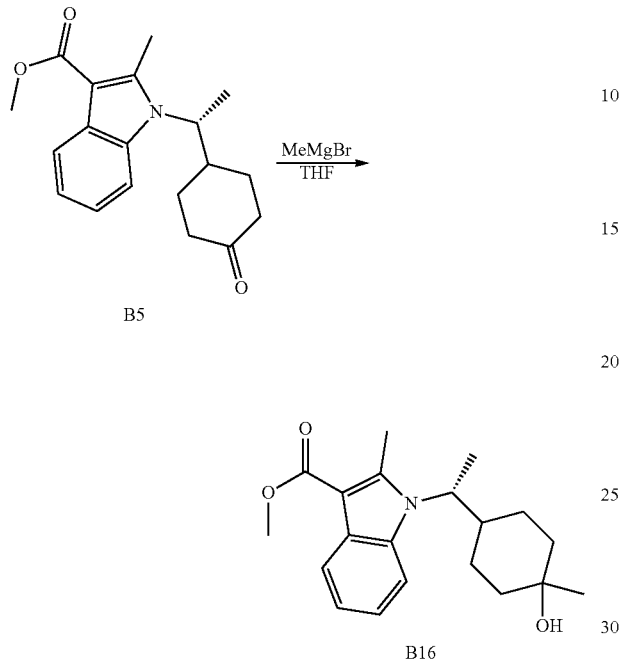

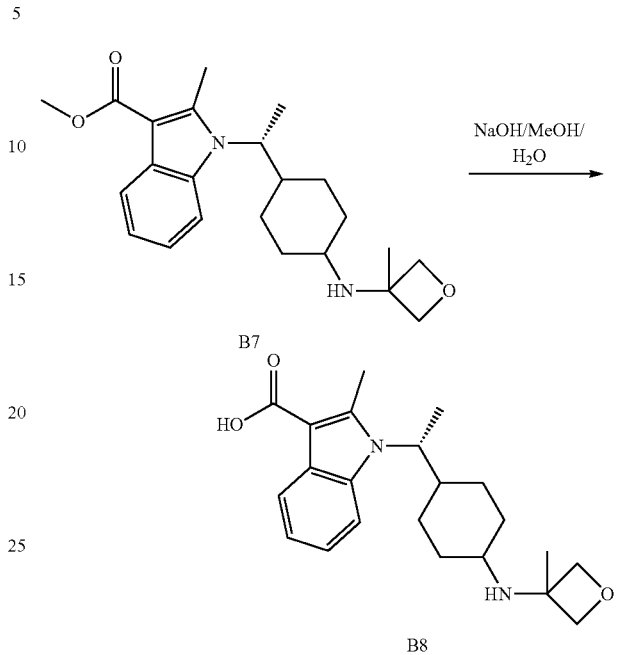

To a solution of methyl (R)-2-methyl-1-(1-(4-oxocyclohexyl)ethyl)-1H-indole-3-carboxylate (200 mg, 638 umol, 1 equiv) in THF (10 mL) was added MeMgBr (3 M, 700 uL, 3.3 equiv) at −78° C. under N2 atmosphere. The mixture was stirred at −78° C. for 1 h under N2 atmosphere. The reaction mixture was quenched by addition of saturated NH₄Cl 20 mL at 0° C. The mixture was extracted with ethyl acetate 60 mL (20 mL*3). The combined organic layers were washed with brine 60 mL (20 mL*3), dried over sodium sulfate, filtered and concentrated under reduced pressure to give B16, methyl (R)-1-(1-(4-hydroxy-4-methylcyclohexyl)ethyl)-2-methyl-1H-indole-3-carboxylate (210 mg, 484 umol) in 76% yield as a yellow solid. LCMS ([M+H]+) m/z: calc'd: 330.20; found 330.3.

To a solution of methyl (R)-2-methyl-1-(1-(4-((3-methyl-oxetan-3-yl)amino)cyclohexyl)ethyl)-1H-indole-3-carboxylate (150 mg, 390 umol, 1.0 equiv, cis/trans mixture) in methanol (3 mL) and water (1.5 mL) was added NaOH (156 mg, 3.9 mmol, 10 equiv). The mixture was stirred at 80° C. for 12 h. The reaction mixture was concentrated. dichloromethane (15 mL) and water (10 mL) were added. The mixture was adjusted to pH=5-6 with HCl (1 M) solution. The mixture was extracted with dichloromethane (20 mL*3). The organic layer was dried by anhydrous sodium sulfate, filtered and concentrated under vacuum to give B7, (R)-2-methyl-1-(1-(4-((3-methyloxetan-3-yl)amino)cyclohexyl)ethyl)-1H-indole-3-carboxylic acid (160.0 mg, crude), as a white solid. LCMS [M+H]+ m/z: calc'd 371.23; found 371.1.

The following intermediates were synthesized using similar conditions as those described above, along with appropriate starting materials.

| Structure and Name | Intermediate | LCMS |
|---|---|---|
| ![structure] 2-methyl-1-((1R)-1-(4-(oxetan-3-ylamino)cyclohexyl)ethyl)-1H-indole-3-carboxylic acid | B17 | LCMS [M + H]+ m/z: calc'd 357.21; found 357.0. |

| Structure and Name | Intermediate | LCMS |
|---|---|---|
| (R)-2-methyl-1-(1-(4-(methyl(3-methyloxetan-3-yl)amino)cyclohexyl)ethyl)-1H-indole-3-carboxylic acid | B18 | LCMS [M + H]$^+$ m/z: calc'd 385.24; found 385.0. |
| 1-((1R)-1-(4-(3-methoxyazetidin-1-yl)cyclohexyl)ethyl)-2-methyl-1H-indole-3-carboxylic acid | B19 | LCMS [M + H]$^+$ m/z: calc'd 371.23; found 371.1. |
| (R)-1-(1-(5-(tert-butylamino)-1,3-dioxan-2-yl)ethyl)-2-methyl-1H-indole-3-carboxylic acid | C14 | LCMS [M + H]$^+$ m/z: calc'd 361.21; found 361.1. |
| (R)-2-methyl-1-(1-(5-((3-methyloxetan-3-yl)amino)-1,3-dioxan-2-yl)ethyl)-1H-indole-3-carboxylic acid | C15 isomer 1 [From C9 isomer 1] | LCMS [M + H]$^+$ m/z: calc'd 397.18; found 397.1 |

-continued

| Structure and Name | Intermediate | LCMS |
|---|---|---|
| (R)-2-methyl-1-(1-(5-((3-methyloxetan-3-yl)amino)-1,3-dioxan-2-yl)ethyl)-1H-indole-3-carboxylic acid | C15 isomer 2 (From C9 isomer 2) | LCMS m/z: calc'd 397.18 [M + Na]$^+$; found 397.1 |
| (R)-1-(1-(5-(dimethylamino)-1,3-dioxan-2-yl)ethyl)-2-methyl-1H-indole-3-carboxylic acid | C16 | LCMS [M + H]$^+$ m/z: calc'd 333.17; found 332.9 |
| (R)-1-(1-(5-(2,2-dimethylazetidin-1-yl)-1,3-dioxan-2-yl)ethyl)-2-methyl-1H-indole-3-carboxylic acid | C17 | LCMS [M + H]$^+$ m/z: calc'd 373.20; found 373.0 |
| | C18 | LCMS [M + H]$^+$ m/z: calc'd 377.22; found 377.0 |

-continued

| Structure and Name | Intermediate | LCMS |
|---|---|---|
| (R)-1-(1-(5-((2-methoxyethyl)(methyl)amino)-1,3-dioxan-2-yl)ethyl)-2-methyl-1H-indole-3-carboxylic acid | C19 | LCMS [M + H]+ m/z: calc'd 319.16; found 318.9 |
| (R)-2-methyl-1-(1-(5-(methylamino)-1,3-dioxan-2-yl)ethyl)-1H-indole-3-carboxylic acid | D14 | LCMS [M + H]+ m/z: calc'd 341.18; found 340.9 |
| (R)-2-methyl-1-(1-(3-(oxetan-3-ylamino)bicyclo[1.1.1]pentan-1-yl)ethyl)-1H-indole-3-carboxylic acid | D15 | LCMS [M + H]+ m/z: calc'd 355.19; found 355.1 |
| (R)-2-methyl-1-(1-(3-(methyl(oxetan-3-yl)amino)bicyclo[1.1.1]pentan-1-yl)ethyl)-1H-indole-3-carboxylic acid | D16 | LCMS [M + H]+ m/z: calc'd 381.17; found 381.1 |

| Structure and Name | Intermediate | LCMS |
|---|---|---|
| (R)-2-methyl-1-(1-(3-(methyl(2,2,2-trifluoroethyl)amino)bicyclo[1.1.1]pentan-1-yl)ethyl)-1H-indole-3-carboxylic acid | E3 | LCMS [M + H]⁺ m/z: calc'd 359.23; found 359.1 |
| (R)-1-(1-(1-(2-hydroxy-2-methylpropyl)piperidin-4-yl)ethyl)-2-methyl-1H-indole-3-carboxylic acid | F2 | LCMS [M + H]⁺ m/z: calc'd 288.15; found 287.9 |
| (R)-2-methyl-1-(1-(tetrahydro-2H-pyran-4-yl)ethyl)-1H-indole-3-carboxylic acid | G2 | LCMS [M + H]⁺ m/z: calc'd 260.12; found 259.9 |
| 2-methyl-1-(1-(oxetan-3-yl)ethyl)-1H-indole-3-carboxylic acid | B20 | LCMS [M + H]⁺ m/z: calc'd 316.18; found 316.0 |
| (R)-1-(1-(4-methoxycyclohexyl)ethyl)-2-methyl-1H-indole-3-carboxylic acid | B21 | LCMS [M + H]⁺ m/z: calc'd 302.17; found 301.9 |

| Structure and Name | Intermediate | LCMS |
|---|---|---|

(R)-1-(1-(4-hydroxycyclohexyl)ethyl)-2-methyl-1H-indole-3-carboxylic acid

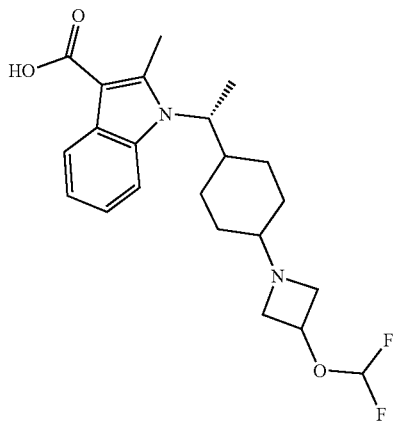 [SMILES: Cc1c(C(=O)O)c2ccccc2n1[C@H](C)C1CCC(N2CC(OC(F)F)C2)CC1]

B22 Isomer 1 (From B12 isomer 1)

LCMS [M + H]+ m/z: calc'd 407.21; found 407.1

(R)-1-(1-(4-(3-(difluoromethoxy)azetidin-1-yl)cyclohexyl)ethyl)-2-methyl-1H-indole-3-carboxylic acid

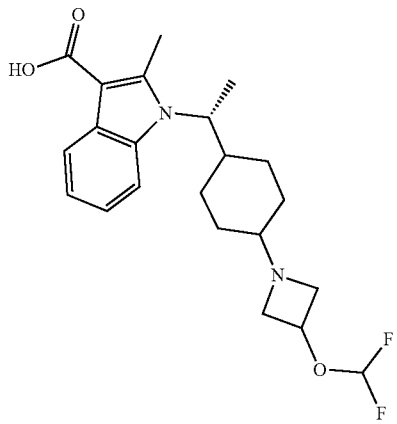 [SMILES: Cc1c(C(=O)O)c2ccccc2n1[C@H](C)C1CCC(N2CC(OC(F)F)C2)CC1]

B22 Isomer 2 (From B12 isomer 2)

LCMS [M + H]+ m/z: calc'd 407.21; found 407.1

(R)-1-(1-(4-(3-(difluoromethoxy)azetidin-1-yl)cyclohexyl)ethyl)-2-methyl-1H-indole-3-carboxylic acid

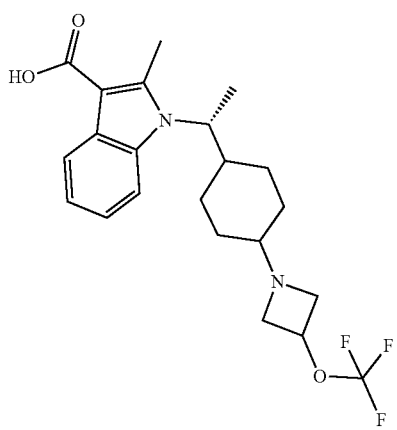 [SMILES: Cc1c(C(=O)O)c2ccccc2n1[C@H](C)C1CCC(N2CC(OC(F)(F)F)C2)CC1]

B23 Isomer 1 (From B13 isomer 1)

LCMS [M + H]+ calc'd. 425.2; found 425.1

| Structure and Name | Intermediate | LCMS |
|---|---|---|
| (R)-2-methyl-1-(1-(4-(3-(trifluoromethoxy)azetidin-1-yl)cyclohexyl)ethyl)-1H-indole-3-carboxylic acid<br>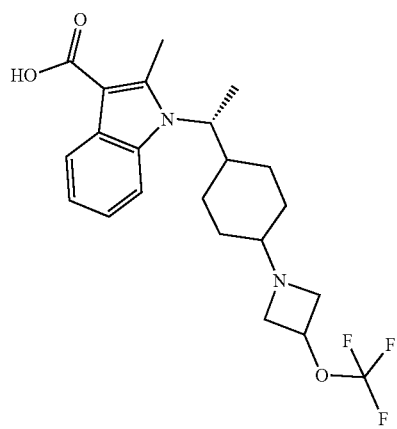 [SMILES: Cc1c(C(=O)O)c2ccccc2n1[C@H](C)C1CCC(N2CC(OC(F)(F)F)C2)CC1]<br>(R)-2-methyl-1-(1-(4-(3-(trifluoromethoxy)azetidin-1-yl)cyclohexyl)ethyl)-1H-indole-3-carboxylic acid | B23 Isomer 2 (From B13 isomer 2) | LCMS [M + H]⁺ calc'd. 425.2; found 425.1 |
| 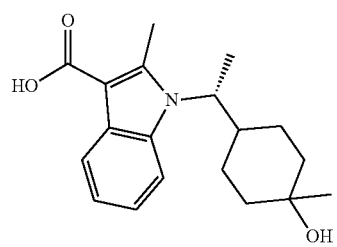 [SMILES: Cc1c(C(=O)O)c2ccccc2n1[C@H](C)C1CCC(C)(O)CC1]<br>(R)-1-(1-(4-hydroxy-4-methylcyclohexyl)ethyl)-2-methyl-1H-indole-3-carboxylic acid | B24 | LCMS [M + H]⁺ m/z: calc'd: 316.18.; found 316.0 |
| 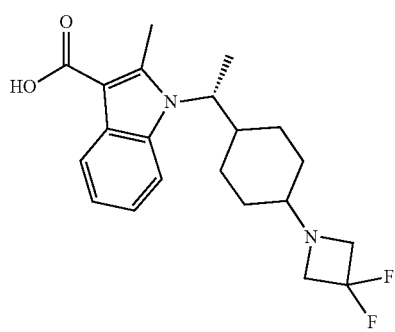 [SMILES: Cc1c(C(=O)O)c2ccccc2n1[C@H](C)C1CCC(N2CC(F)(F)C2)CC1]<br>(R)-1-((R)-1-(4-(3,3-difluoroazetidin-1-yl)cyclohexyl)ethyl)-2-methyl-1H-1l4-indole-3-carboxylic acid | B25 Isomer 1 (From B14 isomer 1) | LCMS [M + H]⁺ m/z: calc'd: 377.2.; found 377.0 |

-continued

| Structure and Name | Intermediate | LCMS |
|---|---|---|
| 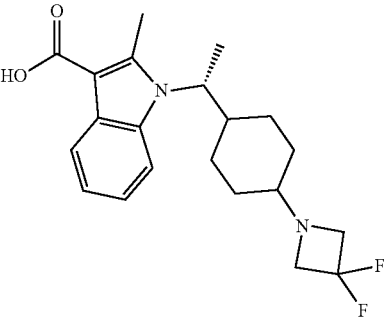 [SMILES: Cc1c(C(=O)O)c2ccccc2n1[C@H](C)C1CCC(N2CC(F)(F)C2)CC1]<br>(R)-1-((R)-1-(4-(3,3-difluoroazetidin-1-yl)cyclohexyl)ethyl)-2-methyl-1H-1l4-indole-3-carboxylic acid | B25 Isomer 2 (From B14 isomer 2) | LCMS [M + H]⁺ m/z: calc'd: 377.2.; found 377.0 |
| 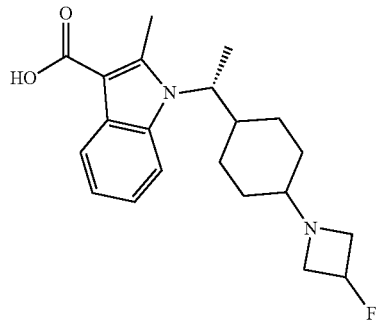 [SMILES: Cc1c(C(=O)O)c2ccccc2n1[C@H](C)C1CCC(N2CC(F)C2)CC1]<br>(R)-1-(1-(4-(3-fluoroazetidin-1-yl)cyclohexyl)ethyl)-2-methyl-1H-indole-3-carboxylic acid | B26 Isomer 1 (From B15 isomer 1) | LCMS [M + H]⁺ m/z: calc'd 359.21; found 359.0 |
| 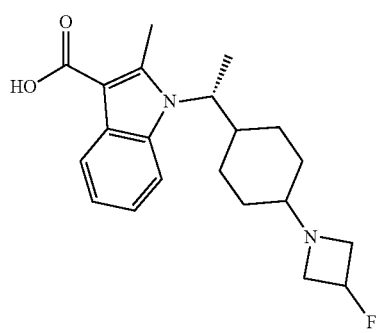 [SMILES: Cc1c(C(=O)O)c2ccccc2n1[C@H](C)C1CCC(N2CC(F)C2)CC1]<br>(R)-1-(1-(4-(3-fluoroazetidin-1-yl)cyclohexyl)ethyl)-2-methyl-1H-indole-3-carboxylic acid | B26 Isomer 2 (From B15 isomer 2) | LCMS [M + H]⁺ m/z: calc'd 359.21; found 359.0 |
| 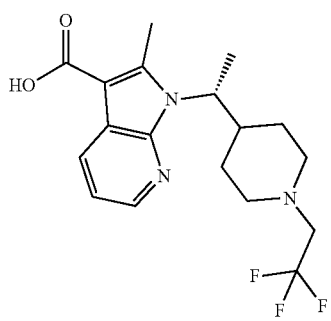 [SMILES: Cc1c(C(=O)O)c2cccnc2n1[C@H](C)C1CCN(CC(F)(F)F)CC1] | H5 | LCMS [M + H]⁺ m/z: calc'd 370.17; found 370.1 |

| Structure and Name | Intermediate | LCMS |
|---|---|---|
| (R)-2-methyl-1-(1-(1-(2,2,2-trifluoroethyl)piperidin-4-yl)ethyl)-1H-pyrrolo[2,3-b]pyridine-3-carboxylic acid 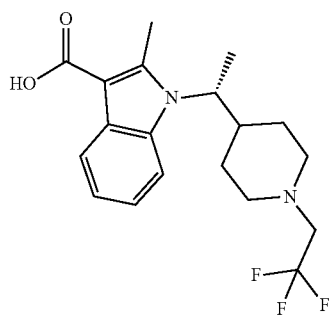 (R)-2-methyl-1-(1-(1-(2,2,2-trifluoroethyl)piperidin-4-yl)ethyl)-1H-indole-3-carboxylic acid | E4 | LCMS [M + H]+ m/z: calc'd 357.21; found 357.2 |
| 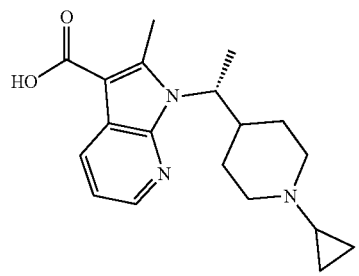 [SMILES: Cc1c(C(=O)O)c2cccnc2n1[C@H](C)C1CCN(C2CC2)CC1] (R)-1-(1-(1-cyclopropylpiperidin-4-yl)ethyl)-2-methyl-1H-pyrrolo[2,3-b]pyridine-3-carboxylic acid | H7 | LCMS [M + H]+ m/z: calc'd 328.19; found 328.0. |

Step 3: Synthesis of (R)-2-methyl-N-((6-methyl-4-(methylthio)-2-oxo-1,2-dihydropyridin-3-yl)methyl)-1-(1-(4-((3-methyloxetan-3-yl)amino)cyclohexyl)ethyl)-1H-indole-3-carboxamide (Example 1, Isomer 1 and Isomer 2)

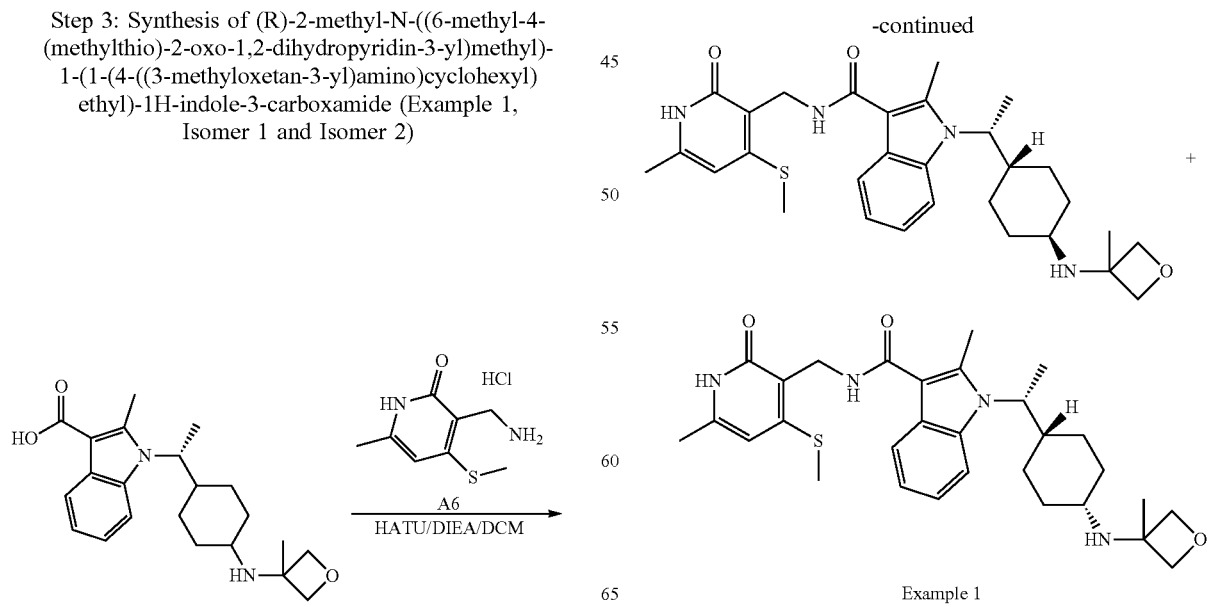

To a solution of (R)-2-methyl-1-(1-(4-((3-methyloxetan-3-yl)amino)cyclohexyl)ethyl)-H-indole-3-carboxylic acid (90 mg, 243 umol, 1.0 equiv, cis/trans mixture) and 3-(aminomethyl)-6-methyl-4-methylsulfanyl-1H-pyridin-2-one (215 mg, 972 umol, 4 equiv, HCl salt) in dichloromethane (2 mL) was added HATU (111 mg, 292 umol, 1.2 equiv) and diisopropyethylamine (157 mg, 1.2 mmol, 5 equiv). The mixture was stirred at 25° C. for 2 h. The reaction was diluted with water (5 mL) and extracted with dichloromethane (10 mL*3). The organic layer was dried over anhydrous sodium sulfate, filtered and concentrated under vacuum before being purified by prep-HPLC (column: Waters Xbridge 150×25 mm Sum; mobile phase A [water (0.05% ammonia hydroxide v/v)] and B [acetonitrile]; gradient B: 35%-65% over 10 min). The cis and trans isomers were separated via SFC. Isomer 1 was purified on a Chiralpak AS-3 100×4.6 mm I.D., 3 um column. The mobile phase A [$CO_2$] and B [ethanol (0.05% diethylamine)]. The gradient was a ramp from 5% to 40% of B in 4.5 min and held at 40% for 2.5 min, and then 5% of B for 1 min at a flow rate of 2.8 mL/min and a column temperature of 40° C. The retention time of Isomer 1 is 3.86 min. Isomer 2 was further purified on a Chiralcel OD-3 100×4.6 mm I.D., 3 um column. The mobile phase A [$CO_2$] and B [ethanol (0.05% diethylamine)]. The column gradient was a ramp from 5% to 40% of B in 4.5 min and held at 40% for 2.5 min, and then 5% of B for 1 min at a flow rate of 2.8 mL/min and a column temperature of 40° C. The retention time of Isomer 2 is 5.27 min.

Isomer 1: (R)-2-methyl-N-((6-methyl-4-(methylthio)-2-oxo-1,2-dihydropyridin-3-yl)methyl)-1-(1-(4-((3-methyloxetan-3-yl)amino)cyclohexyl)ethyl)-1H-indole-3-carboxamide (0.0354 g, 63.3 umol, 26.1% yield) was obtained as a white solid. LCMS [M+H]$^+$ m/z: calc'd 537.28; found 537.1. $^1$H NMR (400 MHz, CDCl$_3$) δ 12.64 (br s, 1H), 7.83 (d, J=7.6 Hz, 1H), 7.45 (d, J=8.0 Hz, 1H), 7.35-7.32 (m, 1H), 7.09-7.02 (m, 2H), 6.00 (s, 1H), 4.72-4.71 (m, 2H), 4.46-4.33 (m, 4H), 4.05-4.03 (m, 1H), 2.72 (s, 3H), 2.54 (br s, 1H), 2.49 (s, 3H), 2.21 (s, 3H), 2.10-1.89 (m, 3H), 1.60 (d, J=7.2 Hz, 3H), 1.49 (s, 3H), 1.19-0.79 (m, 5H).

Isomer 2: (R)-2-methyl-N-((6-methyl-4-(methylthio)-2-oxo-1,2-dihydropyridin-3-yl)methyl)-1-(1-(4-((3-methyloxetan-3-yl)amino)cyclohexyl)ethyl)-1H-indole-3-carboxamide (0.0072 g, 12.7 umol, 5.3% yield) was obtained as a white solid. LCMS [M+H]+m/z: calc'd 537.28; found 537.1. $^1$H NMR (400 MHz, CDCl$_3$) δ12.67 (br s, 1H), 7.84 (d, J=7.2 Hz, 1H), 7.45 (d, J=8.0 Hz, 1H), 7.33-7.32 (m, 1H), 7.10-7.02 (m, 2H), 6.01 (s, 1H), 4.75-4.70 (m, 2H), 4.52-4.24 (m, 5H), 3.01-2.77 (m, 4H), 2.48 (s, 3H), 2.22 (s, 3H), 2.20-1.64 (m, 4H), 1.59 (d, J=6.8 Hz, 3H), 1.48 (s, 3H), 1.33-1.05 (m, 5H).

The following examples were synthesized using the amide coupling procedure described above and using appropriate starting materials.

| Name and Structure | Ex. # | Isomer Separation Method and Retention Time (if any) | LCMS + HNMR |
|---|---|---|---|
| 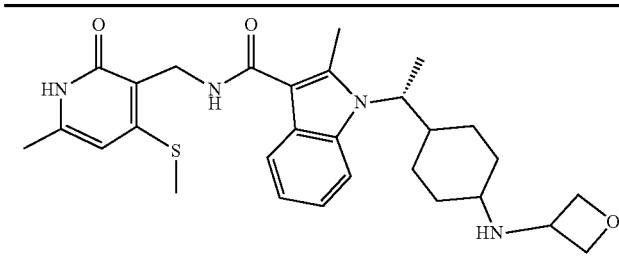<br>(R)-2-methyl-N-((6-methyl-4-(methylthio)-2-oxo-1,2-dihydropyridin-3-yl)methyl)-1-(1-(4-(oxetan-3-ylamino)cyclohexyl)ethyl)-1H-indole-3-carboxamide | 2<br>Isomer 1 | Column: Chiralpak AD-3 100 × 4.6 mm I.D., 3 um Mobile phase: 40% of ethanol (0.05% diethylamine) in $CO_2$ Flow rate: 2.8 mL/min Column temperature: 40° C. Retention Time = 5.06 min | LCMS [M + H]$^+$ m/z: calc'd 523.27; found 523.2; $^1$H NMR (400 MHz, CDCl$_3$) δ 12.76 (br. s., 1H), 7.83 (d, J = 7.6 Hz, 1H), 7.44 (d, J = 8.0 Hz, 1H), 7.35-7.32 (m, 1H), 7.09-7.02 (m, 2H), 6.00 (s, 1H), 4.80-4.76 (m, 4H), 4.40-4.34 (m, 2H), 2.71 (s, 3H), 2.48 (s, 3H), 2.37 (br s, 1H), 2.21 (s, 3H), 2.18-1.91 (m, 2H), 1.59 (d, J = 6.8 Hz, 6H), 1.13-0.79 (m, 5H). |
| 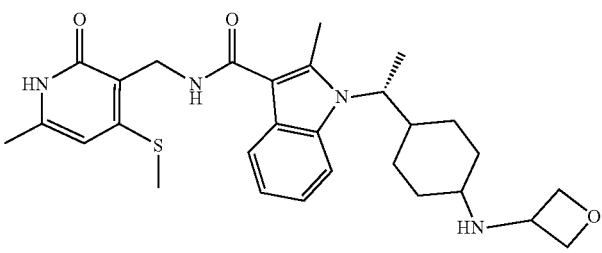 [SMILES: CSc1cc(C)[nH]c(=O)c1CNC(=O)c1c(C)n([C@H](C)C2CCC(NC3COC3)CC2)c2ccccc12]<br>(R)-2-methyl-N-((6-methyl-4-(methylthio)-2-oxo-1,2-dihydropyridin-3-yl)methyl)-1-(1-(4-(oxetan-3-ylamino)cyclohexyl)ethyl)-1H-indole-3-carboxamide | 2<br>Isomer 2 | Column: Chiralpak AD-3 100 × 4.6 mm I.D., 3 um Mobile phase: 40% of ethanol (0.05% diethylamine) in $CO_2$ Flow rate: 2.8 mL/min Column temperature: 40° C. Retention Time = 2.95 min | LCMS [M + H]$^+$ m/z: calc'd 523.27; found 523.2. $^1$H NMR (400 MHz, CDCl$_3$) δ 12.90 (br. s., 1H), 7.83 (d, J = 8.0 Hz, 1H), 7.45 (d, J = 8.0 Hz, 1H), 7.32 (br s, 1H), 7.09-7.01 (m, 2H), 6.01 (s, 1H), 4.83-4.75 (m, 4H), 4.45-4.41 (m, 2H), 4.00-3.98 (m, 2H), 2.84 (s, 3H), 2.48 (s, 3H), 2.29 (br s, 1H), 2.21 (s, 3H), 1.77-1.55 (m, 7H), 1.32-0.86 (m, 5H). |

| Name and Structure | Ex. # | Isomer Separation Method and Retention Time (if any) | LCMS + HNMR |
|---|---|---|---|
| 2-methyl-1-((1R)-1-(4-(methyl(3-methyloxetan-3-yl)amino)cyclohexyl)ethyl)-N-((6-methyl-4-(methylthio)-2-oxo-1,2-dihydropyridin-3-yl)methyl)-1H-indole-3-carboxamide | 3 Isomer 1 | Column: Chiralpak AS-3 100 × 4.6 mm I.D., 3 um Mobile phase: A: $CO_2$ B: ethanol (0.05% diethylamine) Gradient: from 5% to 40% of B in 4.5 min and hold 40% for 2.5 min, then 5% of B for 1 min Flow rate: 2.8 mL/min Column temperature: 40° C. Retention Time = 3.83 min | LCMS [M + H]$^+$ m/z: calc'd 551.30; found 551.1. $^1$H NMR (400 MHz, CDCl$_3$) δ 12.43 (br s, 1H), 7.82 (d, J = 7.2 Hz, 1H), 7.44 (d, J = 7.6 Hz, 1H), 7.32 (s, 1H), 7.10-7.04 (m, 2H), 6.00 (s, 1H), 4.73-4.72 (m, 2H), 4.60 (d, J = 5.2 Hz, 1H), 4.56 (d, J = 5.6 Hz, 1H), 4.14-4.07 (m, 3H), 2.83-2.71 (m, 3H), 2.48 (s, 3H), 2.20-2.10 (m, 6H), 2.02 (s, 3H), 1.82-1.79 (m, 1H), 1.63-1.57 (m, 3H), 1.42-1.39 (m, 5H), 1.05-1.02 (m, 3H), 0.78-0.74 (m, 1H). |
| 2-methyl-1-((1R)-1-(4-(methyl(3-methyloxetan-3-yl)amino)cyclohexyl)ethyl)-N-((6-methyl-4-(methylthio)-2-oxo-1,2-dihydropyridin-3-yl)methyl)-1H-indole-3-carboxamide | 3 Isomer 2 | Column: Chiralcel OD-3 100 × 4.6 mm I.D., 3 um Mobile phase: A: $CO_2$ B: ethanol (0.05% diethylamine) Gradient: from 5% to 40% of B in 4.5 min and hold 40% for 2.5 min, then 5% of B for 1 min Flow rate: 2.8 mL/min Column temperature: 40° C. Retention Time = 5.27 min | LCMS [M + Na]$^+$ m/z: calc'd 573.30; found 573.1. $^1$H NMR (400 MHz, CDCl$_3$) δ 12.22 (br s, 1H), 7.83 (d, J = 8.4 Hz, 1H), 7.44 (d, J = 7.6 Hz, 1H), 7.30-7.26 (m, 1H), 7.09-7.04 (m, 2H), 6.00 (s, 1H), 4.76-4.63 (m, 4H), 4.40-4.38 (m, 1H), 4.13-4.07 (m, 2H), 2.84-2.79 (m, 3H), 2.48 (s, 4H), 2.31-2.30 (m, 1H), 2.21 (s, 3H), 1.97 (s, 3H), 1.78-1.76 (m, 1H), 1.57-1.53 (m, 4H), 1.39-1.25 (m, 6H), 1.16-1.09 (m, 2H), 1.01-0.97 (m, 1H). |
| 1-((1R)-1-(4-(3-methoxyazetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 4 Isomer 1 | Column: Chiralpak AD-3 100 × 4.6 mm I.D., 3 um Mobile phase: 40% of ethanol (0.05% diethylamine) in $CO_2$ Flow rate: 2.8 mL/min Column temperature: 40° C. Retention Time = 3.35 min | LCMS [M + H]$^+$ m/z: calc'd 537.28; found 537.1. $^1$H NMR (400 MHz, CDCl$_3$) δ 12.70 (br s, 1H), 7.82 (d, J = 7.6 Hz, 1H), 7.44 (d, J = 7.6 Hz, 1H), 7.37 (s, 1H), 7.10-7.02 (m, 2H), 6.00 (s, 1H), 4.78-4.71 (m, 2H), 4.03-3.98 (m, 2H), 3.59-3.52 (m, 2H), 3.24 (s, 3H), 2.87-2.80 (m, 2H), 2.72 (s, 3H), 2.48 (s, 3H), 2.18-2.06 (m, 4H), 1.91-1.58 (m, 6H), 1.07-0.73 (m, 5H). |

| Name and Structure | Ex. # | Isomer Separation Method and Retention Time (if any) | LCMS + HNMR |
|---|---|---|---|
| 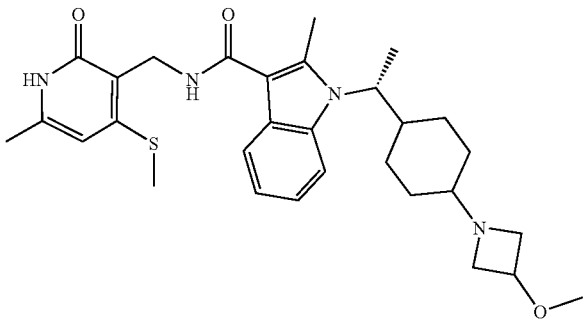 1-((1R)-1-(4-(3-methoxyazetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 4 Isomer 2 | Column: Chiralpak AD-3 100 × 4.6 mm I.D., 3 um Mobile phase: 40% of ethanol (0.05% diethylamine) in $CO_2$ Flow rate: 2.8 mL/min Column temperature: 40° C. Retention Time = 1.77 min | LCMS [M + H]$^+$ m/z: calc'd 537.28; found 537.2. $^1$H NMR (400 MHz, CDCl$_3$) δ 12.50 (br s, 1H), 7.83 (d, J = 7.6 Hz, 1H), 7.45 (d, J = 7.2 Hz, 1H), 7.31 (s, 1H), 7.13-7.01 (m, 2H), 6.00 (s, 1H), 4.80-4.70 (m, 2H), 4.02-4.00 (m, 2H), 3.58-3.47 (m, 2H), 3.25 (s, 3H), 2.79-2.71 (m, 5H), 2.48 (s, 3H), 2.20 (s, 3H), 1.63-1.38 (m, 10H), 1.13-0.74 (m, 3H). |
| 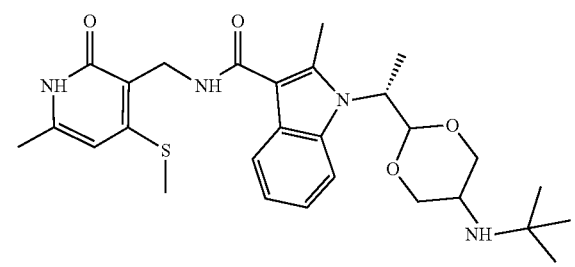 [SMILES: CSc1cc(C)[nH]c(=O)c1CNC(=O)c1c(C)n([C@H](C)C2OCC(NC(C)(C)C)CO2)c2ccccc12] 1-((1R)-1-(5-(tert-butylamino)-1,3-dioxan-2-yl)ethyl)-2-methyl-N-((6-methyl-4-(methylthio)-2-oxo-1,2-dihydropyridin-3-yl)methyl)-1H-indole-3-carboxamide | 5 Isomer 1 | Column: Chiralcel OD-3 100 × 4.6 mm I.D., 3 um Mobile phase: A: $CO_2$ B: ethanol (0.05% diethylamine) Gradient: from 5% to 40% of B in 4.5 min and hold 40% for 2.5 min, then 5% of B for 1 min Flow rate: 2.8 mL/min Column temperature: 40° C. Retention Time = 4.92 min | LCMS [M + H]$^+$ m/z: calc'd 526.26; found 527.1. $^1$H NMR (400 MHz, CD$_3$OD) δ 7.73-7.72 (d, J = 7.6 Hz, 1H), 7.59 (br s, 1H), 7.13-7.05 (m, 2H), 6.29 (s, 1H), 5.03 (br s, 1H), 4.61 (s, 2H), 4.60-4.58 (m, 1H), 4.13 (d, J = 8.0 Hz, 1H), 3.91 (d, J = 7.6 Hz, 1H), 3.42 (t, J = 10.8 Hz, 1H), 3.33-3.32 (m, 1H), 2.97-2.94 (m, 1H), 2.63 (s, 3H), 2.53 (s, 3H), 2.31 (s, 3H), 1.64 (d, J = 7.2 Hz, 3H), 1.08 (s, 9H). |
| 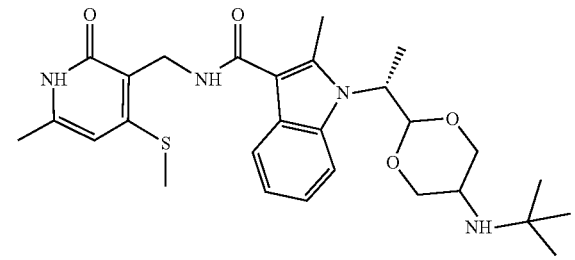 [SMILES: CSc1cc(C)[nH]c(=O)c1CNC(=O)c1c(C)n([C@H](C)C2OCC(NC(C)(C)C)CO2)c2ccccc12] 1-((1R)-1-(5-(tert-butylamino)-1,3-dioxan-2-yl)ethyl)-2-methyl-N-((6-methyl-4-(methylthio)-2-oxo-1,2-dihydropyridin-3-yl)methyl)-1H-indole-3-carboxamide | 5 Isomer 2 | Column: Chiralcel OD-3 100 × 4.6 mm I.D., 3 um Mobile phase: A: $CO_2$ B: ethanol (0.05% diethylamine) Gradient: from 5% to 40% of B in 4.5 min and hold 40% for 2.5 min, then 5% of B for 1 min Flow rate: 2.8 mL/min Column temperature: 40° C. Retention Time = 4.39 min | LCMS [M + H]$^+$ m/z: calc'd 526.26; found 527.1. $^1$H NMR (400 MHz, CD$_3$OD) δ 7.72 (d, J = 7.6 Hz, 1H), 7.62 (br s, 1H), 7.15-7.07 (m, 2H), 6.32 (s, 1H), 5.13 (br s, 1H), 4.62 (s, 2H), 4.60-4.58 (m, 1H), 4.34 (d, J = 11.6 Hz, 1H), 4.12 (d, J = 6.4 Hz, 1H), 3.75-3.70 (m, 1H), 3.45 (br s, 2H), 2.63 (s, 3H), 2.59 (s, 3H), 2.32 (s, 3H), 1.68 (d, J = 7.2 Hz, 3H), 1.29 (s, 9H). |

| Name and Structure | Ex. # | Isomer Separation Method and Retention Time (if any) | LCMS + HNMR |
|---|---|---|---|
| 2-methyl-N-((6-methyl-4-(methylthio)-2-oxo-1,2-dihydropyridin-3-yl)methyl)-1-((1R)-1-(5-((3-methyloxetan-3-yl)amino)-1,3-dioxan-2-yl)ethyl)-1H-indole-3-carboxamide | 6 Isomer 1 (From C15 isomer 1) | N/A | LCMS [M + H]$^+$ m/z: calc'd 541.24; found 541.1. $^1$H NMR (400 MHz, CD$_3$OD) δ 7.72 (d, J = 7.46 Hz, 1H), 7.61 (br s, 1H), 7.06-7.15 (m, 2H), 6.32 (s, 1H), 5.02 (m, 1H), 4.62 (s, 2H), 4.58 (br s, 1H), 4.44 (dd, J = 9.8, 6.0 Hz, 2H), 4.28-4.33 (m, 2H), 4.07-4.13 (m, 1H), 3.89 (br dd, J = 11.0, 2.5 Hz, 1H), 3.35-3.50 (m, 1H), 3.13-3.30 (m, 1H), 2.98 (tt, J = 10.4, 5.0 Hz, 1H), 2.63 (br s, 3H), 2.55 (s, 3H), 2.32 (s, 3H), 1.65 (d, J = 7.2 Hz, 3H), 1.31 (s, 3H). |
| 2-methyl-N-((6-methyl-4-(methylthio)-2-oxo-1,2-dihydropyridin-3-yl)methyl)-1-((1R)-1-(5-((3-methyloxetan-3-yl)amino)-1,3-dioxan-2-yl)ethyl)-1H-indole-3-carboxamide | 6 Isomer 2 (From C15 isomer 2) | N/A | LCMS [M + H]$^+$ m/z: calc'd 541.24; found 541.1. $^1$H NMR (400 MHz, CD$_3$OD) δ 7.70-7.81 (m, 2H), 7.05-7.15 (m, 2H), 6.29 (s, 1H), 5.09-5.14 (m, 1H), 4.52-4.67 (m, 3H), 4.00-4.16 (m, 3H), 3.79-3.93 (m, 3H), 3.67 (br dd, J = 11.29, 1.0 Hz, 1H), 3.51-3.6 (m, 1H), 2.56-2.65 (m, 4H), 2.52-2.55 (m, 3H), 2.28-2.33 (m, 3H), 1.73 (br d, J = 7.8 Hz, 3H), 1.32 (s, 3H). |
| 1-((1R)-1-(5-(dimethylamino)-1,3-dioxan-2-yl)ethyl)-2-methyl-N-((6-methyl-4-(methylthio)-2-oxo-1,2-dihydropyridin-3-yl)methyl)-1H-indole-3-carboxamide | 7 Isomer 1 | Column: Chiralcel OD-3 100 × 4.6 mm I.D., 3 um Mobile phase: A: CO$_2$ B: ethanol (0.05% diethylamine) Gradient: from 5% to 40% of B in 4.5 min and hold 40% for 2.5 min, then 5% of B for 1 min Flow rate: 2.8 mL/min Column temperature: 40° C. Retention Time = 5.23 min | LCMS [M + H]$^+$ m/z: calc'd 499.2; found 498.2. $^1$H NMR (400 MHz, CD$_3$OD) δ 7.72 (d, J = 8.0 Hz, 1H), 7.62 (br s, 1H), 7.21-7.14 (m, 2H), 6.99 (s, 1H), 5.13 (br s, 1H), 4.65-4.63 (m. 1H), 4.62 (s, 2H), 4.51 (d, J = 9.6 Hz, 1H), 4.29 (br s, 1H), 3.89 (t, J = 10.8 Hz, 1H), 3.62 (br s, 1H), 2.75 (s, 6H), 2.71 (s, 3H), 2.56 (s, 3H), 2.33 (s, 3H), 2.05 (br s, 1H), 1.68 (d, J = 7.2 Hz, 3H). |

| Name and Structure | Ex. # | Isomer Separation Method and Retention Time (if any) | LCMS + HNMR |
|---|---|---|---|
| 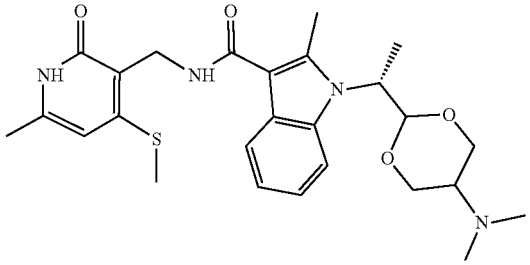<br>1-((1R)-1-(5-(dimethylamino)-1,3-dioxan-2-yl)ethyl)-2-methyl-N-((6-methyl-4-(methylthio)-2-oxo-1,2-dihydropyridin-3-yl)methyl)-1H-indole-3-carboxamide | 7<br>Isomer 2 | Column: Chiralcel OD-3 100 × 4.6 mm I.D., 3 um<br>Mobile phase: A: $CO_2$ B: ethanol (0.05% diethylamine)<br>Gradient: from 5% to 40% of B in 4.5 min and hold 40% for 2.5 min, then 5% of B for 1 min<br>Flow rate: 2.8 mL/min Column temperature: 40° C.<br>Retention Time = 4.66 min | LCMS [M + H]$^+$ m/z: calc'd 499.2; found 498.2. $^1$H NMR (400 MHz, CD$_3$OD) δ 7.71 (d, J = 7Hz, 1H), 7.62 (br s, 1H), 7.13-7.08 (m, 2H), 6.33 (s, 1H), 5.10 (br s, 1H), 4.62 (s, 2H), 4.60 (m, 1H), 4.46 (br s, 1H), 4.26 (d, J = 8.2 Hz, 1H), 3.82 (t, J = 10.4 Hz, 1H), 3.54 (br s, 1H), 3.10 (br s, 1H), 2.62 (s, 9H), 2.56 (s, 3H), 2.33 (s, 3H), 1.68 (d, J = 5.6 Hz, 3H). |
| 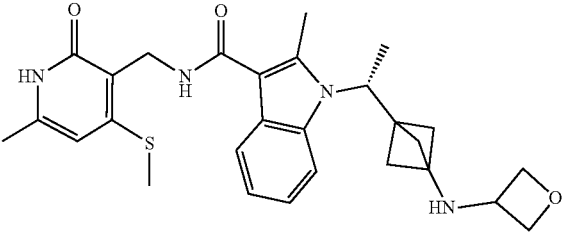 [SMILES: CSc1cc(C)[nH]c(=O)c1CNC(=O)c1c(C)n([C@H](C)C23CC(NC4COC4)(C2)C3)c2ccccc12]<br>(R)-2-methyl-N-((6-methyl-4-(methylthio)-2-oxo-1,2-dihydropyridin-3-yl)methyl)-1-(1-(3-(oxetan-3-ylamino)bicyclo[1.1.1]pentan-1-yl)ethyl)-1H-indole-3-carboxamide | 8 | N/A | LCMS [M + H]$^+$ m/z: calc'd 507.24; found 507.0. $^1$H NMR (400 MHz, CDCl$_3$) δ 13.12 (br s, 1H), 7.79 (d, J = 8.4 Hz, 1H), 7.40 (d, J = 7.6 Hz, 1H), 7.33-6.99 (m, 3H), 5.99 (s, 2H), 4.76-4.63 (m, 5H), 4.32 (t, J = 6.8 Hz, 2H), 3.92-3.91 (m, 1H), 2.78-2.69 (m, 3H), 2.47 (s, 3H), 2.19 (s, 3H), 1.82-1.68 (m, 2H), 1.66-1.61 (m, 7H). |
| 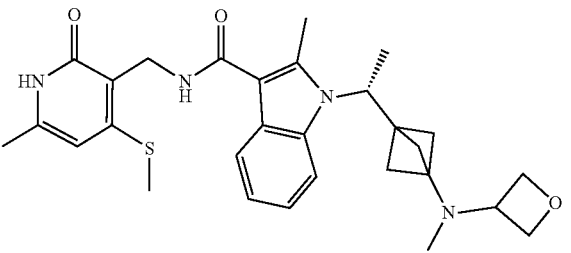 [SMILES: CSc1cc(C)[nH]c(=O)c1CNC(=O)c1c(C)n([C@H](C)C23CC(N(C)C4COC4)(C2)C3)c2ccccc12]<br>(R)-2-methyl-1-(1-(3-(methyl(oxetan-3-yl)amino)bicyclo[1.1.1]pentan-1-yl)ethyl)-N-((6-methyl-4-(methylthio)-2-oxo-1,2-dihydropyridin-3-yl)methyl)-1H-indole-3-carboxamide | 9 | N/A | LCMS [M + H]$^+$ m/z: calc'd 521.25; found 521.1. $^1$H NMR (400 MHz, CDCl$_3$) δ 12.52 (br s, 1H), 7.84 (d, J = 6.8 Hz, 1H), 7.45 (d, J = 7.2 Hz, 1H), 7.34-7.28 (m, 1H), 7.08-7.05 (m, 2H), 6.02 (s, 1H), 4.93-4.67 (m, 3H), 4.59-4.57 (m, 4H), 3.69-3.63 (m, 1H), 2.83-2.73 (m, 3H), 2.50 (s, 3H), 2.24 (s, 3H), 2.07 (s, 3H), 1.70-1.60 (m, 9H). |

-continued

| Name and Structure | Ex. # | Isomer Separation Method and Retention Time (if any) | LCMS + HNMR |
|---|---|---|---|
| 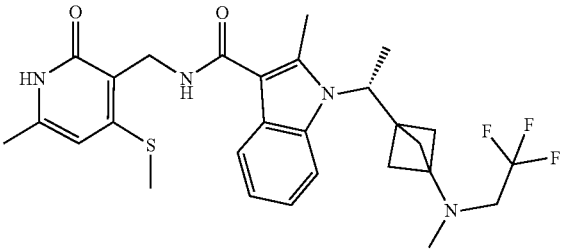 [SMILES: CSc1cc(C)[nH]c(=O)c1CNC(=O)c1c(C)n([C@H](C)C23CC(N(C)CC(F)(F)F)(C2)C3)c2ccccc12]<br>(R)-2-methyl-1-(1-(3-(methyl(2,2,2-trifluoroethyl)amino)bicyclo[1.1.1]pentan-1-yl)ethyl)-N-((6-methyl-4-(methylthio)-2-oxo-1,2-dihydropyridin-3-yl)methyl)-1H-indole-3-carboxamide | 10 | N/A | LCMS [M + H]⁺ m/z: calc'd 547.23; found 547.0. ¹H NMR (400 MHz, CDCl₃) δ 12.46 (br s, 1H), 7.83 (d, J = 8 Hz, 1H), 7.45 (d, J = 8 Hz, 1H), 7.33 (s, 1H), 7.30-7.03 (m, 2H), 6.0 (s, 1H), 4.75-4.68 (m, 3H), 2.94-2.82 (m, 2H), 2.72 (s, 3H), 2.48 (s, 3H), 2.34 (s, 3H), 2.21 (s, 3H), 1.72-1.60 (m, 9H). |
| 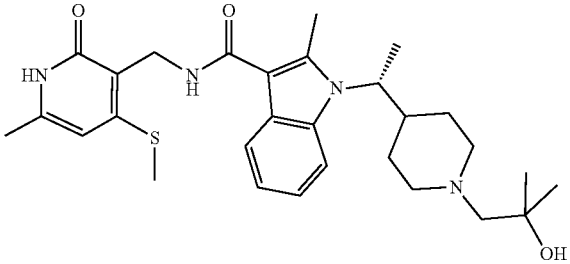 [SMILES: CSc1cc(C)[nH]c(=O)c1CNC(=O)c1c(C)n([C@H](C)C2CCN(CC(C)(C)O)CC2)c2ccccc12]<br>(R)-1-(1-(1-(2-hydroxy-2-methylpropyl)piperidin-4-yl)ethyl)-2-methyl-N-((6-methyl-4-(methylthio)-2-oxo-1,2-dihydropyridin-3-yl)methyl)-1H-indole-3-carboxamide | 11 | N/A | LCMS [M + H]⁺ m/z: calc'd 524.28, found 525.1. ¹H NMR (400 MHz, CDCl₃) δ 11.99 (s, 1H), 7.86-7.84 (d, J = 7.6 Hz, 1H), 7.46-7.44 (d, J = 7.6 Hz, 1H), 7.30 (s, 1H), 7.09-7.04 (m, 2H), 6.00 (s, 1H), 4.75-4.70 (m, 2H), 4.14-4.11 (m, 1H), 3.02-2.99 (m, 1H), 2.74 (s, 3H), 2.70-2.67 (m, 1H), 2.46 (s, 3H), 2.38-2.30 (m, 1H), 2.26-2.25 (m, 2H), 2.22 (s, 3H), 2.17 (m, 1H), 2.10-2.08 (m, 1H), 1.96-1.92 (m, 1H), 1.65 (s, 3H), 1.42-1.39 (m, 1H), 1.13 (s, 3H), 1.11 (s, 3H), 0.93-0.89 (m, 1H). |
| 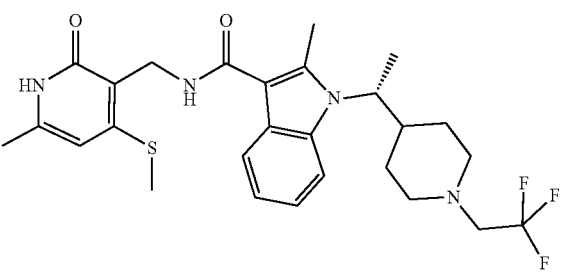 [SMILES: CSc1cc(C)[nH]c(=O)c1CNC(=O)c1c(C)n([C@H](C)C2CCN(CC(F)(F)F)CC2)c2ccccc12]<br>(R)-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide | 12 | N/A | LCMS [M + H]⁺ m/z: calc'd 535.23; found 535.1. ¹H NMR (400 MHz, CD₃OD) δ 7.77 (d, J = 7.2 Hz, 1H), 7.69 (d, J = 8.0 Hz, 1H), 7.23-7.16 (m, 2H), 7.12 (s, 1H), 4.66 (s, 2H), 4.39-4.23 (m, 3H), 3.81-3.78 (m, 1H), 3.51-3.38 (m, 1H), 3.31-3.30 (m, 5H), 2.75 (s, 3H), 2.70 (s, 3H), 2.56 (s, 3H), 2.37-2.33 (m, 1H), 1.90-1.87 (m, 1H, 1.69-1.58 (m, 4H), 1.12-1.09 (m, 1H). |

| Name and Structure | Ex. # | Isomer Separation Method and Retention Time (if any) | LCMS + HNMR |
|---|---|---|---|
| 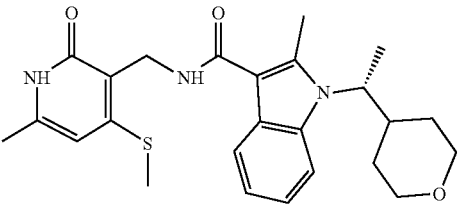 [SMILES: CSc1cc(C)[nH]c(=O)c1CNC(=O)c1c(C)n([C@H](C)C2CCOCC2)c2ccccc12]<br>(R)-2-methyl-N-((6-methyl-4-(methylthio)-2-oxo-1,2-dihydropyridin-3-yl)methyl)-1-(1-(tetrahydro-2H-pyran-4-yl)ethyl)-1H-indole-3-carboxamide | 13 | N/A | LCMS [M + H]⁺ m/z: calc'd 454.21; found 454.0. ¹H NMR (400 MHz, CDCl₃) δ 7.83 (d, J = 7.6 Hz, 1H), 7.46 (d, J = 8.4 Hz, 1H), 7.33-7.01 (m, 3H), 6.00 (s, 1H), 4.76-4.67 (m, 2H), 4.11-4.04 (m ,2H), 3.77-3.74 (m, 1H), 3.44-3.41 (m, 1H), 2.86-2.72 (m, 3H), 2.48-2.42 (m, 4H), 2.20 (s, 3H), 1.90-1.87 (m, 1H), 1.60 (d, J = 6.8 Hz, 3H), 1.44-1.43 (m, 1H), 1.13-1.09 (m, 1H), 0.85-0.82 (m, 1H). |
| 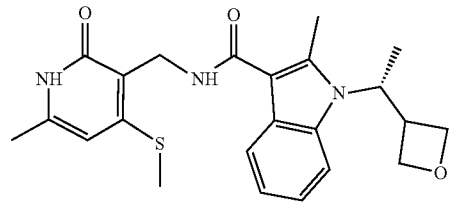 [SMILES: CSc1cc(C)[nH]c(=O)c1CNC(=O)c1c(C)n([C@H](C)C2COC2)c2ccccc12]<br>(R)-2-methyl-N-((6-methyl-4-(methylthio)-2-oxo-1,2-dihydropyridin-3-yl)methyl)-1-(1-(oxetan-3-yl)ethyl)-1H-indole-3-carboxamide | 14<br>Isomer 1 | Chiralpak AD-3 100 × 4.6 mm I.D., 3 um. Mobile phase: A: CO₂ B: ethanol (0.05% diethylamine). Gradient: from 5% to 40% of B in 4.5 min and hold 40% for 2.5 min, then 5% of B for 1 min. Flow rate: 2.8 mL/min Column temperature: 40° C. Retention time = 6.53 min | LCMS [M + H]⁺ m/z: calc'd 426.18; found 426.0. ¹H NMR (400 MHz, CDCl₃) δ 13.14 (br s, 1H), 7.82 (br d, J = 7.8 Hz, 1H), 7.34 (br s, 2H), 7.13-6.98 (m, 2H), 6.00 (s, 1H), 4.94 (t, J = 6.9 Hz, 2H), 4.79-4.64 (m, 2H), 4.49 (br t, J = 5.9 Hz, 2H), 4.09 (t, J = 6.1 Hz, 1H), 3.93 (br s, 1H), 2.85 (br s, 3H), 2.48 (s, 3H), 2.19 (s, 3H), 1.51 (br d, J = 6.5 Hz, 3H). |
| 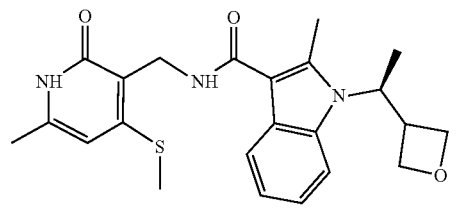 [SMILES: CSc1cc(C)[nH]c(=O)c1CNC(=O)c1c(C)n([C@@H](C)C2COC2)c2ccccc12]<br>(S)-2-methyl-N-((6-methyl-4-(methylthio)-2-oxo-1,2-dihydropyridin-3-yl)methyl)-1-(1-(oxetan-3-yl)ethyl)-1H-indole-3-carboxamide | 14<br>Isomer 2 | Chiralpak AD-3 100 × 4.6 mm I.D., 3 um. Mobile phase: A: CO₂ B: ethanol (0.05% diethylamine). Gradient: from 5% to 40% of B in 4.5 min and hold 40% for 2.5 min, then 5% of B for 1 min. Flow rate: 2.8 mL/min Column temperature: 40° C. Retention time = 5.97 min | LCMS [M + H]⁺ m/z: calc'd 426.18; found 426.0. ¹H NMR (400 MHz, CDCl₃) δ 12.79 (br s, 1H), 7.82 (br d, J = 7.8 Hz, 1H), 7.35 (br d, J = 8.3 Hz, 2H), 7.16-6.99 (m, 2H), 6.00 (s, 1H), 4.94 (dd, J = 6.5, 7.3 Hz, 2H), 4.82-4.64 (m, 2H), 4.49 (br t, J = 5.9 Hz, 2H), 4.10-4.05 (m, 1H), 3.94 (br s, 1H), 2.86 (br s, 3H), 2.48 (s, 3H), 2.20 (s, 3H), 1.54-1.43 (m, 3H). |
| 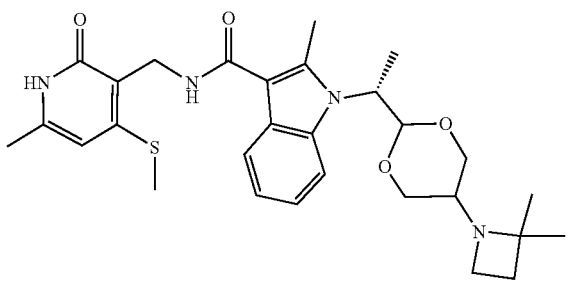<br>(R)-1-(1-(5-(2,2-dimethylazetidin-1-yl)-1,3-dioxan-2-yl)ethyl)-2- | 15<br>Isomer 1<br>(2ⁿᵈ eluting isomer) | column: Waters Xbridge 150 * 25 5 u; mobile phase: [water (0.05% ammonia hydroxide v/v)-ACN]; B%: 45%-70%, 8 min, Column Temp: 30° C. | LCMS [M + H]⁺ m/z: calc'd 539.26; found 539.1. ¹H NMR (400 MHz, CD₃OD) δ 7.69 (d, J = 7.5 Hz, 1H), 7.58 (br s, 1H), 7.14-7.02 (m, 2H), 6.30 (s, 1H), 5.07-5.01 (m, 1H), 4.60 (br s, 3H), 4.10 (br d, J = 10.8 Hz, 1H), 3.88 (br d, J = 9.5 Hz, 1H), 3.43 (t, J = 10.5 Hz, 1H), 3.15 (br d, J = 12.5 Hz, 1H), 3.07 (t, J = 7.2 Hz, 2H), 2.86 (tt, J = 4.9, 10.0 Hz, 1H), |

| Name and Structure | Ex. # | Isomer Separation Method and Retention Time (if any) | LCMS + HNMR |
|---|---|---|---|
| methyl-N-((6-methyl-4-(methylthio)-2-oxo-1,2-dihydropyridin-3-yl)methyl)-1H-indole-3-carboxamide | | | 2.61 (br s, 3H), 2.54 (s, 3H), 2.31 (s, 3H), 1.83 (t, J = 7.0 Hz, 2H), 1.63 (d, J = 7.3 Hz, 3H), 1.23 (s, 3H), 1.22 (s, 3H) |
| 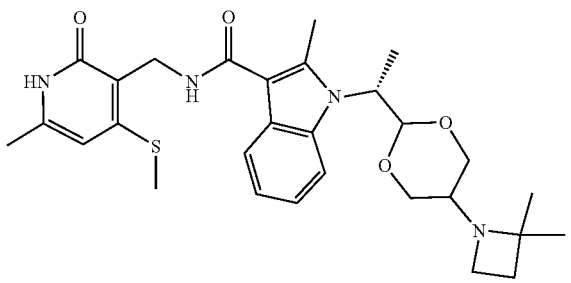<br>(R)-1-(1-(5-(2,2-dimethylazetidin-1-yl)-1,3-dioxan-2-yl)ethyl)-2-methyl-N-((6-methyl-4-(methylthio)-2-oxo-1,2-dihydropyridin-3-yl)methyl)-1H-indole-3-carboxamide | 15 Isomer 2 (1st eluting isomer) | column: Waters Xbridge 150 * 25 5u; mobile phase: [water (0.05% ammonia hydroxide v/v)-ACN]; B%: 45%-70%, 8 min, Column Temp: 30° C. | LCMS [M + H]+ m/z: calc'd 539.26; found 539.1. $^1$H NMR (400 MHz, CD$_3$OD) δ 7.71 (br d, J = 7.3 Hz, 1H), 7.55 (d, J = 8.0 Hz, 1H), 7.16-7.01 (m, 2H), 6.31 (s, 1H), 5.21 (br d, J = 6.8 Hz, 1H), 4.61 (s, 3H), 4.05-3.97 (m, 1H), 3.96-3.88 (m, 1H), 3.74 (br d, J = 12.3 Hz, 1H), 3.60-3.49 (m, 1H), 3.31-3.30 (m, 1H), 3.26-3.13 (m, 2H), 2.67 (s, 3H), 2.54 (s, 3H), 2.31 (s, 3H), 1.91 (br s, 2H), 1.63 (br d, J = 7.0 Hz, 3H), 1.31 (s, 3H), 1.28 (s, 3H) |
| 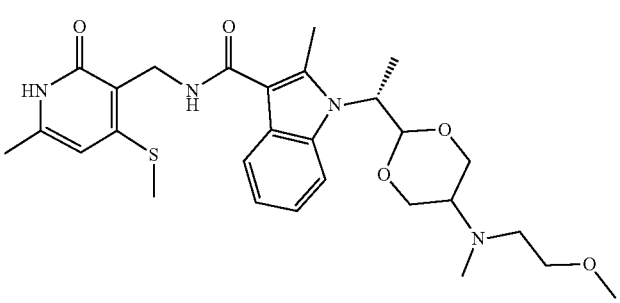<br>(R)-1-(1-(5-((2-methoxyethyl)(methyl)amino-1,3-dioxan-2-yl)ethyl)-2-methyl-N-((6-methyl-4-(methylthio)-2-oxo-1,2-dihydropyridin-3-yl)methyl)-1H-indole-3-carboxamide | 16 Isomer 1 | Chiralpak AD-3 100 × 4.6 mm I.D., 3 um. Mobile phase: 40% ethanol (0.05% diethylamine) in CO$_2$. Flow rate: 2.8 mL/min Column temperature: 40° C. Retention time = 2.19 min | LCMS [M + H]+ m/z: calc'd 543.3; found 543.1. $^1$H NMR (400 MHz, CDCl$_3$) δ 7.73 (d, J = 8 Hz, 1H), 7.61 (s, 1H), 7.14-7.06 (m, 2H), 6.30 (s, 1H), 5.02 (d, J = 16 Hz, 1H), 4.62 (s, 3H), 4.31 (d, J = 12 Hz, 1H), 4.09 (d, J = 8 Hz, 1H), 3.72-3.45 (m, 1H), 3.43-3.42 (m, 3H), 3.34-3.31 (m, 3H), 2.78-2.76 (m, 1H), 2.65-2.63 (m, 5H), 2.55 (s, 3H), 2.32-2.28 (m, 6H), 1.66 (d, J = 8 Hz, 3H) |
| 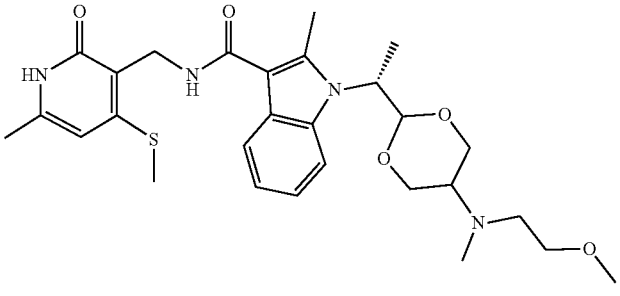<br>(R)-1-(1-(5-((2-methoxyethyl)(methyl)amino- | 16 Isomer 2 | Chiralpak AD-3 100 × 4.6 mm I.D., 3 um. Mobile phase: 40% ethanol (0.05% diethylamine) in CO$_2$. Flow rate: 2.8 mL/min Column temperature: 40° C. Retention time = 1.53 min | LCMS [M + H]+ m/z: calc'd 543.26. found 543.1. $^1$H NMR (400 MHz, CD$_3$OD) δ 7.73 (d, J = 8 Hz, 1H), 7.61 (s, 1H), 7.14-7.06 (m, 2H), 6.31 (s, 1H), 5.03 (d, J = 4 Hz, 1H), 4.63 (s, 3H), 4.31 (d, J = 8 Hz, 1H), 4.09 (d, J = 8 Hz, 1H), 3.72-3.45 (m, 1H), 3.44-3.43 (m, 3H), 3.34-3.32 (m, 3H), 2.80-2.73 (m, 1H), 2.67-2.63 (m, 5H), 2.55 (s, |

-continued

| Name and Structure | Ex. # | Isomer Separation Method and Retention Time (if any) | LCMS + HNMR |
|---|---|---|---|
| 1,3-dioxan-2-yl)ethyl)-2-methyl-N-((6-methyl-4-(methylthio)-2-oxo-1,2-dihydropyridin-3-yl)methyl)-1H-indole-3-carboxamide | | | 3H), 2.32-2.28 (m, 6H), 1.66 (d, J = 8 Hz, 3H). |
| (R)-2-methyl-N-((6-methyl-4-(methylthio)-2-oxo-1,2-dihydropyridin-3-yl)methyl)-1-(1-(5-(methylamino)-1,3-dioxan-2-yl)ethyl)-1H-indole-3-carboxamide | 17 | Chiralpak AD-3 100 × 4.6 mm I.D., 3 um. Mobile phase: A: CO₂ B: ethanol (0.05% diethylamine). Gradient: from 5% to 40% of B in 4.5 min and hold 40% for 2.5 min, then 5% of B for 1 min. Flow rate: 2.8 mL/min Column temperature: 40° C. Retention time = 6.3 min | LCMS [M + H]⁺ m/z: calc'd 485.21: found 485.0. ¹H NMR (400 MHz, CDCl₃) δ 7.81 (d, J = 8.0 Hz, 1H), 7.48 (s, 1H), 7.27 (s, 1H), 7.11-7.02 (m, 2H), 6.00 (s, 1H), 4.90 (s, 1H), 4.72 (d, J = 8.0 Hz, 2H), 4.55 (s, 1H), 4.31-4.28 (m, 1H), 4.10-4.07 (m, 1H), 3.31 (t, J = 8.0 Hz, 1H), 3.09 (m, 1H), 2.85-2.79 (m, 1H), 2.74 (s, 3H), 2.48 (s, 3H), 2.41 (s, 3H), 2.21 (s, 3H), 1.66-1.61 (m, 4H), 1.31-1.26 (m, 1H). |
| 1-((R)-1-(1r,4R)-4-methoxycyclohexyl)ethyl)-2-methyl-N-((6-methyl-4-(methylthio)-2-oxo-1,2-dihydropyridin-3-yl)methyl)-1H-indole-3-carboxamide | 18 Isomer 1 | Column: Chiralpak AD-3 50 × 3 mm I.D., 3 um Column: Chiralpak AD-3 50 × 3 mm I.D., 3 um. Mobile phase: 40% of ethanol (0.05% diethylamine) in CO₂. Flow rate: 2 mL/min Column temperature: 40° C. Retention time = 1.15 min | LCMS [M + H]⁺ m/z: calc'd 482.24; found 482.2. ¹H NMR (400 MHz, CDCl₃) δ 12.77 (br s, 1H), 7.83 (d, J = 8.0 Hz, 1H), 7.46 (d, J = 8.4 Hz, 1H), 7.36 (br s, 1H), 7.11-7.02 (m, 2H), 6.00 (s, 1H), 4.75-4.68 (m, 2H), 4.08-4.03 (m, 1H), 3.31 (s, 3H), 3.06 (s, 1H), 2.85-2.72 (m, 3H), 2.48 (s, 3H), 2.19-2.10 (m, 5H), 1.87-1.84 (m, 1H), 1.59 (d, J = 6.8 Hz, 3H), 1.59-0.76 (m, 6H). |
| 1-((R)-1-((1r,4R)-4-methoxycyclohexyl)ethyl)-2-methyl-N-((6-methyl-4-(methylthio)-2-oxo-1,2-dihydropyridin-3-yl)methyl)-1H-indole-3-carboxamide | 18 Isomer 2 | Column: Chiralpak AD-3 50 × 3 mm I.D., 3 um Column: Chiralpak AD-3 50 × 3 mm I.D., 3 um. Mobile phase: 40% of ethanol (0.05% diethylamine) in CO₂. Gradient from 5% to 40% of B in 2.5 min and hold 40% for 0.35 min, then from 40% to 5% of B for 0.15 min. Flow rate: 2.5 mL/min Column temperature: 40° C. Retention time = 2.41 min | LCMS [M + H]⁺ m/z: calc'd 482.24; found 482.2. ¹H NMR (400 MHz, CDCl₃) δ 12.44 (br s, 1H), 7.84 (d, J = 6.8 Hz, 1H), 7.47 (d, J = 7.2 Hz, 1H), 7.29 (br s, 1H), 7.08-7.03 (m, 2H), 6.00 (s, 1H), 4.76-4.60 (m, 2H), 4.14 (s, 1H), 3.3-3.27 (m, 4H), 2.85-2.73 (m, 3H), 2.48 (s, 3H), 2.21 (s, 3H), 2.03-2.01 (m, 2H), 1.59-1.43 (m, 6H), 1.12-0.80 (m, 4H). |

| Name and Structure | Ex. # | Isomer Separation Method and Retention Time (if any) | LCMS + HNMR |
|---|---|---|---|
| 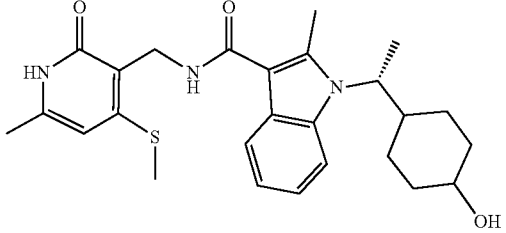 [SMILES: CSc1cc(C)[nH]c(=O)c1CNC(=O)c1c(C)n([C@H](C)C2CCC(O)CC2)c2ccccc12]<br>(R)-1-(1-(4-hydroxycyclohexyl)ethyl)-2-methyl-N-((6-methyl-4-(methlthio)-2-oxo-1,2-dihydropyridin-3-yl)methyl)-1H-indole-3-carboxamide | 19<br>Isomer 1 | Column: Chiralpak AD-3 50 × 3 mm I.D., 3 um Column: Chiralpak AD-3 50 × 3 mm I.D., 3 um. Mobile phase: 40% of ethanol (0.05% diethylamine) in $CO_2$. Flow rate: 2 mL/min Column temperature: 40° C. Retention time = 2.1 min | LCMS [M + H]$^+$ m/z: calc'd 468.22: found 468.0. $^1$H NMR (400 MHz, CDCl$_3$) δ 12.90 (s, 1H), 7.82 (d, J = 8.0, 1H), 7.46-7.44 (m, 1H), 7.36-7.35 (m, 1H), 7.10-7.00 (m, 2H), 6.00 (s, 1H), 4.84-4.60 (m, 2H), 4.03-4.00 (m, 1H), 3.48 (s, 1H), 2.83-2.69 (m, 3H), 2.48 (s, 3H), 2.19 (s, 3H), 2.08-2.03 (m, 2H), 1.60-1.58 (m, 3H), 1.32-1.27 (m, 3H), 1.10-1.07 (m, 1H), 1.00-0.97 (m, 2H), 0.77-0.73 (m, 1H). |
| 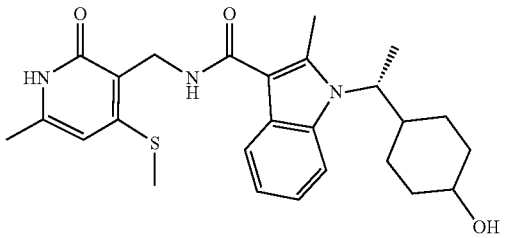 [SMILES: CSc1cc(C)[nH]c(=O)c1CNC(=O)c1c(C)n([C@H](C)C2CCC(O)CC2)c2ccccc12]<br>(R)-1-(1-(4-hydroxycyclohexyl)ethyl)-2-methyl-N-((6-methyl-4-(methylthio)-2-oxo-1,2-dihydropyridin-3-yl)methyl)-1H-indole-3-carboxamide | 19<br>Isomer 2 | Column: Chiralpak AD-3 50 × 3 mm I.D., 3 um. Mobile phase: 40% of ethanol (0.05% diethylamine) in $CO_2$. Flow rate: 2 mL/min. Column temperature: 40° C. Retention time = 0.99 min | LCMS [M + H]$^+$ m/z: calc'd 468.22: found 468.0. $^1$H NMR (400 MHz, CDCl$_3$) δ 13.00 (s, 1H), 7.83 (d, J = 8.0, 1H), 7.46 (d, J = 8.0, 1H), 7.31 (s, 1H), 7.10-7.00 (m, 2H), 6.00 (s, 1H), 4.78-4.67 (m, 2H), 4.17-4.13 (m, 1H), 4.00 (s, 1H), 2.84-2.72 (m, 3H), 2.48 (s, 3H), 2.24-2.20 (m, 4H), 1.85-1.80 (m, 2H), 1.62-1.53 (m, 6H), 1.29-1.20 (m, 3H), 0.83-0.80 (m, 1H). |
| 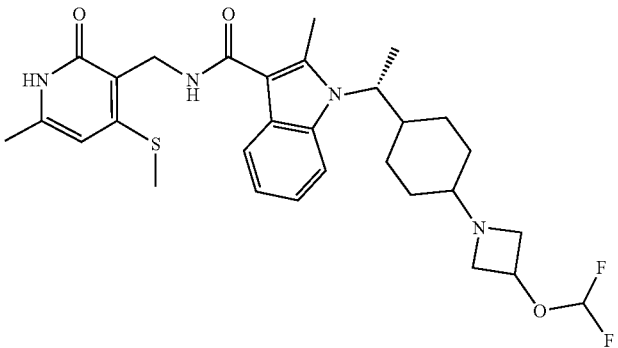 [SMILES: CSc1cc(C)[nH]c(=O)c1CNC(=O)c1c(C)n([C@H](C)C2CCC(N3CC(OC(F)F)C3)CC2)c2ccccc12]<br>(R)-1-(1-(4-(3-(difluoromethoxy)azetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 20<br>Isomer 1<br>(From B22 isomer 1) | Column: Chiralcel OD-3 100 × 4.6 mm I.D., 3 um. Mobile phase: A: $CO_2$ B: ethanol (0.05% diethylamine) Gradient: from 5% to 40% of B in 4.5 min and hold 40% for 2.5 min, then 5% of B for 1 min. Flow rate: 2.8 mL/min. Column temperature: 40° C. Retention time: 4.7 min | LCMS [M + H]$^+$ m/z: calc'd 573.26; found 573.1. $^1$H NMR (400 MHz, CDCl$_3$) δ 12.72 (br s, 1H), 7.82 (d, J = 7.6 Hz, 1H), 7.44 (d, J = 8.0 Hz, 1H), 7.35-7.34 (m, 1H), 7.10-7.02 (m, 2H), 6.16 (t, J = 73.6 Hz, 1H), 6.00 (s, 1H), 4.76-4.70 (m, 3H), 4.05-4.03 (m, 1H), 3.67-3.57 (m, 2H), 3.04-2.97 (m, 2H), 2.72 (s, 3H), 2.48 (s, 3H), 2.19-1.88 (m, 7H), 1.59 (d, J = 7.2 Hz, 3H), 1.08-0.74 (m, 5H). |

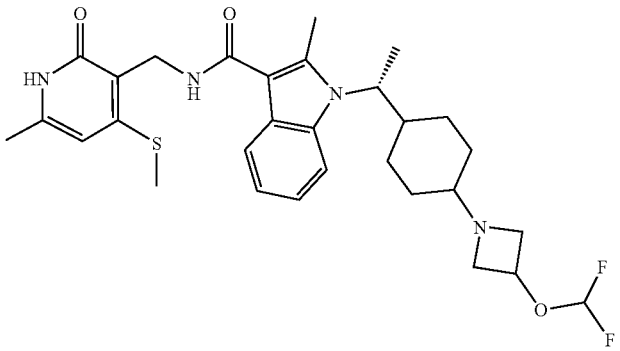 [SMILES: CSc1cc(C)[nH]c(=O)c1CNC(=O)c1c(C)n([C@H](C)C2CCC(N3CC(OC(F)F)C3)CC2)c2ccccc12]

-continued

| Name and Structure | Ex. # | Isomer Separation Method and Retention Time (if any) | LCMS + HNMR |
|---|---|---|---|
| (R)-1-(1-(4-(3-(difluoromethoxy)azetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 20 Isomer 2 (From B22 isomer 2) | Column: Chiralcel OD-3 100 × 4.6 mm I.D., 3 um Mobile phase: A: $CO_2$ B: ethanol (0.05% diethylamine) Gradient: from 5% to 40% of B in 4.5 min and hold 40% for 2.5 min, then 5% of B for 1 min. Flow rate: 2.8 mL/min Column temperature: 40° C. Retention time: 4.4 min | LCMS [M + H]$^+$ m/z: calcd 573.26; found 573.1. $^1$H NMR (400 MHz, CDCl$_3$) δ 12.28 (brs, 1H), 7.83 (d, J = 7.6 Hz, 1H), 7.45 (d, J = 8.0 Hz, 1H), 7.28-7.01 (m, 3H), 6.35-5.98 (m, 2H), 4.78-4.66 (m, 3H), 4.19 (br s, 1H), 3.63-3.54 (m, 2H), 2.92-2.74 (m, 5H), 2.48 (s, 3H), 2.25-2.21 (m, 4H), 1.58-0.74 (m, 11H). |
| (R)-1-(1-(4-(3-(trifluoromethoxy)azetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 21 Isomer 1 (From B23 isomer 1) | N/A | LCMS [M + H]$^+$ calc'd. 591.2; found 591.1 $^1$H NMR (400 MHz, CDCl$_3$) δ 7.82 (br d, J = 7.5 Hz, 1H), 7.44 (br d, J = 8.0 Hz, 1H), 7.36-7.30 (m, 1H), 7.14-7.00 (m, 2H), 6.00 (s, 1H), 4.80-4.65 (m, 3H), 4.20-3.94 (m, 1H), 3.71-3.55 (m, 2H), 3.05 (td, J = 7.0, 13.7 Hz, 2H), 2.71 (s, 3H), 2.48 (s, 3H), 2.19 (s, 3H), 2.07 (br s, 2H), 1.99-1.86 (m, 2H), 1.82-1.76 (m, 1H), 1.58 (br d, J = 7.0 Hz, 3H), 1.55-1.44 (m, 1H), 1.15-0.96 (m, 3H), 0.75 (br t, J = 9.3 Hz, 2H). |
| (R)-1-(1-(4-(3-(trifluoromethoxy)azetidin-1-yl)cyclohexyl)ethyl)-2-methyl-N-((6-methyl-4- | 21 Isomer 2 (From B23 isomer 2) | N/A | LCMS [M + H]$^+$ calc'd. 591.2; found 591.1. $^1$H NMR (400 MHz, CDCl$_3$) δ 7.82 (br d, J = 7.5 Hz, 1H), 7.44 (br d, J = 8.0 Hz, 1H), 7.29 (br s, 1H), 7.16-6.99 (m, 2H), 5.99 (s, 1H), 4.86-4.58 (m, 3H), 4.16 (br s, 1H), 3.64 (br s, 1H), 3.60-3.46 (m, 1H), 3.12-2.88 (m, 2H), 2.86-2.63 (m, 3H), 2.48 (s, 3H), 2.27 (br s, 1H), 2.23-2.15 (m, 3H), 1.76-1.64 (m, 4H), 1.56 (br d, J = 7.0 Hz, 3H), 1.51-1.25 (m, 3H), 1.24-0.98 (m, 2H), 0.72 (br s, 1H). |

| Name and Structure | Ex. # | Isomer Separation Method and Retention Time (if any) | LCMS + HNMR |
|---|---|---|---|
| (methylthio)-2-oxo-1,2-dihydropyridin-3-yl)methyl)-1H-indole-3-carboxamide 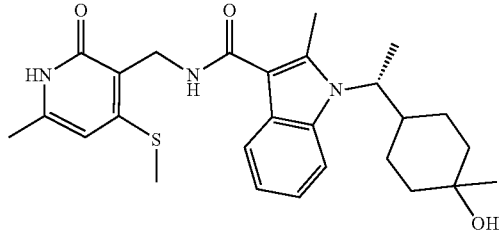<br>(R)-1-(1-(4-hydroxy-4-methylcyclohexyl)ethyl)-2-methyl-N-((6-methyl-4-(methylthio)-2-oxo-1,2-dihydropyridin-3-yl)methyl)-1H-indole-3-carboxamide | 22 Isomer 1 (2$^{nd}$ eluting isomer) | column: Waters X bridge 150 * 25 5u; mobile phase: [water (0.05% ammonia hydroxide v/v)-ACN]; B%: 32%-57%, 7.8 min. Temp: 30° C. | LCMS [M + H]$^+$ m/z: calc'd: 482.24; found 482.1. $^1$H NMR (400 MHz, CD$_3$OD) δ 7.72 (br d, J = 7.6 Hz, 1H), 7.56 (br d, J = 7.6 Hz, 1H), 7.16-6.99 (m, 2H), 6.30 (s, 1H), 4.61 (s, 2H), 4.25-4.07 (m, 1H), 2.62 (s, 2H), 2.53 (s, 3H), 2.30 (s, 3H), 2.21 (br d, J = 11.2 Hz, 1H), 1.91-1.82 (m, 1H), 1.74 (br d, J = 10.4 Hz, 1H), 1.62 (br d, J = 6.8 Hz, 3H), 1.54-1.39 (m, 3H), 1.34-1.25 (m, 1H), 1.24-1.17 (m, 1H), 1.14 (s, 3H), 1.11-1.05 (m, 1H), 0.70 (br d, J = 12.0 Hz, 1H) |
| 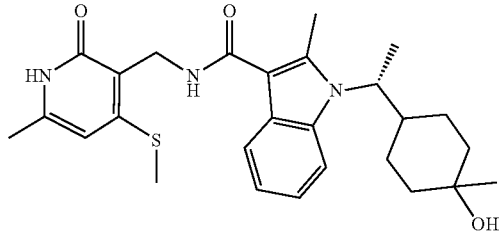<br>(R)-1-(1-(4-hydroxy-4-methylcyclohexyl)ethyl)-2-methyl-N-((6-methyl-4-(methylthio)-2-oxo-1,2-dihydropyridin-3-yl)methyl)-1H-indole-3-carboxamide | 22 Isomer 2 (1$^{st}$ eluting isomer) | column: Waters X bridge 150 * 25 5u; mobile phase: [water (0.05% ammonia hydroxide v/v)-ACN]; B%: 32%-57%, 7.8 min. Temp: 30° C. | LCMS [M + H]$^+$ m/z: calc'd 482.24; found 482.1. $^1$H NMR (400 MHz, CD$_3$OD) δ 7.72 (br d, J = 7.6 Hz, 1H), 7.56 (br d, J = 7.6 Hz, 1H), 7.17-7.02 (m, 2H), 6.30 (s, 1H), 4.61 (s, 2H), 4.27-4.14 (m, 1H), 2.61 (s, 2H), 2.53 (s, 3H), 2.30 (s, 4H), 2.04 (br d, J = 10.8 Hz, 1H), 1.76 (br d, J = 10.8 Hz, 1H), 1.61 (br d, J = 6.8 Hz, 3H), 1.58-1.49 (m, 1H), 1.45 (br d, J = 11.2 Hz, 1H), 1.28 (br d, J = 12.0 Hz, 2H), 1.20 (s, 4H), 1.00-0.87 (m, 2H) |
| 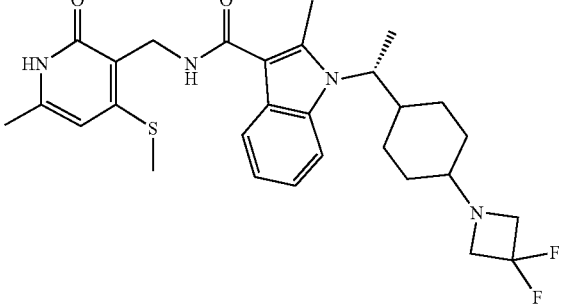<br>(R)-1-(1-(4-(3,3-difluoroazetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 23 Isomer 1 (From B25 isomer 1) | Column: Chiralpak AS-3 100 × 4.6 mm I.D., 3 um. Mobile phase: A: CO$_2$ B: ethanol (0.05% diethylamine). Gradient: from 5% to 40% of B in 4.5 min and hold 40% for 2.5 min, then 5% of B for 1 min. Flow rate: 2.8 mL/min Column temperature 40° C. Retention time = 3.61 min | LCMS [M + H]$^+$ m/z: calc'd 543.25: found 543.1. $^1$H NMR (400 MHz, CDCl$_3$) δ 12.13 (s, 1H), 7.83 (d, J = 8.0 Hz, 1H), 7.44 (d, J = 8.0 Hz, 1H), 7.32 (s, 1H), 7.11-7.04 (m, 2H), 6.00 (s, 1H), 4.77-4.71 (m, 2H), 4.08-4.06 (m, 1H), 3.51 (t, J = 12.0 Hz, 4H), 2.83-2.71 (m, 3H), 2.49 (s, 3H), 2.16-2.11 (m, 4H), 2.08 (m, 1H), 2.00 (s, 1H), 1.86 (m, 3H), 1.27 (m, 1H), 1.17-1.05 (m, 3H), 0.83-0.74 (m, 2H). |

-continued

| Name and Structure | Ex. # | Isomer Separation Method and Retention Time (if any) | LCMS + HNMR |
|---|---|---|---|
| 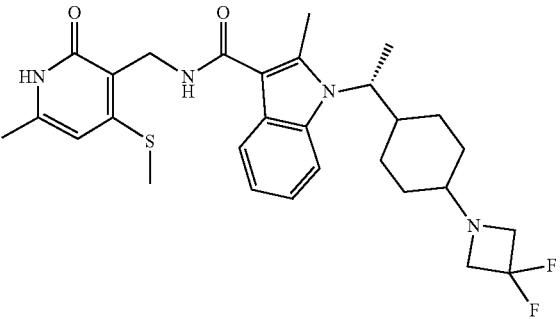 [SMILES: CSc1cc(C)[nH]c(=O)c1CNC(=O)c1c(C)n([C@H](C)C2CCC(N3CC(F)(F)C3)CC2)c2ccccc12]<br>(R)-1-(1-(4-(3,3-difluoroazetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 23 Isomer 2 (From B25 isomer 2) | Column: Chiralpak AD-3 150 × 4.6 mm I.D., 3 um. Mobile phase: A: $CO_2$ B: ethanol (0.05% diethylamine). Gradient: from 5% to 40% of B in 5.5 min and hold 40% for 3.0 min, then 5% of B for 1.5 min. Flow rate: 2.5 mL/min. Column temperature: 40° C. Retention time = 6.16 min | LCMS [M + H]$^+$ m/z: calcd 543.25; found 543.1. $^1$H NMR (400 MHz, CDCl$_3$) δ 12.68 (s, 1H), 7.85 (d, J = 8.0 Hz, 1H), 7.47 (d, J = 7.6 Hz, 1H), 7.31 (s, 1H), 7.11-7.04 (m, 2H), 6.02 (s, 1H), 4.81-4.71 (m, 1H), 3.49-3.43 (m, 4H), 2.85-2.76 (m, 3H), 2.50 (s, 3H), 2.34 (s, 1H), 2.23 (s, 4H), 1.73 (s, 1H), 1.60-1.37 (m, 7H), 1.18-1.16 (m, 2H), 0.75 (s, 1H). |
| 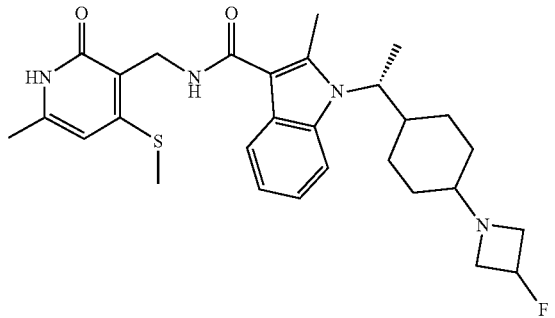 [SMILES: CSc1cc(C)[nH]c(=O)c1CNC(=O)c1c(C)n([C@H](C)C2CCC(N3CC(F)C3)CC2)c2ccccc12]<br>(R)-1-(1-(4-(3-fluoroazetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 24 Isomer 1 (From B26 Isomer 2) | Column: Chiralpak AS-3 100 × 4.6 mm I.D., 3 um. Mobile phase: A: $CO_2$ B: ethanol (0.05% diethylamine). Gradient: from 5% to 40% of B in 4.5 min and hold 40% for 2.5 min, then 5% of B for 1 min. Flow rate: 2.8 mL/min. Column temperature: 40° C. Retention time = 3.54 min | LCMS [M + H]$^+$ m/z: calc'd 524.3; found 525.1. $^1$H NMR (400 MHz, CDCl$_3$) δ 12.73-12.64 (m, 1H), 7.81 (d, J = 7.6 Hz, 1H), 7.45-7.26 (m, 1H), 7.08-7.01 (m, 2H), 6.00 (s, 1H), 5.16-5.01 (m, 1H), 4.74-4.70 (m, 2H), 4.05-4.04 (m, 1H), 3.66-3.61 (m, 2H), 3.11-3.06 (m, 2H), 3.05-2.71 (m, 3H), 2.48 (s, 3H), 2.18 (s, 3H), 2.09-2.07 (m, 1H), 1.90-1.87 (m, 2H), 1.59-1.57 (m, 4H), 1.08-1.04 (m, 3H), 0.78-0.73 (m, 2H). |
| 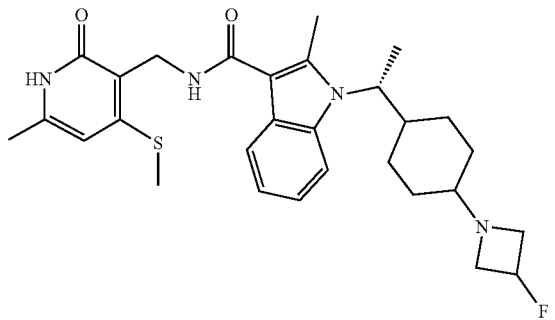 [SMILES: CSc1cc(C)[nH]c(=O)c1CNC(=O)c1c(C)n([C@H](C)C2CCC(N3CC(F)C3)CC2)c2ccccc12]<br>(R)-1-(1-(4-(3-fluoroazetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 24 Isomer 2 (From B26 Isomer 1) | Chiralcel OD-3 100 × 4.6 mm I.D., 3 um. Mobile phase: A: $CO_2$ B: ethanol (0.05% diethylamine). Gradient: from 5% to 40% of B in 4.5 min and hold 40% for 2.5 min, then 5% of B for 1 min. Flow rate: 2.8 mL/min Column temperature: 40° C. Retention time = 4.62 min | LCMS [M + H]$^+$ m/z: calc'd 525.26; found 525.1. $^1$H NMR (400 MHz, CDCl$_3$) δ 12.44 (s, 1H), 7.82 (d, J = 7.6 Hz, 1H), 7.31-7.28 (m, 1H), 7.08-7.01 (m, 2H), 5.99 (s, 1H), 5.16-5.01 (m, 1H), 4.75-4.68 (m, 2H), 4.17-4.15 (m, 1H), 3.62-3.52 (m, 2H), 3.00-2.95 (m, 2H), 2.81-2.71 (m, 3H), 2.47 (s, 3H), 2.26-2.20 (m, 5H), 1.66-1.55 (m, 4H), 1.38-1.35 (m, 4H), 1.12-1.06 (m, 2H), 0.72-0.70 (m, 1H). |

| Name and Structure | Ex. # | Isomer Separation Method and Retention Time (if any) | LCMS + HNMR |
|---|---|---|---|
| 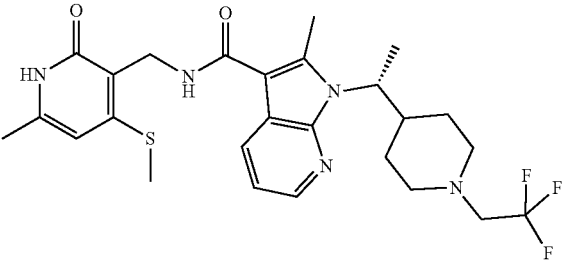 [SMILES: CSc1cc(C)[nH]c(=O)c1CNC(=O)c1c(C)n([C@H](C)C2CCN(CC(F)(F)F)CC2)c2ncccc12]<br>(R)-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-pyrrolo[2,3-b]pyridine-3-carboxamide | 25 | N/A | LCMS [M + H]+ m/z: calc'd 536.22; found 536.1. 1H NMR (400 MHz, CD3OD) δ 8.20 (d, J = 4.0 Hz, 1H), 8.10 (d, J = 8.0 Hz, 1H), 7.14-7.11 (m, 1H), 6.32 (s, 1H), 4.62 (s, 3H), 4.18-4.13 (m, 1H), 3.11-3.06 (m, 1H), 3.05-2.97 (m, 2H), 2.81-2.78 (m, 1H), 2.69 (br s, 3H), 2.56 (s, 3H), 2.43-2.38 (m, 1H), 2.33 (s, 3H), 2.14-2.10 (m, 1H), 2.04-2.00 (m, 1H), 1.68 (br s, 3H), 1.50-1.44 (m, 1H), 1.19-1.15 (m, 1H), 0.88-0.85 (m, 1H). |
| 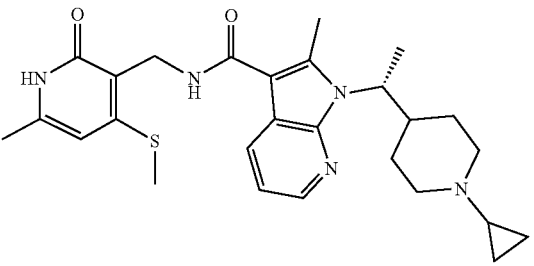 [SMILES: CSc1cc(C)[nH]c(=O)c1CNC(=O)c1c(C)n([C@H](C)C2CCN(C3CC3)CC2)c2ncccc12]<br>(R)-1-(1-(1-cyclopropylpiperidin-4-yl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 26 | N/A | LCMS [M + H]+ m/z: calcd 494.25; found 494.4. 1H NMR (400 MHz, CD3OD) δ 8.20 (dd, J = 5.2, 1.2 Hz, 1H), 8.10 (dd, J = 8.0, 1.2 Hz, 1H), 7.14-7.11 (m, 1H), 6.32 (s, 1H), 4.62 (s, 2H), 4.17-4.11 (m, 1H), 3.18-3.15 (m, 1H), 2.88-2.85 (m, 2H), 2.68 (br s, 3H), 2.58 (s, 3H), 2.33 (s, 3H), 2.29-2.26 (m, 1H), 2.06-1.99 (m, 2H), 1.69 (br s, 3H), 1.64-1.59 (m, 1H), 1.41-1.31 (m, 1H), 1.14-1.03 (m, 1H), 0.91-0.87 (m, 1H), 0.52-0.36 (m, 4H). |

N/A = not applicable

Synthesis of (R)-1-(1-(4-(3-(difluoromethoxy)azetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide (Example 27, Isomer 1)

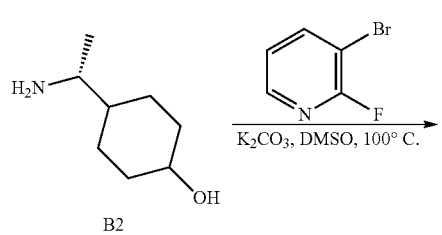

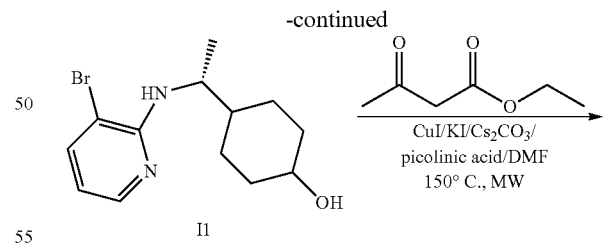

-continued

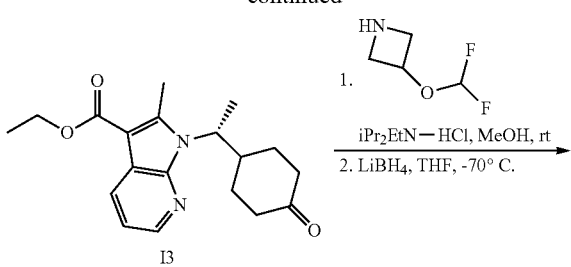

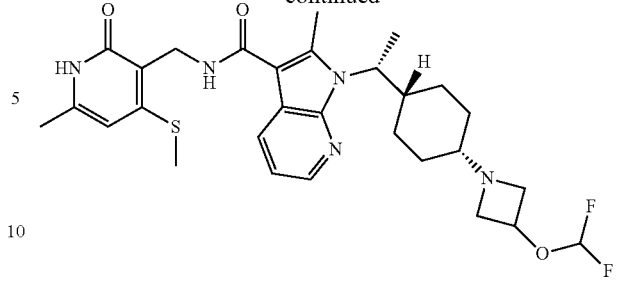

Example 27

Step 1: Synthesis of 4-[(1R)-1-[(3-bromo-2-pyridyl)amino]ethyl]cyclohexanol

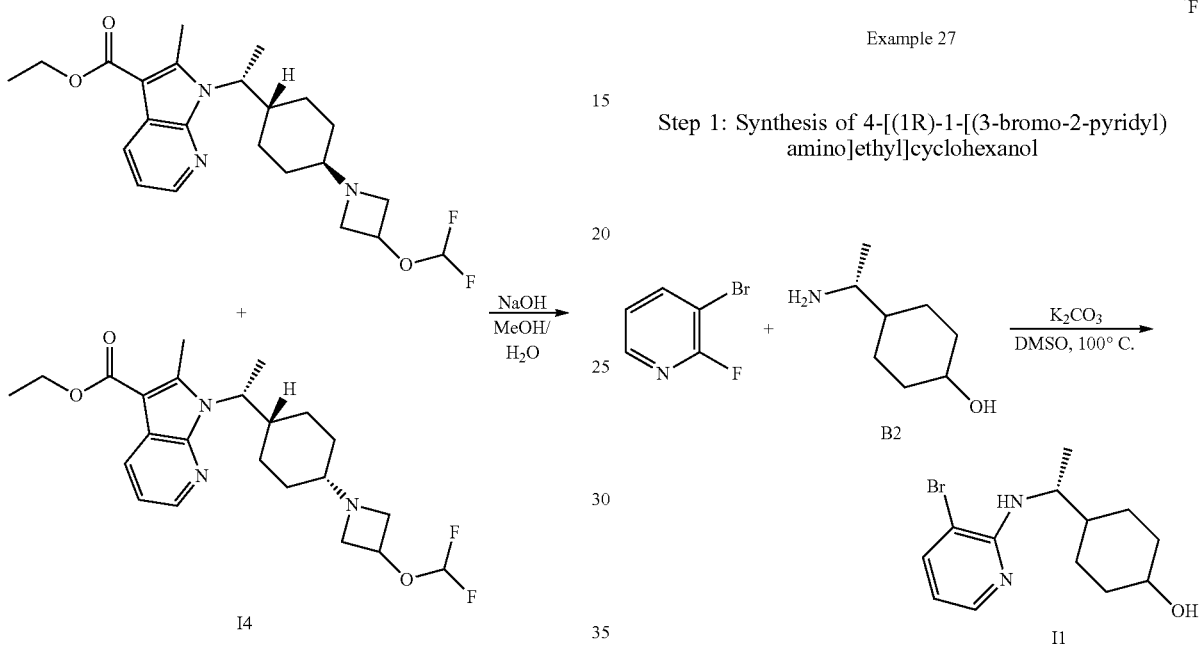

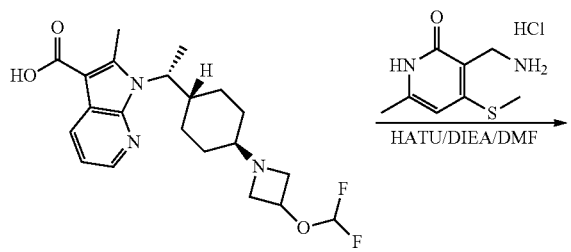

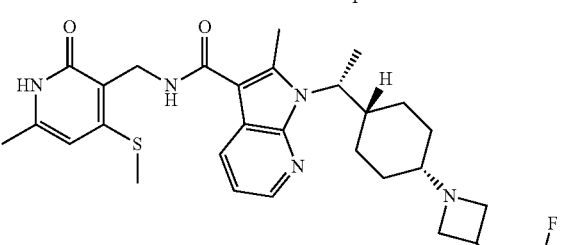

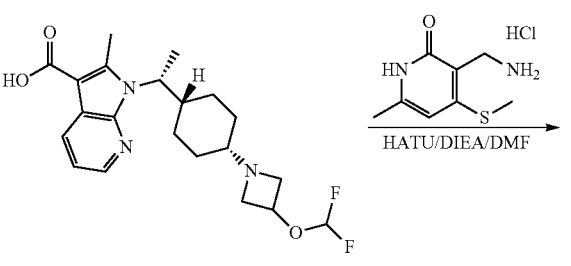

To a mixture of 3-bromo-2-fluoro-pyridine (8.0 g, 45 mmol, 1.0 equiv) and 4-[(1R)-1-aminoethyl]cyclohexanol (18.5 g, 129 mmol, 2.84 equiv) in DMSO (150 mL) was added potassium carbonate (12.6 g, 90.9 mmol, 2 equiv). The reaction was stirred at 100° C. for 17 hours (two batches were run in parallel). After combining the batches, the reaction was quenched with water (150 mL) and the desired product was extracted with ethyl acetate (50 mL×3). The combined organic layers were washed with brine (70 mL×3), dried over sodium sulfate, filtered and concentrated to dryness under reduced pressure. The residue was purified by flash chromatography (SiO₂, petroleum ether/ethyl acetate, 50:1 to 1:1). The title compound, 4-[(1R)-1-[(3-bromo-2-pyridyl)amino]ethyl]cyclohexanol (6.7 g, 16 mmol, 18% yield, 73% purity), was obtained as a yellow oil. LCMS [M+H]⁺ m/z: calc'd 299.07; found 299.2.

Step 2: Synthesis of ethyl 1-[(1R)-1-(4-hydroxycyclohexyl)ethyl]-2-methyl-pyrrolo[2,3-b]pyridine-3-carboxylate (I2)

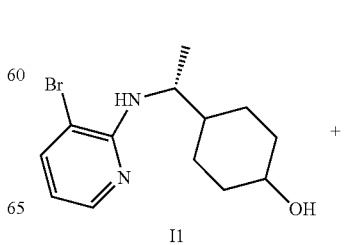

117
-continued

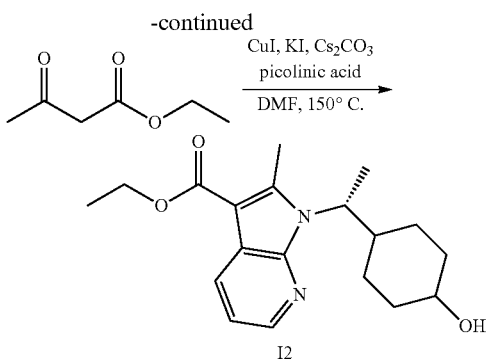

4-[(1R)-1-[(3-bromo-2-pyridyl)amino]ethyl]cyclohexanol (1.0 g, 3.3 mmol, 1 equiv), ethyl 3-oxobutanoate (2.27 g, 17.4 mmol, 2.20 mL, 5.21 equiv), pyridine-2-carboxylic acid (204 mg, 1.66 mmol, 0.5 equiv), potassium iodide (832 mg, 5.01 mmol, 1.5 equiv), cesium carbonate (2.18 g, 6.68 mmol, 2 equiv), copper(I) iodide (320 mg, 1.68 mmol, 0.5 equiv) and dimethylformamide (15 mL) were charged into a microwave tube and the reaction was heated using microwave irradiation at 150° C. for 2 h under nitrogen atmosphere (eight batches were prepared in parallel). The combined batches were quenched with water (150 mL) and the desired product was extracted with ethyl acetate (40 mL×3). The combined organic layers were washed with brine (50 mL×3), dried over sodium sulfate, filtered and concentrated under reduced pressure. The residue was purified by flash chromatography (SiO$_2$, petroleum ether:ethyl acetate, 20:1 to 1:1). The title compound, ethyl 1-[(1R)-1-(4-hydroxycyclohexyl)ethyl]-2-methyl-pyrrolo[2,3-b]pyridine-3-carboxylate (4.0 g, 7.9 mmol, 29% yield, 65% purity), was obtained as a yellow oil. LCMS [M+H]$^+$ m/z: calc'd 331.19; found 331.4.

Step 3: Synthesis of ethyl 2-methyl-1-[(1R)-1-(4-oxocyclohexyl)ethyl]pyrrolo[2,3-b]pyridine-3-carboxylate (I3)

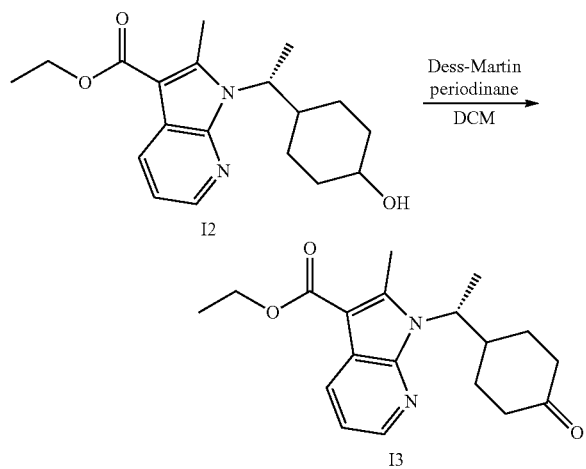

To a solution of ethyl 1-[(1R)-1-(4-hydroxycyclohexyl)ethyl]-2-methyl-pyrrolo[2,3-b]pyridine-3-carboxylate (2.0 g, 6.1 mmol, 1 equiv) in dichloromethane (20 mL) was added Dess-Martin periodinane (3.08 g, 7.26 mmol, 1.2 equiv) at 0° C. and the reaction was stirred at 0° C. for 40

118 min (two batches were prepared in parallel). The combined batches were quenched with saturated Na$_2$SO$_3$ (150 mL) and the desired product was extracted with ethyl acetate (50 mL×3). The combined organic layers were washed with saturated sodium bicarbonate (100 mL) and brine (70 mL×3), dried over sodium sulfate, filtered and concentrated to dryness under reduced pressure. The residue was purified by flash chromatography (SiO$_2$, petroleum ether:ethyl acetate, 20:1 to 3:1). The title compound, ethyl 2-methyl-1-[(1R)-1-(4-oxocyclohexyl)ethyl]pyrrolo[2,3-b]pyridine-3-carboxylate (1.7 g, 5.1 mmol, 42% yield, 98% purity), was obtained as a yellow oil. LCMS [M+H]$^+$ m/z: calc'd 329.18; found 329.4.

Step 4: Synthesis of ethyl 1-[(1R)-1-[4-[3-(difluoromethoxy)azetidin-1-yl]cyclohexyl]ethyl]-2-methyl-pyrrolo[2,3-b]pyridine-3-carboxylate (I4)

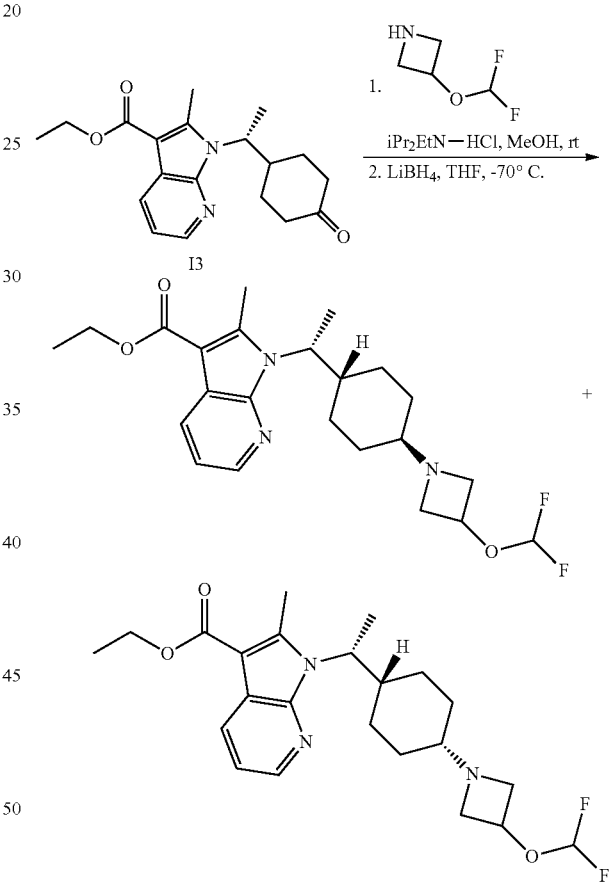

A mixture of 3-(difluoromethoxy)azetidine (140 mg, 1.14 mmol, 2.5 equiv) and N,N-diisopropylethylammonium chloride (590 mg, 4.57 mmol, 795 uL, 10 equiv) in methanol (2 mL) was stirred at 25° C. for 1 hour, then added to a solution of ethyl 2-methyl-1-[(1R)-1-(4-oxocyclohexyl) ethyl]pyrrolo[2,3-b]pyridine-3-carboxylate (150 mg, 457 umol, 1 equiv) in tetrahydrofuran (1 mL). This new mixture was stirred at 25° C. for 1.5 hours, then cooled to −70° C. LiBH$_4$ (15 mg, 689 umol, 1.5 equiv) was added at −70° C., and the reaction was stirred at −70° C. for 30 mins under a nitrogen atmosphere. The reaction was quenched with hydrochloric acid (1 M, 5 mL) and the mixture was stirred for 10 minutes at rt. The mixture was neutralized with saturated aqueous sodium bicarbonate until pH=8. The desired product was extracted with ethyl acetate (10 mL×3) and the combined organic layers were dried over sodium sulfate, filtered and concentrated under vacuum. The residue was purified by preparative TLC (SiO$_2$, petroleum ether: ethyl acetate, 1:1) to give two isomers of the title compound, ethyl 1-[(1R)-1-[4-[3-(difluoromethoxy)azetidin-1-yl]cyclohexyl]ethyl]-2-methyl-pyrrolo[2,3-b]pyridine-3-carboxylate, as yellow oil. Isomer 1 (major): 90 mg, 165 umol, 36% yield, 80% purity. LCMS [M+H]$^+$ m/z: calc'd 436.23; found 436.1. Isomer 2 (minor): LCMS [M+H]$^+$ m/z: calc'd 436.23; found 436.1.

Step 5: Synthesis of 1-[(1R)-1-[4-[3-(difluoromethoxy)azetidin-1-yl]cyclohexyl]ethyl]-2-methyl-pyrrolo[2,3-b]pyridine-3-carboxylic Acid (I5)

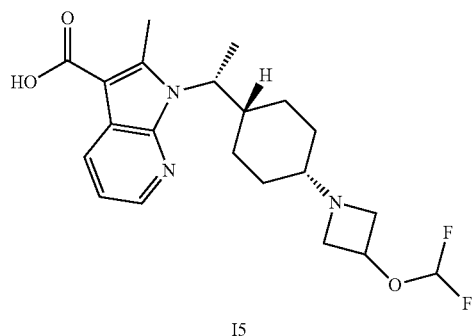

To a solution of the ethyl 1-[(1R)-1-[4-[3-(difluoromethoxy)azetidin-1-yl]cyclohexyl]ethyl]-2-methyl-pyrrolo[2,3-b]pyridine-3-carboxylate major isomer from Step 4 (140 mg, 322 umol, 1 equiv) in methanol (2 mL) was added sodium hydroxide (260 mg, 6.50 mmol, 20 equiv) in water (0.4 mL). The mixture was stirred at 70° C. for 14 h under an nitrogen atmosphere. The reaction mixture was concentrated under vacuum and the residue was neutralized at 0° C. by adding a solution of citric acid dropwise until pH=4. The desired product was extracted with ethylacetate (10 mL×3) and the combined organic layers were dried over sodium sulfate, filtered and concentrated to dryness under vacuum to give Isomer 1 of the title compound, 1-[(1R)-1-[4-[3-(difluoromethoxy)azetidin-1-yl]cyclohexyl]ethyl]-2-methyl-pyrrolo[2,3-b]pyridine-3-carboxylic acid (120 mg, crude) as yellow oil. LCMS (M+H$^+$) m/z: calcd 408.20; found 408.1. Similar conditions using the minor isomer from Step 4 afforded Isomer 2 of the title compound. LCMS [M+H]$^+$ m/z: calcd 408.20; found 408.0.

Step 6: Synthesis of (R)-1-(1-(4-(3-(difluoromethoxy)azetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide (Example 27)

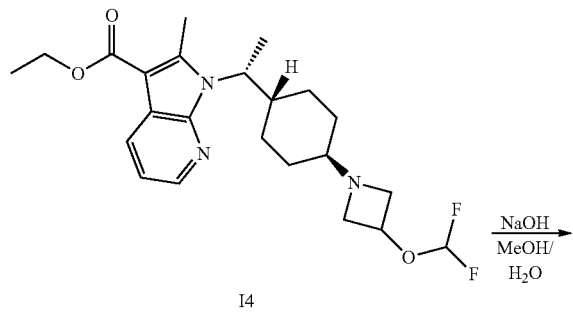

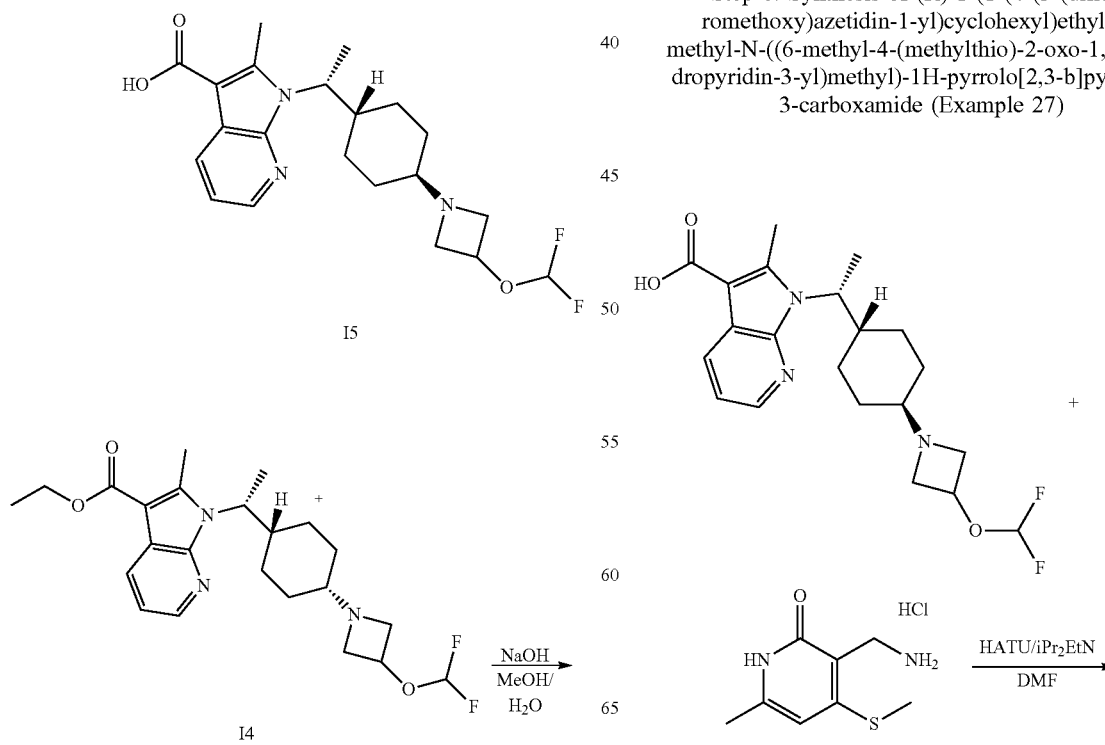

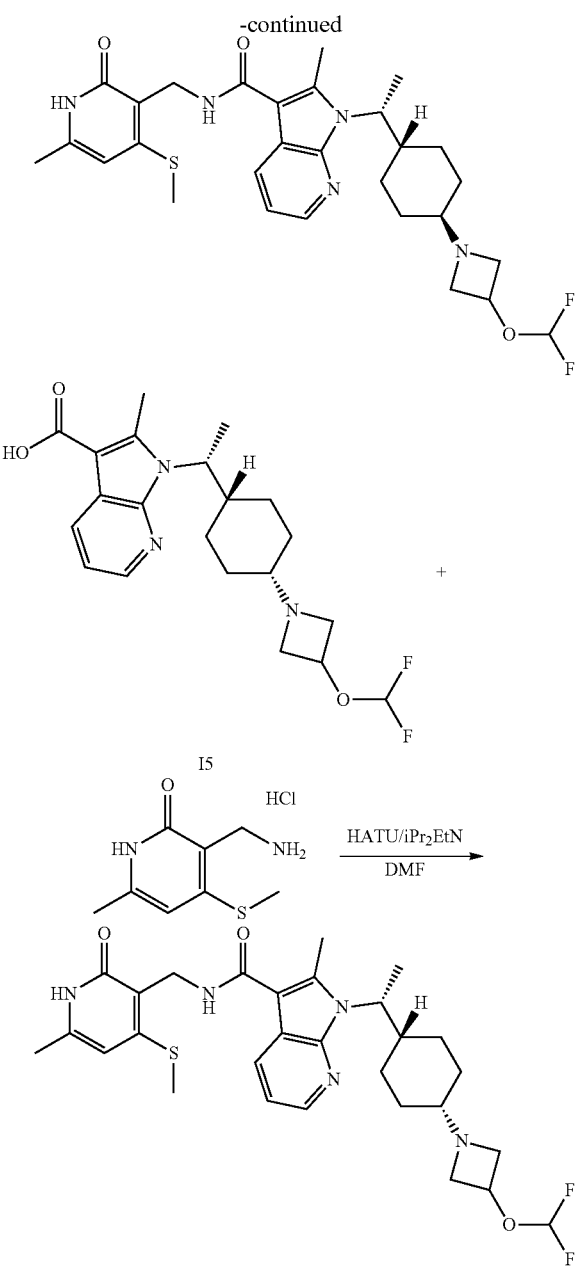

Example 27

A solution of 1-[(1R)-1-[4-[3-(difluoromethoxy)azetidin-1-yl]cyclohexyl]ethyl]-2-methyl-pyrrolo[2,3-b]pyridine-3-carboxylic acid, Isomer 1 from Step 5 (35 mg, 86 umol, 1 equiv), 3-(aminomethyl)-6-methyl-4-methylsulfanyl-1H-pyridin-2-one hydrochloride salt (25 mg, 113 umol, 1.3 equiv), HATU (40 mg, 105 umol, 1.2 equiv), N,N-diisopropylethylamine (75 uL, 431 umol, 5 equiv) in dimethylformamide (2 mL) was degassed (three vacuum and nitrogen refill cycles), and then stirred at 25° C. for 14 h under a nitrogen atmosphere. The reaction was diluted with ethyl acetate (10 mL) and washed with brine (10 mL×3). The organic phase was concentrated under vacuum and the residue was purified by preparative HPLC [column type: Xtimate C18 150×25 mm, Sum, column temperature: 30° C.; mobile phase: water (0.05% ammonia hydroxide v/v)-acetonitrile; gradient acetonitrile: 40% to 80%, over 6.5 min] to give the title compound, (R)-1-(1-(4-(3-(difluoromethoxy)azetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide, Isomer 1 (31 mg, 54 umol, 62% yield, 100% purity) as a white solid. LCMS [M+H]+ m/z: calc'd 574.26; found 574.1. $^1$H NMR (400 MHz, CD$_3$OD) δ 8.20 (d, J=8.0 Hz, 1H), 8.10 (d, J=8.0 Hz, 1H), 7.13-7.10 (m, 1H), 6.39 (t, J=72 Hz, 1H), 6.32 (s, 1H), 5.20 (br s, 1H), 4.74-4.68 (m, 1H), 4.62 (s, 3H), 3.67-3.58 (m, 2H), 3.15-3.08 (m, 2H), 2.68 (s, 3H), 2.55 (s, 3H), 2.32 (s, 3H), 2.23-1.93 (m, 4H), 1.68-1.62 (m, 4H), 1.11-1.05 (m, 1H), 0.96-0.91 (m, 3H).

Isomer 2 of Example 27 was formed using a similar procedure to the above, except starting with Isomer 2 from Step 5. LCMS [M+H]+ m/z: calcd 574.26; found 574.1. $^1$H NMR (400 MHz, CD$_3$OD) δ 8.20 (d, J=8.0 Hz, 1H), 8.09 (d, J=8.0 Hz, 1H), 7.13-7.10 (m, 1H), 6.39 (t, J=72 Hz, 1H), 6.32 (s, 1H), 5.38-5.35 (m, 1H), 4.62 (m, 4H), 3.67-3.60 (m, 2H), 2.71 (s, 3H), 2.56 (s, 3H), 2.33 (s, 3H), 2.21 (t, J=8.0 Hz, 2H), 2.06-2.03 (m, 4H), 1.66-1.61 (m, 4H), 0.94-0.91 (m, 4H).

Synthesis of 1-((R)-1-(4-(3-cyclopropoxyazetidin-1-yl)cyclohexyl)ethyl)-5-fluoro-2-methyl-N-((6-methyl-4-(methylthio)-2-oxo-1,2-dihydropyridin-3-yl)methyl)-1H-pyrrolo[2,3-b]pyridine-3-carboxamide (Example 28, Isomer 1 and 2)

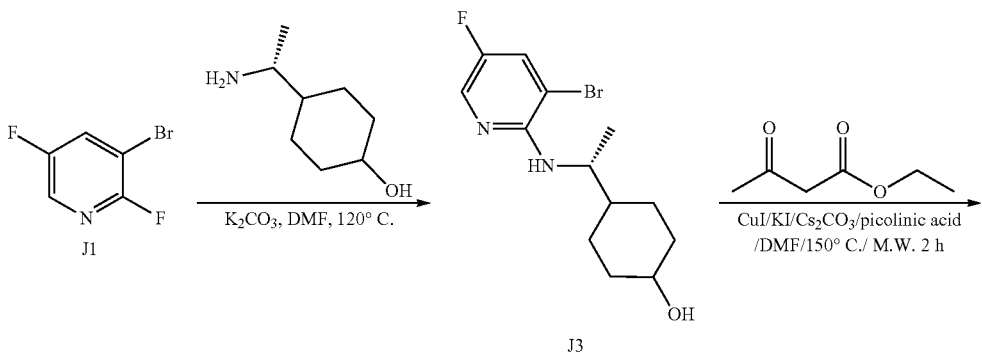

123
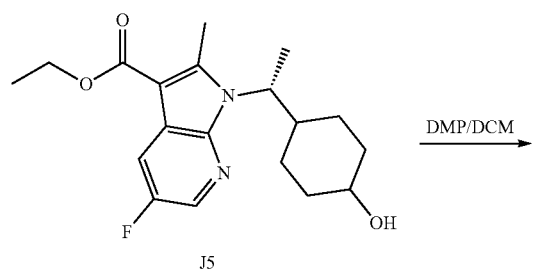
J5
-continued
124
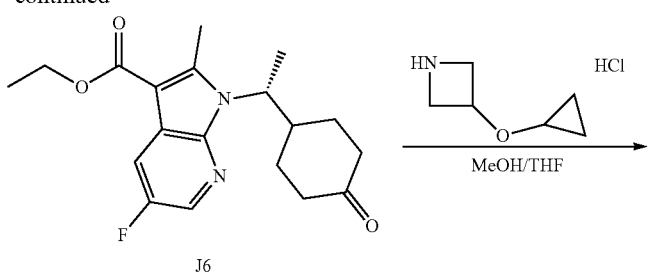
J6
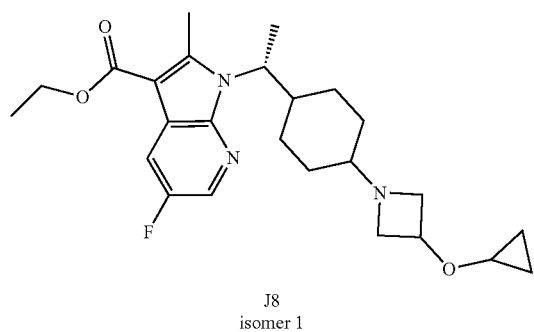
J8
isomer 1
+
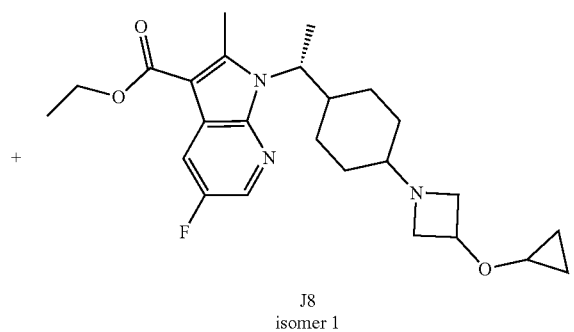
J8
isomer 1
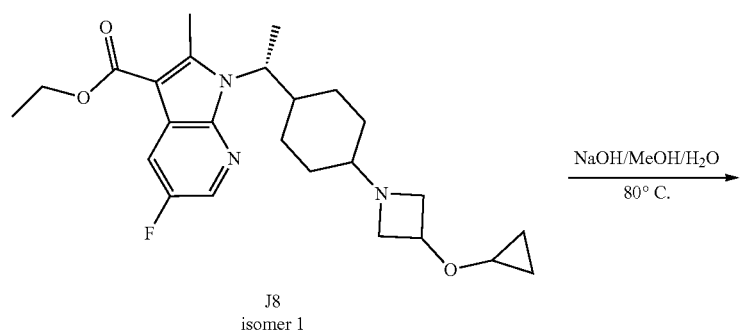
J8
isomer 1
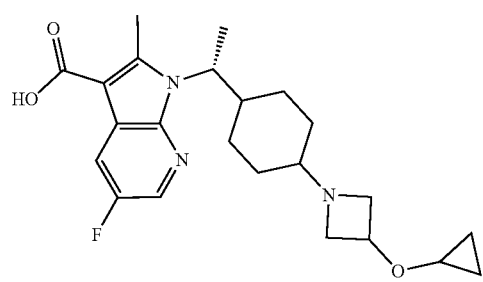
J9
isomer 1
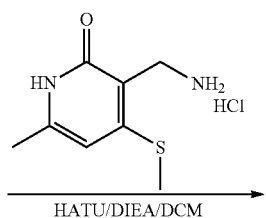
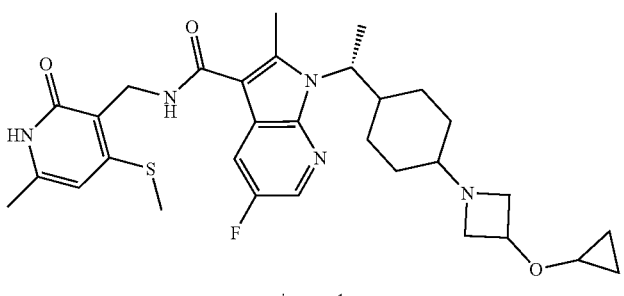
isomer 1

-continued
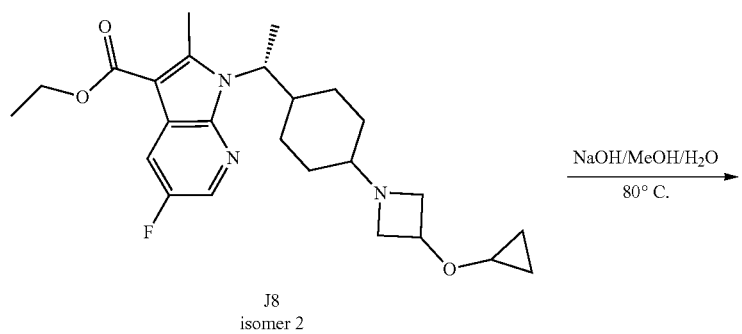
J8
isomer 2
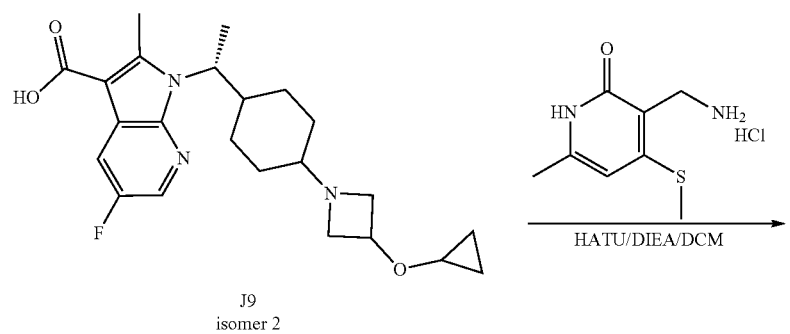
J9
isomer 2
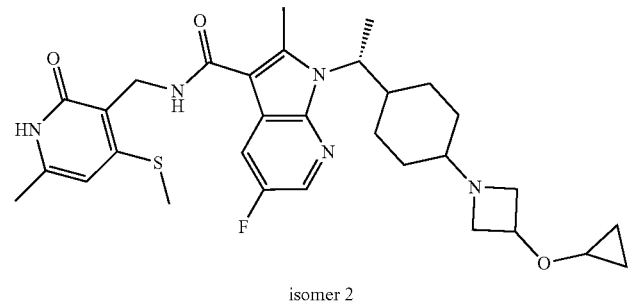
isomer 2

Step 1: 4-[(1R)-1-[(3-Bromo-5-fluoro-2-pyridyl)amino]ethyl]cyclohexanol

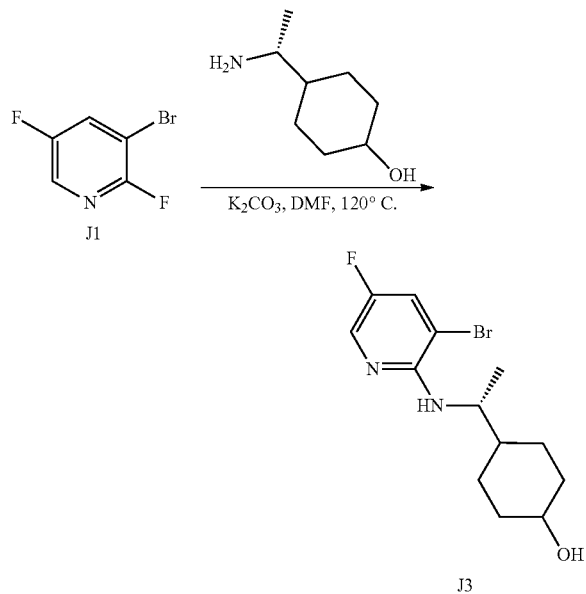

To a solution of 4-[(1R)-1-aminoethyl]cyclohexanol hydrochloride (5.6 g, 30.9 mmol, 1.2 eq) in DMF (25 mL) was added K$_2$CO$_3$ (10.7 g, 77.3 mmol, 3 eq). The mixture was stirred at 15° C. for 0.5 h. 3-Bromo-2,5-difluoropyridine (5 g, 25.8 mmol, 1 eq) was added and the mixture was stirred at 120° C. for 8 h. LCMS detected desired compound. The reaction mixture was concentrated to dryness, H$_2$O (100 mL) was added, and extracted with ethyl acetate (180 mL×3). The combined organic layer was washed with brine (80 mL), dried over Na$_2$SO$_4$, filtered and concentrated. The residue was purified by flash silica gel chromatography (ISCO®; 80 g SepaFlash® Silica Flash Column, eluent of 0-45% ethyl acetate/Petroleum ether gradient @ 60 m/min). 4-[(1R)-1-[(3-Bromo-5-fluoro-2-pyridyl)amino]ethyl]cyclohexanol (5.2 g, 16.23 mmol, 62.96% yield, 99% purity) was obtained as yellow oil. LCMS (M+H$^+$) m/z: calcd 317.06; found 317.1.

Step 2: Ethyl 5-fluoro-1-[(1R)-1-(4-hydroxycyclohexyl)ethyl]-2-methyl-pyrrolo[2,3-b]pyridine-3-carboxylate

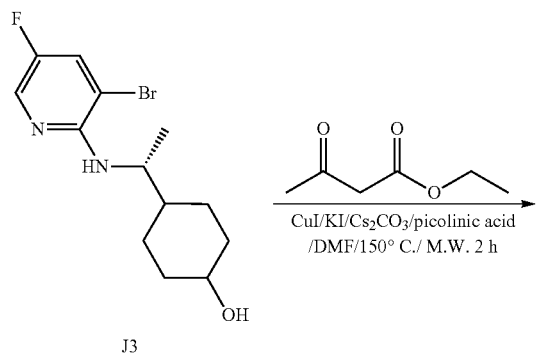

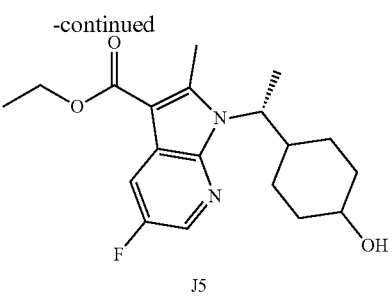

4-[(1R)-1-[(3-Bromo-5-fluoro-2-pyridyl)amino]ethyl]cyclohexanol (1 g, 3.2 mmol, 1 eq), ethyl 3-oxobutanoate (2.1 g, 15.8 mmol, 2.0 mL, 5 eq), KI (785.0 mg, 4.7 mmol, 1.5 eq), picolinic acid (194.1 mg, 1.6 mmol, 0.5 eq), Cs$_2$CO$_3$ (2.1 g, 6.3 mmol, 2 eq) and CuI (300.2 mg, 1.6 mmol, 0.5 eq) in DMF (10 mL) were combined in a microwave tube. The mixture was degassed and purged with N$_2$ (3×). The sealed tube was heated at 150° C. for 1 hour under microwave irradiation. LCMS detected desired compound. The reaction was repeated 5 times at the same scale. The five batches were combined and concentrated to dryness. H$_2$O (50 mL) was added to the residue, extracted with ethyl acetate (100 mL×3). The combined organic phase was washed with brine (50 mL) and concentrated to dryness. The residue was dissolved in DCM (10 mL), and aqueous HCl (50 mL, 1N) was added into the mixture and stirred at 15° C. for 1 h. The mixture was extracted with ethyl acetate (80 mL×3). The combined organic phase was washed with brine (50 mL) and dried (Na$_2$SO$_4$), filtered and concentrated to give ethyl 5-fluoro-1-[(1R)-1-(4-hydroxycyclohexyl)ethyl]-2-methyl-pyrrolo[2,3-b]pyridine-3-carboxylate (3.3 g, crude) as a black brown oil. LCMS (M+H$^+$) m/z: calcd 349.18; found 349.1.

Step 3: Ethyl 5-fluoro-2-methyl-1-[(1R)-1-(4-oxocyclohexyl)ethyl]pyrrolo[2,3-b]pyridine-3-carboxylate

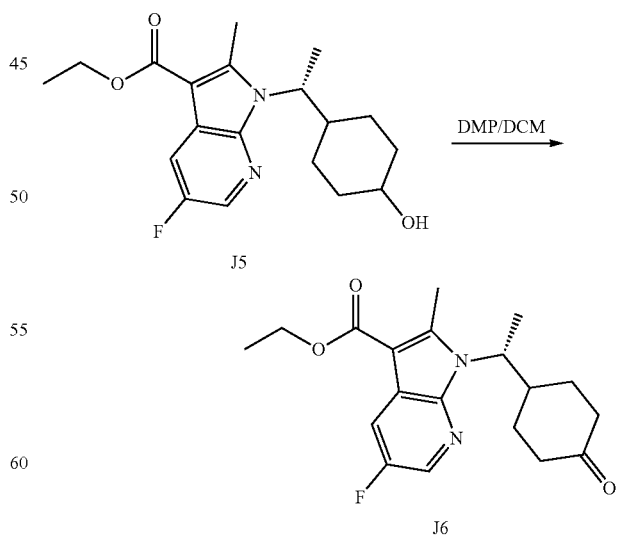

To a solution of ethyl 5-fluoro-1-[(1R)-1-(4-hydroxycyclohexyl)ethyl]-2-methyl-pyrrolo[2,3-b]pyridine-3-carboxylate (3.3 g, 9.5 mmol, 1 eq) in DCM (30 mL) was added DMP (6.0 g, 14.2 mmol, 4.4 mL, 1.5 eq). The mixture was stirred at 15° C. for 1.5 h. LCMS detected desired compound. The mixture was diluted with DCM (50 mL) and washed with sat. Na$_2$S$_2$O$_3$ (30 mL×2). The organic phase was washed with NaHCO$_3$ (30 mL×2) and brine (30 mL). The combined aqueous phase was extracted with ethyl acetate (250 mL×2). The combined organic phase was dried over Na$_2$SO$_4$, filtered and concentrated. The residue was purified by flash silica gel chromatography (ISCO®; 80 g SepaFlash® Silica Flash Column, eluent of 0-28% ethyl acetate/petroleum ether gradient @ 60 m/min). Ethyl 5-fluoro-2-methyl-1-[(1R)-1-(4-oxocyclohexyl)ethyl]pyrrolo[2,3-b]pyridine-3-carboxylate (460 mg, 1.1 mmol, 11.9% yield, 85% purity) was obtained as yellow oil. LCMS (M+H$^+$) m/z: calcd 347.17; found 347.0.

Step 4: Ethyl 1-[(1R)-1-[4-[3-(cyclopropoxy)azetidin-1-yl]cyclohexyl]ethyl]-5-fluoro-2-methyl-pyrrolo[2,3-b]pyridine-3-carboxylate (Isomer 1 and Isomer 2)

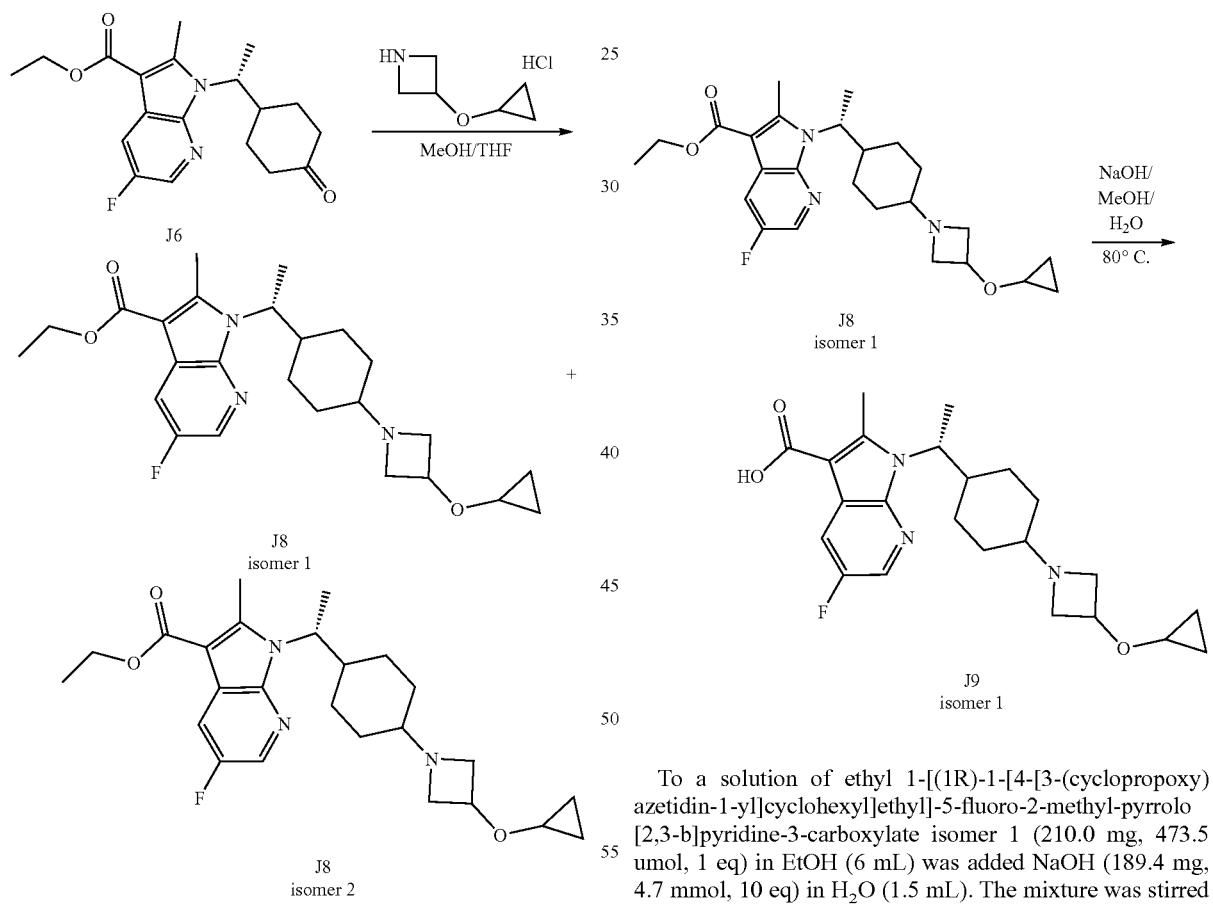

To a solution of 3-(cyclopropoxy)azetidine (933.0 mg, 6.2 mmol, 4 eq, HCl salt) in MeOH (4 mL) was added DIEA (705.2 mg, 5.5 mmol, 950.4 uL, 3.5 eq). The mixture was stirred at 15° C. for 1 h. ethyl 5-fluoro-2-methyl-1-[(1R)-1-(4-oxocyclohexyl)ethyl]pyrrolo[2,3-b]pyridine-3-carboxylate (540.0 mg, 1.6 mmol, 1 eq) in THF (4 mL) was added into the mixture. The mixture was stirred at 15° C. for 1.5 h. LiBH$_4$ (169.8 mg, 7.8 mmol, 5 eq) was added into the mixture at −70° C. The mixture was stirred at −70° C. for 0.5 h. LCMS detected the desired compound. TLC (PE/EA=2/1 and DCM/MeOH=20/1) showed new spots formed. The reaction was quenched with water (20 mL), extracted with ethyl acetate (50 mL×3). The combined organic layer was washed with brine (50 mL), dried over Na$_2$SO$_4$, filtered and concentrated. The residue was purified by prep-TLC (DCM/MeOH=20/1) to give the pure cis and trans isomers separately. Ethyl 1-[(1R)-1-[4-[3-(cyclopropoxy)azetidin-1-yl]cyclohexyl]ethyl]-5-fluoro-2-methyl-pyrrolo[2,3-b]pyridine-3-carboxylate isomer 1 (350.0 mg, 789.1 umol, 50.6% yield, 100% purity) was obtained as a yellow gum; LCMS (M+H$^+$) m/z: calcd 444.26; found 444.2. Ethyl 1-[(1R)-1-[4-[3-(cyclopropoxy)azetidin-1-yl]cyclohexyl]ethyl]-5-fluoro-2-methyl-pyrrolo[2,3-b]pyridine-3-carboxylate isomer 2 (70.0 mg, 140.5 umol, 9.0% yield, 89% purity) was obtained as a yellow gum. LCMS (M+H$^+$) m/z: calcd 444.26; found 444.2.

Step 5: 1-[(1R)-1-[4-[3-(cyclopropoxy)azetidin-1-yl]cyclohexyl]ethyl]-5-fluoro-2-methyl-pyrrolo[2,3-b]pyridine-3-carboxylic Acid Isomer 1

To a solution of ethyl 1-[(1R)-1-[4-[3-(cyclopropoxy)azetidin-1-yl]cyclohexyl]ethyl]-5-fluoro-2-methyl-pyrrolo[2,3-b]pyridine-3-carboxylate isomer 1 (210.0 mg, 473.5 umol, 1 eq) in EtOH (6 mL) was added NaOH (189.4 mg, 4.7 mmol, 10 eq) in H$_2$O (1.5 mL). The mixture was stirred at 80° C. for 12 h. LCMS detected the desired compound. The mixture was cooled to 25° C. and concentrated. The residue was diluted with water (20 mL), adjusted to pH=6-7 with saturated citric acid and extracted with ethyl acetate (40 mL×3). The combined organic layer was washed with brine (30 mL), dried over Na$_2$SO$_4$, filtered and concentrated. 1-[(1R)-1-[4-[3-(cyclopropoxy)azetidin-1-yl]cyclohexyl]ethyl]-5-fluoro-2-methyl-pyrrolo[2,3-b]pyridine-3-carboxylic acid isomer 1 (230.0 mg, crude) was obtained as blue gum. LCMS (M+H$^+$) m/z: calcd 416.23; found 416.2.

Step 6: 1-[(1R)-1-[4-[3-(cyclopropoxy)azetidin-1-yl]cyclohexyl]ethyl]-5-fluoro-2-methyl-N-[(6-methyl-4-methylsulfanyl-2-oxo-1H-pyridin-3-yl)methyl]pyrrolo[2,3-b]pyridine-3-carboxamide Isomer 1

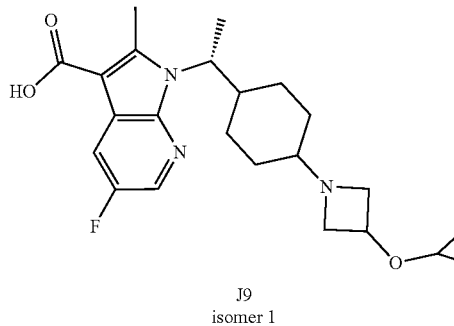

J9
isomer 1

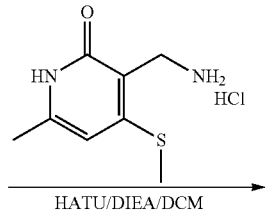

HATU/DIEA/DCM

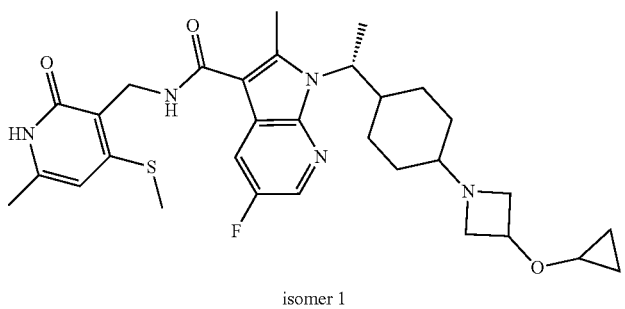

isomer 1

To a mixture of 1-[(1R)-1-[4-[3-(cyclopropoxy)azetidin-1-yl]cyclohexyl]ethyl]-5-fluoro-2-methyl-pyrrolo[2,3-b]pyridine-3-carboxylic acid isomer 1 (230.0 mg, 553.6 umol, 1 eq) and HATU (378.9 mg, 996.4 umol, 1.8 eq) in DCM (15 mL) was added DIEA (286.2 mg, 2.2 mmol, 385.7 uL, 4 eq). The mixture was stirred at 30° C. for 0.5 h. 3-(Aminomethyl)-6-methyl-4-methylsulfanyl-1H-pyridin-2-one (183.3 mg, 830.3 umol, 1.5 eq, HCl salt) was added into the mixture. The mixture was stirred at 30° C. for 12 h. LCMS detected the desired compound. The mixture was diluted with water (20 mL), extracted with DCM (40 mL×3). The combined organic layer was washed with brine (40 mL), dried over $Na_2SO_4$, filtered and concentrated. The residue was purified by prep-TLC (DCM/MeOH=10/1). To give 250 mg (purity: 94%) of the desired compound product. The product was re-purified by prep-HPLC (column: Waters Xbridge 150×25 5u; mobile phase: [water (0.05% ammonia hydroxide v/v)-ACN]; B %: 33%-63%, 7.8 min). 1-[(1R)-1-[4-[3-(Cyclopropoxy)azetidin-1-yl]cyclohexyl]ethyl]-5-fluoro-2-methyl-N-[(6-methyl-4-methylsulfanyl-2-oxo-1H-pyridin-3-yl)methyl]pyrrolo[2,3-b]pyridine-3-carboxamide isomer 1 (211.8 mg, 100% purity) was obtained as white solid. LCMS (M+H+) m/z: calcd 582.28; found 582.1.

$^1$H NMR (400 MHz, CDCl3) δ 12.72 (s, 1H), 8.07 (s, 1H), 7.89 (d, J=8.8 Hz, 1H), 7.36-7.33 (m, 1H), 6.05 (s, 1H), 4.72 (d, J=4.4 Hz, 2H), 4.22-4.19 (m, 1H), 3.63-3.57 (m, 2H), 3.22-3.20 (m, 1H), 2.87-2.79 (m, 5H), 2.51 (s, 3H), 2.28 (s, 3H), 2.09-2.07 (m, 1H), 1.89-1.87 (m, 2H), 1.75 (s, 1H), 1.64-1.57 (m, 4H), 1.05-0.96 (m, 3H), 0.77 (s, 2H), 0.58-0.54 (m, 2H), 0.47-0.42 (m, 2H).

Step 7: 1-[(1R)-1-[4-[3-(cyclopropoxy)azetidin-1-yl]cyclohexyl]ethyl]-5-fluoro-2-methyl-pyrrolo[2,3-b]pyridine-3-carboxylic Acid Isomer 2

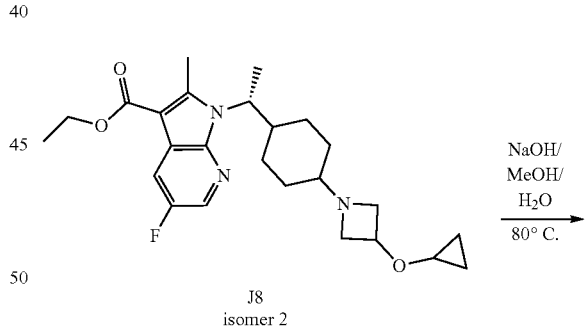

J8
isomer 2

NaOH/MeOH/$H_2O$
80° C.

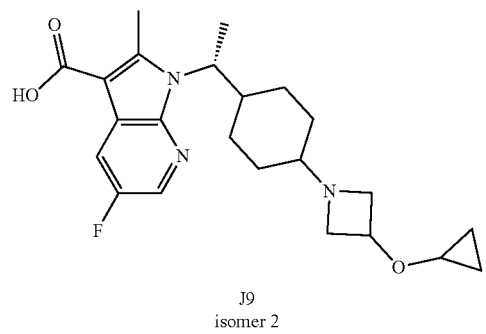

J9
isomer 2

To a solution of ethyl 1-[(1R)-1-[4-[3-(cyclopropoxy)azetidin-1-yl]cyclohexyl]ethyl]-5-fluoro-2-methyl-pyrrolo[2,3-b]pyridine-3-carboxylate isomer 2 (70.0 mg, 157.8 umol, 1 eq) in EtOH (3 mL) was added NaOH (63.1 mg, 1.6 mmol, 10 eq) in H$_2$O (1 mL). The mixture was stirred at 80° C. for 12 h. LCMS detected the desired compound. The mixture was concentrated. The residue was diluted with water (10 mL), adjusted to pH=67 with saturated citric acid, extracted with ethyl acetate (30 mL×3). The combined organic layer was washed with brine (30 mL), dried over Na$_2$SO$_4$, filtered and concentrated. 1-[(1R)-1-[4-[3-(cyclopropoxy)azetidin-1-yl]cyclohexyl]ethyl]-5-fluoro-2-methyl-pyrrolo[2,3-b]pyridine-3-carboxylic acid isomer 2 (70 mg, crude) was obtained as blue solid. LCMS (M+H$^+$) m/z: calcd 416.23; found 416.0.

Step 8: 1-[(1R)-1-[4-[3-(cyclopropoxy)azetidin-1-yl]cyclohexyl]ethyl]-5-fluoro-2-methyl-N-[(6-methyl-4-methylsulfanyl-2-oxo-1H-pyridin-3-yl)methyl]pyrrolo[2,3-b]pyridine-3-carboxamide Isomer 2

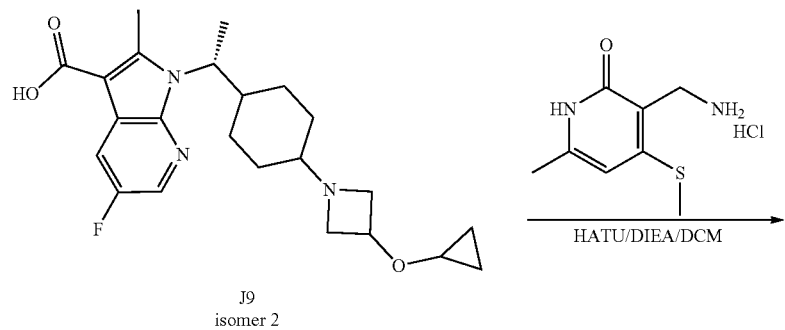

J9
isomer 2

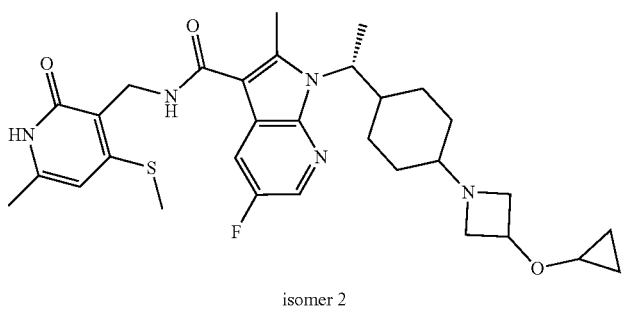

isomer 2

To a mixture of 1-[(1R)-1-[4-[3-(cyclopropoxy)azetidin-1-yl]cyclohexyl]ethyl]-5-fluoro-2-methyl-pyrrolo[2,3-b]pyridine-3-carboxylic acid isomer 2 (70.0 mg, 168.5 umol, 1 eq) and HATU (76.9 mg, 202.2 umol, 1.2 eq) in DCM (4 mL) was added DIEA (108.9 mg, 842.4 umol, 146.72 uL, 5 eq). The mixture was stirred at 30° C. for 0.5 h. 3-(Aminomethyl)-6-methyl-4-methylsulfanyl-1H-pyridin-2-one (55.8 mg, 252.7 umol, 1.5 eq, HCl salt) was added into the mixture. The mixture was stirred at 30° C. for 12 h. LCMS detected the desired compound. The mixture was diluted with water (20 mL), extracted with ethyl acetate (50 mL×3). The combined organic layer was washed with brine (30 mL), dried over Na$_2$SO$_4$, filtered and concentrated. The residue was purified by prep-HPLC (column: Waters Xbridge 150× 25 5u; mobile phase: [water (0.05% ammonia hydroxide v/v)-ACN]; B %: 40%-70%, 7.8 min). 1-[(1R)-1-[4-[3-(Cyclopropoxy)azetidin-1-yl]cyclohexyl]ethyl]-5-fluoro-2-methyl-N-[(6-methyl-4-methylsulfanyl-2-oxo-1H-pyridin-3-yl)methyl]pyrrolo[2,3-b]pyridine-3-carboxamide isomer 2 (53.9 mg, 91.7 umol, 54.5% yield, 99% purity) was obtained as white solid. LCMS (M+H$^+$) m/z: calcd 582.28; found 582.1.

$^1$H NMR (400 MHz, CDCl3) δ 12.71 (s, 1H), 8.04 (s, 1H), 7.86 (dd, J=2.4 Hz, 9.6 Hz, 1H), 7.28 (s, 1H), 6.03 (s, 1H), 4.70 (s, 2H), 4.20-4.17 (m, 2H), 3.58 (s, 1H), 3.50 (s, 1H), 3.22-3.19 (m, 1H), 2.76-2.72 (m, 5H), 2.49 (s, 3H), 2.27 (s, 3H), 2.18 (s, 1H), 1.70 (s, 3H), 1.47-1.34 (m, 3H), 1.13-1.07 (m, 2H), 0.69 (s, 1H), 0.54-0.53 (m, 2H), 0.45-0.43 (m, 2H).

Synthesis of 1-((R)-1-(4-(3-(difluoromethoxy)azetidin-1-yl)cyclohexyl)ethyl)-6-fluoro-2-methyl-N-((6-methyl-4-(methylthio)-2-oxo-1,2-dihydropyridin-3-yl)methyl)-1H-indole-3-carboxamide (Example 29, Single Isomer)
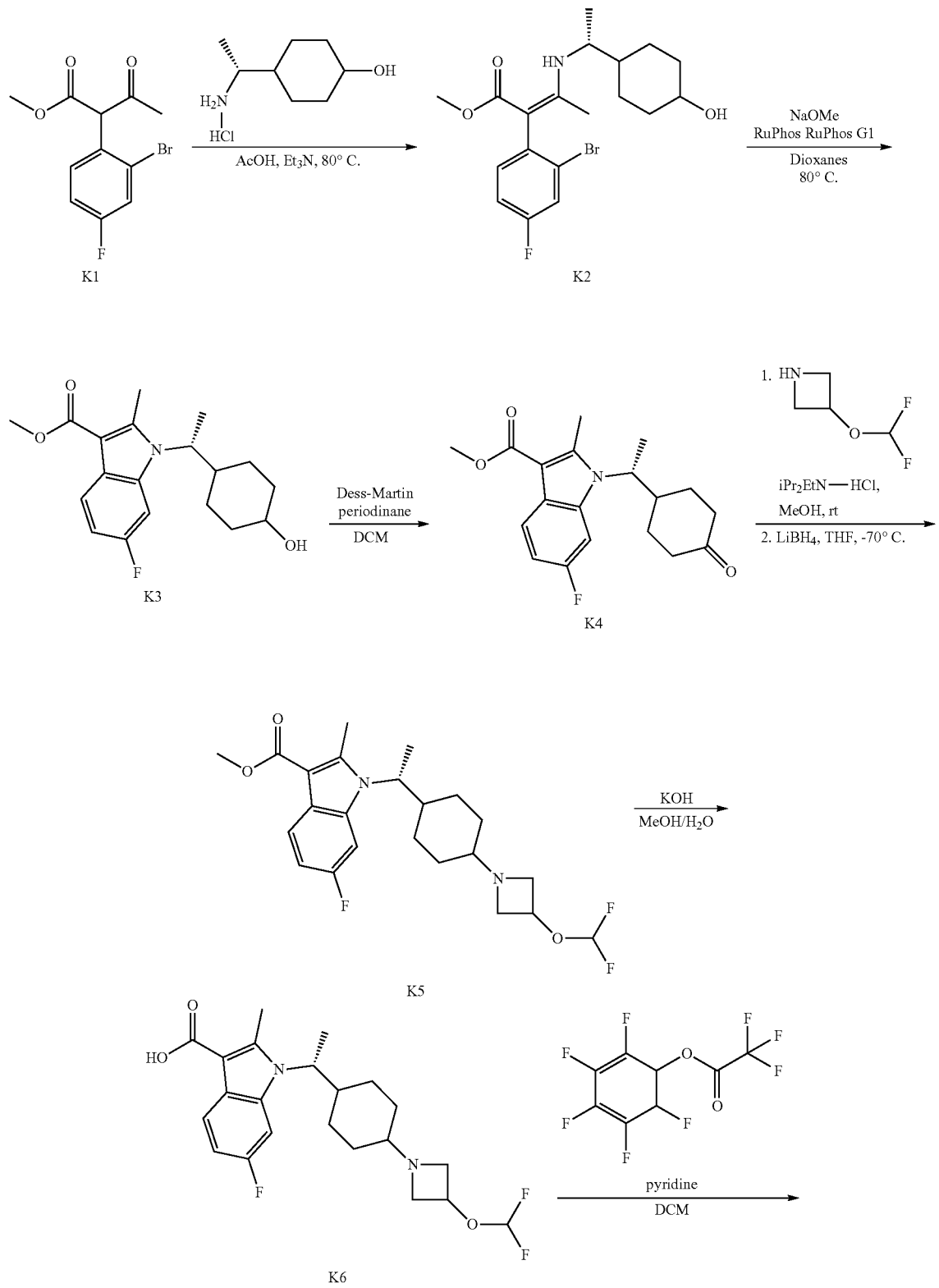

-continued

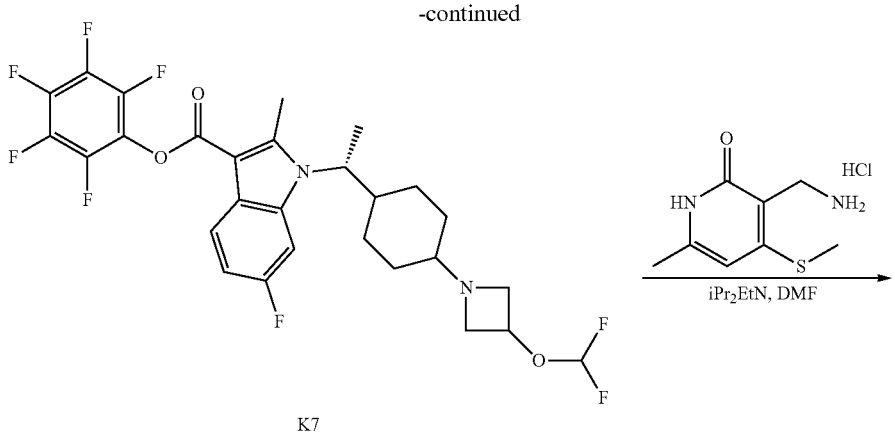

K7

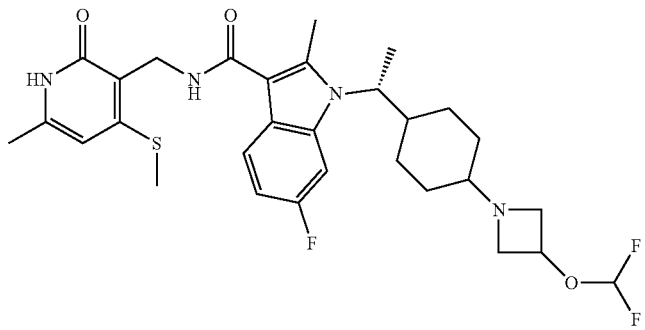

single isomer

Step 1: Synthesis of methyl (R,Z)-2-(2-bromo-4-fluorophenyl)-3-((1-(4-hydroxycyclohexyl)ethyl)amino)but-2-enoate To around bottomed flask was added (R)-4-(1-aminoethyl)cyclohexan-1-ol (0.707 g, 3.94 mmol, 1.0 equiv), t-BuOH (13 mL), triethylamine (0.552 mL, 27.3 mmol, 23 equiv), and methyl 2-(2-bromo-4-fluorophenyl)-3-oxobutanoate (1.14 g, 3.94 mmol, 1.0 equiv) [prepared according to the procedure reported in WO2013120104]. To this solution was added AcOH (0.49 ml, 8.7 mmol, 2.2 equiv) and the reaction was heated overnight at 85° C. before cooling to room temperature and concentrating. The crude residue was purified via silica gel chromatography to afford methyl (R,Z)-2-(2-bromo-4-fluorophenyl)-3-((1-(4-hydroxycyclohexyl)ethyl)amino)but-2-enoate X# (1.42 g, 3.42 mmol, 87%). LCMS [M+H]+m/z: calc'd 414.11; found 414.2.

Step 2: Synthesis of methyl (R)-6-fluoro-1-(1-(4-hydroxycyclohexyl)ethyl)-2-methyl-1H-indole-3-carboxylate

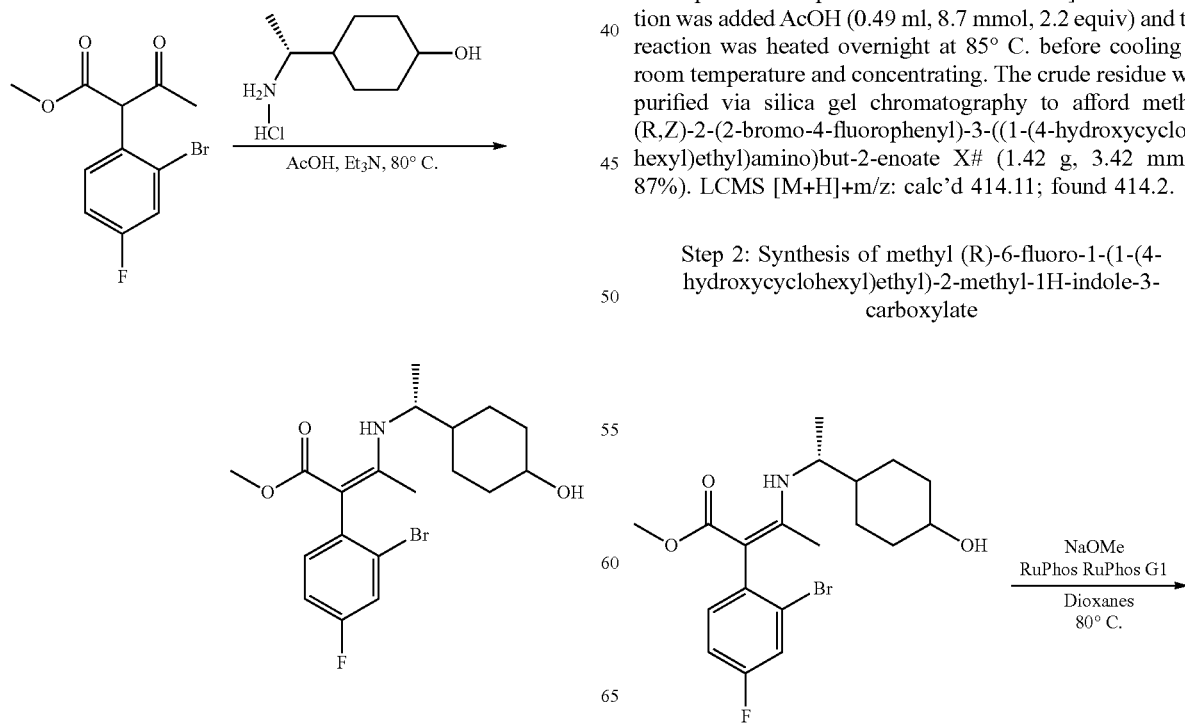

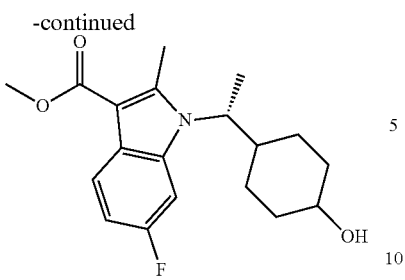

To a resealable vial was added Ruphos (79.7 mg, 171 µmol, 0.05 equiv), Pd-precat. RuPhos G1 (111 mg, 136 µmol, 0.04 equiv), and methyl (2Z)-2-(2-bromo-4-fluorophenyl)-3-{[(1R)-1-(4-hydroxycyclohexyl)ethyl]amino}but-2-enoate (1420 mg, 3.42 mmol, 1.0 equiv) dissolved in dioxanes (11.4 mL). To this solution was added sodium methoxide (277 mg, 5.13 mmol, 1.5 equiv) and the reaction was evacuated/backfilled with nitrogen (3×) before heating to reflux overnight. The solution was cooled to room temperature and diluted with ethyl acetate. The precipitate was filtered off and the filtrate concentrated. The crude residue was purified by flash chromatography to afford methyl 6-fluoro-1-[(1R)-1-(4-hydroxycyclohexyl)ethyl]-2-methyl-1H-indole-3-carboxylate (1033 mg, 90%). LCMS [M+H]+ m/z: calc'd 334.18; found 334.3.

Step 3: Synthesis of methyl (R)-6-fluoro-2-methyl-1-(1-(4-oxocyclohexyl)ethyl)-1H-indole-3-carboxylate

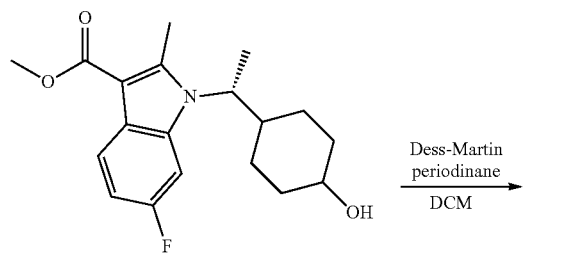

To the mixture of methyl 6-fluoro-1-[(1R)-1-(4-hydroxycyclohexyl)ethyl]-2-methyl-1H-indole-3-carboxylate (890 mg, 2.66 mmol, 1.0 equiv) in dichloromethane (10.6 mL) was added Dess-Martin periodinane (1.35 g, 3.19 mmol, 1.2 equiv) at 0° C. and stirred at 0° C. for 2 h. The reaction was then quenched with isopropanol and warmed to room temperature. The mixture was extracted with ethyl acetate (50 mL×3). The combined organic layers were washed with saturated sodium bicarbonate (100 mL) and brine (70 mL×3), dried over sodium sulfate, filtered and concentrated to dryness under reduced pressure. The residue was purified by column chromatography (SiO2, Petroleum ether/Ethyl acetate=20/1 to 3:1) to give methyl (R)-6-fluoro-2-methyl-1-(1-(4-oxocyclohexyl)ethyl)-1H-indole-3-carboxylate (513 mg, 58%) as a clear oil. LCMS [M+H]+ m/z: calc'd 332.17; found 332.2.

Step 4: Synthesis of methyl 1-((R)-1-(4-(3-(difluoromethoxy)azetidin-1-yl)cyclohexyl)ethyl)-6-fluoro-2-methyl-1H-indole-3-carboxylate (Single Isomer)

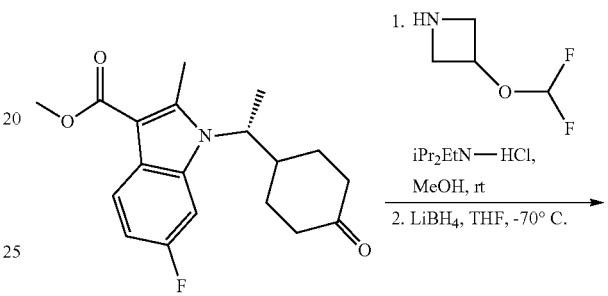

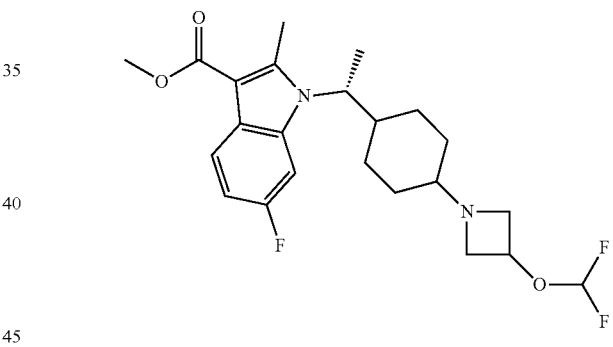

A mixture of 3-(difluoromethoxy)azetidine (132 mg, 1.08 mmol, 4.5 equiv) and N,N-diisopropylethylammonium chloride (174 mg, 1.26 mmol, 5.3 equiv) in methanol (1 mL) was stirred at 25° C. for 1 hour, then added to a solution of methyl (R)-6-fluoro-2-methyl-1-(1-(4-oxocyclohexyl)ethyl)-1H-indole-3-carboxylate (80 mg, 0.241 mmol, 1 equiv) in tetrahydrofuran (1 mL). This new mixture was stirred at 25° C. for 1.5 hours, then cooled to −70° C. LiBH4 (2M in THF) (0.168 mL, 0.337 mmol, 1.4 equiv) was added at −70° C., and the reaction was stirred at −70° C. for 30 min under a nitrogen atmosphere. The reaction was quenched with hydrochloric acid (1 M, 5 mL) and the mixture was stirred for 10 min at rt. The mixture was neutralized with saturated aqueous sodium bicarbonate until pH=8. The desired product was extracted with ethyl acetate (10 mL×3) and the combined organic layers were dried over sodium sulfate, filtered and concentrated under vacuum. The residue was purified via silica gel chromatography to afford methyl 1-((R)-1-(4-(3-(difluoromethoxy)azetidin-1-yl)cyclohexyl)ethyl)-6-fluoro-2-methyl-1H-indole-3-carboxylate (single isomer) (56 mg, 0.127 mmol, 53%). LCMS [M+H]+ m/z: calc'd 439.2; found 439.2.

Step 5: Synthesis of 1-((R)-1-(4-(3-(difluoromethoxy)azetidin-1-yl)cyclohexyl)ethyl)-6-fluoro-2-methyl-1H-indole-3-carboxylic Acid (Single Isomer)

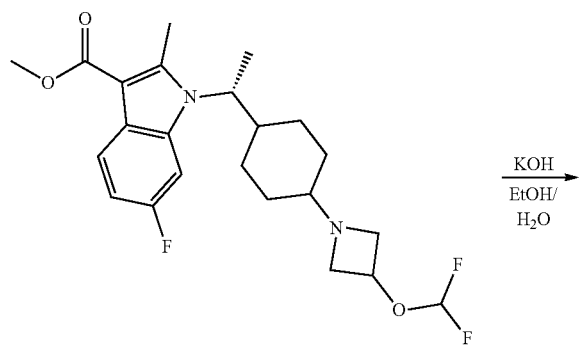

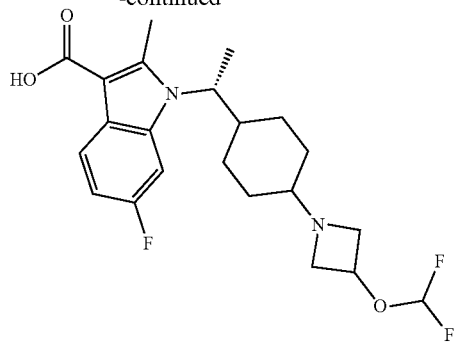

To a solution of methyl 1-((R)-1-(4-(3-(difluoromethoxy)azetidin-1-yl)cyclohexyl)ethyl)-6-fluoro-2-methyl-1H-indole-3-carboxylate single isomer (76 mg, 0.173 mmol, 1.0 equiv) in ethanol (1.3 mL) and water (0.40 mL) was added KOH (58 mg, 1.0 mmol, 6 equiv). The mixture was stirred at 80° C. for 2 h. The reaction mixture was concentrated, and dichloromethane (15 mL) and water (10 mL) were added. The mixture was adjusted to pH=5-6 with hydrochloric acid (1 M) solution. The mixture was extracted with dichloromethane (20 mL*3). The organic layer was dried by anhydrous sodium sulfate, filtered and concentrated under vacuum to give 1-((R)-1-(4-(3-(difluoromethoxy)azetidin-1-yl)cyclohexyl)ethyl)-6-fluoro-2-methyl-1H-indole-3-carboxylic acid (90 mg, crude), as a solid. LCMS [M+H]$^+$ m/z: calc'd 425.21; found 425.2.

Step 6: Synthesis of perfluorophenyl 2-methyl-1-((R)-1-(4-((3-(trifluoromethyl)oxetan-3-yl)amino)cyclohexyl)ethyl)-1H-indole-3-carboxylate

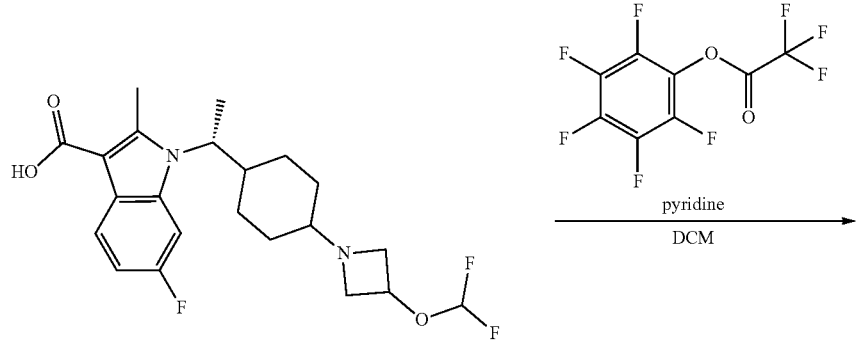

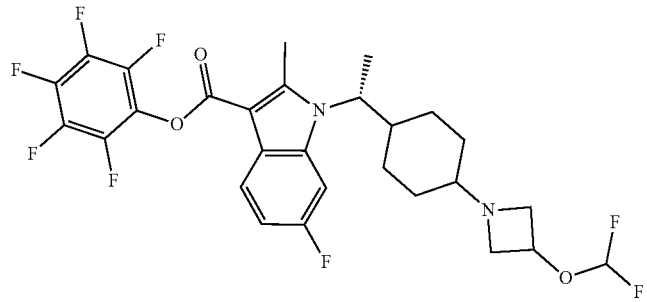

To a stirred solution of 1-((R)-1-(4-(3-(difluoromethoxy)azetidin-1-yl)cyclohexyl)ethyl)-6-fluoro-2-methyl-1H-indole-3-carboxylic acid (70 mg, 164 μmol, 1.0 equiv) in dichloromethane (0.66 mL) was added pyridine (33 μL, 0.41 mmol, 2.5 equiv) followed by dropwise addition of 2,3,4,5,6-pentafluorophenyl 2,2,2-trifluoroacetate (43 μL, 0.248 mmol, 1.5 equiv). This mixture was stirred for 30 min at which time the starting material was consumed. The reaction was then concentrated under reduced pressure. The crude product was directly used in the next step (59 mg, crude). LCMS [M+H]$^+$ m/z: calc'd 591.19; found 591.2.

Step 7: Synthesis of 1-((R)-1-(4-(3-(difluoromethoxy)azetidin-1-yl)cyclohexyl)ethyl)-6-fluoro-2-methyl-N-((6-methyl-4-(methylthio)-2-oxo-1,2-dihydropyridin-3-yl)methyl)-1H-indole-3-carboxamide

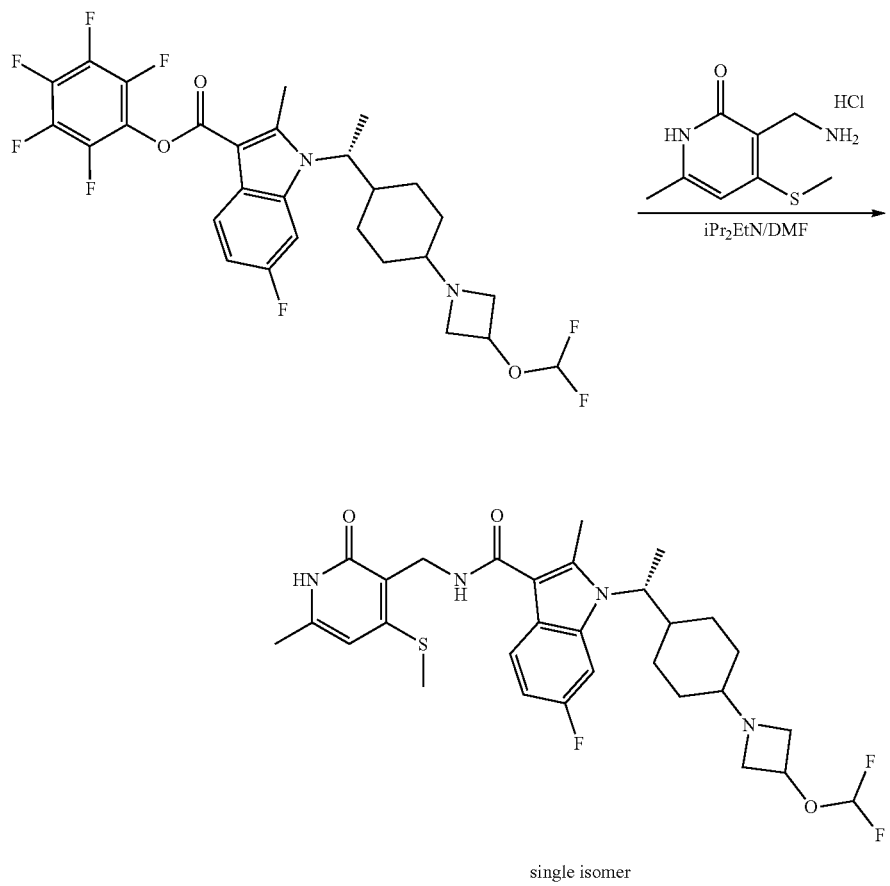

single isomer

To a solution of perfluorophenyl 1-((R)-1-(4-(3-(difluoromethoxy)azetidin-1-yl)cyclohexyl)ethyl)-6-fluoro-2-methyl-1H-indole-3-carboxylate (40 mg, 61 μmol, 1.0 equiv) in dimethyl formamide (166 μL) was added 3-(aminomethyl)-6-methyl-4-(methylsulfanyl)-1,2-dihydropyridin-2-one (34 mg, 182 μmol, 3.0 equiv) followed by diisopropylethylamine (21 μL, 120 μmol, 2.0 equiv). The reaction was stirred at 60° C. for 1 h. The reaction was then diluted with water (10 mL), extracted with dichloromethane (20 mL*4). The combined organic layer was washed with brine (20 mL), dried over sodium sulfate, filtered and concentrated. The crude mixture was purified by column chromatography on silica gel to give 1-((R)-1-(4-(3-(difluoromethoxy)azetidin-1-yl)cyclohexyl)ethyl)-6-fluoro-2-methyl-N-((6-methyl-4-(methylthio)-2-oxo-1,2-dihydropyridin-3-yl)methyl)-1H-indole-3-carboxamide (6.0 mg, 10 μmol, 17% yield) as a white solid. LCMS [M+H]$^+$ m/z: calc'd 591.26; found 591.3.

1H NMR (400 MHz, CDCl3) δ 12.15 (br. s., 1H), 7.75 (dd, J=5.4, 8.8 Hz, 1H), 7.31 (br. s., 1H), 7.12 (d, J=10.3 Hz, 1H), 6.81 (dt, J=2.4, 9.0 Hz, 1H), 6.37-5.95 (m, 2H), 4.73 (td, J=5.7, 11.6 Hz, 2H), 4.03 (br. s., 1H), 3.74-3.61 (m, 2H), 3.09-3.00 (m, 2H), 2.72-2.66 (m, 2H), 2.49 (s, 3H), 2.20 (s, 3H), 2.08 (d, J=7.8 Hz, 1H), 2.00 (br. s., 1H), 1.90 (d, J=10.3 Hz, 1H), 1.57 (d, J=6.8 Hz, 3H), 1.15-1.02 (m, 3H), 0.92-0.71 (m, 3H).

145

The Synthesis of 1-[(1R)-1-[4-[3-(cyclopropoxy)azetidin-1-yl]cyclohexyl]ethyl]-2-methyl-N-[(6-methyl-4-methylsulfanyl-2-oxo-1H-pyridin-3-yl)methyl]pyrrolo[2,3-b]pyridine-3-carboxamide
(Example 30, Single Isomer)

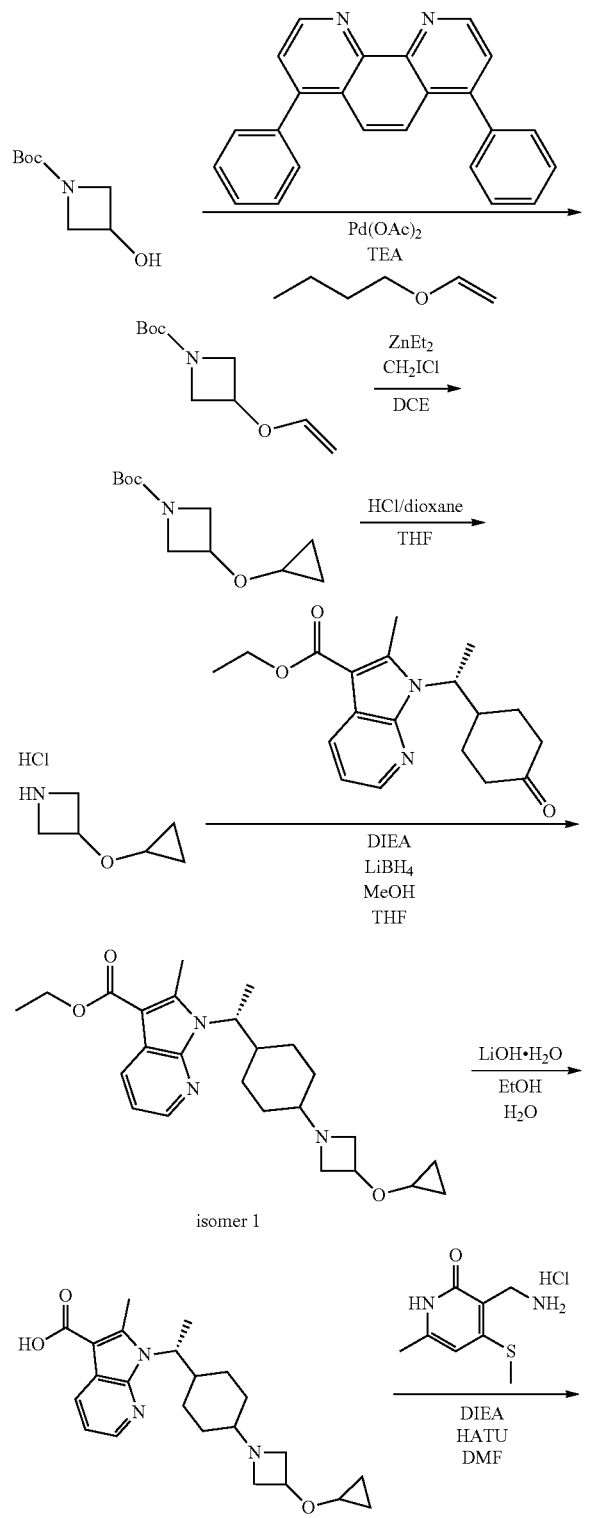

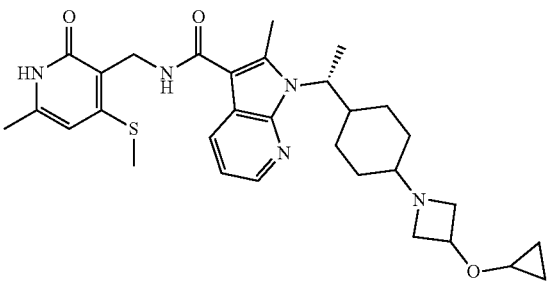

Step 1: tert-Butyl 3-vinyloxyazetidine-1-carboxylate

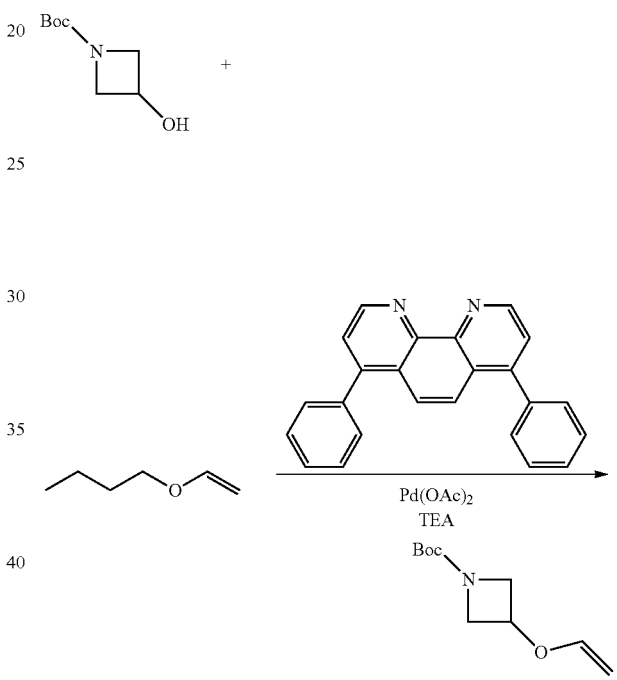

To a solution of tert-butyl 3-hydroxyazetidine-1-carboxylate (1.5 g, 8.66 mmol, 1 eq) in 1-vinyloxybutane (13.08 g, 130.61 mmol, 16.79 mL, 15.08 eq) was added TEA (381.68 mg, 3.77 mmol, 525 uL, 0.44 eq), 4,7-diphenyl-1,10-phenanthroline (120 mg, 361 umol, 0.04 eq) and Pd(OAc)$_2$ (90 mg, 400.87 umol, 0.046 eq). The mixture was purged with N$_2$ for 5 min and stirred at 80° C. for 2 hours under microwave irradiation. TLC showed desired compound was detected. The reaction was repeated 3 times, and the three batches were combined, the mixture was filtered and concentrated under reduced pressure to give a crude residue which was purified by flash silica gel chromatography (ISCO®; 80 g SepaFlash® Silica Flash Column, eluent of 0-20% ethyl acetate/petroleum ether gradient @ 50 mL/min). tert-Butyl 3-vinyloxyazetidine-1-carboxylate (3.5 g, 17.57 mmol, 67.61% yield) was obtained as colorless oil.

$^1$H NMR (400 MHz, CDCl$_3$) δ 6.37 (dd, J=14.4, 6.8 Hz, 1H), 4.59 (tt, J=6.4, 4.0 Hz, 1H), 4.17 (dd, J=10.4, 6.4 Hz, 2H), 4.05-4.10 (m, 1H), 3.96 (dd, J=14.4, 2.4 Hz, 1H), 3.90 (dd, J=10.4, 4.4 Hz, 2H), 1.44 (s, 9H).

Step 2: tert-Butyl 3-(cyclopropoxy)azetidine-1-carboxylate

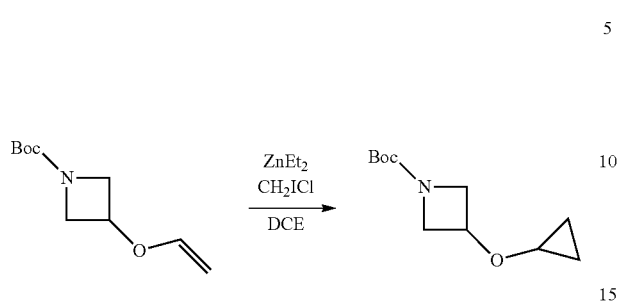

A solution of tert-butyl 3-vinyloxyazetidine-1-carboxylate (1.5 g, 7.53 mmol, 1 eq) and chloro(iodo)methane (4.42 g, 25.05 mmol, 1.82 mL, 3.33 eq) in DCE (20 mL) was cooled to −5° C. Diethylzinc (1 M in toluene, 12.12 mL, 1.61 eq) was added to the solution dropwise at −5° C., and the reaction mixture was stirred at 25° C. for 0.5 hour. The reaction was quenched with $NH_4Cl$ solution (10 mL) at 0° C., concentrated $NH_4OH$ solution (20 mL) was added, and the mixture was extracted with MTBE 45 mL (15 mL×3). The organic layers were washed with $NH_4Cl$ solution (15 mL), dried over $Na_2SO_4$, filtered and concentrated under reduced pressure. The residue was purified by flash silica gel chromatography (ISCO®; 12 g SepaFlash® Silica Flash Column, eluent of 020% ethyl acetate/petroleum ether gradient @12 m/min). tert-Butyl 3-(cyclopropoxy)azetidine-1-carboxylate (220 mg, 1.03 mmol, 13.70% yield) was obtained as a colorless oil.

$^1$H NMR (400 MHz, $CDCl_3$) δ 4.32 (tt, J=6.4, 4.4 Hz, 1H), 4.03-4.15 (m, 2H), 3.85 (dd, J=10.0, 4.4 Hz, 2H), 3.24 (tt, J=6.0, 2.8 Hz, 1H), 1.43 (s, 9H), 0.55-0.64 (m, 2H), 0.44-0.52 (m, 2H).

Step 3: 3-(Cyclopropoxy)azetidine hydrochloride

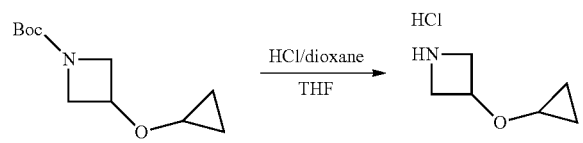 [SMILES: Cl ; CC(C)(C)OC(=O)N1CC(OC2CC2)C1 ; C1CC1OC1CNC1 ; "THF"]

HCl/dioxane (4 M, 4.80 mL, 13.65 eq) was added dropwise at 0° C. to a solution of tert-butyl 3-(cyclopropoxy)azetidine-1-carboxylate (300 mg, 1.41 mmol, 1 eq) in THF (2 mL). The reaction was stirred at 25° C. for 3 hours, diluted with i-PrOH (20 mL) and concentrated under reduced pressure to give 3-(cyclopropoxy)azetidine hydrochloride (200 mg, crude) as a yellow oil.

$^1$H NMR (400 MHz, $CD_3OD$) δ 4.39-4.54 (m, 1H), 4.19 (br dd, J=11.2, 6.8 Hz, 2H), 3.89 (br dd, J=10.8, 5.2 Hz, 2H), 3.25-3.33 (m, 1H), 0.46-0.55 (m, 2H), 0.37-0.46 (m, 2H).

Step 4: Ethyl 1-[(1R)-1-[4-[3-(cyclopropoxy)azetidin-1-yl]cyclohexyl]ethyl]-2-methyl-pyrrolo[2,3-b]pyridine-3-carboxylate

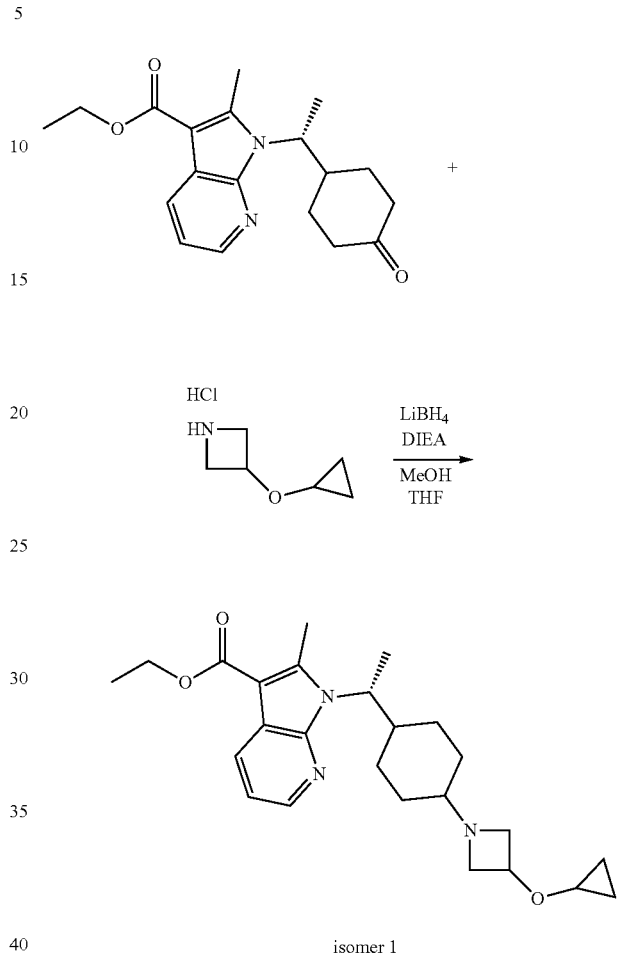

isomer 1

A mixture of 3-(cyclopropoxy)azetidine hydrochloride (850 mg, 5.68 mmol, 3.73 eq) and DIEA (816 mg, 6.32 mmol, 1.1 mL, 4.15 eq) in MeOH (6 mL) was stirred at 20° C. for 1 hr. Ethyl 2-methyl-1-[(1R)-1-(4-oxocyclohexyl)ethyl]pyrrolo[2,3-b]pyridine-3-carboxylate (500 mg, 1.52 mmol, 1 eq) in THF (2 mL) was added, and the mixture stirred at 20° C. for 1.5 h. To the reaction mixture was added $LiBH_4$ (73 mg, 3.35 mmol, 2.2 eq) at −78° C. and stirring continued at −78° C. for 30 min. LCMS showed desired compound. The reaction mixture was quenched by the addition of saturated aqueous $NH_4Cl$ (100 mL) and extracted with EtOAc (30 mL×2). The organic phase was washed with brine (30 mL), dried over anhydrous $Na_2SO_4$, and concentrated. The residue was purified by column chromatography ($SiO_2$, petroleum ether/ethyl acetate=1/1 to 0:1) to give ethyl 1-[(1R)-1-[4-[3-(cyclopropoxy)azetidin-1-yl]cyclohexyl]ethyl]-2-methyl-pyrrolo[2,3-b]pyridine-3-carboxylate isomer 1 (450 mg, 1.06 mmol, 69.45% yield, 100% purity) as yellow oil [LCMS (M+H$^+$) calcd. 462.2; found 462.1] and ethyl 1-[(1R)-1-[4-[3-(cyclopropoxy)azetidin-1-yl]cyclohexyl]ethyl]-2-methyl-pyrrolo[2,3-b]pyridine-3-carboxylate isomer 2 (40 mg, 62.04 umol, 4.07% yield, 66% purity) as yellow oil [LCMS (M+H$^+$) calcd. 462.2; found 462.1].

Step 5: 1-[(1R)-1-[4-[3-(cyclopropoxy)azetidin-1-yl]cyclohexyl]ethyl]-2-methyl-pyrrolo[2,3-b]pyridine-3-carboxylic Acid (Single Isomer)

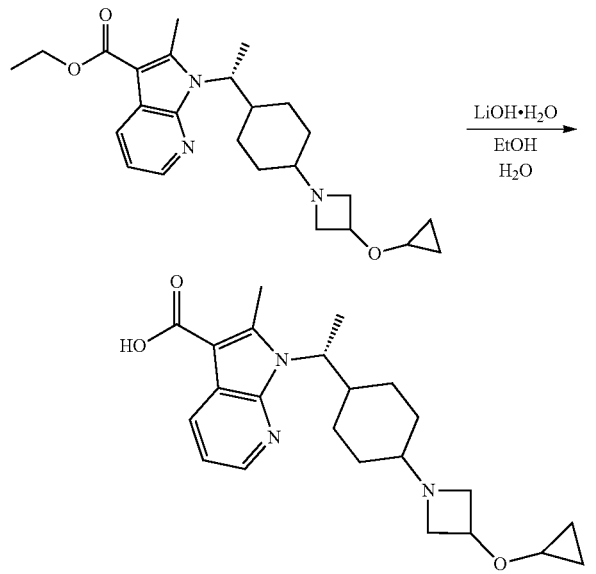

To a solution of ethyl 1-[(1R)-1-[4-[3-(cyclopropoxy)azetidin-1-yl]cyclohexyl]ethyl]-2-methyl-pyrrolo[2,3-b]pyridine-3-carboxylate isomer 1 (120 mg, 281.98 umol, 1 eq) in EtOH (1 mL) was added LiOH.H₂O (112.5 mg, 2.68 mmol, 9.51 eq) in H₂O (0.2 mL). The mixture was stirred at 80° C. for 16 hours. The mixture was concentrated, diluted with H₂O (5 mL) and pH adjusted to 6 with citric acid. The solution was extracted with DCM (10 mL×3). The combined organic layers were dried over Na₂SO₄, filtered and concentrated under reduced pressure to give 1-[(1R)-1-[4-[3-(cyclopropoxy)azetidin-1-yl]cyclohexyl]ethyl]-2-methyl-pyrrolo[2,3-b]pyridine-3-carboxylic acid single isomer (100 mg, crude) as a yellow oil.

LCMS (M+H⁺) m/z: calcd 398.24; found 398.1.

Step 6: 1-[(1R)-1-[4-[3-(Cyclopropoxy)azetidin-1-yl]cyclohexyl]ethyl]-2-methyl-N-[(6-methyl-4-methylsulfanyl-2-oxo-1H-pyridin-3-yl)methyl]pyrrolo[2,3-b]pyridine-3-carboxamide (Single Isomer)

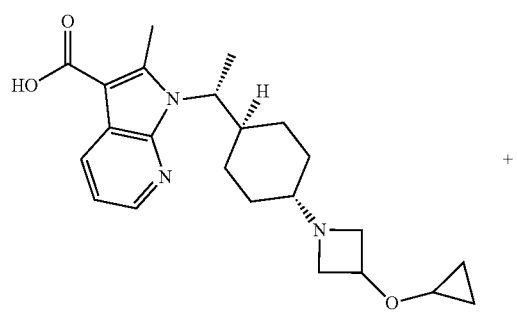

+

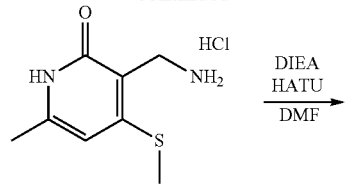

To a solution of 1-[(1R)-1-[4-[3-(cyclopropoxy)azetidin-1-yl]cyclohexyl]ethyl]-2-methyl-pyrrolo[2,3-b]pyridine-3-carboxylic acid (100 mg, 251.57 umol, 1 eq) in DMF (2 mL) was added DIEA (163 mg, 1.26 mmol, 220 uL, 5.02 eq) and HATU (115 mg, 302.45 umol, 1.2 eq). The mixture was stirred at 25° C. for 0.5 hour. 3-(Aminomethyl)-6-methyl-4-methylsulfanyl-1H-pyridin-2-one hydrochloride (85 mg, 385.10 umol, 1.53 eq) was added to the mixture and stirred at 25° C. for 2 hours. The reaction mixture was filtered and the filtrate was purified by prep-HPLC (column: Waters Xbridge 150*25 5u; mobile phase: [water (0.05% ammonia hydroxide v/v)-ACN]; B %: 38%-68%, 6.5 min. Column Temp: 30° C.) to give 1-[(1R)-1-[4-[3-(cyclopropoxy)azetidin-1-yl]cyclohexyl]ethyl]-2-methyl-N-[(6-methyl-4-methylsulfanyl-2-oxo-1H-pyridin-3-yl)methyl]pyrrolo[2,3-b]pyridine-3-carboxamide single isomer (53.3 mg, 94.55 umol, 37.58% yield, 100% purity) as a white solid.

¹H NMR (400 MHz, CD₃OD) δ 8.19 (br d, J=4.0 Hz, 1H), 8.10 (br d, J=7.6 Hz, 1H), 7.12 (br dd, J=7.2, 4.8 Hz, 1H), 6.32 (s, 1H), 4.61 (s, 2H), 4.20 (m, 1H), 4.09 (br s, 1H), 3.62 (br t, J=6.8 Hz, 1H), 3.56 (br t, J=6.8 Hz, 1H), 3.24-3.31 (m, 1H), 2.91-3.03 (m, 2H), 2.72-2.75 (m, 1H), 2.67 (br s, 3H), 2.55 (s, 3H), 2.32 (s, 3H), 2.14 (br d, J=12.0 Hz, 1H), 2.05 (br s, 1H), 1.94 (br d, J=9.6 Hz, 1H), 1.57-1.74 (m, 4H), 1.03-1.18 (m, 2H), 0.95 (br s, 1H), 0.71-0.92 (m, 2H), 0.49-0.56 (m, 2H), 0.42-0.48 (m, 2H).

LCMS (M+H⁺) m/z: calcd 564.29; found 564.3.

Synthesis of 2-methyl-N-((6-methyl-4-(methylthio)-2-oxo-1,2-dihydropyridin-3-yl)methyl)-1-((R)-1-(4-((3-(trifluoromethyl)oxetan-3-yl)amino)cyclohexyl)ethyl)-1H-indole-3-carboxamide (Single Isomer) (Example 130)
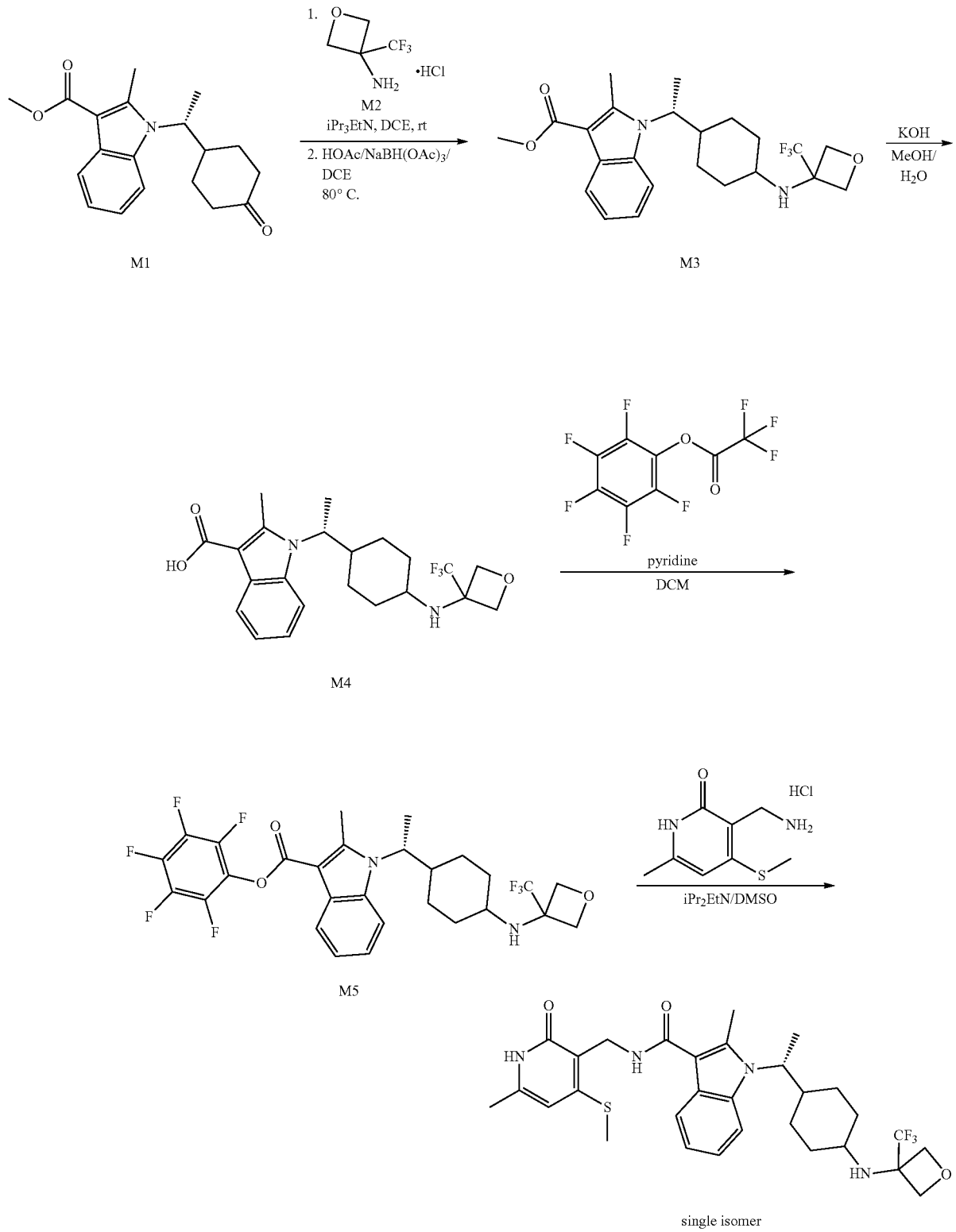

Step 1: Synthesis of methyl 2-methyl-1-((R)-1-(4-((3-(trifluoromethyl)oxetan-3-yl)amino)cyclohexyl)ethyl)-1H-indole-3-carboxylate (Single Isomer)

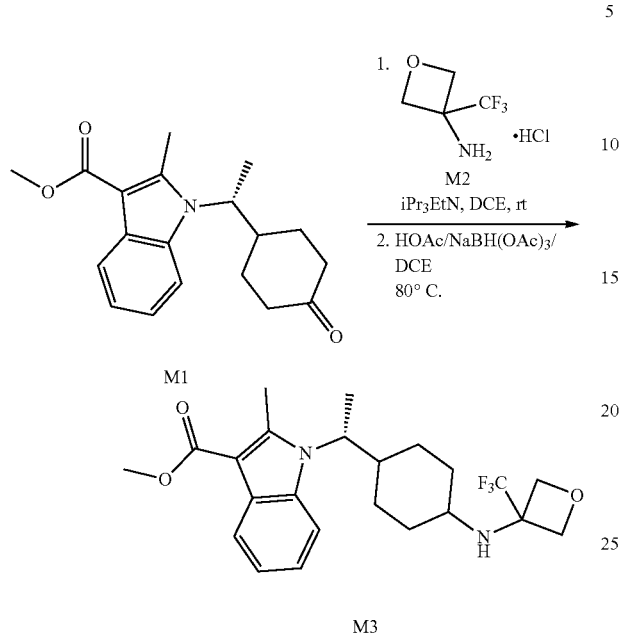

Step 2: Synthesis of 2-methyl-1-((R)-1-(4-((3-(trifluoromethyl)oxetan-3-yl)amino)cyclohexyl)ethyl)-1H-indole-3-carboxylic Acid (Single Isomer)

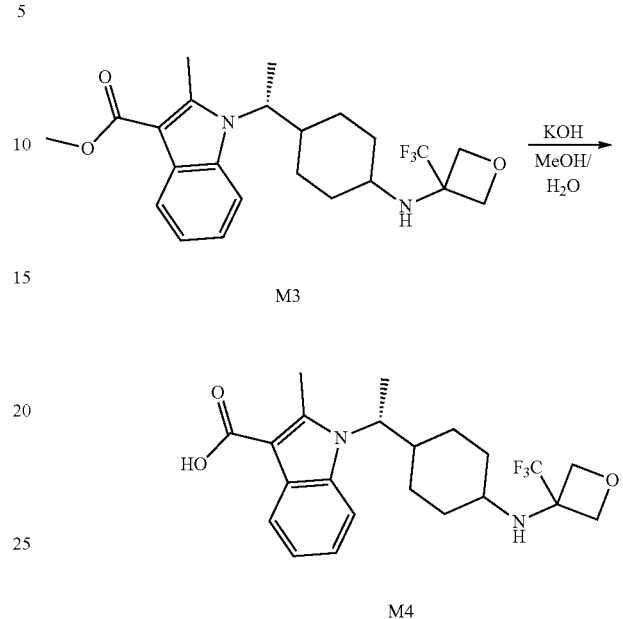

A mixture of [3-(trifluoromethyl)oxetan-3-yl]amine hydrochloride (735 mg, 4.14 mmol) and diisopropylethylamine (754 μL, 4.34 mmol) in dichloroethane (10.3 mL) was stirred at 25° C. for 0.5 h under nitrogen atmosphere. To the reaction was added methyl 2-methyl-1-[(1R)-1-(4-oxocyclohexyl)ethyl]-1H-indole-3-carboxylate (650 mg, 2.07 mmol) and acetic acid (236 μL, 4.14 mmol). This mixture was then stirred at 80° C. for 45 min (mixture now clear light yellow). Then sodium triacetoxyborohydride (438 mg, 2.07 mmol) was added into the reaction mixture and stirred at 80° C. The mixture was diluted with saturated sodium bicarbonate (3 mL) and water (10 mL), extracted with dichloromethane (20 mL×3). The combined organic layer was washed with brine (20 mL), dried over sodium sulfate, filtered and concentrated. The crude was purified by column chromatography on silica gel to give methyl 2-methyl-1-((R)-1-(4-((3-(trifluoromethyl)oxetan-3-yl)amino)cyclohexyl)ethyl)-1H-indole-3-carboxylate (single isomer) (651 mg, 1.17 mmol, 57% yield) as a white solid.

LCMS [M+H]$^+$ m/z: calc'd 438.22; found 439.2.

To a solution of methyl 2-methyl-1-((R)-1-(4-((3-(trifluoromethyl)oxetan-3-yl)amino)cyclohexyl)ethyl)-1H-indole-3-carboxylate single isomer (651 mg, 1.17 mmol, 1.0 equiv) in methanol (3 mL) and water (1.5 mL) was added KOH (786 mg, 14.0 mmol, 12 equiv). The mixture was stirred at 80° C. for 12 h. The reaction mixture was concentrated. Dichloromethane (15 mL) and water (10 mL) were added, and the mixture was adjusted to pH=5-6 with hydrochloric acid (1 M) solution. The mixture was extracted with dichloromethane (20 mL*3). The organic layer was dried by anhydrous sodium sulfate, filtered and concentrated under vacuum to give 2-methyl-1-((R)-1-((1r,4R)-4-((3-(trifluoromethyl)oxetan-3-yl)amino)cyclohexyl)ethyl)-1H-indole-3-carboxylic acid (500 mg, crude), as a white solid. LCMS [M+H]$^+$ m/z: calc'd 425.21; found 425.3.

Step 3: Synthesis of perfluorophenyl 2-methyl-1-((R)-1-(4-((3-(trifluoromethyl)oxetan-3-yl)amino)cyclohexyl)ethyl)-1H-indole-3-carboxylate (Single Isomer)

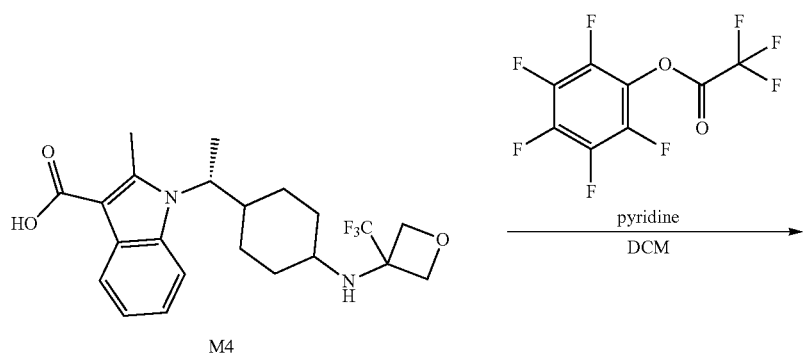

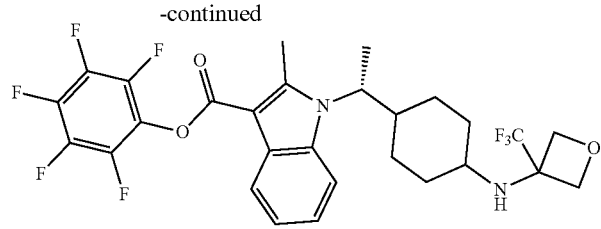

M5

To a stirred solution of 2-methyl-1-[(1R)-1-[4-{[3-(trifluoromethyl)oxetan-3-yl]amino}cyclohexyl]ethyl]-1H-pyrrolo[2,3-b]pyridine-3-carboxylic acid single isomer (500 mg, 1178 μmol, 1.0 equiv) in dichloromethane (4.68 mL) was added pyridine (236 μL, 2.94 mmol, 2.5 equiv) followed by dropwise addition of 2,3,4,5,6-pentafluorophenyl 2,2,2-trifluoroacetate (403 μL, 2.35 mmol, 2.0 equiv). This mixture was stirred for 30 min at which time the starting material was consumed. The reaction was stopped by concentration under reduced pressure. The crude product was directly used in the next step. LCMS [M+H]$^+$ m/z: calc'd 591.19; found 591.14.

Step 4: Synthesis of 2-methyl-N-((6-methyl-4-(methylthio)-2-oxo-1,2-dihydropyridin-3-yl)methyl)-1-((R)-1-(4-((3-(trifluoromethyl)oxetan-3-yl)amino)cyclohexyl)ethyl)-1H-indole-3-carboxamide (Single Isomer)

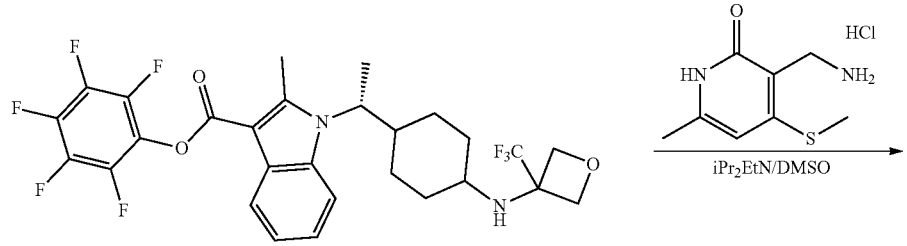

M5

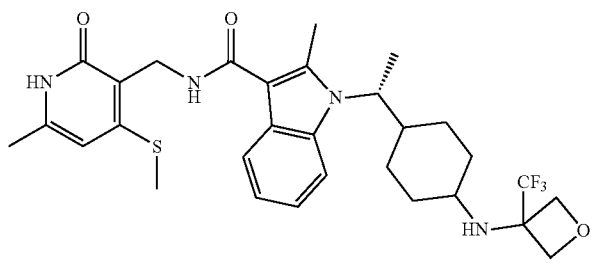

single isomer

To a solution of 2,3,4,5,6-pentafluorophenyl 2-methyl-1-[(1R)-1-(4-{[3-(trifluoromethyl)oxetan-3-yl]amino}cyclohexyl)ethyl]-1H-indole-3-carboxylate single isomer (758 mg, 1158 μmol, 1.0 equiv) in dimethyl sulfoxide (5 mL) was added 3-(aminomethyl)-6-methyl-4-(methylsulfanyl)-1,2-dihydropyridin-2-one (755 mg, 4.10 mmol, 3.5 equiv) followed by ethylbis(propan-2-yl)amine (218 μL, 1.27 mmol, 1.1 equiv). The reaction was stirred overnight at room temperature, followed by heating at 50° C. for 1 h. The reaction was then diluted with water (10 mL), extracted with dichloromethane (20 mL×4). The combined organic layer was washed with brine (20 mL), dried over sodium sulfate, filtered and concentrated. The crude mixture was purified by column chromatography on silica gel to give 2-methyl-N-{[6-methyl-4-(methylsulfanyl)-2-oxo-1,2-dihydropyridin-3-yl]methyl}-1-[(1R)-1-(4-{[3-(trifluoromethyl)oxetan-3-yl]amino}cyclohexyl)ethyl]-1H-indole-3-carboxamide (single isomer) (415 mg, 0.703 mmol, 61% yield) as a white solid. LCMS [M+H]+ m/z: calc'd 591.26; found 591.3. 1H NMR (400 MHz, CDCl3) δ 12.78 (br. s., 1H), 7.84 (d, J=7.8 Hz, 1H), 7.45 (d, J=8.3 Hz, 1H), 7.33 (br. s., 1H), 7.14-6.98 (m, 2H), 6.01 (s, 1H), 4.81-4.62 (m, 4H), 4.49 (t, J=7.8 Hz, 2H), 4.11-3.97 (m, 1H), 2.65 (d, J=9.8 Hz, 1H), 2.48 (s, 3H), 2.21 (s, 3H), 2.09 (d, J=12.2 Hz, 1H), 1.95 (d, J=11.7 Hz, 1H), 1.66-1.55 (m, 6H), 1.31-1.18 (m, 2H), 1.18-1.09 (m, 1H), 1.04 (d, J=13.2 Hz, 1H), 0.98-0.90 (m, 1H), 0.90-0.75 (m, 2H).

The following examples were synthesized using substantially similar procedures as described above, and using appropriate starting materials.

| Name | Ex. # | LCMS | 1H-NMR |
|---|---|---|---|
| (R)-1-(1-hydroxypropan-2-yl)-2-methyl-N-((6-methyl-4-(methylthio)-2-oxo-1,2-dihydropyridin-3-yl)methyl)-1H-indole-3-carboxamide | 31 | (M + H+) m/z: calcd 400.51, found 400.3. | 1H NMR (400 MHz, METHANOL-d4) δ = 7.73 (d, J = 7.3 Hz, 1H), 7.54 (d, J = 7.8 Hz, 1H), 7.20-7.02 (m, 2H), 6.47 (s, 1H), 4.70 (br dd, J = 7.1, 14.4 Hz, 1H), 4.62 (s, 2H), 4.21-4.09 (m, 1H), 3.88 (dd, J = 5.4, 11.7 Hz, 1H), 2.67 (s, 3H), 2.58 (s, 3H), 2.36 (s, 3H), 1.59 (d, J = 7.3 Hz, 3H) |
| (R)-1-(1-methoxypropan-2-yl)-2-methyl-N-((6-methyl-4-(methylthio)-2-oxo-1,2-dihydropyridin-3-yl)methyl)-1H-indole-3-carboxamide | 32 | (M + H+) m/z: calcd 414.53, found 414.2. | 1H NMR (400 MHz, DMSO-d6) δ = 11.78-11.57 (m, 1H), 7.73 (d, J = 7.8 Hz, 1H), 7.68 (br s, 1H), 7.58 (d, J = 7.8 Hz, 1H), 7.12-7.00 (m, 2H), 6.14 (s, 1H), 4.77 (br d, J = 5.4 Hz, 1H), 4.40 (br d, J = 2.9 Hz, 2H), 3.91 (br t, J = 9.5 Hz, 1H), 3.79 (br s, 2H), 3.67 (dd, J = 5.1, 10.0 Hz, 1H), 3.16 (s, 3H), 2.61 (s, 3H), 2.48 (s, 3H), 2.19 (s, 3H), 1.52 (d, J = 7.3 Hz, 3H) |
| (R)-1-(1-ethoxypropan-2-yl)-2-methyl-N-((6-methyl-4-(methylthio)-2-oxo-1,2-dihydropyridin-3-yl)methyl)-1H-indole-3-carboxamide | 33 | (M + H+) m/z: calcd 528.56, found 428.2. | 1H NMR (400 MHz, METHANOL-d4) δ = 7.79-7.68 (m, 1H), 7.53 (d, J = 8.3 Hz, 1H), 7.17-6.95 (m, 2H), 6.34 (s, 1H), 4.82-4.74 (m, 2H), 4.61 (s, 2H), 4.00 (t, J = 9.3 Hz, 1H), 3.79 (dd, J = 4.9, 10.3 Hz, 1H), 3.48-3.37 (m, 1H), 2.91-2.77 (m, 1H), 2.65 (s, 3H), 2.54 (s, 3H), 2.31 (s, 3H), 1.60 (d, J = 7.3 Hz, 3H), 1.01 (t, J = 6.8 Hz, 3H) |
| (S)-2-methyl-N-((6-methyl-4-(methylthio)-2-oxo-1,2-dihydropyridin-3-yl)methyl)-1-(1-(2-methylpyrimidin-5-yl)ethyl)-1H-indole-3-carboxamide | 34 | (M + H+) m/z: calcd 462.19; found 462.3 | 1H NMR (400 MHz, CDCl3) δ 12.52 (brs, 1H), 8.40 (s, 2H), 7.84 (d, J = 7.6 Hz, 1H), 7.44-7.43 (m, 1H), 7.04-6.97 (m, 2H), 6.91 (d, J = 8.0 Hz, 1H), 6.01 (s, 1H), 5.84-5.79 (m, 1H), 4.75-4.74 (m, 2H), 2.77 (s, 3H), 2.71 (s, 3H), 2.45 (s, 3H), 2.20 (s, 3H), 1.98 (d, J = 7.2 Hz, 3H). |
| (R)-2-methyl-N-((6-methyl-4-(methylthio)-2-oxo-1,2-dihydropyridin-3-yl)methyl)-1-(1-(2-methylpyrimidin-5-yl)ethyl)-1H-indole-3-carboxamide | 35 | (M + H+) m/z: calcd 462.19; found 462.3 | 1H NMR (400 MHz, CDCl3) δ 12.68 (brs, 1H), 8.40 (s, 2H), 7.84 (d, J = 8.0 Hz, 1H), 7.43-7.42 (m, 1H), 7.03-6.97 (m, 2H), 6.90 (d, J = 8.0 Hz, 1H), 6.01 (s, 1H), 5.84-5.79 (m, 1H), 4.74 (d, J = 4.0 Hz, 2H), 2.77 (s, 3H), 2.71 (s, 3H), 2.49 (s, 3H), 2.19 (s, 3H), 1.98 (d, J = 7.2 Hz, 3H). |
| 1-((R)-1-(4-hydroxycyclohexyl)ethyl)-2-methyl-N-((6-methyl-4-(methylthio)-2-oxo-1,2-dihydropyridin-3-yl)methyl)-1H- | 36 isomer 1 | (M + H+) m/z: calcd 469.22.; found 469.1 | 1H NMR (400 MHz, CD3OD) δ 8.18 (dd, J = 1.6, 4.4 Hz, 1H), 8.08 (d, J = 7.6 Hz, 1H), 7.10 (dd, J = 4.0, 7.6 Hz, 1H), 6.29 (s, 1H), 4.63 (br s, 2H), 4.06 (br s, 1H), 3.51-3.38 (m, 1H), 2.83-2.70 (m, 1H), |

| Name | Ex. # | LCMS | ¹H-NMR |
|---|---|---|---|
| pyrrolo[2,3-b]pyridine-3-carboxamide | | | 2.65 (br s, 3H), 2.53 (s, 3H), 2.30 (s, 3H), 2.13-1.89 (m, 2H), 1.75-1.59 (m, 4H), 1.37-1.25 (m, 1H), 1.22-1.10 (m, 1H), 1.08-0.81 (m, 3H) |
| 1-((R)-1-(4-hydroxycyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 36 isomer 2 | (M + H+) m/z: calcd: 469.22.; found 469.1 | 1H NMR (400 MHz, CD3OD) δ 8.16 (d, J = 3.6 Hz, 1H), 8.07 (d, J = 8.0 Hz, 1H), 7.08 (dd, J = 4.8, 7.6 Hz, 1H), 6.28 (s, 1H), 4.58 (s, 2H), 4.28-4.03 (m, 1H), 3.86 (br s, 1H), 2.87 (br d, J = 16.8 Hz, 1H), 2.70-2.60 (m, 3H), 2.52 (s, 3H), 2.29 (s, 3H), 1.86-1.72 (m, 2H), 1.64 (br s, 3H), 1.59-1.44 (m, 3H), 1.42-1.07 (m, 2H), 0.72 (br s, 1H) |
| 1-((R)-1-((3R,4R)-3-fluoropiperidin-4-yl)ethyl)-2-methyl-N-((6-methyl-4-(methylthio)-2-oxo-1,2-dihydropyridin-3-yl)methyl)-1H-indole-3-carboxamide | 37 | (M + H+) m/z: calcd 471.22; found 471.3. | 1H NMR (400 MHz, CD3OD) δ 7.75 (d, J = 7.5 Hz, 1H), 7.59 (d, J = 8.3 Hz, 1H), 7.19-7.06 (m, 2H), 6.32 (s, 1H), 4.62-4.42 (m, 3H), 3.28 (br d, J = 6.3 Hz, 2H), 2.78-2.66 (m, 2H), 2.65-2.59 (m, 4H), 2.56 (s, 3H), 2.33 (s, 4H), 1.76 (dd, J = 2.6, 6.9 Hz, 3H), 1.03 (br s, 1H) |
| 1-((1R)-1-((3S)-3-fluoropiperidin-4-yl)ethyl)-2-methyl-N-((6-methyl-4-(methylthio)-2-oxo-1,2-dihydropyridin-3-yl)methyl)-1H-indole-3-carboxamide | 38 | (M + H+) m/z: calcd 471.22; found 471.2. | 1H NMR (400 MHz, MeOD) δ 7.78 (d, J = 7.6 Hz, 1H), 7.67 (d, J = 8.0 Hz, 1H), 7.24-7.10 (m, 2H), 5.41-5.29 (m, 1H), 4.66-4.60 (m, 3H), 4.00-3.73 (m, 2H), 3.50-3.42 (m, 2H), 3.21-3.18 (m, 2H), 3.21-3.18 (m, 2H), 3.04-2.81 (m, 3H), 2.74-2.71 (m, 3H), 2.56 (s, 3H), 1.78-1.66 (m, 3H), 1.40-1.29 (m, 2H), 0.95-0.90 (m, 1H) |
| (R)-1-(1-(1-cyanopiperidin-4-yl)ethyl)-2-methyl-N-((6-methyl-4-(methylthio)-2-oxo-1,2-dihydropyridin-3-yl)methyl)-1H-indole-3-carboxamide | 39 | (M + H+) m/z: calcd 478.23; found 478.1 | 1H NMR (400 MHz, CD3OD) δ 7.73 (br d, J = 7.5 Hz, 1H), 7.50-7.50 (m, 1H), 7.58 (br d, J = 7.5 Hz, 1H), 7.17-7.05 (m, 2H), 6.30 (s, 1H), 4.63-4.60 (m, 2H), 4.23 (br dd, J = 7.0, 10.5 Hz, 1H), 3.58-3.33 (m, 1H), 3.25-3.08 (m, 1H), 3.10- 3.07 (m, 1H), 2.81 (br t, J = 11.5 Hz, 1H), 2.62 (s, 3H), 2.54 (s, 3H), 2.44 (br d, J = 11.5 Hz, 1H), 2.31 (s, 3H), 2.19-1.99 (m, 1H), 1.63 (br d, J = 7.0 Hz, 3H), 1.59-1.38 (m, 1H), 1.33-1.09 (m, 1H), 0.88 (br d, J = 14.5 Hz, 1H). |
| 1-((1R)-1-(4-hydroxycyclohexyl)ethyl)-2,6-dimethyl-N-((6-methyl-4-(methylthio)-2-oxo-1,2-dihydropyridin-3-yl)methyl)-1H-pyrrolo[2,3-b]pyridine-3-carboxamide | 40 | (M + H+) m/z: calcd 483.62, found 483.3. | 1H NMR (400 MHz, METHANOL-d4) δ = 8.93-8.84 (m, 1H), 8.65 (tt, J = 1.5, 7.8 Hz, 1H), 8.14-8.08 (m, 1H), 8.07-7.87 (m, 1H), 7.04 (br d, J = 4.9 Hz, 1H), 6.43 (s, 1H), 6.26 (s, 1H), 4.59 (s, 1H), 4.44 (s, 1H), 3.88 (br s, 1H), 3.55-3.40 (m, 1H), 2.65 (s, 4 H), 2.61-2.55 (m, 4H), 2.51 (s, 1H), 2.34 (s, 2H), 2.29 (s, 1H), 2.24-1.95 (m, 2H), 1.92-1.48 (m, 5 H), 1.46-0.79 (m, 4H) |
| 7-((R)-1-(4-methoxycyclohexyl)ethyl)-6-methyl-N-((6-methyl-4-(methylthio)-2-oxo-1,2-dihydropyridin-3-yl)methyl)-7H-pyrrolo[2,3-d]pyrimidine-5-carboxamide | 41 isomer 1 | (M + H+) m/z: calcd 484.23; found 484.2 | 1H NMR (400 MHz, CD3OD) δ 9.02 (s, 1H), 8.72 (s, 1H), 6.31 (s, 1H), 4.60 (s, 2H), 4.17 (br s, 1H), 3.31 (s, 3H), 3.20-3.07 (m, 1H), 2.69 (br s, 3H), 2.60-2.52 (m, 3H), 2.31 (s, 3H), 2.21-2.10 (m, 2H), 1.88 (br s, 1H), 1.68 (br d, J = 6.5 Hz, 3H), 1.34-1.16 (m, 3H), 0.96 (br s, 3H). |
| 7-((R)-1-(4-methoxycyclohexyl)ethyl)-6-methyl-N-((6-methyl-4-(methylthio)-2-oxo-1,2-dihydropyridin-3- | 41 isomer 2 | (M + H+) m/z: calcd 484.23; found 484.2 | 1H NMR (400 MHz, CD3OD δ 9.02 (s, 1H), 8.70 (s, 1H), 6.31 (s, 1H), 4.63-4.57 (m, 2H), 4.22 (br s, 1H), 3.42 (br s, 1H), 3.27 (s, 3H), 2.69 (s, 3H), 2.54 (s, 3H), |

-continued

| Name | Ex. # Example # | LCMS LCMS | ¹H-NMR NMR |
|---|---|---|---|
| yl)methyl)-7H-pyrrolo[2,3-d]pyrimidine-5-carboxamide | | | 2.31 (s, 3H), 2.02 (br d, J = 14.6 Hz, 1H), 1.85-1.78 (m, 1H), 1.77-1.71 (m, 1H), 1.67 (br d, J = 6.6 Hz, 3H), 1.56-1.40 (m, 2H), 1.35-1.05 (m, 3H), 0.69 (br d, J = 11.8 Hz, 1H). |
| 1-((R)-1-((3R,4R)-3-fluoro-1-methylpiperidin-4-yl)ethyl)-2-methyl-N-((6-methyl-4-(methylthio)-2-oxo-1,2-dihydropyridin-3-yl)methyl)-1H-indole-3-carboxamide | 42 | (M + H+) m/z: calcd 485.23; found 485.4. | 1H NMR (400 MHz, CD3OD) δ 7.76 (d, J = 8.0 Hz, 1H), 7.58 (d, J = 7.8 Hz, 1H), 7.23-7.10 (m, 2H), 6.33 (s, 1H), 4.68 (br d, J = 5.0 Hz, 2H), 4.58-4.51 (m, 1H), 3.17 (br dd, J = 5.3, 10.5 Hz, 2H), 2.88-2.72 (m, 1H), 2.65 (s, 2H), 2.56 (m, 6H), 2.33 (s, 3H), 2.29 (s, 3H), 2.14 (br dd, J = 6.0, 10.5 Hz, 1H), 1.76 (dd, J = 2.8, 7.0 Hz, 3H), 1.21-1.02 (m, 2H). |
| 1-((1R)-1-((3S)-3-fluoro-1-methylpiperidin-4-yl)ethyl)-2-methyl-N-((6-methyl-4-(methylthio)-2-oxo-1,2-dihydropyridin-3-yl)methyl)-1H-indole-3-carboxamide | 43 | (M + H+) m/z: calcd 485.23; found 485.1. | 1H NMR (400 MHz, CDCl3) δ 12.47 (brs, 1H), 7.88-7.85 (m, 1H), 7.38 (d, J = 7.6 Hz, 1H), 7.14-7.05 (m, 2H), 6.01 (s, 1H), 5.01-4.68 (m, 2H), 4.57-4.56 (m, 1H), 3.31-2.83 (m, 2H), 2.71 (s, 3H), 2.49 (s, 3H), 2.31-2.22 (m, 8H), 1.86-1.53 (m, 7H). |
| 6-fluoro-1-((R)-1-(4-hydroxycyclohexyl)ethyl)-2-methyl-N-((6-methyl-4-(methylthio)-2-oxo-1,2-dihydropyridin-3-yl)methyl)-1H-indole-3-carboxamide | 44 isomer 1 | (M + H+) m/z: calcd: 486.22; found 486.2. | 1H NMR (400 MHz, CDCl3) δ 7.68 (dd, J = 5.6, 8.6 Hz, 1H), 7.15 (d, J = 9.8 Hz, 1H), 6.92 (dt, J = 2.0, 9.0 Hz, 1H), 6.76 (br. s., 1H), 6.41 (s, 1H), 4.72 (d, J = 10.3 Hz, 2H), 4.11-3.96 (m, 1H), 3.60-3.46 (m, 1H), 2.66 (s, 2H), 2.56 (s, 3H), 2.46 (s, 3H), 2.09 (d, J = 8.3 Hz, 3H), 1.78 (d, J = 10.3 Hz, 1H), 1.58 (d, J = 7.3 Hz, 3H), 1.40-1.24 (m, 1H), 1.17-1.01 (m, 3H), 0.90-0.75 (m, 1H). |
| 6-fluoro-1-((R)-1-(4-hydroxycyclohexyl)ethyl)-2-methyl-N-((6-methyl-4-(methylthio)-2-oxo-1,2-dihydropyridin-3-yl)methyl)-1H-indole-3-carboxamide | 44 isomer 2 | (M + H+) m/z: calcd: 486.22; found 486.2. | 1H NMR (400 MHz, CDCl3) δ 7.70-7.60 (m, 1H), 7.16 (d, J = 10.3 Hz, 1H), 6.93 (d, J = 2.4 Hz, 1H), 6.72 (br. s., 1H), 6.48 (s, 1H), 4.72 (br. s., 2H), 4.19-4.09 (m, 1H), 4.04 (br. s., 1H), 2.72-2.62 (m, 2H), 2.57 (s, 3H), 2.50 (s, 3H), 2.21-2.05 (m, 2H), 1.93-1.75 (m, 3H), 1.64-1.49 (m, 4H), 1.40-1.28 (m, 1H), 1.25-1.12 (m, 1H), 1.12-1.03 (m, 0H), 0.85-0.75 (m, 1H). |
| (R)-1-(1-(4,4-difluorocyclohexyl)ethyl)-2-methyl-N-((6-methyl-4-(methylthio)-2-oxo-1,2-dihydropyridin-3-yl)methyl)-1H-indole-3-carboxamide | 45 | (M + H+) m/z: calcd 488.21: found 488.0 | 1H NMR (400 MHz, CDCl3) δ 12.01 (s, 1H), 7.83 (d, J = 8.0, 1H), 7.72 (d, J = 8.0, 1H), 7.28 (s, 1H), 7.08-7.02 (m, 2H), 5.98 (s, 1H), 4.75-4.64 (m, 2H), 4.11 (m, 1H), 2.83-2.70 (m, 3H), 2.46 (s, 3H), 2.29 (m, 1H), 2.20 (s, 3H), 2.08-2.05 (m, 2H), 1.85-1.80 (m, 2H), 1.61-1.60 (m, 4H), 1.23-1.18 (m, 2H), 1.10-1.04 (m, 2H) |
| (R)-1-(1-(4-(dimethylamino)phenyl)ethyl)-2-methyl-N-((6-methyl-4-(methylthio)-2-oxo-1,2-dihydropyridin-3-yl)methyl)-1H-indole-3-carboxamide | 46 | (M + H+) m/z: calcd 489.22; found 489.1. | 1H NMR (400 MHz, CDCl3) δ 7.74 (d, J = 8.0 Hz, 1H), 7.27-7.25 (m, 1H), 6.97-6.87 (m, 5H), 6.56 (d, J = 8.8 Hz, 2H), 5.93 (s, 1H), 5.73-5.67 (m, 1H), 4.67-4.65 (m, 2H), 2.84 (s, 6H), 2.66 (s, 3H), 2.40 (s, 3H), 2.13 (s, 3H), 1.80 (d, J = 6.8 Hz, 3H) |
| (S)-1-(1-(4-(dimethylamino)phenyl)ethyl)-2-methyl-N-((6-methyl-4-(methylthio)-2-oxo-1,2-dihydropyridin-3-yl)methyl)-1H-indole-3-carboxamide | 47 | (M + H+) m/z: calcd 489.22; found 489.1. | 1H NMR (400 MHz, CDCl3) δ 7.74 (d, J = 6.8 Hz, 1H), 7.29-7.26 (m, 1H), 6.98-6.87 (m, 5H), 6.57-6.55 (m, 2H), 5.92 (s, 1H), 5.72-5.67 (m, 1H), 4.67-4.62 (m, 2H), 2.83 (s, 6H), 2.66 (s, 3H), 2.40 (s, 3H), 2.17-2.12 (m, 3H), 1.81-1.79 (m, 3H). |

-continued

| Name | Ex. # | LCMS | ¹H-NMR |
|---|---|---|---|
| (R)-1-(1-(1-cyclopropylpiperidin-4-yl)ethyl)-2-methyl-N-((6-methyl-4-(methylthio)-2-oxo-1,2-dihydropyridin-3-yl)methyl)-1H-indole-3-carboxamide | 48 | (M + H+) m/z: calcd 493.26, found 493.3 | 1H NMR (400 MHz, DMSO-d6) δ = 11.65 (br. s., 2H), 8.90 (br. s., 2H), 7.85-7.43 (m, 3H), 7.20-6.90 (m, 2H), 6.12 (s, 1H), 4.64-4.46 (m, 0H), 4.38 (d, J= 2.0 Hz, 2H), 4.26-4.04 (m, 1H), 3.68-3.45 (m, 1H), 3.29 (d, J = 11.7 Hz, 1H), 3.22-2.84 (m, 2H), 2.83-2.61 (m, 2H), 2.56 (s, 2H), 2.46 (s, 2H), 2.35-2.22 (m, 0H), 2.22-2.09 (m, 3H), 2.06-1.89 (m, 0H), 1.56 (d, J = 6.4 Hz, 3H), 1.32-1.02 (m, 1H), 1.01-0.64 (m, 4H) |
| 2-methyl-N-((6-methyl-4-(methylthio)-2-oxo-1,2-dihydropyridin-3-yl)methyl)-1-((R)-1-(3-(oxetan-3-ylamino)cyclobutyl)ethyl)-1H-indole-3-carboxamide | 49 single isomer | (M + H+) m/z: calcd 495.24; found 495.1 | 1H NMR (400 MHz, CD3OD) δ 7.72 (br d, J = 8.0 Hz, 1H), 7.61-7.50 (m, 1H), 7.09 (br d, J = 5.0 Hz, 2H), 6.33 (s, 1H), 5.36 (br t, J = 4.5 Hz, 1H), 4.81-4.70 (m, 2H), 4.68-4.64 (m, 2H), 4.54-4.41 (m, 2H), 3.98-3.88 (m, 1H), 2.77-2.68 (m, 3H), 2.56 (s, 3H), 2.52-2.47 (m, 1H), 2.33 (s, 3H), 2.30 (br d, J = 3.0 Hz, 1H), 2.21 (t, J = 7.5 Hz, 1H), 2.18-2.12 (m, 1H), 2.05 (br d, J = 5.0 Hz, 1H), 1.92-1.89 (m, 1H), 1.60-1.52 (m, 3H) |
| (R)-7-(1-(1-cyclopropylpiperidin-4-yl)ethyl)-6-methyl-N-((6-methyl-4-(methylthio)-2-oxo-1,2-dihydropyridin-3-yl)methyl)-7H-pyrrolo[2,3-d]pyrimidine-5-carboxamide | 50 | (M + H+) m/z: calcd 495.25; found 495.5. | 1H NMR (400 MHz, CD3OD) δ 9.05 (s, 1H), 8.74 (s, 1H), 6.33 (s, 1H), 4.63 (br s, 1H), 4.61 (s, 2H), 3.42-3.34 (m, 4H), 3.17-2.89 (m, 1H), 2.72 (br s, 3H), 2.57 (s, 3H), 2.33 (s, 3H), 2.23 (br s, 1H), 1.73 (br d, J = 6.8 Hz, 3H), 1.55 (br s, 1H), 1.35-0.92 (m, 3H), 0.79 (br s, 4H). |
| 1-((R)-1-(4-(dimethylamino)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 51 isomer 1 | (M + H+) m/z: calcd 496.27; found 496.3 | 1H NMR (400 MHz, CD3OD) δ 8.19 (dd, J = 1.5, 4.8 Hz, 1H), 8.09 (br d, J = 8.0 Hz, 1H), 7.11 (dd, J = 4.8, 8.0 Hz, 1H), 6.31 (s, 1H), 4.61 (s, 2H), 4.10 (br s, 1H), 3.34 (br d, J = 1.6 Hz, 1H), 2.67 (br s, 3H), 2.55 (s, 3H), 2.32 (s, 3H), 2.27 (s, 6H), 2.24-2.15 (m, 2H), 2.11-2.01 (m, 1H), 1.79-1.60 (m, 4H), 1.40-1.26 (m, 1H), 1.17 (br d, J = 11.6 Hz, 1H), 1.03 (br d, J = 12.8 Hz, 2H), 0.89 (br d, J = 12.0 Hz, 1H) |
| 1-((R)-1-(4-(dimethylamino)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 51 isomer 2 | (M + H+) m/z: calcd 496.27; found 496.3 | 1H NMR (400 MHz, CD3OD) δ 8.17 (br s, 1H), 8.08 (d, J = 7.6 Hz, 1H), 7.09 (br s, 1H), 6.30 (s, 1H), 4.60 (s, 2H), 4.37 (br s, 1H), 3.33-3.32 (m, 1H), 2.71 (br s, 3H), 2.53 (s, 3H), 2.30 (s, 3H), 2.27 (s, 6H), 2.24-2.06 (m, 1H), 1.86-1.49 (m, 8H), 1.43-1.26 (m, 1H), 1.07 (br s, 1H), 0.92 (br s, 1H) |
| (R)-1-(1-(1-(2-hydroxyethyl)piperidin-4-yl)ethyl)-2-methyl-N-((6-methyl-4-(methylthio)-2-oxo-1,2-dihydropyridin-3-yl)methyl)-1H-indole-3-carboxamide | 52 | (M + H+) m/z: calcd 497.25; found 497.1. | 1H NMR (400 MHz, CDCl3) δ 12.44 (brs, 1H), 7.82 (d, J = 8.4 Hz, 1H), 7.43 (d, J = 8.0 Hz, 1H), 7.29-7.24 (m, 1H), 7.06-7.00 (m, 2H), 5.98 (s, 1H), 4.78-4.62 (m, 2H), 4.11-4.07 (m, 1H), 3.54 (s, 2H), 3.01-2.98 (m, 1H), 2.82-2.65 (m, 4H), 2.46-2.44 (m, 5H), 2.19 (s, 4H), 2.09-2.03 (m, 1H), 1.97-1.94 (m, 1H), 1.80-1.75 (m, 2H), 1.58-1.57 (m, 3H), 1.38-1.35 (m, 1H), 1.03-0.95 (m, 1H). |
| 5-chloro-1-((R)-1-(4-hydroxycyclohexyl)ethyl)-2-methyl-N-((6-methyl-4-(methylthio)-2-oxo-1,2-dihydropyridin-3-yl)methyl)-1H- | 53 isomer 1 | (M + Na+) m/z: calcd 503.18: found 503.1 | 1H NMR (400 MHz, CDCl3) δ 11.92 (s, 1H), 8.13 (d, J = 10.8 Hz, 2H), 7.32 (s, 1H), 6.05-6.02 (m, 1H), 4.71 (m, 2H), 3.51 (m, 1H), 2.74 (m, 2H), 2.52-2.46 (m, 3H), 2.29-2.26 (m, 3H), 2.07 (m, 2H), |

| Name | Ex. # | LCMS | ¹H-NMR |
|---|---|---|---|
| pyrrolo[2,3-b]pyridine-3-carboxamide | | | 1.75-1.73 (m, 1H), 1.63-1.59 (m, 3H), 1.43 (m, 1H), 1.31 (m, 1H), 1.05-0.97 (m, 3H), 0.94-0.81 (m, 1H). |
| 5-chloro-1-((R)-1-(4-hydroxycyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 53 isomer 2 | (M + Na+) m/z: calcd 503.18: found 503.1 | 1H NMR (400 MHz, CDCl3) δ 11.49 (s, 1H), 8.14 (d, J = 15.6 Hz, 2H), 7.34-7.32 (m, 1H), 6.02 (s, 1H), 4.68 (s, 2H), 3.99 (s, 2H), 2.76 (s, 3H), 2.50 (s, 3H), 2.29-2.27 (m, 3H), 1.81 (m, 2H), 1.63-1.61 (m, 3H), 1.33-1.12 (m, 4H), 0.74 (m, 1H). |
| (R)-2-methyl-N-((6-methyl-4-(methylthio)-2-oxo-1,2-dihydropyridin-3-yl)methyl)-1-(1-(2,2,2-trifluoroethyl)azetidin-3-yl)ethyl)-1H-indole-3-carboxamide | 54 | (M + H+) m/z: calcd 507.20; found 507.1. | 1H NMR (400 MHz, CD3OD) δ 7.69 (d, J = 8.0 Hz, 1H), 7.51 (d, J = 8.0 Hz, 1H), 7.08-7.04 (m, 2H), 6.28 (s, 1H), 5.32 (s, 1H), 4.59 (s, 2H), 3.36 (s, 2H), 3.12-3.05 (m, 4H), 2.83-2.80 (m, 1H), 2.69 (s, 3H), 2.52 (s, 3H), 2.29 (s, 3H), 1.52 (d, J = 8.0 Hz, 3H). |
| (S)-2-methyl-N-((6-methyl-4-(methylthio)-2-oxo-1,2-dihydropyridin-3-yl)methyl)-1-(1-(2,2,2-trifluoroethyl)azetidin-3-yl)ethyl)-1H-indole-3-carboxamide | 55 | (M + H+) m/z: calcd 507.20; found 507.3. | 1H NMR (400 MHz, CD3OD) δ 7.69 (d, J = 8.0 Hz, 1H), 7.51 (d, J = 8.0 Hz, 1H), 7.09-7.04 (m, 2H), 6.28 (s, 1H), 5.32 (s, 1H), 4.59 (s, 2H), 3.36 (s, 2H), 3.12-3.05 (m, 4H), 2.83-2.80 (m, 1H), 2.69 (s, 3H), 2.52 (s, 3H), 2.29 (s, 3H), 1.52 (d, J = 8.0 Hz, 3H). |
| 1-((R)-1-((3S,4R)-1-cyclopropyl-3-fluoropiperidin-4-yl)ethyl)-2-methyl-N-((6-methyl-4-(methylthio)-2-oxo-1,2-dihydropyridin-3-yl)methyl)-1H-indole-3-carboxamide | 56 | (M + H+) m/z: calcd 571.27; found 571.1 | 1H NMR (400 MHz, CDCl3) δ 13.00 (s, 1H), 7.88-7.85 (m, 1H), 7.40-7.32 (m, 2H), 7.11-7.02 (m, 2H), 6.00 (s, 1H), 4.98-4.55 (m, 3H), 3.86-2.84 (m, 3H), 2.70 (s, 3H), 2.48 (s, 3H), 2.42-2.38 (m, 1H), 2.20 (s, 3H), 2.10-1.82 (m, 2H), 1.65 (d, J = 7.2 Hz, 3H), 1.59-1.26 (m, 2H), 0.85-0.80 (m, 1H), 0.50-0.39 (m, 4H). |
| (R)-1-(1-(1-cyclopropylpiperidin-4-yl)ethyl)-6-fluoro-2-methyl-N-((6-methyl-4-(methylthio)-2-oxo-1,2-dihydropyridin-3-yl)methyl)-1H-indole-3-carboxamide | 57 | (M + H+) m/z: calcd: 511.25; found 511.3. | 1H NMR (400 MHz, CDCl3) δ 12.96-12.73 (m, 1H), 7.76 (dd, J = 5.4, 8.8 Hz, 1H), 7.35-7.28 (m, 1H), 7.14 (d, J = 10.3 Hz, 1H), 6.80 (t, J = 8.1 Hz, 1H), 6.02 (s, 1H), 4.80-4.63 (m, 2H), 4.07 (dd, J = 6.8, 10.3 Hz, 1H), 3.14 (d, J = 11.2 Hz, 1H), 2.84 (d, J = 11.7 Hz, 1H), 2.65 (s, 2H), 2.49 (s, 3H), 2.24-2.14 (m, 4H), 1.99-1.88 (m, 2H), 1.59-1.49 (m, 4H), 1.40-1.22(m, 2H), 1.11-0.97 (m, 1H), 0.92 (d, J = 12.7 Hz, 1H), 0.49-0.36 (m, 3H). |
| (R)-1-(1-(1-cyclopropylpiperidin-4-yl)ethyl)-5-fluoro-2-methyl-N-((6-methyl-4-(methylthio)-2-oxo-1,2-dihydropyridin-3-yl)methyl)-1H-pyrrolo[2,3-b]pyridine-3-carboxamide | 58 | (M + H+) m/z: calcd 512.66, found 512.3. | 1H NMR (400 MHz, METHANOL-d4) δ = 8.08 (s, 1H), 7.83 (dd, J = 2.7, 9.5 Hz, 1H), 6.30 (s, 1H), 4.58 (s, 2H), 3.13 (br d, J = 11.7 Hz, 1H), 2.85 (br d, J = 12.2 Hz, 1H), 2.66 (s, 3H), 2.54 (s, 3H), 2.31 (s, 2H), 2.29-2.21 (m, 1H), 2.07-1.90 (m, 2H), 1.73-1.54 (m, 4 H), 1.42-1.24 (m, 2H), 1.06 (dq, J = 4.2, 12.3 Hz, 1H), 0.86 (br d, J = 13.2 Hz, 1H), 0.54-0.28 (m, 4H) |
| (R)-1-(1-(1-(2,2-difluoroethyl)piperidin-4-yl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 59 | (M + H+) m/z: calcd: 518.23.; found 518.1 | 1H NMR (400 MHz, CD3OD) δ 8.16 (d, J = 3.6 Hz, 1H), 8.07 (d, J = 8.0 Hz, 1H), 7.08 (dd, J = 4.8, 8.0 Hz, 1H), 6.28 (s, 1H), 6.10-5.74 (m, 1H), 4.58 (s, 2H), 4.11 (br s, 1H), 3.05 (br d, J = 11.6 Hz, 1H), 2.78-2.70 (m, 2H), 2.68-2.64 (m, 3H), 2.54-2.45 (m, 3H), 2.29 (s, 3H), 2.26-2.18 (m, 1H), 2.05-1.90 (m, 2H), 1.65 (br s, 3H), 1.41 (br d, J = 10.8 Hz, 1H), 1.14-1.06 (m, 3H), 0.84 (br d, J = 13.2 Hz, 1H) |

| Name | Ex. # | LCMS | ¹H-NMR |
|---|---|---|---|
| 1-((R)-1-(4-(difluoromethoxy)cyclohex-yl)ethyl)-2-methyl-N-((6-methyl-4-(methylthio)-2-oxo-1,2-dihydropyridin-3-yl)methyl)-1H-indole-3-carboxamide | 60 isomer 1 | (M + H+) m/z: calcd 518.22; found 518.4. | 1H NMR (400 MHz, CDCl3) δ 12.52 (brs, 1H), 7.84 (d, J = 8.0 Hz, 1H), 7.44 (d, J = 8.0 Hz, 1H), 7.30 (s, 1H), 7.09-7.02 (m, 2H), 6.20 (t, J = 75.6 Hz, 1H), 6.00 (s, 1H), 4.77-4.671 (m, 2H), 4.36 (s, 1H), 4.16-4.11 (m, 1H), 2.84-2.73 (m, 3H), 2.47 (s, 3H), 2.26-2.20 (m, 4H), 2.04-2.01 (m, 1H), 1.88-1.85 (m, 1H), 1.73-1.69 (m, 1H), 1.60-1.59 (m, 3H), 1.53-1.49 (m, 2H), 1.26-1.17 (m, 2H), 0.87-0.84 (m, 1H). |
| 1-((R)-1-(4-(difluoromethoxy)cyclohex-yl)ethyl)-2-methyl-N-((6-methyl-4-(methylthio)-2-oxo-1,2-dihydropyridin-3-yl)methyl)-1H-indole-3-carboxamide | 60 isomer 2 | (M + H+) m/z: calcd 518.2; found 518.1. | 1H NMR (400 MHz, MeOD) δ 7.73 (d, J = 6.4Hz, 1H), 7.59 (d, J = 8Hz, 1H), 7.14-7.06 (m, 2H), 6.53-6.15 (m, 2H), 4.62 (s, 1H), 4.17-4.14 (m, 1H), 3.98-3.97 (m, 1H), 2.69-2.57 (m, 5H), 2.33 (s, 3H), 2.33-2.13 (m, 1H), 2.13-2.11 (m, 2H), 1.81 (d, J = 9.2 Hz, 1H), 1.62 (d, J = 7.2 Hz, 3H), 1.48-1.38 (m, 1H), 1.31-1.28 (m, 3H), 1.25-1.24 (m, 1H), 0.95-0.90 (m, 2H). |
| (R)-1-(1-(4-(tert-butylamino)cyclohexyl)eth-yl)-2-methyl-N-((6-methyl-4-(methylthio)-2-oxo-1,2-dihydropyridin-3-yl)methyl)-1H-indole-3-carboxamide | 61 | (M + H+) m/z: calcd 523.30, found 523.2. | 1H NMR (400 MHz, CDCl3) δ 7.79-7.77 (d, J = 7.6 Hz, 1H), 7.44-7.42 (d, J = 7.2 Hz, 1H), 7.10-7.03 (m, 2H), 6.01 (s, 1H), 4.78-4.65 (m, 2H), 4.06-4.01 (m, 1H), 2.70 (s, 3H), 2.49 (s, 3H), 2.46 (s, 1H), 2.22 (s, 3H), 2.17-1.95 (m, 2H), 1.58-1.56 (m, 5H), 1.12 (s, 11H), 0.95-0.81 (m, 3H). |
| 2-methyl-N-((6-methyl-4-(methylthio)-2-oxo-1,2-dihydropyridin-3-yl)methyl)-1-((R)-1-(4-(oxetan-3-ylamino)cyclohexyl)ethyl)-1H-pyrrolo[2,3-b]pyridine-3-carboxamide | 62 isomer 1 | (M + H+) m/z: calcd 524.26; found 524.5. | 1H NMR (400 MHz, CDCl3) δ 8.12 (d, J = 4.0 Hz, 1H), 8.03 (d, J = 7.6 Hz, 1H), 7.29 (m, 1H), 6.91 (dd, J = 4.8, 7.6 Hz, 1H), 5.95 (s, 1H), 4.78-4.58 (m, 4H), 4.37-4.24 (m, 2H), 3.95 (m, 1H), 2.99-2.46 (m, 4H), 2.42 (s, 3H), 2.28 (m, 1H), 2.15 (s, 3H), 2.07-1.95 (m, 1H), 1.82 (br d, J = 11.6 Hz, 1H), 1.69-1.43 (m, 7H), 1.20-0.96 (m, 2H), 0.90 (br d, J = 12.4 Hz, 1H), 0.84-0.66 (m, 2H). |
| 2-methyl-N-((6-methyl-4-(methylthio)-2-oxo-1,2-dihydropyridin-3-yl)methyl)-1-((R)-1-(4-(oxetan-3-ylamino)cyclohexyl)ethyl)-1H-pyrrolo[2,3-b]pyridine-3-carboxamide | 62 isomer 2 | (M + H+) m/z: calcd 524.26; found 524.5. | 1H NMR (400 MHz, CDCl3) δ 8.13 (br s, 1H), 8.03 (d, J = 8.0 Hz, 1H), 7.27 (br s, 1H), 6.91 (m, 1H), 5.95 (s, 1H), 4.78-4.57 (m, 4H), 4.43-4.26 (m, 2H), 3.97-3.87 (m, 1H), 3.65 (q, J = 7.2 Hz, 1H), 2.85-2.56 (m, 4H), 2.42 (s, 3H), 2.16 (s, 3H), 1.63-1.38 (m, 9H), 1.31-1.12 (m, 3H), 1.05-0.92 (m, 1H), 0.77 (br s, 1H). |
| 6-methyl-N-((6-methyl-4-(methylthio)-2-oxo-1,2-dihydropyridin-3-yl)methyl)-7-((R)-1-(4-(oxetan-3-ylamino)cyclohexyl)ethyl)-7H-pyrrolo[2,3-d]pyrimidine-5-carboxamide | 63 single isomer | (M + H+) calcd. 525.2; found 525.1. | 1H NMR (400 MHz, CD3OD) δ 9.03 (s, 1H), 8.72 (s, 1H), 6.32 (s, 1H), 5.00-4.92 (m, 1H), 4.87-4.73 (m, 3H), 4.61 (s, 2H), 4.47 (td, J = 6.4, 11.0 Hz, 2H), 4.06 (quin, J = 6.8 Hz, 1H), 2.75-2.65 (m, 3H), 2.56 (s, 3H), 2.39 (br d, J = 3.4 Hz, 1H), 2.35-2.24 (m, 3H), 2.19-1.99 (m, 1H), 1.99-1.90 (m, 1H), 1.69 (br d, J = 6.5 Hz, 4H), 1.25-1.06 (m, 2H), 1.00-0.85 (m, 3H) |
| (R)-1-(1-(1-(3-fluorocyclobutyl)piperidin-4-yl)ethyl)-2-methyl-N-((6-methyl-4-(methylthio)-2-oxo-1,2-dihydropyridin-3-yl)methyl)-1H-indole-3-carboxamide | 64 isomer 1 | (M + H+) m/z: calcd 525.27, found 525.3 | |
| 1-((R)-1-(1-(3-fluorocyclobutyl)piperidin- | 64 isomer 2 | (M + H+) m/z: calcd | |

| Name | Ex. # | LCMS | ¹H-NMR |
|---|---|---|---|
| 4-yl)ethyl)-2-methyl-N-((6-methyl-4-(methylthio)-2-oxo-1,2-dihydropyridin-3-yl)methyl)-1H-indole-3-carboxamide | | 525.27, found 525.3 | |
| 1-((R)-1-(4-(3-fluoroazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 65 single isomer | (M + H+) m/z: calcd 526.27; found 526.4 | 1H NMR (400 MHz, CD3OD) δ 8.17 (d, J = 3.5 Hz, 1H), 8.08 (br d, J = 8.0 Hz, 1H), 7.10 (br dd, J = 4.8, 7.8 Hz, 1H), 6.30 (s, 1H), 5.17-4.97 (m, 1H), 4.60 (br s, 2H), 4.07 (br s, 1H), 3.63-3.52 (m, 2H), 3.25-3.14 (m, 2H), 2.67 (m, 3H), 2.53 (s, 3H), 2.30 (s, 3H), 2.14-2.07 (m, 2H), 1.94-1.91 (m, 1H), 1.65-1.60 (m, 4H), 1.13-1.11 (m, 3H), 1.07-1.04 (m, 1H), 0.94-0.86 (m, 2H) |
| (R)-1-(1-(1-(3-fluorocyclobutyl)piperidin-4-yl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 66 | (M + H+) m/z: calcd 526.26; found 526.2 | 1H NMR (400 MHz, CD3OD) δ 8.18 (d, J = 4.0 Hz, 1H), 8.08 (d, J = 8.0 Hz, 1H), 7.12-7.09 (m, 1H), 6.30 (s, 1H), 5.15-4.99 (m, 1H), 4.60 (s, 2H), 4.17-4.10 (m, 1H), 3.03-2.98 (m, 2H), 2.74-2.67 (m, 4H), 2.54 (s, 3H), 2.31 (s, 3H), 2.26-2.24 (m, 2H), 2.21-2.17 (m, 1H), 2.08-2.02 (m, 1H), 1.90-1.84 (m, 1H), 1.67 (br s, 3H), 1.43-1.30 (m, 4H), 1.14-1.06 (m, 1H), 0.93-0.88 (m, 1H). |
| 1-((R)-1-(4-(2-methoxyethoxy)cyclohexyl)ethyl)-2-methyl-N-((6-methyl-4-(methylthio)-2-oxo-1,2-dihydropyridin-3-yl)methyl)-1H-indole-3-carboxamide | 67 isomer 1 | (M + H+) m/z: calcd 526.27; found 526.3 | 1H NMR (400 MHz, CDCl3) δ 13.10 (br, 1H), 7.82 (d, J = 7.6 Hz, 1H), 7.46 (d, J = 8.0Hz, 1H), 7.31 (s, 1H), 7.06-6.99 (m, 2H), 4.77-4.67 (m, 1H), 4.16-4.12 (m, 1H), 3.51 (m, 5H), 3.38 (s, 3H), 2.84-2.72 (m, 3H), 2.47 (s, 3H), 2.22-2.18 (m, 4H), 2.00 (s, 1H), 1.75-1.71 (m, 2H), 1.57 (d, J = 6.8 Hz, 3H), 1.47-0.79 (m, 6H). |
| 1-((R)-1-(4-(2-methoxyethoxy)cyclohex-yl)ethyl)-2-methyl-N-((6-methyl-4-(methylthio)-2-oxo-1,2-dihydropyridin-3-yl)methyl)-1H-indole-3-carboxamide | 67 isomer 2 | (M + H+) m/z: calcd 526.27; found 526.2 | 1H NMR (400 MHz, CDCl3) δ 13.00 (s, 1H), 7.75 (d, J = 8 Hz, 1H), 7.38 (d, J = 8.4 Hz, 1H), 7.32-7.30 (m, 1H), 7.03-6.93 (m, 2H), 5.92 (s, 1H), 4.70-4.62 (m, 2H), 3.99-3.97 (m, 1H), .3.52-3.49 (m, 2H), 3.44-3.42 (m, 2H), 3.41 (s, 3H), 3.30-3.29 (m, 1H), 3.12-2.64 (m, 3H), 2.41 (s, 3H), 2.09-2.05 (m, 6H), 1.79-1.76 (m, 1H), 1.52-1.51 (m, 3H), 1.02-1.00 (m, 1H), 0.97-0.95 (m, 3H), 0.72-0.69 (m, 1H). |
| 7-((R)-1-(4-(3-fluoroazetidin-1-yl)cyclohexyl)ethyl)-6-methyl-N-((6-methyl-4-(methylthio)-2-oxo-1,2-dihydropyridin-3-yl)methyl)-7H-pyrrolo[2,3-d]pyrimidine-5-carboxamide | 68 single isomer | (M + H+) m/z: calcd: 527.25.; found 527.6 | 1H NMR (400 MHz, CD3OD) δ 9.00 (s, 1H), 8.68 (s, 1H), 6.29 (s, 1H), 5.16-4.97 (m, 1H), 4.57 (s, 3H), 3.67-3.49 (m, 2H), 3.26-3.13 (m, 2H), 2.67 (br s, 3H), 2.53 (s, 3H), 2.29 (s, 3H), 2.17-2.03 (m, 2H), 1.92 (br d, J = 12.0 Hz, 1H), 1.70-1.59 (m, 4H), 1.35-0.97 (m, 3H), 0.95-0.70 (m, 3H) |
| (R)-5-chloro-1-(1-(1-cyclopropylpiperidin-4-yl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 69 | (M + H+) m/z: calcd 528.21; found 528.2 | 1H NMR (400 MHz, CDCl3) δ 12.65 (br, 1H), 8.15-8.11 (m, 2H), 7.36 (s, 1H), 6.03 (s, 1H), 4.71-4.68 (m, 2H), 3.97 (s, 2H), 3.12-3.09 (m, 1H), 2.82-2.71 (m, 4H), 2.49 (s, 3H), 2.25-2.20 (m, 4H), 1.95-1.90 (m, 2H), 1.63-1.51 (m, 2H), 1.30-1.25 (m, 3H), 0.88-0.36 (m, 6H). |
| 1-((R)-1-((R)-1-cyclopropyl-3,3-difluoropiperidin-4-yl)ethyl)-2-methyl-N-((6-methyl-4-(methylthio)-2-oxo-1,2-dihydropyridin-3- | 70 | (M + H+) m/z: calcd 530.23; found 530.1 | 1H NMR (400 MHz, CD3OD) δ 8.25-8.20 (m, 1H), 8.11 (d, J = 8.0 Hz, 1H), 7.14 (dd, J = 4.6, 7.9 Hz, 1H), 6.32 (s, 1H), 4.65 (br s, 1H), 4.61 (s, 2H), 3.31-3.21 (m, 2H), 2.87-2.78 (m, 1H), 2.66 (s, |

| Name | Ex. # | LCMS | ¹H-NMR |
|---|---|---|---|
| yl)methyl)-1H-pyrrolo[2,3-b]pyridine-3-carboxamide | | | 3H), 2.60-2.45 (m, 4H), 2.33 (s, 3H), 2.07 (br t, J = 12.3 Hz, 1H), 1.84 (br d, J = 4.8 Hz, 3H), 1.70 (br s, 1H), 1.32-1.20 (m, 1H), 0.88 (br s, 1H), 0.55-0.35 (m, 4H) |
| 1-((R)-1-((S)-1-cyclopropyl-3,3-difluoropiperidin-4-yl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 70 | (M + H+) m/z: calcd 530.23; found 530.2. | 1H NMR (400 MHz, CD3OD) δ 8.19 (d, J = 3.5 Hz, 1H), 8.08 (d, J = 7.8 Hz, 1H), 7.10 (dd, J = 4.9, 7.9 Hz, 1H), 6.32 (s, 1H), 4.86-4.83 (m, 1H), 4.62 (s, 2H), 3.21-3.14 (m, 1H), 3.04 (dt, J = 4.4, 11.5 Hz, 1H), 2.71 (s, 3H), 2.56 (s, 3H), 2.44-2.25 (m, 5H), 2.17 (br d, J = 13.9 Hz, 1H), 1.75-1.65 (m, 4H), 1.63-1.52 (m, 1H), 1.45-1.29 (m, 1H), 0.54-0.44 (m, 3H), 0.40-0.32 (m, 1H). |
| 2-methyl-1-((R)-1-((2S,4S)-1-methyl-2-(trifluoromethyl)piperidin-4-yl)ethyl)-N-((6-methyl-4-(methylthio)-2-oxo-1,2-dihydropyridin-3-yl)methyl)-1H-indole-3-carboxamide | 71 | (M + H+) calcd.535.1; found 535.2 | 1H NMR (400 MHz, CD3OD) δ 7.75 (br d, J = 7.8 Hz, 1H), 7.60 (br d, J = 7.5 Hz, 1H), 7.19-7.06 (m, 2H), 6.32 (s, 1H), 4.63 (s, 2H), 4.26 (br dd, J = 7.3, 10.3 Hz, 1H), 2.82 (br d, J = 7.8 Hz, 1H), 2.77 (br s, 1H), 2.63 (s, 3H), 2.55 (s, 3H), 2.46 (br d, J = 11.0 Hz, 1H), 2.37 (s, 3H), 2.32 (s, 3H), 2.10 (br t, J = 12.2 Hz, 1H), 1.66 (br d, J = 6.8 Hz, 3H), 1.53-1.28 (m, 1H), 1.22-1.16 (m, 1H), 1.13 (br s, 1H), 0.84 (br d, J = 13.6 Hz, 1H) |
| 2-methyl-N-((6-methyl-4-(methylthio)-2-oxo-1,2-dihydropyridin-3-yl)methyl)-1-((R)-1-(4-(2-oxopyrrolidin-1-yl)cyclohexyl)ethyl)-1H-indole-3-carboxamide | 72 single isomer | (M + H+) m/z: calcd: 535.27; found 535.1 | 1H NMR (400 MHz, CD3OD) δ 7.73 (br d, J = 7.6 Hz, 1H), 7.54 (br d, J = 8.0 Hz, 1H), 7.14-7.01 (m, 2H), 6.27-6.20 (m, 1H), 4.58 (d, J = 2.0 Hz, 2H), 4.16-4.08 (m, 1H), 3.81-3.70 (m, 1H), 3.36-3.31 (m, 1H), 3.28-3.20 (m, 1H), 2.58 (s, 3H), 2.49 (s, 3H), 2.33-2.27 (m, 2H), 2.26 (s, 3H), 2.23-2.09 (m, 2H), 2.02-1.83 (m, 3H), 1.73 (br d, J = 12.0 Hz, 1H), 1.58 (br d, J = 7.2 Hz, 3H), 1.39 (br d, J = 12 Hz, 1H), 1.28-1.12 (m, 2H), 0.94 (br s, 2H) |
| (R)-6-methyl-N-((6-methyl-4-(methylthio)-2-oxo-1,2-dihydropyridin-3-yl)methyl)-7-(1-(1-(2,2,2-trifluoroethyl)piperidin-4-yl)ethyl)-7H-pyrrolo[2,3-d]pyrimidine-5-carboxamide | 73 | (M + H+) m/z: calcd 537.22; found 537.1 | 1H NMR (400 MHz, CD3OD) δ 9.02 (s, 1H), 8.71 (s, 1H), 6.31 (s, 1H), 4.59 (s, 2H), 3.08 (br d, J = 11.6 Hz, 1H), 3.02-2.94 (m, 2H), 2.86-2.71 (m, 2H), 2.69 (s, 3H), 2.54 (s, 3H), 2.43-2.34 (m, 1H), 2.31 (s, 3H), 2.21-2.07 (m, 1H), 1.99 (br d, J = 12.4 Hz, 1H), 1.68 (br d, J = 6.8 Hz, 3H), 1.44 (dq, J = 4.1, 12.4 Hz, 1H), 1.36-1.25 (m, 2H), 1.22-1.12 (m, 1H), 0.84 (br d, J = 12.4 Hz, 1H). |
| 2-methyl-N-((6-methyl-4-(methylthio)-2-oxo-1,2-dihydropyridin-3-yl)methyl)-1-((R)-1-(4-(2-oxooxazolidin-3-yl)cyclohexyl)ethyl)-1H-indole-3-carboxamide | 74 single isomer | (M + H+) m/z: calcd: 537.25; found 537.2 | 1H NMR (400 MHz, CD3OD) δ 7.72 (br d, J = 7.6 Hz, 1H), 7.60-7.48 (m, 1H), 7.15-6.99 (m, 2H), 6.26 (s, 1H), 4.58 (br d, J = 1.6 Hz, 2H), 4.35-4.08 (m, 3H), 3.59-3.38 (m, 3H), 2.70-2.55 (m, 3H), 2.50 (s, 3H), 2.27 (s, 3H), 2.24-2.08 (m, 2H), 1.89-1.79 (m, 1H), 1.59 (br d, J = 7.2 Hz, 3H), 1.56-1.44 (m, 2H), 1.30-1.12 (m, 2H), 1.02-0.88 (m, 2H) |
| 2-methyl-N-((6-methyl-4-(methylthio)-2-oxo-1,2-dihydropyridin-3-yl)methyl)-1-((R)-1-(4- | 75 isomer 1 | (M + H+) m/z: calcd 537.28; found 537.1. | 1H NMR (400 MHz, CDCl3) δ 12.56 (brs, 1H), 7.83 (d, J = 7.6 Hz, 1H), 7.45 (d, J = 7.6 Hz, 1H), 7.34-7.31 (m, 1H), 7.10-7.02 (m, |

-continued

| Name | Ex. # | LCMS | ¹H-NMR |
|---|---|---|---|
| morpholinocyclohexyl)ethyl)-1H-indole-3-carboxamide | | | 2H), 6.01 (s, 1H), 4.79-4.68 (m, 2H), 4.08-4.06 (m, 1H), 3.70 (t, J = 4.0 Hz, 4H), 2.84-2.71 (m, 3H), 2.53-2.49 (m, 7H), 2.21-2.03 (m, 7H), 1.59 (d, J = 7.2 Hz, 3H), 1.32-1.26 (m, 2H), 1.11-0.77 (m, 4H). |
| 2-methyl-N-((6-methyl-4-(methylthio)-2-oxo-1,2-dihydropyridin-3-yl)methyl)-1-((R)-1-(4-morpholinocyclohexyl)ethyl)-1H-indole-3-carboxamide | 75 isomer 2 | (M + H+) m/z: calcd 537.28; found 537.1. | 1H NMR (400 MHz, CDCl3) δ 12.39 (brs, 1H), 7.83 (d, J = 7.2 Hz, 1H), 7.47 (d, J = 8.4 Hz, 1H), 7.32-7.29 (m, 1H), 7.10-7.04 (m, 2H), 6.00 (s, 1H), 4.80-4.65 (m, 2H), 4.29-4.25 (m, 1H), 3.72 (s, 4H), 2.84-2.76 (m, 3H), 2.48 (s, 3H), 2.42 (s, 4H), 2.22-1.87 (m, 6H), 1.56 (d, J = 8.4 Hz, 3H), 1.29-0.82 (m, 6H). |
| 1-((R)-1-(4-(3-methoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 76 isomer 1 | (M + H+) m/z: calcd 538.28; found 538.1 | 1H NMR (400 MHz, CD3OD) δ 8.19 (br d, J = 4.0 Hz, 1H), 8.10 (br d, J = 7.6 Hz, 1H), 7.16-7.09 (m, 1H), 6.32 (s, 1H), 4.89-4.81 (m, 1H), 4.62 (s, 3H), 4.00 (m, 1H), 3.63-3.49 (m, 2H), 3.25 (s, 3H), 2.95 (m, 2H), 2.67 (br s, 3H), 2.56 (s, 3H), 2.32 (s, 3H), 2.14 (br d, J = 12.8 Hz, 1H), 2.05 (br d, J = 3.2 Hz, 1H), 1.99-1.89 (m, 1H), 1.75-1.59 (m, 3H), 1.75-1.59 (m, 1H), 1.15-0.70 (m, 5H). |
| 1-((R)-1-(4-(3-methoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 76 isomer 2 | (M + H+) m/z: calcd 538.28; found 538.5. | 1H NMR (400 MHz, CD3OD) δ 8.19 (br d, J = 4.3 Hz, 1H), 8.09 (dd, J = 1.4, 7.9 Hz, 1H), 7.11 (dd, J = 4.8, 8.0 Hz, 1H), 6.32 (s, 1H), 4.89-4.87 (m, 1H), 4.62-4.28 (s, 3H), 4.06-3.98 (m, 1H), 3.64-3.52 (m, 2H), 3.26 (s, 3H), 2.88 (br s, 2H), 2.71 (br s, 3H), 2.56 (s, 3H), 2.33 (s, 3H), 2.26 (br s, 1H), 1.81-1.53 (m, 7H), 1.38 (br s, 1H), 1.33-1.21 (m, 1H), 1.17-1.03 (m, 1H), 0.80 (br s, 1H). |
| 7-((R)-1-(4-(3-methoxyazetidin-1-yl)cyclohexyl)ethyl)-6-methyl-N-((6-methyl-4-(methylthio)-2-oxo-1,2-dihydropyridin-3-yl)methyl)-7H-pyrrolo[2,3-d]pyrimidine-5-carboxamide | 77 single isomer | (M + H+) m/z: calcd 539.27; found 539.1. | 1H NMR (400 MHz, CD3OD) δ 9.04 (s, 1H), 8.72 (s, 1H), 6.33 (s, 1H), 4.61 (s, 2H), 4.08 (quin, J = 5.6 Hz, 1H), 3.86-3.76 (m, 2H), 3.28 (s, 3H), 2.70 (br s, 3H), 2.60-2.56 (m, 3H), 2.43-2.28 (m, 5H), 2.24-2.14 (m, 1H), 2.08-2.00 (m, 1H), 1.77-1.66 (m, 4H), 1.37-1.29 (m, 3H), 1.23-1.11 (m, 2H), 1.03-0.87 (m, 3H). |
| 1-((R)-1-(5-(3,3-dimethylazetidin-1-yl)-1,3-dioxan-2-yl)ethyl)-2-methyl-N-((6-methyl-4-(methylthio)-2-oxo-1,2-dihydropyridin-3-yl)methyl)-1H-indole-3-carboxamide | 78 isomer 1 | (M + H+) m/z: calcd 539.26; found 539.1 | 1H NMR (400 MHz, CD3OD) δ 7.69 (br d, J = 7.8 Hz, 1H), 7.58 (br s, 1H), 7.15-7.00 (m, 2H), 6.29 (s, 1H), 5.06-5.00 (m, 1H), 4.60 (s, 3H), 4.10 (br d, J = 8.3 Hz, 1H), 3.90 (br d, J = 9.0 Hz, 1H), 3.38 (br t, J = 10.7 Hz, 1H), 3.12 (br s, 1H), 3.01 (s, 4H), 2.65-2.55 (m, 4H), 2.53 (s, 3H), 2.30 (s, 3H), 1.63 (br d, J = 7.0 Hz, 3H), 1.18 (s, 6H) |
| 1-((R)-1-(5-(3,3-dimethylazetidin-1-yl)-1,3-dioxan-2-yl)ethyl)-2-methyl-N-((6-methyl-4-(methylthio)-2-oxo-1,2-dihydropyridin-3-yl)methyl)-1H-indole-3-carboxamide | 78 isomer 2 | (M + H+) m/z: calcd 539.26; found 539.1 | 1H NMR (400 MHz, CD3OD) δ 7.74-7.51 (m, 2H), 7.15-7.00 (m, 2H), 6.30 (s, 1H), 5.34 (br s, 1H), 4.61 (br s, 3H), 4.10 (br d, J = 8.3 Hz, 1H), 3.90 (br d, J = 8.3 Hz, 1H), 3.42-3.34 (m, 1H), 3.13 (br s, 1H), 3.02 (s, 4H), 2.61 (br s, 4H), 2.54 (s, 3H), 2.31 (s, 3H), 1.63 (br d, J = 7.0 Hz, 3H), 1.18 (s, 6H) |
| 1-((R)-1-(4-((R)-3-fluoropyrrolidin-1-yl)cyclohexyl)ethyl)-2-methyl-N-((6-methyl-4-(methylthio)-2-oxo-1,2- | 79 isomer 1 | (M + H+) m/z: calcd 539.28; found 539.2 | 1H NMR (400 MHz, CDCl3) δ 12.63 (br, 1H), 7.81 (d, J = 7.6 Hz, 1H), 7.44 (d, J = 8.0 Hz, 1H), 7.35-7.34 (m, 1H), 7.09-7.01 (m, 2H), 5.99 (s, 1H), 5.21-5.05 (m, 1H), |

| Name | Ex. # | LCMS | ¹H-NMR |
|---|---|---|---|
| dihydropyridin-3-yl)methyl)-1H-indole-3-carboxamide | | | 4.77-4.70(m, 2H), 4.21-4.02 (m, 1H), 2.97-2.71 (m, 6H), 2.48-2.32 (m, 4H), 2.10-1.99 (m, 9H), 1.58 (d, J = 6.7 Hz, 3H), 1.30-0.78 (m, 4H |
| 1-((R)-1-(4-((R)-3-fluoropyrrolidin-1-yl)cyclohexyl)ethyl)-2-methyl-N-((6-methyl-4-(methylthio)-2-oxo-1,2-dihydropyridin-3-yl)methyl)-1H-indole-3-carboxamide | 79 isomer 2 | (M + H+) m/z: calcd 539.28; found 539.2 | 1H NMR (400 MHz, CDCl3) δ 12.70 (br, 1H), 7.82 (d, J = 8.0 Hz, 1H), 7.46 (d, J = 8.0 Hz, 1H), 1.16 (s, 1H), 7.08-7.01 (m, 2H), 5.99 (s, 1H), 5.22-5.08 (m, 1H), 4.79-4.65 (m, 2H), 4.25-4.21 (m, 1H), 2.84-2.47 (m, 6H), 2.47 (s, 3H), 2.20-2.01 (m, 9H), 1.86-1.84 (m, 1H), 1.56 (d, J = 6.8 Hz, 3H), 1.25-0.80 (m, 4H). |
| 1-((R)-1-(4-(3-fluoro-3-methylazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 80 single isomer | (M + H+) m/z: calcd. 540.2; found 540.1. | 1H NMR (400 MHz, CD3OD) δ 8.19 (d, J = 3.8 Hz, 1H), 8.10 (br d, J = 7.5 Hz, 1H), 7.12 (t, J = 6.0 Hz, 1H), 6.32 (s, 1H), 4.62 (s, 2H), 4.09 (br s, 1H), 3.34 (br s, 2H), 3.32-3.22 (m, 3H), 2.68 (br s, 3H), 2.56 (s, 3H), 2.32 (s, 3H), 2.19-2.03 (m, 2H), 1.94 (br d, J = 9.8 Hz, 1H), 1.75-1.59 (m, 4H), 1.57-1.49 (d, J = 20 Hz, 3H), 1.23-1.06 (m, 2H), 0.96 (br s, 1H), 0.91-0.68 (m, 2H). |
| (R)-1-(1-(1-(3,3-difluorocyclobutyl)piperidin-4-yl)ethyl)-2-methyl-N-((6-methyl-4-(methylthio)-2-oxo-1,2-dihydropyridin-3-yl)methyl)-1H-indole-3-carboxamide | 81 | (M + H+) m/z: calcd 543.26, found 543.3 | 1H NMR (400 MHz, DMSO-d6) δ = 11.64 (br. s., 1H), 7.72 (d, J= 7.3 Hz, 1H), 7.67-7.45 (m, 2H), 7.17-6.93 (m, 2H), 6.11 (s, 1H), 4.37 (d, J = 3.4 Hz, 2H), 4.13 (br. s., 1H), 2.99 (d, J = 5.9 Hz, 2H), 2.85 (br. s., 1H), 2.75-2.51 (m, 4H), 2.46 (s, 3H), 2.39-2.08 (m, 6H), 1.89 (br. s., 2H), 1.83-1.61 (m, 2H), 1.59-1.44 (m, 4H), 1.43-1.19 (m, 2H), 1.07-0.60 (m, 4H) |
| 7-fluoro-1-((R)-1-(4-(3-fluoroazetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 82 single isomer | (M + H+) m/z: calcd 543.25; found 543.1. | 1H NMR (400 MHz, MeOD) δ 12.95 (s, 1H), 7.53 (d, J = 8.0 Hz, 1H), 7.32-7.31 (m, 1H), 6.87-6.73 (m, 2H), 5.93 (s, 1H), 5.08-4.92 (m, 1H), 4.65-4.63 (m, 2H), 4.00-3.97 (m, 1H), 3.58-3.52 (m, 2H), 2.99-2.96 (m, 2H), 2.71-2.63 (m, 3H), 2.41 (s, 3H), 2.07 (s, 3H), 1.95-1.79 (m, 4H), 1.53-1.42 (m, 3H), 0.98-0.95 (m, 3H), 0.70-0.68 (m, 2H). |
| (R)-6-fluoro-1-(1-(4-(3-fluoroazetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 83 single isomer | (M + H+) m/z: calcd: 543.26; found 543.3. | 1H NMR (500 MHz, CDCl3) δ 12.49-12.31 (m, 1H), 7.75 (dd, J = 5.4, 8.8 Hz, 1H), 7.31 (br. s., 1H), 7.12 (d, J = 9.8 Hz, 1H), 6.81 (dt, J = 2.2, 8.9 Hz, 1H), 6.03 (s, 1H), 5.24-4.97 (m, 1H), 4.79-4.48 (m, 2H), 4.03 (br. s., 1H), 3.80-3.64 (m, 1H), 3.15 (br. s., 1H), 2.68 (s, 2H), 2.49 (s, 2H), 2.23 (s, 3H), 2.08 (d, J = 10.3 Hz, 2H), 1.92 (d, J = 11.7 Hz, 1H), 1.65-1.51 (m, 3H), 1.32-1.20 (m, 2H), 1.16-1.01 (m, 2H), 0.93-0.70 (m, 2H). |
| 5-fluoro-1-((R)-1-(4-(3-fluoroazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 84 isomer 1 | (M + H+) m/z: calcd 518.22; found 518.4. | 1H NMR (400 MHz, MeOD) δ 8.15 (s, 1H), 7.84 (dd, J = 9.2 Hz, 2.4 Hz, 1H), 6.94 (s, 1H), 5.49-5.30 (m, 1H), 4.65-4.23 (m, 7H), 3.27-3.15 (m, 1H), 2.94-2.71 (m, 8H), 2.52 (s, 3H), 2.28-2.16 (m, 2H), 1.90-1.87 (m, 1H), 1.70 (d, J = 5.6 Hz, 3H), 1.32-1.24 (m, 2H), 1.06 (s, 3H). |
| 5-fluoro-1-((R)-1-(4-(3-fluoroazetidin-1-yl)cyclohexyl)ethyl)-2-methyl-N-((6-methyl-4-(methylthio)-2-oxo-1,2- | 84 isomer 2 | (M + H+) m/z: calcd 518.22; found 518.4. | 1H NMR (400 MHz, MeOD) δ 8.14 (s, 1H), 7.84 (dd, J = 9.2 Hz, 2.4 Hz, 1H), 6.85 (s, 1H), 5.44-5.30 (m, 1H), 4.64-4.23 (m, 7H), 3.26-3.15 (m, 1H), 2.92-2.66 (m, 8H), |

-continued

| Name | Example # | LCMS | ¹H-NMR |
|---|---|---|---|
| dihydropyridin-3-yl)methyl)-1H-pyrrolo[2,3-b]pyridine-3-carboxamide | | | 2.59-2.49 (m, 3H), 2.27-2.25 (m, 2H), 1.90-1.84 (m, 1H), 1.69 (d, J = 5.6 Hz, 3H), 1.34-1.24 (m, 2H), 1.04-1.01 (s, 3H). |
| 1-((R)-1-(5-(3,3-difluoroazetidin-1-yl)-1,3-dioxan-2-yl)ethyl)-2-methyl-N-((6-methyl-4-(methylthio)-2-oxo-1,2-dihydropyridin-3-yl)methyl)-1H-indole-3-carboxamide | 85 isomer 1 | (M + H+) m/z: calcd 547.21; found 547.0 | 1H NMR (400 MHz, CDCl3) δ 7.79 (d, J = 7.2 Hz, 1H), 7.47 (brs, 1H), 7.22 (brs, 1H), 7.10-7.01 (m, 2H), 6.04 (s, 1H), 4.87 (s, 1H), 4.69 (s, 2H), 4.53 (s, 1H), 4.09-4.06 (m, 1H), 3.87 (d, J = 9.2 Hz, 1H), 3.57 (t, J = 11.2 Hz, 4H), 3.40 (t, J = 10.4 Hz, 1H), 3.19 (t, J = 10.4 Hz, 1H), 2.71-2.62 (m, 5H), 2.48 (s, 3H), 2.25 (s, 3H), 1.61 (d, J = 7.2 Hz, 3H). |
| 1-((R)-1-(5-(3,3-difluoroazetidin-1-yl)-1,3-dioxan-2-yl)ethyl)-2-methyl-N-((6-methyl-4-(methylthio)-2-oxo-1,2-dihydropyridin-3-yl)methyl)-1H-indole-3-carboxamide | 85 isomer 2 | (M + H+) m/z: calcd 547.21; found 547.0 | 1H NMR (400 MHz, CDCl3) δ 7.81 (d, J = 7.6 Hz, 1H), 7.47 (brs, 1H), 7.22 (brs, 1H), 7.10-7.02 (m, 2H), 6.02 (s, 1H), 4.89-4.86 (m, 1H), 4.69 (s, 2H), 4.53 (s, 1H), 4.09-4.06 (m, 1H), 3.87 (d, J = 9.3 Hz, 1H), 3.57 (t, J = 11.2 Hz, 4H), 3.40 (t, J = 10.4 Hz, 1H), 3.19 (t, J = 10.4 Hz, 1H), 2.72-2.63 (m, 5H), 2.48 (s, 3H), 2.23 (s, 3H), 1.61 (d, J = 7.2 Hz, 3H). |
| (R)-N-((4-(ethylthio)-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide | 86 | (M + H+30) m/z: calcd 549.24; found 549.1. | 1H NMR (400 MHz, DMSO) δ 11.67 (s, 1H), 7.75-7.74 (d, J = 4.0 Hz, 1H), 7.64-7.59 (m, 2H), 7.09-7.02 (m, 2H), 6.15 (s, 1H), 4.39 (s, 2H), 4.18-4.14 (m, 1H), 3.10-2.98 (m, 5H), 2.69 (s, 2H), 2.59 (s, 3H), 2.35 (m, 1H), 2.18 (s, 4H), 2.02 (m, 1H), 1.99 (m, 1H), 1.54-1.53 (m, 3H), 1.41-1.38 (m,1H), 1.29-1.26 (m, 4H), 1.06 (m, 1H), 0.68-0.65 (m, 1H) |
| (R)-2,4-dimethyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide | 87 | (M + H+) m/z: calcd 549.2; found 549.1. | 1H NMR (400 MHz, CDCCl3) δ 12.59-12.51 (m, 1H), 7.23 (s, 1H), 7.00-6.96 (m, 1H), 6.82 (d, J = 6.8 Hz, 1H), 6.68-6.67 (m, 1H), 5.98 (s, 1H), 4.73-4.63 (m, 1H), 3.99-3.97 (m, 1H), 3.06 (d, J = 43.6 Hz, 1H), 2.92-2.87 (m, 2H), 2.74 (d, J = 12 Hz, 1H), 2.51-2.47 (m, 6H), 2.41-2.36 (m, 3H), 2.19-2.11 (m, 4H), 1.96 (d, J = 14.8 Hz, 1H), 1.44-1.42 (m, 1H) 1.30-1.26 (m, 3H) 1.25-1.01 (m, 1H) 1.00-1.00 (m, 1H) .0.88-0.86 (m, 1H). |
| (R)-2-methyl-N-((6-methyl-4-(methylthio)-2-oxo-1,2-dihydropyridin-3-yl)methyl)-1-(1-(1-(3,3,3-trifluoropropyl)piperidin-4-yl)ethyl)-1H-indole-3-carboxamide | 88 | (M + H+) m/z: calcd 549.67, found 549.3. | 1H NMR (400 MHz, DMSO-d6) δ = 11.65 (br s, 1H), 7.74 (br d, J = 7.3 Hz, 1H), 7.64 (br t, J = 4.6 Hz, 1H), 7.59 (br d, J = 7.8 Hz, 1H), 7.14-6.95 (m, 2H), 6.12 (s, 1H), 4.43-4.37 (m, 2H), 4.33 (t, J = 5.1 Hz, 1H), 4.21-4.09 (m, 1H), 2.95 (br d, J = 10.8 Hz, 1H), 2.66 (br d, J = 11.2 Hz, 1H), 2.54 (s, 3H), 2.48 (s, 3H), 2.46-2.39 (m, 3H), 2.23-2.15 (m, 4H), 1.98-1.88 (m, 2H), 1.63 (br t, J = 10.8 Hz, 1H), 1.54 (br d, J = 6.8 Hz, 3H), 1.38-1.27 (m, 1H), 0.68 (br d, J = 13.2 Hz, 1H) |
| 6-methyl-N-((6-methyl-4-(methylthio)-2-oxo-1,2-dihydropyridin-3-yl)methyl)-7-((R)-1-(4-((2,2,2-trifluoroethyl)amino)cyclohexyl)ethyl)-7H-pyrrolo[2,3-d]pyrimidine-5-carboxamide | 89 single isomer | (M + H+) m/z: calcd 551.23; found 551.1. | 1H NMR (400 MHz, CD3OD) δ 8.92 (s, 1H), 8.61 (s, 1H), 6.21 (s, 1H), 4.50 (s, 3H), 3.14-3.07 (q, J = 10.0 Hz, 2H), 2.59 (s, 3H), 2.45 (s, 3H), 2.37 (s, 1H), 2.22 (s, 3H), 2.04-1.94 (m, 4H), 1.69-1.57 (m, 2H), 1.10-1.05 (m, 2H), 0.86-0.79 (m, 3H). |
| 1-((R)-1-(4-(3-methoxy-3-methylazetidin-1- | 90 isomer 1 | (M + H+) m/z: calcd | 1H NMR (400 MHz, CDCl3) δ 13.09 (br, 1H), 7.81(d, J = 8.0 Hz, |

| Name | Ex. # Example # | LCMS LCMS | ¹H-NMR NMR |
|---|---|---|---|
| yl)cyclohexyl)ethyl)-2-methyl-N-((6-methyl-4-(methylthio)-2-oxo-1,2-dihydropyridin-3-yl)methyl)-1H-indole-3-carboxamide | | 551.30; found 551.2. | 1H), 7.43-7.38 (m, 2H), 7.08-6.99 (m, 2H), 5.99 (s, 1H), 4.72 (s, 2H), 4.06-4.01 (m, 1H), 3.18-3.11 (m, 5H), 3.01-2.96 (m, 2H), 2.71-2.47 (m, 3H), 2.17-2.15 (m, 6H), 1.90-1.87 (m, 2H), 1.57 (d, J = 6.8 Hz, 3H), 1.42 (s, 3H), 1.07-1.04 (m, 3H), 0.77-0.75 (m, 2H) |
| 1-((R)-1-(4-(3-methoxy-3-methylazetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 90 isomer 2 | (M + H+) m/z: calcd 551.30. found 276.0. | 1H NMR (400 MHz, CDCl3) δ 12.50 (br, 1H), 7.82 (d, J = 7.2 Hz, 1H), 7.45 (d, J = 7.6 Hz, 1H), 7.29-7.26 (m ,1H), 7.08-7.01 (m, 2H), 5.99 (s, 1H), 4.79-4.66 (m, 2H), 4.20 (s, 1H), 3.18 (s, 3H), 3.11-3.04 (m, 2H), 2.92-2.86 (m, 2H), 2.74 (s, 3H), 2.47 (m, 3H), 2.20 (s, 5H), 1.57-1.55 (m, 4H), 1.45-1.36 (m, 6H), 1.13-0.72 (m, 4H). |
| 1-((R)-1-(4-(3-ethoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 91 isomer 1 | (M + H+) m/z: calcd 552.29; found 552.3 | 1H NMR (400 MHz, CD3OD) δ 8.17 (d, J = 3.5 Hz, 1H), 8.08 (br d, J = 8.0 Hz, 1H), 7.10 (br dd, J = 4.5, 7.5 Hz, 1H), 6.30 (s, 1H), 4.59 (s, 2H), 4.08-4.02 (m, 1H), 3.59-3.50 (m, 2H), 3.41 (q, J = 7.0 Hz, 2H), 2.95-2.87 (m, 2H), 2.71-2.65 (m, 3H), 2.53 (s, 3H), 2.30 (s, 3H), 2.21-2.06 (m, 1H), 2.06-1.85 (m, 2H), 1.74-1.51 (m, 4H), 1.18-1.13 (m, 3H), 1.13-1.08 (m, 3H), 1.07-0.99 (m, 1H), 0.97-0.66 (m, 3H) |
| 1-((R)-1-(4-(3-ethoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 91 isomer 2 | (M + H+) m/z: calcd 552.29; found 552.2 | 1H NMR (400 MHz, CD3OD) δ 8.17 (br d, J = 4.5 Hz, 1H), 8.07 (dd, J = 1.5, 8.0 Hz, 1H), 7.09 (dd, J = 4.8, 7.8 Hz, 1H), 6.30 (s, 1H), 4.60 (s, 2H), 4.07 (br d, J = 6.0 Hz, 1H), 3.65-3.58 (m, 1H), 3.55 (br s, 1H), 3.43 (q, J = 7.0 Hz, 2H), 2.87 (br s, 2H), 2.69 (br s, 3H), 2.54 (s, 3H), 2.30 (s, 3H), 2.24-2.19 (m, 1H), 2.07-1.95 (m, 1H), 1.71 (br s, 1H), 1.67-1.58 (m, 4H), 1.55-1.48 (m, 1H), 1.34-1.27 (m, 3H), 1.16 (t, J = 7.0 Hz, 3H), 1.06 (br s, 1H), 0.90 (br t, J = 7.0 Hz, 1H), 0.77 (br s, 1H) |
| (R)-6-fluoro-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide | 92 | (M + H+) m/z: calcd: 553.23; found 552.9. | 1H NMR (400 MHz, CDCl3) δ 12.91 (br. s., 1H), 7.81-7.71 (m, 1H), 7.12 (d, J = 9.8 Hz, 1H), 6.80 (t, J = 8.3 Hz, 1H), 6.02 (s, 1H), 4.80-4.61 (m, 2H), 4.08 (dd, J = 7.3, 10.3 Hz, 1H), 3.08 (d, J = 10.8 Hz, 1H), 2.93 (q, J = 9.8 Hz, 2H), 2.77 (d, J = 11.7 Hz, 1H), 2.68 (s, 3H), 2.49 (s, 3H), 2.38 (t, J = 11.0 Hz, 1H), 2.20 (s, 3H), 2.16-2.08 (m, 2H), 1.95 (d, J = 12.2 Hz, 1H), 1.74 (br. s., 1H), 1.57 (d, J = 7.3 Hz, 3H), 1.49-1.37 (m, 1H), 1.20-1.07 (m, 1H), 0.92 (d, J = 12.7 Hz, 1H). |
| N-((4-((fluoromethyl)thio)-6-methyl-2-oxo-1,2-dihydropyridin-3-yl)methyl)-1-((R)-1-(4-(3-methoxyazetidin-1-yl)cyclohexyl)ethyl)-2-methyl-1H-indole-3-carboxamide | 93 single isomer | (M + H+) m/z: calcd 555.73, found 555.3. | 1H NMR (400 MHz, DMSO-d6) δ 11.81 (s, 1H), 7.73 (d, J = 6.8 Hz, 1H), 7.63-7.55 (m, 2H), 7.10-7.00 (m, 2H), 6.25 (s, 1H), 6.13-5.97 (m, 1H), 4.40 (dd, J = 2.2, 4.6 Hz, 2H), 4.13-4.04 (m, 1H), 3.90-3.82 (m, 1H), 3.49-3.36 (m, 2H), 3.11 (s, 3H), 2.78-2.64 (m, 2H), 2.57 (s, 3H), 2.20 (s, 3H), 2.16-2.06 (m, 1H), 2.04-1.95 (m, 1H), 1.92-1.75 (m, 2H), 1.53 (d, J = 6.8 Hz, 3H), 1.51-1.47 (m, 1H), 1.18-1.02 (m, 2H), 1.00-0.87 (m, 2H), 0.83-0.72 (m, 2H), 0.65-0.51 (m, 1H) |

-continued

| Name | Ex. # Example # | LCMS LCMS | ¹H-NMR NMR |
|---|---|---|---|
| 5-fluoro-1-((R)-1-(4-(3-methoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 94 isomer 1 | (M + H+) m/z: calcd 556.27; found 556.2. | 1H NMR (400 MHz, CDCl3) δ 12.09-12.01 (m, 1H), 7.99 (s, 1H), 7.81 (d, J = 9.2 Hz, 1H), 7.45-7.22 (m, 1H), 5.96 (s, 1H), 4.63-4.58 (m, 2H), 3.96-3.93 (m, 1H), 3.56-3.51 (m, 2H), 3.17 (s, 3H), 2.83-2.67 (m, 5H), 2.42 (s, 3H), 2.20 (s, 3H), 1.80-1.66 (m, 1H), 1.60-1.56 (m, 3H), 1.53-1.52 (m, 4H), 1.18-1.49 (m, 1H), 0.91-0.70 (m, 5H). |
| 5-fluoro-1-((R)-1-(4-(3-methoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 94 isomer 2 | (M + H+) m/z: calcd 556.27; found 556.2. | 1H NMR (400 MHz, CDCl3) δ 11.67-11.60 (m, 1H), 7.98-7.82 (m, 1H), 7.80 (d, J = 9.6 Hz, 1H), 7.19-7.16 (m, 1H), 5.96 (s, 1H), 4.66-4.61 (m, 2H), 4.01-3.97 (m, 2H), 3.95-3.20 (m, 2H), 3.18 (s, 3H), 2.89-2.69 (m, 6H), 2.42 (s, 3H), 2.21 (s, 3H), 1.96-1.58 (m, 4H), 1.42-1.07 (m, 4H), 0.81-0.65 (m, 2H). |
| 1-((R)-1-(4-(3,3-difluoropyrrolidin-1-yl)cyclohexyl)ethyl)-2-methyl-N-((6-methyl-4-(methylthio)-2-oxo-1,2-dihydropyridin-3-yl)methyl)-1H-indole-3-carboxamide | 95 single isomer | (M + H+) calcd. 557; found 557.1 | 1H NMR (400 MHz, CD3OD) δ 7.74 (br d, J = 7.3 Hz, 1H), 7.58 (br d, J = 8.3 Hz, 1H), 7.18-7.01 (m, 2H), 6.32 (s, 1H), 4.63 (s, 2H), 4.15 (m, 1H), 2.97 (br t, J = 13.4 Hz, 2H), 2.87-2.69 (m, 2H), 2.62 (s, 2H), 2.56 (s, 3H), 2.33 (s, 3H), 2.31-2.15 (m, 3H), 2.10 (br d, J = 10.3 Hz, 3H), 1.78 (br s, 1H), 1.64 (br d, J = 7.0 Hz, 3H), 1.37-1.10 (m, 3H), 1.10-0.82 (m, 3H). |
| 1-((R)-1-(4-(3-(difluoromethyl)azetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 96 single isomer | (M + H+) m/z: calcd 558.26; found 558.1. | 1H NMR (400 MHz, CD3OD) δ 8.20 (d, J = 8.0 Hz, 1H), 8.10 (d, J = 8.0 Hz, 1H), 7.14-7.10 (m, 1H), 6.32 (s, 1H), 6.01 (t, J = 56.0 Hz, 1H), 4.62 (s, 3H), 3.42-3.37 (m, 2H), 3.20-3.15 (m, 3H), 2.91-2.82 (m, 1H), 2.68 (s, 3H), 2.56 (s, 3H), 2.33 (s, 3H), 2.16-1.92 (m, 4H), 1.68-1.61 (m, 4H), 1.16-1.09 (m, 1H), 0.99-0.85 (m, 3H). |
| (R)-4-cyano-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide | 97 | (M + H+) m/z: calcd 560.22; found 560.1. | 1H NMR (400 MHz, DMSO-d6) δ 11.54 (d, 1H), 7.96 (d, J = 8.4Hz, 2H), 7.49 (d, J = 7.2 Hz, 1H), 7.21-7.17 (m, 1H), 6.10 (s, 1H), 4.39-4.34 (m, 2H), 4.17-4.13 (m, 1H), 3.10-2.97 (m, 2H), 2.73-2.70 (m, 1H), 2.46 (s, 3H), 2.43-2.34 (m, 4H), 2.17 (s, 3H), 2.03-1.87 (m, 2H), 1.53 (d, J = 6.8 Hz, 3H), 1.48-0.66 (m, 4H). |
| 5-chloro-1-((R)-1-(4-(3-fluoroazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 98 single isomer | (M + H+) m/z: calcd 560.2; found 560.3. | 1H NMR (400 MHz, CDCl3) δ 12.97-12.95 (m, 1H), 8.14 (d, J = 12.8 Hz, 2H), 7.42-7.40 (m, 1H), 6.04 (s, 1H), 5.19-5.15 (m, 1H), 5.03-5.00 (m, 2H), 3.65-3.59 (m, 2H), 3.07-3.06 (m, 2H), 2.76 (s, 3H), 2.50 (s, 3H), 2.25 (s, 3H), 2.07-1.86 (m, 4H), 1.62-1.55 (m, 4H), 1.06-0.96 (m, 3H), 0.78-0.76 (m, 2H). |
| N-((4-(cyclopropylthio)-6-methyl-2-oxo-1,2-dihydropyridin-3-yl)methyl)-1-((R)-1-(4-(3-methoxyazetidin-1-yl)cyclohexyl)ethyl)-2-methyl-1H-indole-3-carboxamide | 99 single isomer | (M + H+) m/z: calcd: 563.31; found 563.0. | 1H NMR (400 MHz, CDCl3) δ 12.88 (br. s., 1H), 7.83 (d, J = 7.8 Hz, 1H), 7.44 (d, J = 8.3 Hz, 1H), 7.36 (br. s., 1H), 7.12-7.00 (m, 2H), 6.43 (s, 1H), 4.64 (t, J = 5.4 Hz, 2H), 4.12-3.93 (m, 2H), 3.65-3.47 (m, 2H), 3.24 (s, 3H), 2.91-2.66 (m, 5H), 2.18 (s, 3H), 2.16-2.02 (m, 2H), 1.92 (br. s., 2H), 1.58 (s, 3H), 1.20-0.97 (m, 5H), 0.86-0.68 (m, 4H). |
| 1-((R)-1-(4-(3-cyclopropoxyazetidin-1-yl)cyclohexyl)ethyl)-2- | 100 single isomer | (M + H+) m/z: calcd 563.30; | 1H NMR (400 MHz, CD3OD) δ 7.62 (d, J = 8.0 Hz, 1H), 7.43 (s, d, J = 8.0 Hz, 1H), 7.00-6.93 (m, |

-continued

| Name | Example # | LCMS | NMR |
|---|---|---|---|
| methyl-N-((6-methyl-4-(methylthio)-2-oxo-1,2-dihydropyridin-3-yl)methyl)-1H-indole-3-carboxamide | | found 563.1 | 2H), 6.17 (s, 1H), 4.50 (s, 2H), 4.08-3.99 (m, 2H), 3.49-3.40 (m, 2H), 3.15-3.13 (m, 1H), 2.86-2.79 (m, 2H), 2.49 (s, 3H), 2.42 (s, 3H), 2.18 (s, 3H), 2.11-1.79 (m, 4H), 1.49 (d, J = 8.0 Hz, 4H), 1.06-0.58 (m, 5H), 0.39-0.32 (m, 4H). |
| (R)-4-methoxy-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide | 101 | (M + H+) m/z: calcd 565.24; found 565.1. | 1H NMR (400 MHz, CDCl3) δ 8.33-8.24 (m, 1H), 7.11-6.94 (m, 2H), 6.53 (d, J = 8.0, 1H), 5.98 (s, 1H), 4.74-4.64 (m, 2H), 4.18-4.13 (m, 1H), 3.52 (s, 3H), 3.07 (d, J = 8.0, 1H), 3.09-2.91 (m, 3H), 2.88-2.74 (m, 4H), 2.44 (s, 3H), 2.36 (m, 1H), 2.25-2.20 (m, 4H), 2.09 (m, 1H), 1.96-1.93 (m, 1H), 1.58-1.56 (m, 3H), 1.42 (m, 1H), 1.11-1.10 (m, 1H), 0.93-0.88 (m, 1H). |
| 7-((R)-1-(4-(3-cyclopropoxyazetidin-1-yl)cyclohexyl)ethyl)-6-methyl-N-((6-methyl-4-(methylthio)-2-oxo-1,2-dihydropyridin-3-yl)methyl)-7H-pyrrolo[2,3-d]pyrimidine-5-carboxamide | 102 isomer 1 | (M + H+) m/z: calcd 565.25; found 565.3. | 1H NMR (400 MHz, CD3OD) δ 9.01 (s, 1H), 8.70 (s, 1H), 6.30 (s, 1H), 4.80-4.87 (m, 1H), 4.59 (s, 2H), 4.18 (quin, J = 6.0 Hz, 1H), 3.50-3.64 (m, 2H), 3.23-3.36 (m, 2H), 2.94 (dt, J = 14.0, 7.2 Hz, 2H), 2.68 (br s, 3H), 2.54 (s, 3H), 2.31 (s, 3H), 2.11 (br d, J = 12.6 Hz, 1H), 2.03 (br t, J = 10.4 Hz, 1H), 1.93 (br d, J = 12.0 Hz, 1H), 1.58-1.73 (m, 4H), 0.98-1.20 (m, 2H), 0.84-0.97 (m, 2H), 0.76 (br d, J = 11.4 Hz, 1H), 0.47-0.53 (m, 2H), 0.39-0.47 (m, 2H). |
| 7-((R)-1-(4-(3-cyclopropoxyazetidin-1-yl)cyclohexyl)ethyl)-6-methyl-N-((6-methyl-4-(methylthio)-2-oxo-1,2-dihydropyridin-3-yl)methyl)-7H-pyrrolo[2,3-d]pyrimidine-5-carboxamide | 102 isomer 2 | (M + H+) m/z: calcd 565.25; found 565.1. | 1H NMR (400 MHz, CD3OD) δ 9.01 (s, 1H), 8.69 (s, 1H), 6.31 (s, 1H), 4.89 (br d, J = 2.4 Hz, 1H), 4.59 (s, 2H), 4.21 (quin, J = 6.0 Hz, 1H), 3.53-3.65 (m, 2H), 3.23-3.30 (m, 2H), 2.88 (dt, J = 17.2, 6.8 Hz, 2H), 2.72 (s, 3H), 2.54 (s, 3H), 2.31 (s, 3H), 2.25 (br s, 1H), 1.71 (br s, 1H), 1.65 (br d, J = 6.4 Hz, 3H), 1.48-1.63 (m, 3H), 1.33-1.45 (m, 1H), 1.19-1.30 (m, 1H), 1.09 (br d, J = 10.6 Hz, 1H), 0.77 (br s, 1H), 0.49-0.55 (m, 2H), 0.39-0.47 (m, 2H). |
| (R)-4-chloro-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide | 103 | (M + H+) m/z: calcd 569.2; found 569.1. | 1H NMR (400 MHz, CDCCl3) δ 12.41-12.38 (m, 1H), 7.32 (d, J = 8.4 Hz, 1H), 7.03-6.92 (m, 2H), 5.94 (s, 1H), 4.68 (s, 1H), 4.02-3.98 (m, 1H), 3.09 (d, J = 10.8 Hz, 1H), 2.95-2.88 (m, 2H), 2.78 (d, J = 11.6 Hz, 1H), 2.46-2.44 (m, 6H), 2.36-2.20 (m, 1H), 2.11-2.07 (m, 5H), 1.96 (d, J = 12.4 Hz, 1H), 1.63-1.57 (m, 3H), 1.43-1.30 (m, 1H), 1.11-1.10 (m, 1H) 0.96-0.90 (m, 1H). |
| 1-((R)-1-(4-((3R,4R)-3-fluoro-4-methoxypyrrolidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 104 isomer 1 | (M + H+) m/z: calcd 570.28; found 570.4. | 1H NMR (400 MHz, CD3OD) δ 8.20 (d, J = 3.8 Hz, 1H), 8.10 (br d, J = 8.0 Hz, 1H), 7.12 (br dd, J = 5.1, 7.4 Hz, 1H), 6.32 (s, 1H), 5.00 (br s, 1H), 4.62 (s, 2H), 4.10 (br s, 1H), 3.98-3.86 (m, 1H), 3.38 (d, J = 3.0 Hz, 3H), 3.26-3.14 (m, 1H), 3.07-2.92 (m, 1H), 2.86-2.63 (m, 4H), 2.56 (s, 3H), 2.42-2.35 (m, 1H), 2.33 (s, 3H), 2.20-2.02 (m, 3H), 1.84-1.60 (m, 4H), 1.38-1.13 (m, 3H), 1.06-0.83 (m, 3H). |
| 1-((R)-1-(4-((3R,4R)-3-fluoro-4-methoxypyrrolidin-1-yl)cyclohexyl)ethyl)-2-methyl-N-((6-methyl-4- | 104 isomer 2 | (M + H+) m/z: calcd 570.28; found 570.3. | 1H NMR (400 MHz, CD3OD) δ 8.19 (br s, 1H), 8.10 (br d, J = 7.8 Hz, 1H), 7.12 (br d, J = 7.3 Hz, 1H), 6.32 (s, 1H), 5.02 (br s, 1H), 4.62 (s, 2H), 4.30 (br s, 1H), 3.95 |

| Name | Ex. # Example # | LCMS LCMS | ¹H-NMR NMR |
|---|---|---|---|
| (methylthio)-2-oxo-1,2-dihydropyridin-3-yl)methyl)-1H-pyrrolo[2,3-b]pyridine-3-carboxamide | | | (br d, J = 18.3 Hz, 1H), 3.40 (br d, J = 2.8 Hz, 3H), 3.24-3.11 (m, 1H), 3.01-2.91 (m, 1H), 2.72 (br s, 4H), 2.56 (s, 3H), 2.33 (s, 4H), 2.17 (br s, 1H), 1.90-1.60 (m, 8H), 1.33 (br d, J = 10.5 Hz, 1H), 1.20 (br d, J = 6.3 Hz, 2H), 0.85 (br s, 1H) |
| (R)-N-((4-((difluoromethyl)thio)-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide | 105 | (M + H+) m/z: calcd: 571.21; found 571.1. | 1H NMR (400 MHz, CD3OD) δ 7.77 (br d, J = 7.5 Hz, 1H), 7.62-7.55 (m, 1H), 7.42 (s, 1H), 7.28 (s, 1H), 7.17-7.08 (m, 2H), 6.41 (s, 1H), 4.63 (br s, 2H), 4.22 (br s, 1H), 3.16-3.08 (m, 1H), 3.06-2.96 (m, 2H), 2.80 (br d, J = 11.5 Hz, 1H), 2.63 (s, 3H), 2.46-2.38 (m, 1H), 2.32 (s, 4H), 2.15-1.98 (m, 2H), 1.64 (d, J = 6.8 Hz, 3H), 1.47 (br d, J = 10.0 Hz, 1H), 1.32 (br s, 1H), 1.16 (br s, 1H), 0.00-0.00 (m, 1H) |
| 5-chloro-1-((R)-1-(4-(3-methoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 106 isomer 1 | (M + H+) m/z: calcd 572.24: found 572.2 | 1H NMR (400 MHz, CDCl3) δ 8.07-8.04 (d, J = 10.4 Hz, 2H), 7.31-7.29 (m, 1H), 5.95 (s, 1H), 4.61 (s, 1H), 3.94-3.91 (m, 1H), 3.52-3.47 (m, 2H), 3.16 (s, 3H), 2.80-2.68 (m, 5H), 2.42 (s, 3H), 2.18-2.15 (m, 3H), 1.98-1.92 (m, 1H), 1.82 (m, 2H), 1.19-1.16 (m, 5H), 1.01-0.99 (m, 2H), 0.89-0.86 (m, 1H), 0.73-0.69 (m, 3H). |
| 5-chloro-1-((R)-1-(4-(3-methoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 106 isomer 2 | (M + H+) m/z: calcd 572.24: found 572.2 | 1H NMR (400 MHz, CDCl3) δ 8.07-8.04 (d, J = 12 Hz, 2H), 7.25 (s, 1H), 5.95 (s, 1H), 4.62 (s, 2H), 3.93 (s, 1H), 3.50-3.40 (m, 1H), 3.00 (s, 3H), 2.68 (m, 5H), 2.42 (s, 3H), 2.19-2.13 (m, 4H), 1.95-1.92 (m, 1H), 1.19 (s, 9H), 1.08-1.01 (m, 3H), 0.83-0.79 (m, 1H), 0.63 (m, 1H). |
| 5-chloro-1-((R)-1-(4-((R)-3-fluoropyrrolidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 107 single isomer | (M + H+) m/z: calcd 574.23: found 574.2 | 1H NMR (400 MHz, CDCl3) δ 8.14-8.10 (m,, 2H), 7.43-7.40 (m, 1H), 6.04 (s, 1H), 5.20-5.07 (m, 1H), 4.70 (s, 2H), 3.95 (s, 1H), 2.92-2.76 (m, 6H), 2.50 (s, 3H), 2.25 (s, 3H), 2.10-2.01 (m, 5H), 1.76-1.72 (m, 2H), 1.62 (s, 2H), 1.27 (m, 2H), 1.07-0.96 (m, 2H), 0.81 (m, 1H). |
| 7-((R)-1-(4-(3-(difluoromethoxy)azetidin-1-yl)cyclohexyl)ethyl)-6-methyl-N-((6-methyl-4-(methylthio)-2-oxo-1,2-dihydropyridin-3-yl)methyl)-7H-pyrrolo[2,3-d]pyrimidine-5-carboxamide | 108 single isomer | (M + H+) m/z: calcd 575.25; found 575. | 1H NMR (400 MHz, CD3OD) δ 9.02 (s, 1H), 8.71 (s, 1H), 6.59-6.22 (m, 2H), 4.76 (br d, J = 6.0 Hz, 1H), 4.60 (s, 2H), 3.77-3.76 (m, 1H), 3.74 (br d, J = 7.0 Hz, 1H), 3.26 (br d, J = 13.6 Hz, 2H), 3.14 (s, 1H), 2.69 (br s, 3H), 2.55 (s, 3H), 2.31 (s, 3H), 2.13 (br s, 1H), 1.99 (br s, 1H), 1.68 (br d, J = 6.5 Hz, 4H), 1.38 (d, J = 7.0 Hz, 3H), 1.19-1.08 (m, 2H), 0.96 (br s, 2H) |
| (R)-N-((4-(cyclobutylthio)-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide | 109 | (M + H+) m/z: calcd 575.26; found 575.1 | 1H NMR (400 MHz, CDCl3) δ 7.85 (d, J = 6.8 Hz,1H), 7.44 (d, J = 7.6 Hz, 1H), 7.29 (s, 1H), 7.10-7.03 (m, 2H), 5.86 (s, 1H), 4.741-4.650 (m, 2H), 4.13-4.10 (m, 1H), 3.97-3.93 (m, 1H), 2.95-2.91 (m, 3H), 2.71 (m, 3H) 2.55-2.53 (m, 2H), 2.22-1.94 (m, 10H), 1.60 (m, 3H) 1.45 (m, 1H), 1.15-1.12 (m, 1H), 0.94-0.91 (m, 1H). |
| 2-methyl-N-((6-methyl-4-(methylthio)-2-oxo-1,2-dihydropyridin-3-yl)methyl)-1-((R)-1-(4-(3-(trifluoromethyl)azetidin- | 110 single isomer | (M + H+) m/z: calcd 576.25; found 576.3 | 1H NMR (400 MHz, CD3OD) δ 8.19-8.15 (m, 1H), 8.08 (br d, J = 7.6 Hz, 1H), 7.16-7.02 (m, 1H), 6.30 (s, 1H), 4.60 (s, 3H), 4.08 (br s, 1H), 3.53-3.39 (m, 2H), 3.26- |

| Name | Ex. # | LCMS | ¹H-NMR |
|---|---|---|---|
| 1-yl)cyclohexyl)ethyl)-1H-pyrrolo[2,3-b]pyridine-3-carboxamide | | | 3.17 (m, 3H), 2.73-2.60 (m, 3H), 2.53 (s, 3H), 2.30 (s, 3H), 2.16-2.01 (m, 2H), 1.95-1.86 (m, 1H), 1.71-1.52 (m, 4H), 1.19-0.99 (m, 2H), 0.98-0.64 (m, 3H) |
| 1-((1R)-1-(4-(3-cyclopropoxypyrrolidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 111 single isomer | (M + H+) m/z: calcd 578.31; found 578.1. | 1H NMR (400 MHz, CD3OD) δ 8.08 (d, J = 8.0 Hz, 1H), 7.99 (d, J = 8.0 Hz, 1H), 7.01-6.98 (m, 1H), 6.19 (s, 1H), 4.50 (s, 2H), 4.05-4.01 (m, 1H), 3.17-3.15 (m, 1H), 2.71-2.56 (m, 7H), 2.43-2.38 (m, 4H), 2.20 (s, 3H), 2.04-1.89 (m, 4H), 1.73-1.68 (m, 2H), 1.56 (s, 3H), 1.24-1.02 (m, 3H), 0.88-0.74 (m, 3H), 0.40-0.33 (m, 4H). |
| 1-((R)-1-(4-(3-(tert-butoxy)azetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 112 isomer 1 | (M + H+) m/z: calcd 580.32; found 580.3 | 1H NMR (400 MHz, CD3OD) δ 8.17 (br d, J = 4.0 Hz, 1H), 8.08 (br d, J = 7.8 Hz, 1H), 7.10 (br dd, J = 4.8, 7.5 Hz, 1H), 6.30 (s, 1H), 4.60 (s, 2H), 4.28 (quin, J = 6.4 Hz, 1H), 4.07 (br s, 1H), 3.66 (br t, J = 6.5 Hz, 1H), 3.59 (br t, J = 5.6 Hz, 1H), 2.98-2.84 (m, 2H), 2.66 (br s, 3H), 2.54 (s, 3H), 2.31 (s, 3H), 2.11 (br t, J = 11.4 Hz, 2H), 1.95 (br d, J = 11.0 Hz, 1H), 1.65 (br s, 4H), 1.36-1.27 (m, 1H), 1.15 (s, 9H), 1.12-1.00 (m, 2H), 1.00-0.91 (m, 1H), 0.91-0.69 (m, 2H) |
| 1-((R)-1-(4-(3-(tert-butoxy)azetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 112 isomer 2 | (M + H+) m/z: calcd 580.32; found 580.3 | 1H NMR (400 MHz, CD3OD) δ 8.16 (br d, J = 3.8 Hz, 1H), 8.07 (dd, J = 1.3, 8.0 Hz, 1H), 7.09 (dd, J = 4.8, 8.0 Hz, 1H), 6.30 (s, 1H), 4.60 (s, 2H), 4.36-4.21 (m, 2H), 3.69-3.49 (m, 2H), 2.80 (br t, J = 6.7 Hz, 1H), 2.77-2.65 (m, 4H), 2.54 (s, 3H), 2.30 (s, 3H), 2.24-2.16 (m, 1H), 1.72 (br d, J = 3.8 Hz, 1H), 1.62 (br d, J = 13.1 Hz, 4H), 1.54 (br s, 2H), 1.41-1.27 (m, 2H), 1.22 (br dd, J = 10.0, 13.6 Hz, 1H), 1.16 (s, 9H), 1.11-1.00 (m, 1H), 0.77 (br s, 1H) |
| 1-((R)-1-(4-(3-cyclopropoxyazetidin-1-yl)cyclohexyl)ethyl)-7-fluoro-2-methyl-N-((6-methyl-4-(methylthio)-2-oxo-1,2-dihydropyridin-3-yl)methyl)-1H-indole-3-carboxamide | 113 isomer 1 | (M + H+) m/z: calcd 581.29: found 581.3 | 1H NMR (400 MHz, CDCl3) δ 12.72 (s, 1H), 7.61-7.59 (m, 1H), 7.39-7.37 (m, 1H), 6.95-6.93 (m, 1H), 6.86-6.81 (m, 1H), 6.00 (s, 1H), 4.76-4.71 (m, 2H), 4.21-4.18 (m, 1H), 4.06 (m, 1H), 3.57 (m, 2H), 3.21-3.19 (m, 1H), 2.85-2.79 (m, 2H), 2.71 (s, 2H), 2.45 (s, 3H), 2.15 (s, 3H), 2.06-2.04 (m, 2H), 1.89-1.85 (m, 2H), 1.74 (s, 3H), 1.60-1.58 (m, 2H), 1.51-1.49 (m, 1H), 1.31-1.29 (m, 1H), 1.04-1.02 (m, 2H), 0.76-0.74 (m, 1H), 0.55 (s, 2H), 0.44-0.43 (m, 2H). |
| 1-((R)-1-(4-(3-cyclopropoxyazetidin-1-yl)cyclohexyl)ethyl)-7-fluoro-2-methyl-N-((6-methyl-4-(methylthio)-2-oxo-1,2-dihydropyridin-3-yl)methyl)-1H-indole-3-carboxamide | 113 isomer 2 | (M + H+) m/z: calcd 581.29: found 581.3 | 1H NMR (400 MHz, CDCl3) δ 12.50 (s, 1H), 7.55-7.49 (m, 1H), 7.22 (m, 1H), 6.90-6.87 (m, 1H), 6.78-6.72 (m, 1H), 5.92 (s, 1H), 4.68-4.59 (m, 2H), 4.14 (s, 2H), 3.52-3.45 (m, 2H), 3.15-3.14 (s, 1H), 2.72-2.62 (m, 3H), 2.41 (s, 3H), 2.09-1.96 (m, 4H), 1.62-1.57 (m, 4H), 1.49-1.36 (m, 2H), 1.33-1.19 (m, 2H), 1.05 (m, 2H), 0.82-0.78 (m, 3H), 0.76 (m, 1H), 0.48 (m, 2H), 0.38-0.36 (m, 2H) |
| (R)-4-(difluoromethyl)-2-methyl-N-((6-methyl-4-(methylthio)-2-oxo-1,2-dihydropyridin-3-yl)methyl)-1-(1-(1-(2,2,2- | 114 | (M + H+) m/z: calcd 585.22; found 585.2. | 1H NMR (400 MHz, CDCl3) δ 7.49-7.43 (m, 1H), 7.35-7.33 (m, 1H), 7.16-7.08 (m, 1H), 6.76 (m, 1H), 5.94 (s, 1H), 5.29-5.27 (m, 1H), 4.63-4.60 (m, 2H), 3.94 |

-continued

| Name | Ex. # | LCMS | ¹H-NMR |
|---|---|---|---|
| trifluoroethyl)piperidin-4-yl)ethyl)-1H-indole-3-carboxamide | | | (m, 1H), 3.00-2.89 (m, 1H), 2.89-2.86 (m, 2H), 2.86-2.84 (m, 1H), 2.43-2.39 (m, 5H), 2.19-2.13 (m, 1H), 1.98-1.94 (m, 11H), 0.79-0.74 (m, 3H). |
| 1-((R)-1-(4-(3-(difluoromethoxy)azetidin-1-yl)cyclohexyl)ethyl)-2,5-dimethyl-N-((6-methyl-4-(methylthio)-2-oxo-1,2-dihydropyridin-3-yl)methyl)-1H-pyrrolo[2,3-b]pyridine-3-carboxamide | 115 single isomer | (M + H+) m/z: calcd 588.73, found 588.3. | 1H NMR (400 MHz, METHANOL-d4) δ =8.02 (d, J = 1.5 Hz, 1H), 7.92 (s, 1H), 6.55 (s, 1H), 6.36 (s, 1H), 6.28 (s, 1H), 6.18 (s, 1H), 4.68 (quin, J = 6.0 Hz, 1H), 4.59 (s, 2H), 3.61 (br t, J = 6.6 Hz, 1H), 3.56 (br t, J = 7.1 Hz, 1H), 3.08 (ddd, J = 5.9, 8.1, 13.9 Hz, 2H), 2.53 (s, 3H), 2.39 (s, 3H), 2.29 (s, 3H), 2.16-2.01 (m, 2H), 1.95-1.86 (m, 1H), 1.68-1.55 (m, 4H), 1.16-1.00 (m, 3H), 0.99-0.91 (m, 1H), 0.89-0.69 (m, 3H) |
| 1-((R)-1-(4-(3-(2,2-difluoroethoxy)azetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 116 single isomer | (M + H+) m/z: calcd 588.27; found 588.6 | 1H NMR (400 MHz, CD3OD) δ 8.19 (dd, J1 = 4.8 Hz, J2 = 1.2 Hz, 1H), 8.09 (d, J = 7.6 Hz, 1H), 7.13-7.10 (m, 1H), 6.32 (s, 1H), 8.19 (tt, J1 = 55.2 Hz, J2 = 4.0 Hz, 1H), 4.93-4.82 (m, 2H), 4.62 (s, 2H), 4.21-4.15 (m, 1H), 3.67-3.53 (m, 4H), 3.03-2.96 (m, 2H), 2.68 (br s, 3H), 2.53 (s, 3H), 2.32 (s, 3H), 2.16-2.13 (m, 1H), 2.08-2.02 (m, 1H), 1.96-1.93 (m, 1H), 1.69-1.62 (m, 4H), 1.19-1.05 (m, 2H), 1.02-0.96 (m, 1H), 0.91-0.75 (m, 2H). |
| 1-((S)-1-(4-(3-(difluoromethoxy)azetidin-1-yl)cyclohexyl)propyl)-2-methyl-N-((6-methyl-4-(methylthio)-2-oxo-1,2-dihydropyridin-3-yl)methyl)-1H-pyrrolo[2,3-b]pyridine-3-carboxamide | 117 single isomer | (M + H+) m/z: calcd 588.27; found 588.1. | 1H NMR (400 MHz, CDCl3) δ 12.56 (s, 1H), 8.22-8.09 (m, 2H), 7.41-7.34 (m, 1H), 6.99-6.96 (m, 1H), 6.15 (t, J = 73.6 Hz, 1H), 6.02 (s, 1H), 4.76-4.67 (m, 3H), 3.65-3.58 (m, 3H), 3.01-2.97 (m, 2H), 2.83-2.74 (m, 3H), 2.67-2.61 (m, 1H), 2.49 (s, 3H), 2.20 (s, 3H), 2.15-1.97 (m, 1H), 1.96-1.85 (m, 4H), 1.51 (s, 1H), 1.04-0.96 (m, 3H), 0.76-0.75 (m, 2H), 0.59-0.53 (m, 3H). |
| 1-((R)-1-(4-(3-(difluoromethoxy)azetidin-1-yl)cyclohexyl)propyl)-2-methyl-N-((6-methyl-4-(methylthio)-2-oxo-1,2-dihydropyridin-3-yl)methyl)-1H-pyrrolo[2,3-b]pyridine-3-carboxamide | 118 single isomer | (M + H+) m/z: calcd 588.27; found 588.1. | 1H NMR (400 MHz, CDCl3) δ 12.85 (s, 1H), 8.21-8.09 (m, 2H), 7.42-7.39 (m, 1H), 6.98-6.94 (m, 1H), 6.14 (t, J = 73.6 Hz, 1H), 6.02 (s, 1H), 4.71-4.66 (m, 3H), 3.63-3.55 (m, 3H), 3.01-2.96 (m, 2H), 2.83-2.74 (m, 3H), 2.65-2.60 (m, 1H), 2.48 (s, 3H), 2.19-1.85 (m, 8H), 1.52 (s, 1H), 1.03-0.95 (m, 3H), 0.76-0.74 (m, 2H), 0.59-0.53 (m, 3H). |
| 1-((R)-1-(4-((R)-3-(difluoromethoxy)pyrrolidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 119 single isomer | (M + H+) m/z: calcd 588.27; found 588.1 | 1H NMR (400 MHz, CD3OD) δ 8.17 (dd, J = 1.3, 4.5 Hz, 1H), 8.08 (br d, J = 7.8 Hz, 1H), 7.10 (br dd, J = 4.8, 7.8 Hz, 1H), 6.55-6.17 (t, J = 75.2 Hz, 1H), 6.29 (s, 1H), 4.74-4.67 (m, 1H), 4.60 (s, 2H), 4.07 (br s, 1H), 2.87-2.74 (m, 4H), 2.72-2.60 (m, 3H), 2.53 (s, 3H), 2.51-2.45 (m, 1H), 2.30 (s, 3H), 2.24-1.98 (m, 4H), 1.95-1.83 (m, 1H), 1.78 (br d, J = 12.0 Hz, 1H), 1.66 (br s, 3H), 1.38-1.08 (m, 3H), 1.06-0.78 (m, 2H) |
| 1-((R)-1-(4-((S)-3-(difluoromethoxy)pyrrolidin-1-yl)cyclohexyl)ethyl)-2-methyl-N-((6-methyl-4-(methylthio)-2-oxo-1,2-dihydropyridin-3- | 120 single isomer | (M + H+) m/z: calcd: 588.27.; found 588.2 | 1H NMR (400 MHz, CD3OD) δ 8.16 (dd, J = 1.2, 4.8 Hz, 1H), 8.06 (br d, J = 7.6 Hz, 1H), 7.08 (br dd, J = 4.8, 7.6 Hz, 1H), 6.34 (s, 1H), 6.28 (s, 1H), 4.69 (br s, 1H), 4.58 (s, 2H), 4.05 (br s, 1H), 2.88-2.72 |

| Name | Example # | LCMS | 1H-NMR |
|---|---|---|---|
| yl)methyl)-1H-pyrrolo[2,3-b]pyridine-3-carboxamide | | | (m, 3H), 2.72-2.57 (m, 3H), 2.51 (s, 3H), 2.49-2.43 (m, 1H), 2.28 (s, 3H), 2.23-1.97 (m, 4H), 1.93-1.83 (m, 1H), 1.77 (br d, J = 10.8 Hz, 1H), 1.73-1.47 (m, 3H), 1.47-1.14 (m, 2H), 1.13-1.01 (m, 1H), 1.00-0.65 (m, 3H) |
| 1-((R)-1-(4-(3-(difluoromethoxy)azetidin-1-yl)cyclohexyl)ethyl)-7-fluoro-2-methyl-N-((6-methyl-4-(methylthio)-2-oxo-1,2-dihydropyridin-3-yl)methyl)-1H-indole-3-carboxamide | 121 isomer 1 | (M + H+) m/z: calcd 591.25; found 591.1. | 1H NMR (400 MHz, CDCl3) δ 13.24 (s, 1H), 7.61-7.59 (m, 1H), 7.40-7.27 (m, 1H), 6.94-6.80 (m, 2H), 6.34-5.97 (m, 2H), 6.36-5.99 (m, 2H), 4.73-4.64 (m, 3H), 4.06 (s, 1H), 3.65-3.58 (m, 2H), 3.01-2.95 (m, 2H), 2.70 (s, 3H), 2.48 (s, 3H), 2.13 (s, 3H), 2.05-2.02 (m, 2H), 2.00-1.90 (m, 2H), 1.60-1.50 (m, 3H), 1.04-1.02 (m, 3H), 0.76-0.74 (m, 2H). |
| 1-((R)-1-(4-(3-(difluoromethoxy)azetidin-1-yl)cyclohexyl)ethyl)-7-fluoro-2-methyl-N-((6-methyl-4-(methylthio)-2-oxo-1,2-dihydropyridin-3-yl)methyl)-1H-indole-3-carboxamide | 121 isomer 2 | (M + H+) m/z: calcd 591.25; found 591.1. | 1H NMR (400 MHz, CDCl3) δ 12.53-12.52 (m, 1H), 7.63 (d, J = 8.0 Hz, 1H), 7.31 (d, J = 6.4 Hz, 1H), 6.96-6.94 (m, 1H), 6.86-6.80 (m, 1H), 6.36-5.99 (m, 2H), 4.78-4.65 (m, 3H), 4.20 (s, 1H), 3.63-3.50 (m, 2H), 2.92-2.88 (m, 2H), 2.73 (s, 3H), 2.47 (s, 3H), 2.18-2.00 (m, 5H), 1.66-1.63 (m, 8H), 1.57-1.48 (m, 3H), 1.43-1.41 (m, 1H), 1.26-1.12 (m, 2H), 0.75-0.74 (m, 1H). |
| 1-((R)-1-(4-(3-(difluoromethoxy)azetidin-1-yl)cyclohexyl)ethyl)-5-fluoro-2-methyl-N-((6-methyl-4-(methylthio)-2-oxo-1,2-dihydropyridin-3-yl)methyl)-1H-pyrrolo[2,3-b]pyridine-3-carboxamide | 122 single isomer | (M + H+) m/z: calcd 592.25; found 592.2 | 1H NMR (400 MHz, CDCl3) δ 12.48 (s, 1H), 8.56 (s, 1H), 7.88 (d, J = 8.0 Hz, 1H), 7.34-7.31 (m, 1H), 6.34-5.97 (m, 2H), 4.71-4.70 (m, 2H), 3.95 (s, 1H), 3.66-3.59 (m, 2H), 3.03-2.95 (m, 2H), 2.76 (s, 3H), 2.50 (s, 3H), 2.28 (s, 3H), 2.10-1.93 (m, 1H), 1.87-1.85 (m, 2H), 1.63-1.54 (m, 3H), 1.26 (s, 3H), 1.05-0.96 (m, 3H), 0.77-0.75 (m, 2H). |
| 6-methyl-N-((6-methyl-4-(methylthio)-2-oxo-1,2-dihydropyridin-3-yl)methyl)-7-((R)-1-(4-(3-(trifluoromethoxy)azetidin-1-yl)cyclohexyl)ethyl)-7H-pyrrolo[2,3-d]pyrimidine-5-carboxamide | 123 isomer 1 | (M + H+) m/z: calcd 593.24; found 593.0 | 1H NMR (400 MHz, CD3OD) δ 9.01 (s, 1H), 8.70 (s, 1H), 6.30 (s, 1H), 4.93 (br s, 1H), 4.85-4.77 (m, 1H), 4.59 (s, 2H), 4.14 (br s, 1H), 3.71-3.57 (m, 2H), 3.19 (dt, J = 5.7, 9.0 Hz, 2H), 2.68 (br s, 3H), 2.56-2.52 (m, 3H), 2.31 (s, 3H), 2.16-2.05 (m, 2H), 1.93 (br d, J = 12.1 Hz, 1H), 1.67 (br d, J = 6.4 Hz, 3H), 1.62 (br s, 1H), 1.21-0.99 (m, 2H), 0.98-0.84 (m, 2H), 0.77 (br d, J = 11.6 Hz, 1H) |
| 6-methyl-N-((6-methyl-4-(methylthio)-2-oxo-1,2-dihydropyridin-3-yl)methyl)-7-((R)-1-(4-(3-(trifluoromethoxy)azetidin-1-yl)cyclohexyl)ethyl)-7H-pyrrolo[2,3-d]pyrimidine-5-carboxamide | 123 isomer 2 | (M + H+) m/z: calcd 593.24; found 593.0 | 1H NMR (400 MHz, CD3OD) δ 9.01 (s, 1H), 8.70 (s, 1H), 6.31 (s, 1H), 4.92-4.89 (m, 1H), 4.81 (quin, J = 5.7 Hz, 1H), 4.59 (s, 2H), 4.21-3.97 (m, 1H), 3.71-3.57 (m, 2H), 3.24-3.15 (m, 2H), 2.68 (br s, 3H), 2.54 (s, 3H), 2.31 (s, 3H), 2.16-2.05 (m, 2H), 1.98-1.86 (m, 1H), 1.67 (br d, J = 6.5 Hz, 3H), 1.62 (br s, 1H), 1.22-0.99 (m, 2H), 0.98-0.66 (m, 3H) |
| 5-chloro-1-((R)-1-(4-(3-cyclopropoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 124 single isomer | (M + H+) m/z: calcd 598.25; found 598.2. | 1H NMR (400 MHz, CDCl3) δ 12.02 (s, 1H), 8.14-8.11 (m, 2H), 7.38-7.16 (m, 1H), 6.02 (s, 1H), 4.69 (d, J = 4.8 Hz, 2H), 4.20-4.17 (m, 1H), 3.62-3.56 (m, 2H), 3.20-3.18 (m, 1H), 2.84-2.74 (m, 5H), 2.49 (s, 3H), 2.24 (s, 3H), 2.08-2.06 (m, 1H), 1.88-1.85 (m, 2H), 1.61-1.55 (m, 5H), 1.04-0.96 (m, 3H), 0.76-0.74 (m, 2H), 0.54-0.52 (m, 2H), 0.45-0.42 (m, 2H). |
| 1-((R)-1-(4-(3-(difluoromethoxy)azetidin- | 125 isomer 1 | (M + H+) m/z: calcd | 1H NMR (400 MHz, CDCl3) δ 12.79 (s, 1H), 7.94-7.93 (m, 1H), |

-continued

| Name | Example # | LCMS | NMR |
|---|---|---|---|
| 1-yl)cyclohexyl)ethyl)-5-methoxy-2-methyl-N-((6-methyl-4-(methylthio)-2-oxo-1,2-dihydropyridin-3-yl)methyl)-1H-pyrrolo[2,3-b]pyridine-3-carboxamide | | 604.27; found 604.2 | 7.69 (s, 1H), 7.40 (s, 1H), 6.34-5.87 (m, 2H), 4.71 (s, 3H), 3.81 (s, 3H), 3.75-3.57 (m, 2H), 3.02-2.94 (m, 2H), 2.74 (m, 2H), 2.48 (s, 3H), 2.20 (s, 3H), 1.92 (m, 1H), 1.86-1.84 (m, 3H), 1.63-1.53 (m, 4H), 1.05-0.99 (m, 3H), 0.77 (s, 2H). |
| 1-((R)-1-(4-(3-(difluoromethoxy)azetidin-1-yl)cyclohexyl)ethyl)-5-methoxy-2-methyl-N-((6-methyl-4-(methylthio)-2-oxo-1,2-dihydropyridin-3-yl)methyl)-1H-pyrrolo[2,3-b]pyridine-3-carboxamide | 125 isomer 2 | (M + H+) m/z: calcd 604.27; found 604.2 | 1H NMR (400 MHz, CDCl3) δ 7.91-7.88 (m, 1H), 7.73-7.71 (m, 1H), 7.30 (s, 1H), 6.27-5.90 (m, 2H), 4.68-4.63 (m, 3H), 3.72 (s, 3H), 3.63-3.58 (m, 2H), 3.00-2.83 (m, 2H), 2.67 (s, 3H), 2.42 (s, 3H), 2.17-2.13 (m, 3H), 2.00 (m, 2H), 1.78 (m, 2H), 1.24-1.16 (m, 7H), 0.94-0.91 (m, 2H), 0.81-0.71 (m, 1H). |
| 5-chloro-1-((R)-1-(4-(3-cyclobutoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 126 single isomer | (M + H+) m/z: calcd 612.27; found 612.4. | 1H NMR (400 MHz, CD3OD) δ 8.11 (dd, J = 2.0, 16.3 Hz, 2H), 6.31 (s, 1H), 4.86-4.81 (m, 1H), 4.58 (s, 2H), 4.04 (br t, J = 6.0 Hz, 1H), 3.91 (quin, J = 7.3 Hz, 1H), 3.61-3.45 (m, 2H), 2.96-2.85 (m, 2H), 2.65 (br s, 3H), 2.55 (s, 3H), 2.31 (s, 3H), 2.19-2.08 (m, 3H), 2.02 (br s, 1H), 1.95-1.83 (m, 3H), 1.73-1.57 (m, 5H), 1.56-1.46 (m, 1H), 1.21 (br s, 1H), 1.13-0.98 (m, 2H), 0.94-0.68 (m, 3H). |
| (R)-6-bromo-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide | 127 | (M + H+) m/z: calcd 615.14; found 615.0 | 1H NMR (400 MHz, CDCl3) δ 11.87 (s, 1H), 7.72-7.70 (m, 1H), 7.56-7.52 (s, 1H), 7.15 (d, J= 7.6 Hz, 1H), 6.02 (s, 1H), 4.76-4.65 (m, 2H), 4.10-4.05 (m, 1H), 3.08 (d, J = 11.6 Hz, 1H), 2.97-2.89 (m, 2H), 2.80-2.75 (m, 2H), 2.67 (s, 2H), 2.49 (s, 4H), 2.20 (m, 3H), 2.13-2.11 (m, 2H), 1.96 (d, J = 12 Hz, 1H), 1.43-1.40 (m, 1H), 1.14-1.12 (m, 1H), 0.90 (d, J = 13.6 Hz, 1H) |
| (R)-4-bromo-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide | 128 | (M + H+) m/z: calcd 615.14; found 615.1. | 1H NMR (400 MHz, CDCl3) δ 12.44 (br, 1H), 7.35 (d, J = 8.4 Hz, 1H), 7.18 (d, J = 6.8 Hz, 1H), 6.93-6.89 (m, 2H), 5.94 (s, 1H), 4.68 (br, 2H), 4.01-3.97 (m, 1H), 3.07 (d, J = 11.2 Hz, 1H), 2.95-2.88 (m, 2H), 2.77 (d, J = 10.8 Hz, 1H), 2.46-2.36 (m, 7H), 2.10-1.92 (m, 6H), 1.56 (d, J = 6.8 Hz, 3H), 1.42-0.97 (m, 4H). |
| 1-((R)-1-(4-(3-(tert-butoxy)azetidin-1-yl)cyclohexyl)ethyl)-5-chloro-2-methyl-N-((6-methyl-4-(methylthio)-2-oxo-1,2-dihydropyridin-3-yl)methyl)-1H-pyrrolo[2,3-b]pyridine-3-carboxamide | 129 single isomer | (M + H+) m/z: calcd 614.3; found 614.4. | 1H NMR (400 MHz, CDCl3) δ 13.24-13.22 (m, 1H), 8.13 (d, J = 10.4 Hz, 2H), 7.43-7.40 (m, 1H), 6.03 (s, 1H), 4.70-4.69 (m, 2H), 4.27-4.23 (m, 1H), 4.22 (s, 1H), 3.62-3.54 (m, 2H), 2.78-2.69 (m, 5H), 2.49 (s, 3H), 2.23 (s, 3H), 2.03-2.00 (m, 2H), 1.88-1.61 (m, 2H), 1.58-1.55 (m, 4H), 1.14 (s, 9H), 1.02-0.98 (m, 2H), 0.95-0.74 (m, 2H). |
| (R)-2-methyl-N-((6-methyl-4-(methylthio)-2-oxo-1,2-dihydropyridin-3-yl)methyl)-1-(1-(1-(1-methylcyclopropyl)piperidin-4-yl)ethyl)-1H-pyrrolo[2,3-b]pyridine-3-carboxamide | 131 | (M + H+) m/z: calcd 508.27; found 508.5 | 1H NMR (400 MHz, CD3OD) δ 8.09 (dd, J1 = 4.8 Hz, J2 = 1.6 Hz, 1H), 7.98 (dd, J1 = 8.0 Hz, J2 = 1.2 Hz, 1H), 7.03-6.99 (m, 1H), 6.21 (s, 1H), 4.50 (s, 2H), 4.05-3.98 (m, 1H), 2.85-2.82 (m, 1H), 2.62-2.52 (m, 4H), 2.48-2.40 (m, 5H), 2.21 (s, 3H), 2.17-2.08 (m, 1H), 1.94-1.91 (m, 1H), 1.57 (br s, 3H), 1.24-1.20 (m, 1H), 0.97-0.89 (m, 4H), 0.81-0.75 (m, 1H), 0.49-0.45 (m, 1H), 0.41-0.38 (m, 1H), 0.28-0.20 (m, 2H). |
| 1-((R)-1-(4-cyclopropoxycyclohex- | 132 single | (M + H+) m/z: calcd: | 1H NMR (400 MHz, CD3OD) δ 7.70 (br d, J = 7.6 Hz, 1H), 7.53 |

| Name | Ex. # | LCMS | ¹H-NMR |
|---|---|---|---|
| yl)ethyl)-2-methyl-N-((6-methyl-4-(methylthio)-2-oxo-1,2-dihydropyridin-3-yl)methyl)-1H-indole-3-carboxamide | isomer | 508.26; found 508.1 | (br d, J = 8.0 Hz, 1H), 7.14-6.98 (m, 2H), 6.27 (s, 1H), 4.62-4.53 (m, 2H), 4.11 (br dd, J = 7.2, 10.4 Hz, 1H), 3.40-3.31 (m, 2H), 2.62-2.53 (m, 3H), 2.51 (s, 3H), 2.27 (s, 3H), 2.24-2.05 (m, 3H), 1.83 (br s, 1H), 1.58 (br d, J = 6.8 Hz, 3H), 1.36-1.05 (m, 3H), 0.94-0.86 (m, 2H), 0.48-0.38 (m, 4H) |
| (R)-2-methyl-N-((6-methyl-4-(methylthio)-2-oxo-1,2-dihydropyridin-3-yl)methyl)-1-(1-(1-(oxetan-3-yl)piperidin-4-yl)ethyl)-1H-indole-3-carboxamide | 133 | (M + H+) m/z: calcd 508.7; found 509.2. | 1H NMR (400 MHz, CDCl3) δ 12.31-12.28 (m 1H), 7.85-7.83 (d, J = 8.0 Hz, 1H), 7.45-7.43(d, J = 8.0 Hz, 1H), 7.29-7.26 (d, J = 12.0 Hz, 1H), 7.10-7.02 (m, 2H), 6.00 (s, 1H), 4.75-4.53 (m, 6H), 4.15-4.10 (m, 1H), 3.40-3.37 (m, 1H), 2.86-2.71 (m, 4H), 2.53-2.48 (m, 4H), 2.21-2.17 (m, 4H), 2.02-1.98 (d, J = 16.0 Hz, 1H), 1.90-1.83 (m, 1H), 1.61-1.59 (m, 4H), 1.54-1.43 (m, 1H), 1.20-1.10 (m, 1H), 0.96-0.94 (d, J = 8 Hz, 1H). |
| 4-((R)-1-(2-methyl-3-(((6-methyl-4-(methylthio)-2-oxo-1,2-dihydropyridin-3-yl)methyl)carbamoyl)-1H-indol-1-yl)ethyl)cyclohexyl acetate | 134 isomer 1 | (M + H+) m/z: calcd 510.23; found 510.2 | 1H NMR (400 MHz, CD3OD) δ 7.73 (br d, J = 7.5 Hz, 1H), 7.57 (br d, J = 7.8 Hz, 1H), 7.16-7.01 (m, 2H), 6.29 (s, 1H), 4.86-4.82 (m, 1H), 4.61 (s, 2H), 4.24-4.16 (m, 1H), 2.62 (s, 3H), 2.53 (s, 3H), 2.40-2.32 (m, 1H), 2.30 (s, 3H), 2.04 (s, 3H), 2.01-1.89 (m, 2H), 1.71-1.57 (m, 5H), 1.52-1.39 (m, 1H), 1.30 (br t, J = 13.3 Hz, 1H), 1.19-1.06 (m, 1H), 0.79 (br d, J = 12.0 Hz, 1H) |
| 4-((R)-1-(2-methyl-3-(((6-methyl-4-(methylthio)-2-oxo-1,2-dihydropyridin-3-yl)methyl)carbamoyl)-1H-indol-1-yl)ethyl)cyclohexyl acetate | 134 isomer 2 | (M + H+) m/z: calcd 510.23; found 510.2 | 1H NMR (400 MHz, CD3OD) δ 7.73 (br d, J = 7.5 Hz, 1H), 7.57 (br d, J = 7.8 Hz, 1H), 7.17-7.02 (m, 2H), 6.30 (s, 1H), 4.67-4.56 (m, 3H), 4.21-4.11 (m, 1H), 2.78-2.57 (m, 3H), 2.53 (s, 3H), 2.30 (s, 3H), 2.29-2.23 (m, 1H), 2.19-2.03 (m, 2H), 1.96 (s, 3H), 1.76 (br d, J = 11.8 Hz, 1H), 1.62 (br d, J = 7.0 Hz, 3H), 1.51-1.38 (m, 1H), 1.35-1.20 (m, 1H), 1.17-1.05 (m, 1H), 1.01-0.89 (m, 2H) |
| (R)-1-(1-(1-(2-hydroxyacetyl)piperidin-4-yl)ethyl)-2-methyl-N-((6-methyl-4-(methylthio)-2-oxo-1,2-dihydropyridin-3-yl)methyl)-1H-indole-3-carboxamide | 135 | (M + H+) m/z: calcd 511.65, found 511.3. | 1H NMR (400 MHz, METHANOL-d4) δ = 7.74 (br d, J = 7.3 Hz, 1H), 7.59 (br d, J = 7.8 Hz, 1H), 7.19-6.93 (m, 2H), 6.39 (br s, 1H), 4.59 (s, 2H), 4.30-4.00 (m, 3H), 3.77 (br d, J = 13.7 Hz, 1 H), 3.45 (br d, J = 13.2 Hz, 1H), 3.10-2.92 (m, 1H), 2.78-2.63 (m, 2H), 2.61-2.46 (m, 6H), 2.32 (s, 3H), 2.11-1.96 (m, 1H), 1.59 (br d, J = 6.8 Hz, 3H), 1.43-1.11 (m, 2H), 1.10-0.74 (m, 2H) |
| (R)-1-(1-(4-(3-hydroxyazetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 136 single isomer | (M + H+) m/z: calcd 523.27; found 523.2 | 1H NMR (400 MHz, DMSO-d6) δ 11.68 (br, 1H), 7.74-7.72 (m, 1H), 7.65-7.57 (m, 2H), 7.07-7.01 (m, 2H), 6.13 (s, 1H), 5.19 (s, 1H), 4.38 (s, 2H), 4.11-4.07 (m, 2H), 2.68 (s, 1H), 2.58 (s, 3H), 2.33 (s, 1H), 2.19-2.13 (m, 5H), 1.84-1.54 (m, 4H), 1.48-0.48 (m, 10H). |
| 2-methyl-N-((6-methyl-4-(methylthio)-2-oxo-1,2-dihydropyridin-3-yl)methyl)-1-((R)-1-(4-(oxetan-3-yloxy)cyclohexyl)ethyl)-1H-indole-3-carboxamide | 137 isomer 1 | (M + H+) m/z: calcd 524.25; found 524.2 | 1H NMR (400 MHz, CDCl3) δ 12.54 (br, 1H), 7.83(d, J = 7.6 Hz, 1H), 7.44 (d, J = 7.6 Hz, 1H), 7.30-7.26 (m, 1H), 7.08-7.01 (m, 2H), 6.00 (s, 1H), 4.76-4.55 (m, 8H), 4.16-4.15 (m, 1H), 3.46 (s, 1H), 2.84-2.75 (m, 3H), 2.48 (s, 3H), 2.21 (s, 4H), 1.84-1.79 (m, 2H), 1.51-1.46 (m, 4H), 1.15-0.81 (m, 3H). |

-continued

| Name | Ex. # Example # | LCMS LCMS | ¹H-NMR NMR |
|---|---|---|---|
| 2-methyl-N-((6-methyl-4-(methylthio)-2-oxo-1,2-dihydropyridin-3-yl)methyl)-1-((R)-1-(4-(oxetan-3-yloxy)cyclohexyl)ethyl)-1H-indole-3-carboxamide | 137 isomer 2 | (M + H+) m/z: calcd 524.25; found 524.2. | 1H NMR (400 MHz, CDCl3) δ 12.36 (br, 1H), 7.82 (d, J = 7.6 Hz, 1H), 7.44 (d, J = 8.0 Hz, 1H), 7.30-7.26 (m, 1H), 7.11-7.00 (m, 2H), 5.99 (s, 1H), 4.72-4.58 (m, 6H), 4.05-4.01 (m, 1H), 3.15 (s, 1H), 2.75-2.69 (m, 3H), 2.48 (s, 3H), 2.11-1.98 (m, 5H), 1.68-1.65 (m, 1H), 1.30-0.77 (m, 9H). |
| 1-((R)-1-(4-(3-cyanoazetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 138 isomer 1 | (M + H+) m/z: calcd 532.27; found 266.5. | 1H NMR (400 MHz, CDCl3) δ 7.81 (d, J = 7.2 Hz, 1H), 7.43 (d, J = 7.6 Hz, 1H), 7.10-7.04 (m, 2H), 6.00 (s, 1H), 4.73-4.69 (m, 2H), 4.05-4.02 (m, 1H), 3.57-3.51 (m, 2H), 3.26-3.18 (m, 3H), 2.71 (s, 3H), 2.48 (s, 3H), 2.22 (s, 3H), 2.06-1.85 (m, 4H), 1.58 (d, J = 7.2 Hz, 3H), 1.26-0.74 (m, 7H). |
| 1-((R)-1-(4-(3-cyanoazetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 138 isomer 2 | (M + H+) m/z: calcd 532.27; found 532.0. | 1H NMR (400 MHz, CDCl3) δ 12.29 (br, 1H), 7.82 (d, J = 7.2 Hz, 1H), 7.43 (d, J = 7.2 Hz, 1H), 7.15-7.02 (m, 2H), 6.00 (s, 1H), 4.79-4.66 (m, 2H), 4.17-4.12 (m, 1H), 3.51-3.46 (m, 2H), 3.17 (s, 3H), 2.82-2.74 (m, 3H), 2.48 (s, 3H), 2.27-2.21 (m, 5H), 1.57 (d, J = 6.8 Hz, 3H), 1.41-0.70 (m, 7H). |
| 1-((R)-1-(4-(5-oxa-1-azaspiro[2.3]hexan-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 139 isomer 1 | (M + H+) m/z: calcd 536.70; found 536.1. | 1H NMR (400 MHz, CD3OD) δ 8.24-8.17 (m, 1H), 8.11 (m, 1H), 7.17-7.06 (m, 1H), 6.31 (s, 1H), 5.05-4.93 (m, 1H), 4.78-4.66 (m, 2H), 4.61 (s, 2H), 4.09 (br s, 1H), 2.89-2.59 (m, 4H), 2.55 (d, J = 1.2 Hz, 3H), 2.32 (s, 3H), 2.26 (br d, J = 13.2 Hz, 1H), 2.18 (br d, J = 12.4 Hz, 1H), 1.99-1.87 (m, 2H), 1.76-1.56 (m, 4H), 1.54 (m, 1H), 1.47 (s, 1H), 1.45-1.32 (m, 1H), 1.27-0.70 (m, 4H) |
| 1-((R)-1-(4-(5-oxa-1-azaspiro[2.3]hexan-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 139 isomer 2 | (M + H+) m/z: calcd 536.70; found 536.1. | 1H NMR (400 MHz, CD3OD) δ 8.22-8.16 (m, 1H), 8.14-8.05 (m, 1H), 7.11 (m, 1H), 6.31 (s, 1H), 5.02-4.92 (m, 1H), 4.84-4.71 (m, 2H), 4.62 (d, J = 2.4 Hz, 2H), 4.28 (br s, 1H), 2.96-2.63 (m, 4H), 2.55 (d, J = 0.8 Hz, 3H), 2.32 (s, 3H), 2.11-1.90 (m, 2H), 1.79 (br d, J = 11.2 Hz, 3H), 1.74-1.58 (m, 5H), 1.51 (br s, 1H), 1.45 (s, 1H), 1.41-1.19 (m, 2H), 0.98-0.75 (m, 1H) |
| (R)-1-(1-(1-(3-methoxycyclobutyl)piperidin-4-yl)ethyl)-2-methyl-N-((6-methyl-4-(methylthio)-2-oxo-1,2-dihydropyridin-3-yl)methyl)-1H-indole-3-carboxamide | 140 | (M + H+30) m/z: calcd 537.29, found 537.3 | 1H NMR (400 MHz ,DMSO-d6) δ = 11.64 (br. s., 1H), 7.80-7.45 (m, 3H), 7.03 (quin, J = 7.3 Hz, 2H), 6.11 (s, 1H), 4.57-4.43 (m, 0H), 4.42-4.30 (m, 2H), 4.20-4.05 (m, 1H), 3.77 (br. s., 0H), 3.49 (quin, J = 7.0 Hz, 1H), 3.12-3.02 (m, 2H), 2.94-2.78 (m, 1H), 2.74-2.52 (m, 4H), 2.46 (s, 3H), 2.37-2.07 (m, 5H), 2.04-1.80 (m, 2H), 1.76-1.60 (m, 1H), 1.58-1.19 (m, 6H), 1.07-0.88 (m, 1H), 0.83 (d, J = 6.4 Hz, 1H), 0.67 (d, J = 12.2 Hz, 1H) |
| (R)-1-(1-(1-(3-methoxycyclobutyl)piperidin-4-yl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 141 | (M + H+) m/z: calcd 538.28; found 538.1. | 1H NMR (400 MHz, CD3OD) δ 8.19 (d, J = 4.0 Hz, 1H), 8.10 (d, J = 8.0 Hz, 1H), 7.12 (dd, J = 4.6, 7.9 Hz, 1H), 6.32 (s, 1H), 5.21 (br s, 1H), 4.73-4.64 (m, 1H), 4.61-4.55 (m, 2H), 3.69-3.59 (m, 1H), 3.23 (s, 3H), 3.06 (br d, J = 8.5 Hz, 1H), 2.82-2.66 (m, 4H), 2.56 (s, 3H), 2.53-2.36 (m, 3H), 2.33 (s, |

| Name | Ex. # Example # | LCMS LCMS | ¹H-NMR NMR |
|---|---|---|---|
| | | | 3H), 2.12-1.92 (m, 2H), 1.83-1.61 (m, 6H), 1.44 (br d, J = 18.6 Hz, 1H), 1.13 (br d, J = 10.3 Hz, 1H), 0.93 (br d, J = 12.3 Hz, 1H). |
| (R)-1-(1-(1-(dimethylglycyl)piperidin-4-yl)ethyl)-2-methyl-N-((6-methyl-4-(methylthio)-2-oxo-1,2-dihydropyridin-3-yl)methyl)-1H-indole-3-carboxamide | 142 | (M + H+) m/z: calcd 538.72, found 538.4. | 1H NMR (400 MHz, METHANOL-d4) δ = 7.73 (br d, J = 7.8 Hz, 1H), 7.61 (br d, J = 7.3 Hz, 1H), 7.18-7.01 (m, 2H), 6.41 (d, J = 2.0 Hz, 1H), 4.61 (s, 2H), 4.25 (br d, J = 17.6 Hz, 3H), 3.75 (br d, J = 13.7 Hz, 1H), 3.43 (br d, J = 13.7 Hz, 1H), 3.24-3.07 (m, 1H), 2.92 (br d, J = 12.7 Hz, 5H), 2.84-2.68 (m, 2H), 2.67-2.51 (m, 6H), 2.33 (s, 2H), 2.10 (br d, J = 12.7 Hz, 1H), 1.63 (br d, J = 6.8 Hz, 3H), 1.47-1.19 (m, 2H), 1.15-0.86 (m, 2H) |
| 4-((R)-1-(2-methyl-3-(((6-methyl-4-(methylthio)-2-oxo-1,2-dihydropyridin-3-yl)methyl)carbamoyl)-1H-indol-1-yl)ethyl)cyclohexyl butyrate | 143 isomer 1 | (M + H+) m/z: calcd: 538.27.; found 538.3 | 1H NMR (400 MHz, CD3OD) δ 7.71 (br d, J = 7.6 Hz, 1H), 7.55 (br d, J = 8.0 Hz, 1H), 7.20-6.95 (m, 2H), 6.27 (s, 1H), 4.92 (br d, J = 3.2 Hz, 1H), 4.67-4.54 (m, 2H), 4.27-4.12 (m, 1H), 2.77-2.57 (m, 3H), 2.51 (s, 3H), 2.36-2.29 (m, 2H), 2.28-2.26 (m, 3H), 2.03-1.85 (m, 2H), 1.71-1.62 (m, 3H), 1.60 (br d, J = 6.8 Hz, 4H), 1.50-1.39 (m, 1H), 1.39-1.19 (m, 2H), 1.19-1.05 (m, 1H), 1.00-0.89 (m, 3H), 0.77 (br d, J = 10.8 Hz, 1H) |
| 4-((R)-1-(2-methyl-3-(((6-methyl-4-(methylthio)-2-oxo-1,2-dihydropyridin-3-yl)methyl)carbamoyl)-1H-indol-1-yl)ethyl)cyclohexyl butyrate | 143 isomer 2 | (M + H+) m/z: calcd: 538.27.; found 538.3 | 1H NMR (400 MHz, CD3OD) δ 7.71 (br d, J = 7.6 Hz, 1H), 7.59-7.47 (m, 1H), 7.13-6.99 (m, 2H), 6.27 (s, 1H), 4.59 (s, 3H), 4.14 (m, 1H), 2.74-2.56 (m, 3H), 2.51 (s, 3H), 2.28 (s, 3H), 2.20 (br t, J = 7.2 Hz, 2H), 2.14-2.02 (m, 2H), 1.73 (br d, J = 10.8 Hz, 1H), 1.66-1.47 (m, 6H), 1.46-1.36 (m, 1H), 1.29-1.20 (m, 1H), 1.14-1.02 (m, 1H), 0.94 (br s, 2H), 0.89 (t, J = 7.6 Hz, 3H) |
| 4-((R)-1-(2-methyl-3-(((6-methyl-4-(methylthio)-2-oxo-1,2-dihydropyridin-3-yl)methyl)carbamoyl)-1H-indol-1-yl)ethyl)cyclohexyl isobutyrate | 144 isomer 1 | (M + H+) m/z: calcd: 538.27.; found 538.3 | 1H NMR (400 MHz, CD3OD) δ 7.71 (br d, J = 7.6 Hz, 1H), 7.54 (br d, J = 8.0 Hz, 1H), 7.13-6.98 (m, 2H), 6.25 (s, 1H), 4.94-4.88 (m, 1H), 4.58 (d, J = 2.0 Hz, 2H), 4.22-4.09 (m, 1H), 2.59 (s, 3H), 2.55-2.50 (m, 1H), 2.49 (s, 3H), 2.39-2.30 (m, 1H), 2.26 (s, 3H), 1.97-1.85 (m, 2H), 1.63 (br s, 1H), 1.59 (br d, J = 6.8 Hz, 3H), 1.49-1.39 (m, 1H), 1.35-1.19 (m, 2H), 1.14 (d, J = 2.4 Hz, 3H), 1.12 (br d, J = 2.8 Hz, 4H), 0.75 (br d, J = 12.0 Hz, 1H) |
| 4-((R)-1-(2-methyl-3-(((6-methyl-4-(methylthio)-2-oxo-1,2-dihydropyridin-3-yl)methyl)carbamoyl)-1H-indol-1-yl)ethyl)cyclohexyl isobutyrate | 144 isomer 2 | (M + H+) m/z: calcd: 538.27.; found 538.3 | 1H NMR (400 MHz, CD3OD) δ 7.71 (br d, J = 7.6 Hz, 1H), 7.54 (br d, J = 8.0 Hz, 1H), 7.15-6.99 (m, 2H), 6.24 (s, 1H), 4.63-4.52 (m, 3H), 4.20-3.99 (m, 1H), 2.75-2.53 (m, 3H), 2.49 (s, 3H), 2.42 (td, J = 6.8, 14.0 Hz, 1H), 2.26 (s, 3H), 2.14-1.96 (m, 2H), 1.69 (br d, J = 9.6 Hz, 1H), 1.58 (br d, J = 6.8 Hz, 3H), 1.47-1.33 (m, 1H), 1.29-1.11 (m, 2H), 1.07 (d, J = 5.2 Hz, 4H), 1.05 (d, J = 5.2 Hz, 3H), 0.97-0.85 (m, 2H) |
| 2-methyl-N-((6-methyl-4-(methylthio)-2-oxo-1,2-dihydropyridin-3-yl)methyl)-1-((R)-1-(4-((1-methylazetidin-3- | 145 isomer 1 | (M + H+) m/z: calcd 538.28; found 538.2. | 1H NMR (400 MHz, CDCl3) δ 8.23-8.01 (m, 2H), 7.41-7.35 (m, 2H), 6.99 (s, 1H), 6.03-6.01 (m, 1H), 4.71 (s, 2H), 4.15-4.05 (m, 2H), 3.71-3.67 (m, 5H), 2.92- |

| Name | Ex. # | LCMS | 1H-NMR |
|---|---|---|---|
| yl)oxy)cyclohexyl)ethyl)-1H-pyrrolo[2,3-b]pyridine-3-carboxamide | | | 2.86 (m, 4H), 2.80-2.49 (m, 12H), 2.23-1.83 (m, 4H), 1.25-1.15 (m, 4H). |
| 2-methyl-N-((6-methyl-4-(methylthio)-2-oxo-1,2-dihydropyridin-3-yl)methyl)-1-((R)-1-(4-((1-methylazetidin-3-yl)oxy)cyclohexyl)ethyl)-1H-pyrrolo[2,3-b]pyridine-3-carboxamide | 145 isomer 2 | (M + H+) m/z: calcd 538.28; found 577.1. | 1H NMR (400 MHz, CDCl3) δ 12.70 (s, 1H), 8.20-8.10 (m, 2H), 7.38-7.35 (m, 1H), 7.00-6.97 (m, 1H), 6.03 (s, 1H), 4.72 (s, 2H), 4.37-4.33 (m, 1H), 4.16-4.14 (m, 2H), 3.60-3.50 (m, 3H), 2.89-2.81 (m, 6H), 2.49 (s, 3H), 2.24 (s, 3H), 1.84 (d, J = 12.4 Hz, 2H), 1.66-1.59 (m, 6H), 1.26-1.23 (m, 1H), 1.04 (s, 1H), 0.79-0.77 (m, 1H). |
| (R)-1-(1-(1-(ethylsulfonyl)piperidin-4-yl)ethyl)-2-methyl-N-((6-methyl-4-(methylthio)-2-oxo-1,2-dihydropyridin-3-yl)methyl)-1H-indole-3-carboxamide | 146 | LCMS (M + H+) m/z: calcd 545.23; found 545.1 | 1H NMR (400 MHz, CD3OD) δ 7.74 (br d, J = 7.5 Hz, 1H), 7.58 (br d, J = 8.0 Hz, 1H), 7.16-7.04 (m, 2H), 6.29 (s, 1H), 4.61 (s, 2H), 4.34-4.16 (m, 1H), 3.83 (br d, J = 12.0 Hz, 1H), 3.53 (br d, J = 12.0 Hz, 1H), 2.96 (q, J = 7.5 Hz, 2H), 2.86 (dt, J = 2.5, 12.5 Hz, 1H), 2.77-2.65 (m, 1H), 2.60 (s, 3H), 2.53 (s, 3H), 2.51-2.40 (m, 1H), 2.30 (s, 3H), 2.10 (br d, J = 13.0 Hz, 1H), 1.63 (br d, J = 7.0 Hz, 3H), 1.50-1.32 (m, 1H), 1.27 (t, J = 7.5 Hz, 3H), 1.18-1.00 (m, 1H), 1.00-0.86 (m, 1H) |
| 2-methyl-1-((R)-1-(4-((1-methyl-1H-pyrazol-4-yl)oxy)cyclohexyl)ethyl)-N-((6-methyl-4-(methylthio)-2-oxo-1,2-dihydropyridin-3-yl)methyl)-1H-pyrrolo[2,3-b]pyridine-3-carboxamide | 147 isomer 1 | (M + H+) m/z: calcd 549.26: found 549.2 | 1H NMR (400 MHz, CDCl3) δ 13.00 (s, 1H), 8.20-8.19 (m, 1H), 8.11-8.09 (m, 1H), 7.36 (s, 1H), 7.17 (s, 1H), 7.02-6.96 (m, 2H), 6.02 (s, 1H), 4.71 (s, 2H), 4.06 (s, 2H), 3.79 (s, 3H), 2.80 (s, 3H), 2.48 (s, 3H), 2.21 (s, 3H), 2.14-2.11 (m, 1H), 1.88-1.80 (m, 3H), 1.67-1.54 (m, 5H), 1.27-1.16 (m, 2H), 0.79-0.76 (m, 1H). |
| 2-methyl-1-((R)-1-(4-((1-methyl-1H-pyrazol-4-yl)oxy)cyclohexyl)ethyl)-N-((6-methyl-4-(methylthio)-2-oxo-1,2 dihydropyridin-3-yl)methyl)-1H-pyrrolo[2,3-b]pyridine-3-carboxamide | 147 isomer 2 | (M + H+) m/z: calcd 549.26: found 549.2 | 1H NMR (400 MHz, CDCl3) δ 12.18 (s, 1H), 8.22-8.21 (m, 1H), 8.12-8.10 (m, 1H), 7.39-7.36 (m, 1H), 7.16 (s, 1H), 7.02-7.00 (m, 2H), 6.02 (s, 1H), 4.71 (s, 2H), 3.79 (s, 3H), 3.74-3.70 (m, 1H), 2.77 (s, 3H), 2.49 (s, 3H), 2.25-2.18 (m, 5H), 1.95-1.92 (m, 1H), 1.72-1.63 (m, 2H), 1.44 (m, 1H), 1.32-1.05 (m, 5H), 0.89 (m, 1H). |
| 1-((R)-1-(4-(3-(dimethylamino)azetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 148 isomer 1 | (M + H+) m/z: calcd 550.79, found 550.4. | 1H NMR (400 MHz, METHANOL-d4) δ = 7.79-7.68 (m, 1H), 7.54 (br d, J = 7.8 Hz, 1H), 7.19-7.06 (m, 2H), 6.42 (s, 1H), 4.61 (s, 2H), 4.59-4.42 (m, 4H), 4.31 (quin, J = 7.3 Hz, 1H), 4.18-4.07 (m, 1H), 3.28-3.18 (m, 1H), 2.99-2.91 (m, 1H), 2.86 (s, 6H), 2.61-2.54 (m, 5H), 2.33 (s, 3H), 2.28-2.07 (m, 4H), 1.59 (br d, J = 6.8 Hz, 3H), 1.41-1.26 (m, 1H), 1.23-1.10 (m, 1H), 1.03-0.78 (m, 3H) |
| 1-((1R)-1-(4-(3-(dimethylamino)azetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 148 isomer 2 | (M + H+) m/z: calcd 550.79, found 550.4. | 1H NMR (400 MHz, METHANOL-d4) δ = 7.73 (br d, J = 7.3 Hz, 1H), 7.56 (br d, J = 7.8 Hz, 1H), 7.18-7.04 (m, 2H), 6.39 (s, 1H), 4.61 (s, 2H), 4.58-4.41 (m, 4H), 4.27-4.10 (m, 2H), 3.28-3.18 (m, 1H), 2.82 (s, 6H), 2.74-2.67 (m, 1H), 2.59 (s, 2H), 2.57-2.53 (m, 3H), 2.33 (s, 3H), 2.31-2.03 (m, 4H), 1.85-1.77 (m, 1H), 1.62 (br d, J = 6.8 Hz, 3H), 1.43-1.14 (m, 3H), 1.08-0.83 (m, 3H) |
| 2-methyl-N-((6-methyl-4-(methylthio)-2-oxo-1,2- | 149 isomer 1 | (M + H+) calcd. | 1H NMR (400 MHz, CDCl3) δ 7.84 (br d, J = 7.0 Hz, 1H), 7.47 |

| Name | Ex. # | LCMS | ¹H-NMR |
|---|---|---|---|
| dihydropyridin-3-yl)methyl)-1-((1R)-1-(4-((3-methyltetrahydrofuran-3-yl)amino)cyclohexyl)ethyl)-1H-indole-3-carboxamide | | 551.3; found 551.2. | (br d, J = 8.0 Hz, 1H), 7.32 (s, 1H), 7.19-6.96 (m, 2H), 6.02 (s, 1H), 4.73 (br d, J = 5.5 Hz, 2H), 3.9 (m, 3H), 3.61-3.34 (m, 2H), 2.87-2.64 (m, 3H), 2.50 (m, 4H), 2.22 (s, 3H), 2.12-1.79 (m, 4H), 1.72-1.64 (m, 3H), 1.55-1.49 (m, 1H), 1.26 (br s, 3H), 1.16-0.98 (m, 2H), 0.94-0.48 (m, 3H). |
| 2-methyl-N-((6-methyl-4-(methylthio)-2-oxo-1,2-dihydropyridin-3-yl)methyl)-1-((1R)-1-(4-((3-methyltetrahydrofuran-3-yl)amino)cyclohexyl)ethyl)-1H-indole-3-carboxamide | 149 isomer 2 | | 1H NMR (400 MHz, CDCl3) δ 7.85 (br d, J = 6.8 Hz, 1H), 7.47 (br d, J = 7.8 Hz, 1H), 7.08 (br d, J = 4.5 Hz, 2H), 6.02 (s, 1H), 4.73 (br d, J = 18.6 Hz, 2H), 4.25 (br s, 1H), 4.01-3.82 (m, 2H), 3.60 (br s, 1H), 3.47 (br s, 1H), 2.76 (s, 3H), 2.50 (s, 3H), 2.32 (m, 1H), 2.24 (s, 3H), 2.00-1.68 (m, 5H), 1.54-1.41 (m, 3H), 1.40-1.22 (m, 5H), 1.07 (br s, 2H), 0.91 (br s, 2H). |
| 1-((R)-1-((2s,5S)-5-(6-oxa-1-azaspiro[3.3]heptan-1-yl)-1,3-dioxan-2-yl)ethyl)-2-methyl-N-((6-methyl-4-(methylthio)-2-oxo-1,2-dihydropyridin-3-yl)methyl)-1H-indole-3-carboxamide | 150 isomer 1 | (M + H+) m/z: calcd 553.24: found 553.0. | 1H NMR (400 MHz, CDCl3) δ 11.80 (s, 1H), 7.83 (d, J = 8.0, 1H), 7.45 (d, J = 4.0, 1H), 7.22 (m, 1H), 7.10-7.04 (m, 2H), 5.99 (s, 1H), 5.09 (m, 1H), 4.90-4.85 (m, 2H), 4.73-4.67 (m, 5H), 4.26 (m, 1H), 3.94-3.91 (m, 1H), 3.71-3.68 (m, 1H), 3.22-3.20 (m, 1H), 3.12-3.10 (m, 1H), 2.74 (s, 3H), 2.49-2.48 (m, 4H), 2.36-2.32 (m, 2H), 2.22 (s, 3H), 1.26 (m, 5H). |
| 1-((R)-1-((2r,5R)-5-(6-oxa-1-azaspiro[3.3]heptan-1-yl)-1,3-dioxan-2-yl)ethyl)-2-methyl-N-((6-methyl-4-(methylthio)-2-oxo-1,2-dihydropyridin-3-yl)methyl)-1H-indole-3-carboxamide | 150 isomer 2 | (M + H+) m/z: calcd 553.24: found 553.0. | 1H NMR (400 MHz, CDCl3)δ 11.58 (s, 1H), 7.82 (d, J = 8.0, 1H), 7.52-7.48 (m, 1H), 7.23 (m, 1H), 7.09-7.05(m, 2H), 5.99 (s, 1H), 4.93 (m, 1H), 4.82 (d, J = 8.0 1H), 4.75 (m, 1H), 4.72 (m, 2H), 4.70 (m, 2H), 4.64 (m, 1H), 4.42 (m, 1H), 4.16 (m, 1H), 3.53-3.48 (m, 1H), 3.28 (m, 1H), 3.01-2.98 (m, 3H), 2.74 (s, 3H), 2.47 (s, 3H), 2.30-2.28 (m, 2H), 2.27 (s, 3H), 1.26 (m, 6H). |
| 1-((S)-1-((2s,5R)-5-(6-oxa-1-azaspiro[3.3]heptan-1-yl)-1,3-dioxan-2-yl)ethyl)-2-methyl-N-((6-methyl-4-(methylthio)-2-oxo-1,2-dihydropyridin-3-yl)methyl)-1H-indole-3-carboxamide | 151 isomer 1 | (M + H+) m/z: calcd 553.24: found 553.0. | 1H NMR (400 MHz, CDCl3) δ 11.74 (s, 1H), 7.84 (d, J = 4.0, 1H), 7.46 (d, J = 8.0, 1H), 7.22 (s, 1H), 7.12-7.05 (m, 2H), 6.02-5.99 (m, 1H), 5.10 (m, 1H), 4.90-4.85 (m, 2H), 4.72-4.69 (m, 5H), 4.26 (m, 1H), 4.11 (m, 1H), 3.94-3.91 (m, 1H), 3.62-3.67 (m, 1H), 3.22-3.20 (m, 1H), 3.12-3.10 (m, 1H), 2.74 (s, 3H), 2.47 (s, 3H), 2.34-2.31 (m, 2H), 2.22-2.20 (m, 4H), 1.25 (m, 5H). |
| 1-((S)-1-((2r,5S)-5-(6-oxa-1-azaspiro[3.3]heptan-1-yl)-1,3-dioxan-2-yl)ethyl)-2-methyl-N-((6-methyl-4-(methylthio)-2-oxo-1,2-dihydropyridin-3-yl)methyl)-1H-indole-3-carboxamide | 151 isomer 2 | (M + H+) m/z: calcd 553.24: found 553.0. | 1H NMR (400 MHz, CDCl3) δ 11.46-11.41 (m, 1H), 7.82 (m, 1H), 7.52 (m, 1H), 7.09 (m, 1H), 7.07 (m, 2H), 5.99 (s, 1H), 5.39 (m, 1H), 4.94 (m, 1H), 4.81 (m, 1H), 4.76 (m, 1H), 4.71 (m, 1H), 4.64-4.63 (m, 2H), 4.55 (m, 1H), 4.40-4.37 (m, 1H), 4.12 (m, 1H), 3.51 (m, 1H), 3.29 (m, 1H), 3.00 (s, 3H), 2.74 (s, 3H), 2.48 (s, 3H), 2.28-2.20 (m, 5H), 2.02-2.00 (m, 1H), 1.26 (m, 10H), 0.88-0.86 (m, 1H). |
| 1-((R)-1-((3R,4R)-3-fluoro-1-(3-methoxycyclobutyl)piperidin-4-yl)ethyl)-2-methyl-N-((6-methyl-4-(methylthio)-2-oxo-1,2-dihydropyridin-3-yl)methyl)-1H-indole-3-carboxamide | 152 | (M + H+) m/z: calcd 555.27; found 555.4. | 1H NMR (400 MHz, CD3OD) δ 7.81-7.72 (m, 1H), 7.57 (d, J = 8.0 Hz, 1H), 7.19-7.09 (m, 2H), 6.32 (s, 1H), 4.71-4.63 (m, 2H), 4.58-4.49 (m, 1H), 3.68-3.59 (m, 1H), 3.26-3.12 (m, 4H), 2.75 (s, 1H), 2.67-2.58 (m, 4H), 2.56 (s, 3H), 2.54-2.36 (m, 4H), 2.33 (s, 3H), 1.99-1.90 (m, 1H), 1.78-1.60 (m, 6H), 1.18-0.99 (m, 2H). |

| Name | Ex. # | LCMS | ¹H-NMR |
|---|---|---|---|
| 1-((R)-1-((3S,4R)-3-fluoro-1-(3-methoxycyclobutyl)piperidin-4-yl)ethyl)-2-methyl-N-((6-methyl-4-(methylthio)-2-oxo-1,2 dihydropyridin-3-yl)methyl)-1H-indole-3-carboxamide | 153 | (M + H+) m/z: calcd 555.27; found 555.1. | 1H NMR (400 MHz, CDCl3) δ 7.81-7.78 (m, 1H), 7.34-7.24 (m, 1H), 7.06-6.97 (m, 2H), 5.93 (s, 1H), 4.93-4.49 (m, 4H), 3.83-3.23 (m, 2H), 3.15-3.13 (m, 3H), 3.10-2.76 (m, 1H), 2.64 (s, 4H), 2.41 (s, 3H), 2.29-2.27 (m, 4H), 2.14 (s, 3H), 1.81-1.72 (m, 4H), 1.53-1.21 (m, 3H), 0.81-0.70 (m, 1H). |
| 1-((R)-1-(4-((3-(fluoromethyl)oxetan-3-yl)amino)cyclohexyl)ethyl)-2-methyl-N-((6-methyl-4-(methylthio)-2-oxo-1,2-dihydropyridin-3-yl)methyl)-1H-indole-3-carboxamide | 154 isomer 1 | (M + H+) m/z: calcd: 555.28; found 555.3. | 1H NMR (500 MHz, CDCl3) δ 7.84 (br d, J = 7.9 Hz, 1H), 7.45 (br d, J = 8.5 Hz, 1H), 7.32 (br s, 1H), 7.09 (br s, 1H), 7.08-7.02 (m, 1H), 7.12-7.00 (m, 2H), 6.01 (s, 1H), 4.71 (s, 2H), 4.62 (s, 1H), 4.55 (br d, J = 3.1 Hz, 1H), 4.47-4.39 (m, 2H), 4.27-4.17 (m, 1H), 3.00 (br s, 1H), 2.31 (br d, J = 9.8 Hz, 1H), 2.21 (s, 2H), 2.18 (s, 1H), 1.84-1.76 (m, 1H), 1.59 (br d, J = 7.3 Hz, 3H), 1.31 (br d, J = 4.3 Hz, 1H), 0.94-0.83 (m, 1H). |
| 1-((R)-1-(4-((3-(fluoromethyl)oxetan-3-yl)amino)cyclohexyl)ethyl)-2-methyl-N-((6-methyl-4-(methylthio)-2-oxo-1,2 dihydropyridin-3-yl)methyl)-1H-indole-3-carboxamide | 154 isomer 2 | (M + H+) m/z: calcd: 555.28; found 555.3. | 1H NMR (500 MHz, CDCl3) δ 12.47-12.18 (m, 1H), 7.90-7.78 (m, 1H), 7.49-7.40 (m, 1H), 7.30 (br s, 1H), 7.34-7.28 (m, 1H), 7.13-7.00 (m, 2H), 6.01 (s, 1H), 4.73 (br s, 3H), 4.63 (br s, 1H), 4.55-4.35 (m, 5H), 4.10-4.00 (m, 1H), 2.71 (s, 3H), 2.49 (s, 3H), 2.23-2.21 (m, 3H), 2.20-2.14 (m, 1H), 2.11-2.06 (m, 1H), 1.93-1.87 (m, 1H), 1.62-1.58 (m, 4H), 1.27-1.19 (m, 2H), 1.17-1.08 (m, 1H), 1.06-1.00 (m, 1H), 0.95-0.77 (m, 2H). |
| 1-((R)-1-(4-((3-(fluoromethyl)oxetan-3-yl)amino)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 155 isomer 1 | (M + H+) m/z: calcd 556.71; found 556.3. | 1H NMR (400 MHz, CD3OD) δ 8.19 (dd, J = 1.2, 4.5 Hz, 1H), 8.10 (br d, J = 7.6 Hz, 1H), 7.12 (dd, J = 4.8, 7.6 Hz, 1H), 6.31 (s, 1H), 4.77 (s, 1H), 4.65 (s, 1H), 4.61 (s, 2H), 4.57-4.38 (m, 4H), 4.09 (br s, 1H), 2.78-2.51 (m, 8H), 2.32 (s, 3H), 2.12 (br d, J = 11.6 Hz, 1H), 1.88 (br d, J = 11.6 Hz, 1H), 1.75-1.50 (m, 4H), 1.31-1.11 (m, 2H), 0.93 (br s, 3H) |
| 1-((R)-1-(4-((3-(fluoromethyl)oxetan-3-yl)amino)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 155 isomer 2 | (M + H+) m/z: calcd 556.71; found 556.3 | 1H NMR (400 MHz, CD3OD) δ 8.20 (br s, 1H), 8.10 (br d, J = 7.2 Hz, 1H), 7.12 (br s, 1H), 6.32 (s, 1H), 4.76 (s, 1H), 4.68-4.58 (m, 5H), 4.56 (br s, 1H), 4.48 (d, J = 6.4 Hz, 1H), 4.44 (br d, J = 5.6 Hz, 1H), 2.91 (br s, 1H), 2.74 (br s, 3H), 2.55 (s, 3H), 2.32 (s, 3H), 1.87-1.56 (m, 8H), 1.34 (br s, 2H), 1.13 (br d, J = 5.6 Hz, 1H), 0.90 (br s, 1H) |
| 7-((R)-1-(4-((3-(fluoromethyl)oxetan-3-yl)amino)cyclohexyl)ethyl)-6-methyl-N-((6-methyl-4-(methylthio)-2-oxo-1,2-dihydropyridin-3-yl)methyl)-7H-pyrrolo[2,3-d]pyrimidine-5-carboxamide | 156 isomer 1 | (M + H+) m/z: calcd 557.26; found 557.2. | 1H NMR (400 MHz, CD3OD) δ 9.04 (s, 1H), 8.71 (s, 1H), 6.31 (s, 1H), 4.77 (s, 1H), 4.65 (s, 1H), 4.59 (s, 2H), 4.49-4.55 (m, 2H), 4.43 (dd, J = 6.4, 17.6 Hz, 2H), 4.15 (br s, 1H), 2.79-2.51 (m, 8H), 2.32 (s, 3H), 2.11 (br d, J = 10.8 Hz, 1H), 1.88 (br d, J = 11.6 Hz, 1H), 1.73-1.49 (m, 4H), 1.31-1.10 (m, 2H), 0.93 (br d, J = 5.2 Hz, 3H) |
| 7-((R)-1-(4-((3-(fluoromethyl)oxetan-3-yl)amino)cyclohexyl)ethyl)-6-methyl-N-((6-methyl-4-(methylthio)-2-oxo-1,2-dihydropyridin-3- | 156 isomer 2 | (M + H+) m/z: calcd 557.26; found 557.1. | 1H NMR (400 MHz, CD3OD) δ 9.03 (s, 1H), 8.72 (s, 1H), 6.32 (s, 1H), 4.79-4.75 (m, 1H), 4.66-4.52 (m, 6H), 4.50-4.49 (m, 1H), 4.46 (dd, J = 6.4, 14.0 Hz, 1H), 2.96-2.87 (m, 1H), 2.76 (s, 3H), |

| Name | Example # | LCMS | 1H-NMR |
|---|---|---|---|
| yl)methyl)-7H-pyrrolo[2,3-d]pyrimidine-5-carboxamide | | | 2.56 (s, 3H), 2.32 (s, 3H), 1.87-1.54 (m, 8H), 1.36 (br d, J = 4.4 Hz, 2H), 1.23-1.11 (m, 1H), 0.92 (br s, 1H). |
| 1-((R)-1-(4-(3-cyclopropyl-3-fluoroazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 157 single isomer | (M + H+) m/z: calcd: 566.29.; found 566.1 | 1H NMR (400 MHz, CD3OD) δ 8.18 (br d, J = 4.0 Hz, 1H), 8.09 (br d, J = 7.6 Hz, 1H), 7.16-7.01 (m, 1H), 6.30 (s, 1H), 4.60 (s, 2H), 4.08 (br s, 1H), 3.28 (br d, J = 5.6 Hz, 2H), 3.25-3.20 (m, 2H), 2.67 (br s, 3H), 2.54 (s, 3H), 2.31 (s, 3H), 2.20-1.87 (m, 3H), 1.74-1.61 (m, 3H),1.59-1.56 (m, 1H) 1.31-1.21 (m, 1H), 1.15 (br d, J = 6.4 Hz, 2H), 1.13-1.01 (m, 2H), 0.95 (br s, 1H), 0.89-0.80 (m, 1H), 0.56 (br d, J = 8.0 Hz, 2H), 0.48-0.36 (m, 2H). |
| 1-((R)-1-(4-(3-hydroxy-3-isopropylazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide | 158 single isomer | (M + H+) m/z: calcd 566.78, found 566.3. | 1H NMR (400 MHz, METHANOL-d4) δ = 8.24-8.16 (m, 1H), 8.11 (br d, J = 7.8 Hz, 1H), 7.13 (br dd, J = 4.6, 8.1 Hz, 1H), 6.40 (s, 1H), 4.61 (s, 2H), 4.25 (br dd, J = 2.2, 11.0 Hz, 1H), 4.17 (br dd, J = 2.7, 11.0 Hz, 1H), 4.05 (d, J = 10.3 Hz, 1H), 3.97 (d, J = 10.3 Hz, 1H), 3.89 (dd, J = 5.4, 10.8 Hz, 1H), 3.85-3.77 (m, 1H), 3.00 (br d, J = 5.9 Hz, 2H), 2.77-2.61 (m, 4H), 2.56 (s, 3H), 2.34 (s, 3H), 2.28-2.08 (m, 2H), 2.02-1.78 (m, 3H), 1.67 (br s, 3H), 1.41-1.17 (m, 3H), 0.95 (t, J = 7.1 Hz, 3H), 0.88 (t, J = 6.6 Hz, 3H) |
| 6-fluoro-1-((R)-1-(4-((3-(hydroxymethyl)oxetan-3-yl)amino)cyclohexyl)ethyl)-2-methyl-N-((6-methyl-4-(methylthio)-2-oxo-1,2-dihydropyridin-3-yl)methyl)-1H-indole-3-carboxamide | 159 isomer 1 | (M + H+) m/z: calcd: 571.28 ; found 571.3. | 1H NMR (400 MHz, CDCl3) δ 12.35-12.07 (m, 1H), 7.76 (dd, J = 5.6, 8.6 Hz, 1H), 7.24 (br. s., 1H), 7.12 (d, J = 10.3 Hz, 1H), 6.86-6.78 (m, 1H), 6.03 (s, 1H), 4.81-4.61 (m, 2H), 4.48 (br. s., 2H), 4.42-4.31 (m, 2H), 4.05-3.98 (m, 1H), 3.86 (br. s., 2H), 2.66 (s, 2H), 2.58 (br. s., 1H), 2.49 (s, 3H), 2.29-2.17 (m, 3H), 2.07 (d, J = 12.2 Hz, 2H), 1.93 (d, J = 12.7 Hz, 1H), 1.57 (s, 3H), 1.31 (br. s., 1H), 1.18-1.06 (m, 1H), 1.05-0.94 (m, 2H), 0.90-0.68 (m, 4H). |
| 6-fluoro-1-((R)-1-(4-((3-(hydroxymethyl)oxetan-3-yl)amino)cyclohexyl)ethyl)-2-methyl-N-((6-methyl-4-(methylthio)-2-oxo-1,2-dihydropyridin-3-yl)methyl)-1H-indole-3-carboxamide | 159 isomer 2 | (M + H+) m/z: calcd: 571.28 ; found 571.3. | 1H NMR (400 MHz, CDCl3) δ 12.55-12.37 (m, 1H), 7.83-7.68 (m, 1H), 7.12 (d, J = 10.3 Hz, 1H), 6.82 (t, J = 8.1 Hz, 1H), 6.03 (s, 1H), 4.80-4.63 (m, 2H), 4.57-4.42 (m, 2H), 4.41-4.33 (m, 1H), 4.19 (br. s., 1H), 3.84 (br. s., 1H), 2.92 (br. s., 1H), 2.71 (s, 2H), 2.49 (s, 3H), 2.24 (s, 3H), 2.08 (br. s., 1H), 1.83 (d, J = 8.8 Hz, 1H), 1.63 (br. s., 2H), 1.57 (s, 4H), 1.15-0.79 (m, 4H). |
| 1-((R)-1-(4-(3-(1H-1,2,3-triazol-1-yl)azetidin-1-yl)cyclohexyl)ethyl)-2-methyl-N-((6-methyl-4-(methylthio)-2-oxo-1,2-dihydropyridin-3-yl)methyl)-1H-indole-3-carboxamide | 160 single isomer | (M + H+) m/z: calcd 574.29; found 574.3 | 1H NMR (400 MHz, CD3OD) δ 8.12 (d, J = 0.8 Hz, 1H), 7.76-7.71 (m, 2H), 7.55 (br d, J = 7.9 Hz, 1H), 7.13-7.03 (m, 2H), 6.28 (s, 1H), 5.26 (quin, J = 6.9 Hz, 1H), 4.61 (d, J = 2.1 Hz, 2H), 4.18-4.07 (m, 1H), 3.84 (td, J = 7.7, 19.3 Hz, 2H), 3.64-3.55 (m, 2H), 2.61 (s, 3H), 2.52 (s, 3H), 2.29 (s, 3H), 2.23 (br d, J = 10.4 Hz, 2H), 2.13 (br d, J = 10.5 Hz, 1H), 1.96 (br d, J = 10.8 Hz, 1H), 1.66-1.57 (m, 4H), 1.21-1.07 (m, 2H), 0.98-0.74 (m, 3H) |
| 2-methyl-N-((6-methyl-4-(methylthio)-2-oxo-1,2- | 161 single | (M + H+) m/z: calcd: | 1H NMR (400 MHz, DMSO-d6) δ 11.67 (s, 1H), 8.18 (d, J = 4.0 Hz, |

| Name | Ex. # | LCMS | ¹H-NMR |
|---|---|---|---|
| dihydropyridin-3-yl)methyl)-1-((R)-1-(4-((1-(trifluoromethyl)cyclopropyl)amino)cyclohexyl)ethyl)-1H-pyrrolo[2,3-b]pyridine-3-carboxamide | isomer | 576.25; found 576.6 | 1H), 8.06 (d, J = 8.0 Hz, 1H), 7.81 (br t, J = 4.4 Hz, 1H), 7.09 (dd, J = 4.8, 8 Hz, 1H), 6.13 (s, 1H), 4.38 (br d, J = 4.8 Hz, 2H), 4.03 (br s, 1H), 2.65 (br d, J = 16 Hz, 4H), 2.56 (br s, 1H), 2.47 (s, 3H), 2.41-2.24 (m, 1H), 2.18 (s, 3H), 2.07-1.85 (m, 2H), 1.71-1.52 (m, 4H), 1.29-1.21 (m, 1H), 1.14-0.98 (m, 2H), 0.96-0.84 (m, 3H), 0.80 (br s, 3H) |
| 2-methyl-N-((6-methyl-4-(methylthio)-2-oxo-1,2-dihydropyridin-3-yl)methyl)-1-((R)-1-(4-(3-(methylsulfonyl)azetidin-1-yl)cyclohexyl)ethyl)-1H-indole-3-carboxamide | 162 isomer 1 | (M + H+) m/z: calcd 585.25; found 585.1. | 1H NMR (400 MHz, CD3OD) δ 7.74 (d, J = 8.0 Hz, 1H), 7.57 (d, J = 8.0 Hz, 1H), 7.12-7.07 (m, 2H), 6.33 (s, 1H), 5.37-5.35 (m, 1H), 4.63 (s, 2H), 4.15-4.11 (m, 2H), 3.66-3.57 (m, 2H), 3.52-3.47 (m, 2H), 2.91 (s, 3H), 2.62 (s, 3H), 2.56 (s, 3H), 2.33 (s, 3H), 2.23-2.14 (m, 4H), 2.04-2.02 (m, 2H), 1.96-1.93 (m, 1H), 1.63 (d, J = 8.0 Hz, 4H), 0.94-0.90 (m, 1H). |
| 2-methyl-N-((6-methyl-4-(methylthio)-2-oxo-1,2-dihydropyridin-3-yl)methyl)-1-((R)-1-(4-(3-(methylsulfonyl)azetidin-1-yl)cyclohexyl)ethyl)-1H-indole-3-carboxamide | 162 isomer 2 | (M + H+) m/z: calcd 585.25; found 585.1. | 1H NMR (400 MHz, CD3OD) δ 7.74 (d, J = 8.0 Hz, 1H), 7.56 (d, J = 8.0 Hz, 1H), 7.11-7.08 (m, 2H), 6.33 (s, 1H), 5.37-5.35 (m, 1H), 4.63 (s, 2H), 4.26 (br s, 1H), 4.07-4.04 (m, 1H), 3.60-3.53 (m, 2H), 3.44-3.38 (m, 2H), 2.97 (s, 3H), 2.64 (s, 3H), 2.56 (s, 3H), 2.37 (s, 1H), 2.33 (s, 3H), 2.21 (t, J = 8.0 Hz, 1H), 2.05 (br s, 1H), 1.72 (br s, 2H), 1.62 (d, J = 8.0 Hz, 4H), 1.53-1.50 (m, 1H), 1.17-1.14 (m, 1H), 0.93-0.90 (m, 1H). |
| 2-methyl-N-((6-methyl-4-(methylthio)-2-oxo-1,2-dihydropyridin-3-yl)methyl)-1-((R)-1-(4-((3-(trifluoromethyl)oxetan-3-yl)amino)cyclohexyl)ethyl)-1H-pyrrolo[2,3-b]pyridine-3-carboxamide | 163 isomer 1 | (M + H+) m/z: calcd: 592.26; found 592.3. | 1H NMR (500 MHz, CDCl3) δ 12.67 (br. s., 1H), 8.25-8.18 (m, 1H), 8.11 (dd, J = 1.5, 7.8 Hz, 1H), 7.36 (br. s., 1H), 6.99 (dd, J = 4.9, 7.8 Hz, 1H), 6.03 (s, 1H), 4.71 (dd, J = 7.1, 8.6 Hz, 4H), 4.50 (t, J = 7.6 Hz, 2H), 2.90-2.55 (m, 5H), 2.50 (s, 3H), 2.22 (s, 3H), 2.11 (d, J = 9.8 Hz, 1H), 1.93 (d, J = 11.7 Hz, 1H), 1.74-1.55 (m, 4H), 1.34-1.20 (m, 1H), 0.99 (q, J = 11.2 Hz, 3H), 0.83 (d, J = 10.3 Hz, 1H). |
| 2-methyl-N-((6-methyl-4-(methylthio)-2-oxo-1,2-dihydropyridin-3-yl)methyl)-1-((R)-1-(4-((3-(trifluoromethyl)oxetan-3-yl)amino)cyclohexyl)ethyl)-1H-pyrrolo[2,3-b]pyridine-3-carboxamide | 163 isomer 2 | (M + H+) m/z: calcd: 592.26; found 592.3. | 1H NMR (500 MHz, CDCl3) δ 12.75 (br. s., 1H), 8.21 (br. s., 1H), 8.17-8.04 (m, 1H), 7.37 (br. s., 1H), 6.99 (dd, J = 4.9, 7.8 Hz, 1H), 6.03 (s, 1H), 4.79-4.68 (m, 4H), 4.58-4.47 (m, 2H), 3.08-2.78 (m, 4H), 2.49 (s, 3H), 2.23 (s, 3H), 1.82 (br. s., 1H), 1.65 (br. s., 6 H), 1.37 (br. s., 2H), 1.07 (dd, J = 5.1, 13.9 Hz, 1H), 0.90 (d, J = 9.3 Hz, 1H). |
| 6-methyl-N-((6-methyl-4-(methylthio)-2-oxo-1,2-dihydropyridin-3-yl)methyl)-7-((R)-1-(4-((3-(trifluoromethyl)oxetan-3-yl)amino)cyclohexyl)ethyl)-7H-pyrrolo[2,3-d]pyrimidine-5-carboxamide | 164 isomer 1 | (M + H+) m/z: calcd 593.24; found 593.1 | 1H NMR (400 MHz, CD3OD) δ 9.03 (s, 1H), 8.84-8.55 (m, 1H), 6.32 (s, 1H), 4.68 (dd, J = 7.0, 10.8 Hz, 2H), 4.62-4.51 (m, 4H), 4.18 (br s, 1H), 2.69 (br s, 3H), 2.62 (br s, 3H), 2.55 (s, 3H), 2.32 (s, 3H), 2.11 (br d, J = 9.5 Hz, 1H), 1.98-1.91 (m, 1H), 1.73-1.61 (m, 4H), 1.38-1.03 (m, 3H), 1.02-0.85 (m, 3H) |
| 6-methyl-N-((6-methyl-4-(methylthio)-2-oxo-1,2-dihydropyridin-3-yl)methyl)-7-((R)-1-(4-((3-(trifluoromethyl)oxetan-3-yl)amino)cyclohexyl)ethyl)- | 164 isomer 2 | (M + H+) m/z: calcd 593.24; found 593.1 | 1H NMR (400 MHz, CD3OD) δ 9.01 (s, 1H), 8.70 (s, 1H), 6.30 (s, 1H), 4.71-4.64 (m, 2H), 4.61-4.54 (m, 4H), 4.42-4.21 (m, 1H), 3.01-2.90 (m, 1H), 2.73 (s, 3H), 2.54 (s, 3H), 2.30 (s, 3H), 1.81 (br d, J = 8.8 Hz, 1H), 1.67 (br d, J = |

| Name | Ex. # | LCMS | $^1$H-NMR |
|---|---|---|---|
| Name | Example # | LCMS | NMR |
| 7H-pyrrolo[2,3-d]pyrimidine-5-carboxamide | | | 6.5 Hz, 6H), 1.49-0.98 (m, 4H), 0.84 (br s, 1H) |

EZH2 Assays

IC$_{50}$ Measurements for Inhibitors Using EZH2

EZH2 biochemical assay (IC$_{50}$): Compound potencies were assessed through incorporation of $^3$H-SAM into a biotinylated H3 peptide. Specifically, 30 pM PRC2 containing wt EZH2 (pentameric complex prepared in-house) was pre-incubated with 450 nM SAM, 450 nM $^3$H-SAM, 2 µM H3K27me3 activating peptide (H$_2$N-RKQLATKAAR(Kme3)SAPATGGVKKP-amide) and compounds (as 10 point duplicate dose response titrations in DMSO, final assay 0.8% DMSO (v/v)) for 3-5 h in 50 mM Tris (pH 8.5), 1 mM DTT, 0.07 mM Brij-35, 0.1% BSA, and 0.8% DMSO in a total volume of 12.5 µl. Reaction was initiated with biotinylated H3 substrate peptide (H$_2$N-RKQLATKAAR(Kme1)SAPATGGVKKP-NTPEGBiot) as a 2 µM stock in 12.5 µl of buffer and allowed to react at room temperature for 18-22 h. Quenching was accomplished by addition of 20 µl of STOP solution (50 mM Tris (pH 8.5), 200 mM EDTA, 2 mM SAH). 35 µl of the quenched solution was transferred to streptavidin coated FlashPlates (PerkinElmer), incubated 1-2 h, washed, and read in a TopCount Reader (PerkinElmer). IC$_{50}$s were calculated in Genedata Screener using non-linear least square four parameter fits, where the four parameters were IC$_{50}$, Hill slope, pre-transitional baseline (0% INH), and post-transitional baseline (100% INH).

Table 1 shows the activity of selected compounds of this invention in the EZH2 activity inhibition assays. IC$_{50}$ values are reported as follows: "A" indicates an IC$_{50}$ value of less than 0.5 nM; "B" indicates an IC$_{50}$ value of 0.5 nM to 5 nM; "C" indicates an IC$_{50}$ value of greater than 5 nM for each enzyme; and "ND" is not determined.

TABLE 1

IC$_{50}$ values for selected compounds.

| Example | EZH2 (IC$_{50}$) |
|---|---|
| 1 (isomer 1) | A |
| 1 (isomer 2) | A |
| 2 (isomer 1) | A |
| 2 (isomer 2) | A |
| 3 (isomer 1) | A |
| 3 (isomer 2) | A |
| 4 (isomer 1) | A |
| 4 (isomer 2) | A |
| 5 (isomer 1) | B |
| 5 (isomer 2) | A |
| 6 (isomer 1) | A |
| 6 (isomer 2) | B |
| 7 (isomer 1) | B |
| 7 (isomer 2) | A |
| 8 | A |
| 9 | A |
| 10 | A |
| 11 | A |
| 12 | A |
| 13 | A |
| 14 (isomer 1) | A |
| 14 (isomer 2) | C |
| 15 (isomer 1) | A |
| 15 (isomer 2) | A |
| 16 (isomer 1) | A |
| 16 (isomer 2) | C |
| 17 | A |
| 18 (isomer 1) | A |
| 18 (isomer 2) | A |
| 19 (isomer 1) | A |
| 19 (isomer 2) | A |
| 20 (isomer 1) | A |
| 20 (isomer 2) | A |
| 21 (isomer 1) | A |
| 21 (isomer 2) | A |
| 22 (isomer 1) | A |
| 22 (isomer 2) | A |
| 23 (isomer 1) | B |
| 23 (isomer 2) | A |
| 24 (isomer 1) | A |
| 24 (isomer 2) | A |
| 25 | A |
| 26 | A |
| 27 (isomer 1) | A |
| 27 (isomer 2) | ND |
| 28 (isomer 1) | A |
| 28 (isomer 2) | A |
| 29 | A |
| 30 | A |
| 31 | C |
| 32 | A |
| 33 | B |
| 34 | C |
| 35 | C |
| 36 (isomer 1) | A |
| 36 (isomer 2) | A |
| 37 | A |
| 38 | A |
| 39 | A |
| 40 | B |
| 41 (isomer 1) | A |
| 41 (isomer 2) | A |
| 42 | A |
| 43 | A |
| 44 (isomer 1) | A |
| 44 (isomer 2) | A |
| 45 | A |
| 46 | A |
| 47 | B |
| 48 | A |
| 49 | B |
| 50 | A |
| 51 (isomer 1) | A |
| 51 (isomer 2) | A |
| 52 | A |
| 53 (isomer 1) | A |
| 53 (isomer 2) | A |
| 54 | B |
| 55 | B |
| 56 | A |
| 57 | A |
| 58 | A |
| 59 | A |

TABLE 1-continued

IC$_{50}$ values for selected compounds.

| Example | EZH2 (IC$_{50}$) |
|---|---|
| 60 (isomer 1) | A |
| 60 | A |
| 61 | A |
| 62 (isomer 1) | A |
| 62 | B |
| 63 | A |
| 64 (isomer 1) | A |
| 64 (isomer 2) | A |
| 65 | A |
| 66 | A |
| 67 (isomer 1) | A |
| 67 (isomer 2) | A |
| 68 | A |
| 69 | A |
| 70 (isomer 1) | A |
| 70 (isomer 2) | B |
| 71 | A |
| 72 | A |
| 73 | A |
| 74 | A |
| 75 (isomer 1) | A |
| 75 (isomer 2) | A |
| 76 (isomer 1) | A |
| 76 (isomer 2) | B |
| 77 | A |
| 78 (isomer 1) | A |
| 78 (isomer 2) | C |
| 79 (isomer 1) | A |
| 79 (isomer 2) | A |
| 80 | A |
| 81 | A |
| 82 | A |
| 83 | A |
| 84 (isomer 1) | A |
| 84 (isomer 2) | A |
| 85 (isomer 1) | A |
| 85 (isomer 2) | B |
| 86 | B |
| 87 | B |
| 88 | A |
| 89 | A |
| 90 (isomer 1) | A |
| 90 (isomer 2) | A |
| 91 (isomer 1) | A |
| 91 (isomer 2) | A |
| 92 | A |
| 93 | A |
| 94 (isomer 1) | A |
| 94 (isomer 2) | B |
| 95 | A |
| 96 | A |
| 97 | C |
| 98 | A |
| 99 | A |
| 100 | A |
| 101 | B |
| 102 (isomer 1) | A |
| 102 (isomer 2) | A |
| 103 | A |
| 104 (isomer 1) | B |
| 104 (isomer 2) | B |
| 105 | B |
| 106 (isomer 1) | A |
| 106 (isomer 2) | A |
| 107 | A |
| 108 | A |
| 109 | A |
| 110 | A |
| 111 | A |
| 112 (isomer 1) | A |
| 112 (isomer 2) | A |
| 113 (isomer 1) | A |
| 113 (isomer 2) | A |
| 114 | C |
| 115 | A |
| 116 | A |
| 117 | B |
| 118 | A |
| 119 | A |
| 120 | A |
| 121 (isomer 1) | A |
| 121 (isomer 2) | B |
| 122 | A |
| 123 (isomer 1) | A |
| 123 (isomer 2) | A |
| 124 | A |
| 125 (isomer 1) | A |
| 125 (isomer 2) | A |
| 126 | A |
| 127 | A |
| 128 | B |
| 129 | A |
| 130 | A |
| 131 | A |
| 132 | A |
| 133 | A |
| 134 (isomer 1) | A |
| 134 (isomer 2) | A |
| 135 | A |
| 136 | A |
| 137 (isomer 1) | A |
| 137 (isomer 2) | A |
| 138 (isomer 1) | B |
| 138 (isomer 2) | A |
| 139 (isomer 1) | A |
| 139 (isomer 2) | B |
| 140 | A |
| 141 | A |
| 142 | A |
| 143 (isomer 1) | A |
| 143 (isomer 2) | A |
| 144 (isomer 1) | A |
| 144 (isomer 2) | A |
| 145 (isomer 1) | B |
| 145 (isomer 2) | A |
| 146 | A |
| 147 (isomer 1) | A |
| 147 (isomer 2) | A |
| 148 (isomer 1) | A |
| 148 (isomer 2) | A |
| 149 (isomer 1) | A |
| 149 (isomer 2) | A |
| 150 (isomer 1) | B |
| 150 (isomer 2) | A |
| 151 (isomer 1) | B |
| 151 (isomer 2) | C |
| 152 | A |
| 153 | A |
| 154 (isomer 1) | A |
| 154 (isomer 2) | A |
| 155 (isomer 1) | A |
| 155 (isomer 2) | B |
| 156 (isomer 1) | A |
| 156 (isomer 2) | A |
| 157 | A |
| 158 | A |
| 159 (isomer 1) | A |
| 159 (isomer 2) | A |
| 160 | A |
| 161 | A |
| 162 (isomer 1) | A |
| 162 (isomer 2) | B |
| 163 (isomer 1) | A |
| 163 (isomer 2) | B |
| 164 (isomer 1) | A |
| 164 (isomer 2) | B |

EC$_{50}$ Measurements for Inhibitors in HeLa Cell Assays

H3K27me3 Alpha Hela Assay (AlphaLISA). Ten different doses of each test compound (in a series of 3-fold dilutions) were plated in duplicate 384-well tissue culture treated plates (Catalog #6007680; Perkin Elmer, Waltham, Mass.). Hela cells grown in culture were trypsinized and counted using a Countess® cell counter (Catalog #C10281; Life Technologies, Grand Island, N.Y.). Cell were diluted to 67,000 cells per mL in 10% DMEM (Catalog #10569-010 Life Technologies, Grand Island, N.Y.) and 15 μL (1,000 cells) were plated into each well using the Biotek Micro-Flo™ Select Dispenser (BioTek Instruments, Inc. Vermont, USA),) of the 384-well plate. Plates were incubated at 37° C./5% $CO_2$ for 72 hrs. One of the duplicate plates was processed for HeLa assay and the other for viability.

5 μL of Cell-Histone Lysis buffer (1×) (Catalog #AL009F1 Perkin Elmer; Waltham, Mass.) per well was added to the plate processed for AlphaLISA and the plate was incubated at RT for 30 minutes on a plate shaker with low speed (Model #4625-Q Thermo Scientific; Waltham, Mass.). Then, 10 μL per well Histone Extraction buffer (catalog #AL009F2; Perkin Elmer; Waltham, Mass.) was added and the plate further incubated at RT for 20 min on plate shaker with low speed. Next, 10 μL of 5× mix of anti-K27me3 acceptor beads plus Biotinylated anti-Histone H3 (C-ter) Antibody (diluted to 3 nM final) (Catalog #AL118 Perkin Elmer; Waltham, Mass.) was added in each well. Dilution of the acceptor beads and anti-Histone H3 was done in 1× Histone Detection buffer (Catalog #AL009F3 Perkin Elmer; Waltham, Mass.) which was produced by diluting the 10× stock provided. The plate was sealed with an aluminum plate sealer and incubated at 23° C. for 60 min. Next, 10 μL 5× solution of Streptavidin Donor beads were added (Catalog #6760002 Perkin Elmer; Waltham, Mass.) (20 μg/mL final in 1× Histone Detection Buffer), =plate was sealed with Aluminum plate sealer and incubated at 23° C. for 30 min. The plates were then read using an EnVision-Alpha Reader (model #2104 Perkin Elmer; Waltham, Mass.).

Cell viability was assayed by adding 15 μL of Cell Titer Glo ((Catalog #G9241 Promega Madison, Wis.) to each well with cells with media. The plates were incubated at RT for 15-20 minutes on a plate shaker at low speed. The plates were then read using an EnVision-Alpha Reader (model #2104 Perkin Elmer; Waltham, Mass.).

Data from both assays was analyzed using Genedata (Basel, Switzerland). Data files were imported to Genedata and assay conditions were specified. A unique Analysis ID was created and the data files analysed to measure dose-dependent inhibition of H3K27me3 mark and cell viability respectively. Readout of DMSO wells were used to normalize the data. Resulting curves were fitted using Smart fit application (Genedata; Basel, Switzerland). The data was checked for quality, validated and integrated in excel format using Stardrop (Optibruim, Cambridge, UK).

Table 2 shows the activity of selected compounds of this invention in the HeLa cell assays described above. EC$_{50}$ values are reported as follows: "A" indicates an EC$_{50}$ value of less than 10 nM; "B" indicates an EC$_{50}$ value of 10 nM to 100 nM; "C" indicates an EC$_{50}$ value of greater than 100 nM; and "ND" is not determined.

TABLE 2

EC$_{50}$ values for selected compounds.

| Example | EZH2 Cell H3K27me3 Alpha HeLa (EC50 K27me3) |
|---|---|
| 1 (isomer 1) | A |
| 1 (isomer 2) | B |
| 2 (isomer 1) | A |
| 2 (isomer 2) | B |
| 3 (isomer 1) | A |
| 3 (isomer 2) | B |
| 4 (isomer 1) | A |
| 4 (isomer 2) | B |
| 5 (isomer 1) | B |
| 5 (isomer 2) | A |
| 6 (isomer 1) | A |
| 6 (isomer 2) | C |
| 7 (isomer 1) | C |
| 7 (isomer 2) | A |
| 8 | A |
| 9 | A |
| 10 | A |
| 11 | B |
| 12 | A |
| 13 | A |
| 14 (isomer 1) | B |
| 14 (isomer 2) | C |
| 15 (isomer 1) | A |
| 15 (isomer 2) | C |
| 16 (isomer 1) | A |
| 16 (isomer 2) | C |
| 17 | A |
| 18 (isomer 1) | A |
| 18 (isomer 2) | A |
| 19 (isomer 1) | A |
| 19 (isomer 2) | A |
| 20 (isomer 1) | A |
| 20 (isomer 2) | B |
| 21 (isomer 1) | A |
| 21 (isomer 2) | B |
| 22 (isomer 1) | A |
| 22 (isomer 2) | A |
| 23 (isomer 1) | B |
| 23 (isomer 2) | A |
| 24 (isomer 1) | A |
| 24 (isomer 2) | A |
| 25 | A |
| 26 | A |
| 27 (isomer 1) | A |
| 27 (isomer 2) | ND |
| 28 (isomer 1) | A |
| 28 (isomer 2) | B |
| 29 | A |
| 30 | A |
| 31 | C |
| 32 | B |
| 33 | B |
| 34 | C |
| 35 | C |
| 36 (isomer 1) | B |
| 36 (isomer 2) | A |
| 37 | B |
| 38 | B |
| 39 | B |
| 40 | C |
| 41 (isomer 1) | A |
| 41 (isomer 2) | A |
| 42 | A |
| 43 | B |
| 44 (isomer 1) | A |
| 44 (isomer 2) | A |
| 45 | A |
| 46 | B |
| 47 | C |
| 48 | A |
| 49 | C |
| 50 | A |

TABLE 2-continued

EC$_{50}$ values for selected compounds.

| Example | EZH2 Cell H3K27me3 Alpha HeLa (EC50 K27me3) |
|---|---|
| 51 (isomer 1) | B |
| 51 (isomer 2) | C |
| 52 | C |
| 53 (isomer 1) | B |
| 53 (isomer 2) | A |
| 54 | B |
| 55 | B |
| 56 | A |
| 57 | A |
| 58 | A |
| 59 | A |
| 60 (isomer 1) | A |
| 60 | A |
| 61 | B |
| 62 (isomer 1) | B |
| 62 | C |
| 63 | B |
| 64 (isomer 1) | B |
| 64 (isomer 2) | B |
| 65 | A |
| 66 | B |
| 67 (isomer 1) | B |
| 67 (isomer 2) | A |
| 68 | A |
| 69 | A |
| 70 (isomer 1) | A |
| 70 (isomer 2) | C |
| 71 | A |
| 72 | B |
| 73 | A |
| 74 | B |
| 75 (isomer 1) | B |
| 75 (isomer 2) | B |
| 76 (isomer 1) | A |
| 76 (isomer 2) | C |
| 77 | B |
| 78 (isomer 1) | B |
| 78 (isomer 2) | C |
| 79 (isomer 1) | A |
| 79 (isomer 2) | B |
| 80 | B |
| 81 | B |
| 82 | A |
| 83 | A |
| 84 (isomer 1) | A |
| 84 (isomer 2) | B |
| 85 (isomer 1) | B |
| 85 (isomer 2) | C |
| 86 | B |
| 87 | A |
| 88 | B |
| 89 | B |
| 90 (isomer 1) | B |
| 90 (isomer 2) | C |
| 91 (isomer 1) | A |
| 91 (isomer 2) | B |
| 92 | A |
| 93 | B |
| 94 (isomer 1) | A |
| 94 (isomer 2) | C |
| 95 | A |
| 96 | A |
| 97 | C |
| 98 | A |
| 99 | B |
| 100 | A |
| 101 | B |
| 102 (isomer 1) | A |
| 102 (isomer 2) | B |
| 103 | A |
| 104 (isomer 1) | B |
| 104 (isomer 2) | C |
| 105 | B |
| 106 (isomer 1) | A |
| 106 (isomer 2) | B |
| 107 | B |
| 108 | A |
| 109 | B |
| 110 | B |
| 111 | B |
| 112 (isomer 1) | A |
| 112 (isomer 2) | B |
| 113 (isomer 1) | A |
| 113 (isomer 2) | B |
| 114 | C |
| 115 | A |
| 116 | A |
| 117 | B |
| 118 | A |
| 119 | A |
| 120 | B |
| 121 (isomer 1) | A |
| 121 (isomer 2) | C |
| 122 | A |
| 123 (isomer 1) | A |
| 123 (isomer 2) | A |
| 124 | A |
| 125 (isomer 1) | A |
| 125 (isomer 2) | ND |
| 126 | A |
| 127 | B |
| 128 | B |
| 129 | A |
| 130 | A |
| 131 | A |
| 132 | A |
| 133 | A |
| 134 (isomer 1) | A |
| 134 (isomer 2) | A |
| 135 | C |
| 136 | C |
| 137 (isomer 1) | A |
| 137 (isomer 2) | A |
| 138 (isomer 1) | B |
| 138 (isomer 2) | B |
| 139 (isomer 1) | B |
| 139 (isomer 2) | B |
| 140 | B |
| 141 | B |
| 142 | C |
| 143 (isomer 1) | A |
| 143 (isomer 2) | A |
| 144 (isomer 1) | A |
| 144 (isomer 2) | A |
| 145 (isomer 1) | C |
| 145 (isomer 2) | C |
| 146 | A |
| 147 (isomer 1) | A |
| 147 (isomer 2) | A |
| 148 (isomer 1) | B |
| 148 (isomer 2) | B |
| 149 (isomer 1) | B |
| 149 (isomer 2) | B |
| 150 (isomer 1) | C |
| 150 (isomer 2) | A |
| 151 (isomer 1) | C |
| 151 (isomer 2) | C |
| 152 | A |
| 153 | A |
| 154 (isomer 1) | B |
| 154 (isomer 2) | A |
| 155 (isomer 1) | A |
| 155 (isomer 2) | B |
| 156 (isomer 1) | A |
| 156 (isomer 2) | B |
| 157 | B |

TABLE 2-continued

EC$_{50}$ values for selected compounds.

| Example | EZH2 Cell H3K27me3 Alpha HeLa (EC50 K27me3) |
|---|---|
| 158 | C |
| 159 (isomer 1) | B |
| 159 (isomer 2) | B |
| 160 | A |
| 161 | B |
| 162 (isomer 1) | B |
| 162 (isomer 2) | C |
| 163 (isomer 1) | A |
| 163 (isomer 2) | B |
| 164 (isomer 1) | A |
| 164 (isomer 2) | B |

Residence Time Measurements

EZH2 residence time assay: Compound residence times were assessed by monitoring the recovery of enzyme activity following a 100-fold dilution of pre-formed enzyme-inhibitor complex (dilution reaction), and comparing it to the activity of an undiluted control with the same final concentrations of all reagents (control reaction). Enzyme activity was measured by incorporation of $^3$H-SAM into a biotinylated H3 peptide. For the dilution reaction, 20 nM PRC2 containing wt EZH2 (pentameric complex prepared in-house) was pre-incubated with 1 µM activating peptide (H$_2$N-RKQLATKAAR(Kme3)SAPATGGVKKP-amide) and compound at 600 times its K$_i$ for 2 h in 40 µL of buffer (50 mM Tris pH 8.5, 4 mM DTT, 1 mM MgCl$_2$, 0.07 mM Brij-35, and 0.1 mg/mL BSA), then diluted 100-fold and the reaction initiated by transferring 1.4 µL to a 138.6 µL volume of buffer containing 1 µM activating peptide, 5.05 µM substrate peptide (H$_2$N-RKQLAT-KAARKSAPATGGVKKP-NTPEGbiot), 1.01 µM SAM, and 1.01 µM $^3$H-SAM. For the control reaction, 0.202 nM PRC2 was pre-incubated with 1 µM activating peptide, 1.01 µM SAM, 1.01 µM $^3$H-SAM, and compound at 6.06 times its K$_i$ for 2 h in 138.6 µL of buffer, then the reaction was initiated by the addition of 1.4 µL 500 µM substrate peptide in water. Reactions were quenched at various time points spanning up to 10 hours, by transferring 8 µL aliquots from the reaction vessel to a plate containing 8 µL per well of STOP solution (50 mM Tris pH 8.5, 200 mM EDTA, 2 mM SAH). After the last time point, 12 µL of the quenched solutions were transferred to a streptavidin coated FlashPlate (PerkinElmer) containing 40 µL per well of STOP solution, incubated 1-8 h, washed, and read in a TopCount plate reader (PerkinElmer). A custom script was used to fit control reaction progress data to a straight line and dilution reaction progress data:

$$y = v_s t + \frac{v_i - v_s}{k_{obs}}(1 - e^{-k_{obs} t}) + \text{background}$$

Where y is the product formed, t is the reaction time, $v_i$ is the initial velocity, $v_s$ is the steady state velocity, and $k_{obs}$ is the rate constant for the transition from the initial velocity phase of the curve to the steady state velocity phase of the curve. In fitting the dilution reaction progress data, $v_s$ was constrained to the slope of the line fitted to the control reaction progress data. The fitted value of $k_{obs}$ was then transformed into residence time:

$$\tau = \frac{[EI] - \frac{1}{K_i}[E][I]}{k_{obs}[EI]}$$

Where τ is residence time, $K_i$ is the inhibition constant, [EI] is the calculated equilibrium concentration of enzyme-inhibitor complex, [E] is the calculated equilibrium concentration of free enzyme, and [I] is the calculated equilibrium concentration of free inhibitor.

Table 3 shows residence time and the activity of values for selected compounds of this invention in the EZH2 residence time assay and in the HeLa cell assays described above.

Table 3. Residence time values for selected compounds. Residence time values are reported as follows: "A" indicates at value of greater than 35 hours; "B" indicates a t value of greater than 5 hours but less or equal than 35 hours; "C" indicates a t value of greater than 0.5 hours but less or equal than 5 hours; "D" indicates a t value of less or equal than 0.5 hours; and "ND" is not determined. EC$_{50}$ values are reported as follows: "A" indicates an EC$_{50}$ value of less than 5 nM; "B" indicates an EC$_{50}$ value equal or greater than 5 nM but less than 25 nM; "C" indicates an EC$_{50}$ value equal or greater than 25 nM but less than 125 nM; "D" indicates an EC$_{50}$ value of greater than 125 nM; and "ND" is not determined.

TABLE 3

| Example | Residence Time | EC$_{50}$ Cellular Activity |
|---|---|---|
| 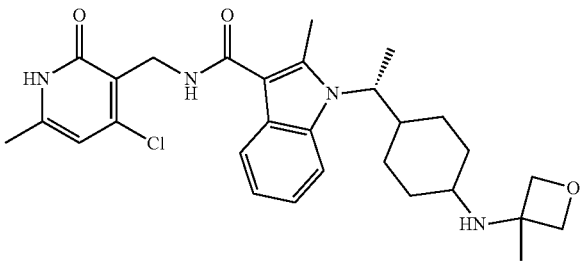 Comparator 1 (isomer 1) | D | C |

TABLE 3-continued
| Example | Residence Time | EC$_{50}$ Cellular Activity |
|---|---|---|
| 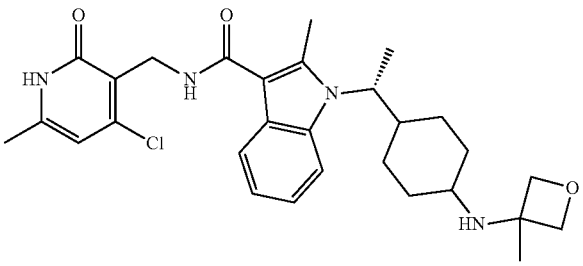 Comparator 1 (isomer 2) | B | B |
| 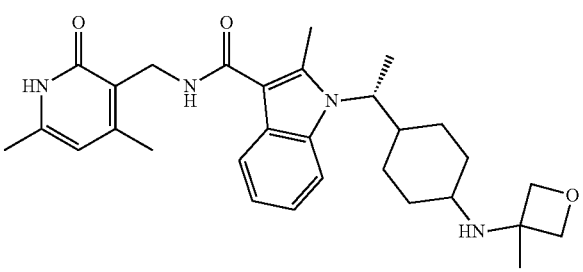 Comparator 2 (isomer 1) | D | C |
| 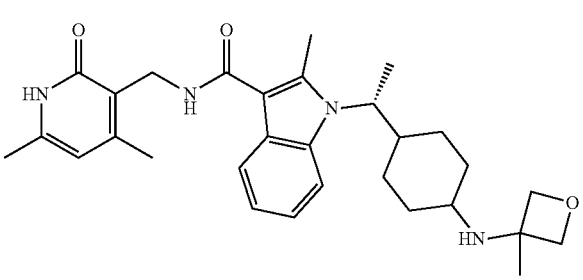 Comparator 2 (isomer 2) | B | A |
| 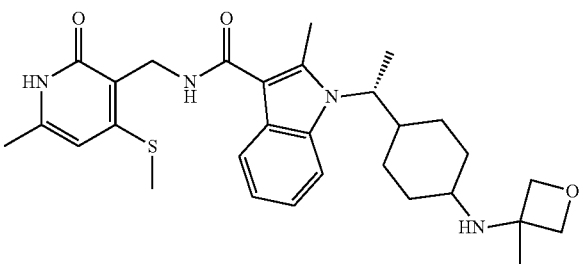 1 (isomer 1) | A | A |
| 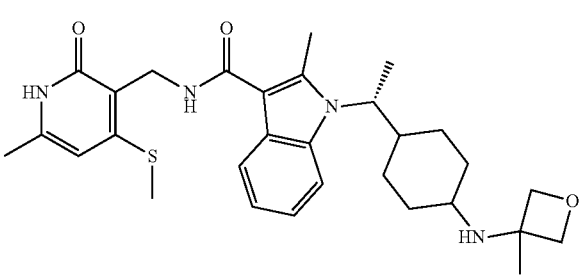 1 (isomer 2) | B | B |

TABLE 3-continued
| Example | Residence Time | EC$_{50}$ Cellular Activity |
|---|---|---|
| 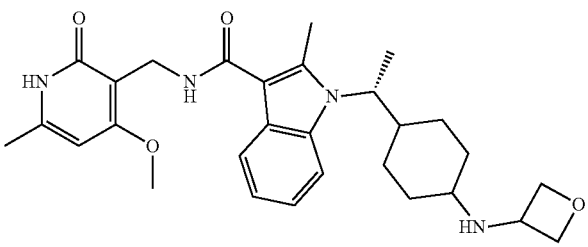 Comparator 3 (isomer 1) | D | D |
| 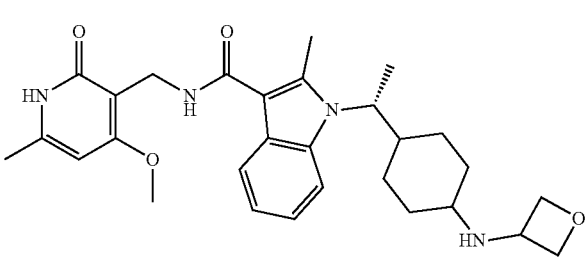 Comparator 3 (isomer 2) | C | C |
| 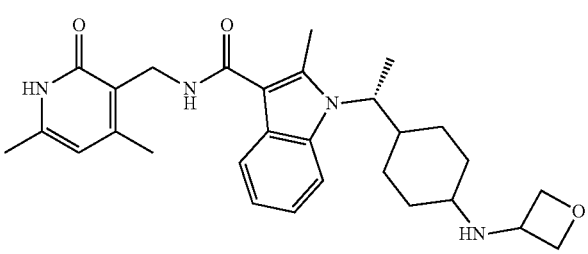 Comparator 4 (isomer 1) | D | D |
| 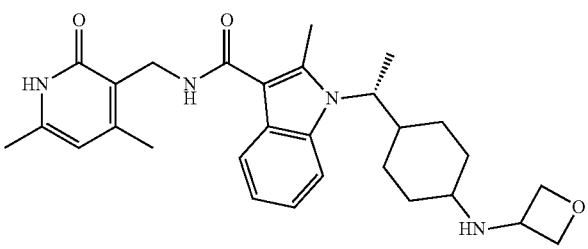 Comparator 4 (isomer 2) | C | C |
| 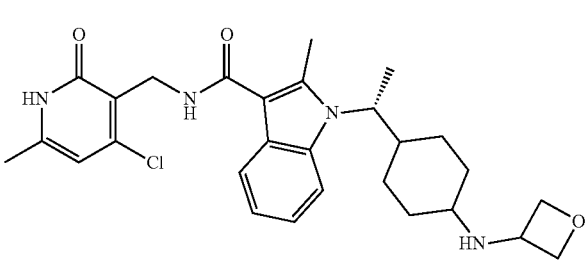 Comparator 5 (isomer 1) | D | D |

TABLE 3-continued

| Example | Residence Time | EC$_{50}$ Cellular Activity |
|---|---|---|
| Comparator 5 (isomer 2) | C | C |
| 2 (isomer 1) | A | A |
| 2 (isomer 2) | C | C |
| Comparator 6 (isomer 1) | C | B |
| Comparator 21 (isomer 1) | C | B |

TABLE 3-continued

| Example | Residence Time | EC$_{50}$ Cellular Activity |
|---|---|---|
| Comparator 7 (isomer 1) | D | D |
| Comparator 7 (isomer 2) | C | D |
| 4 (isomer 1) | A | A |
| 4 (isomer 2) | C | B |

TABLE 3-continued
| Example | Residence Time | EC$_{50}$ Cellular Activity |
|---|---|---|
| 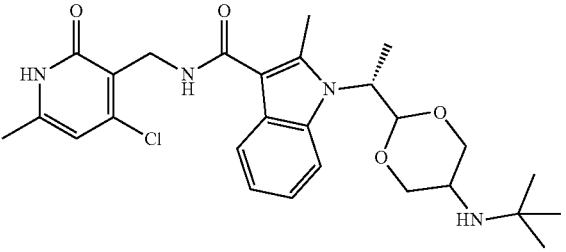<br>Comparator 8 (isomer 1) | C | B |
| 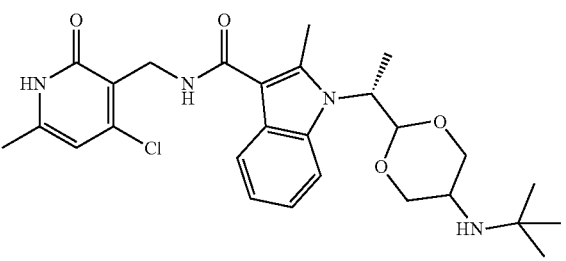<br>Comparator 8 (isomer 1) | ND | B |
| 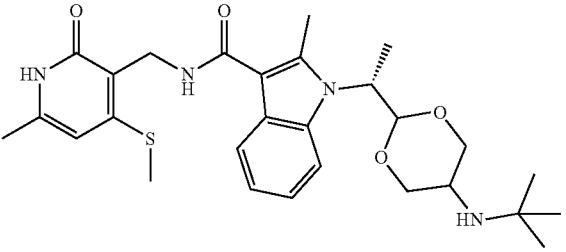<br>5 (isomer 1) | D | C |
| 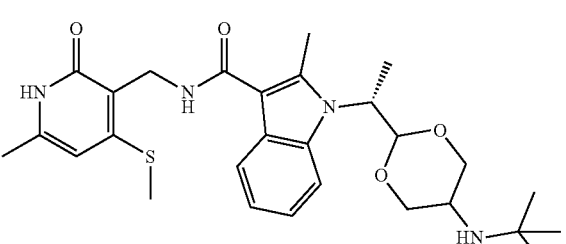<br>5 (isomer 2) | A | A |
| 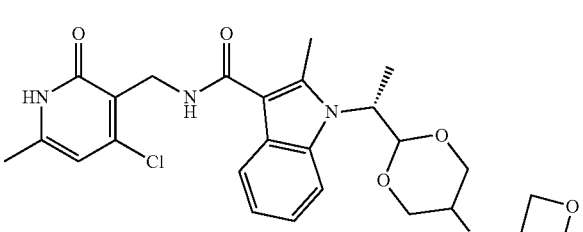<br>Comparator 9 (isomer 1) | D | D |

TABLE 3-continued
| Example | Residence Time | EC$_{50}$ Cellular Activity |
|---|---|---|
| 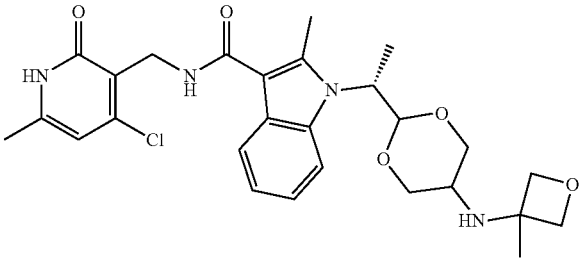 Comparator 9 (isomer 2) | B | B |
| 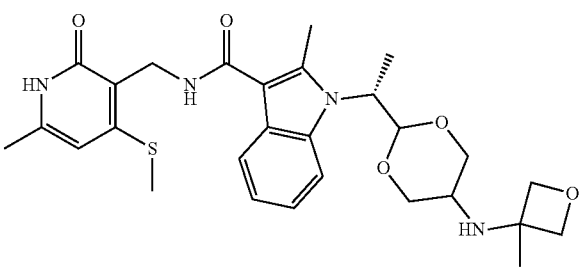 6 (isomer 1) | A | A |
| 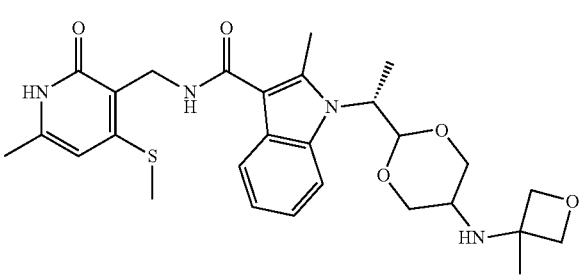 6 (isomer 2) | D | D |
| 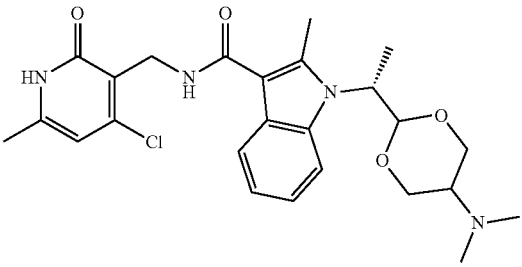 Comparator 10 (isomer 1) | D | D |
| 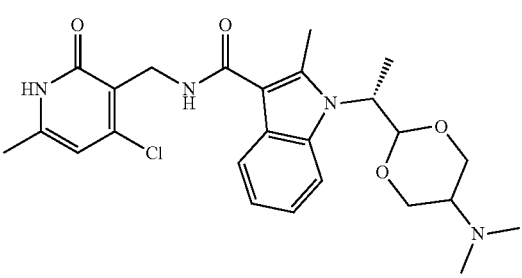 Comparator 10 (isomer 2) | D | C |

TABLE 3-continued
| Example | Residence Time | EC$_{50}$ Cellular Activity |
|---|---|---|
| 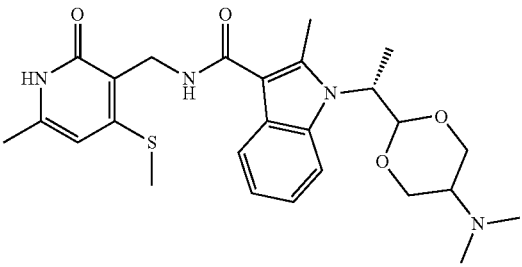 7 (isomer 1) | D | D |
| 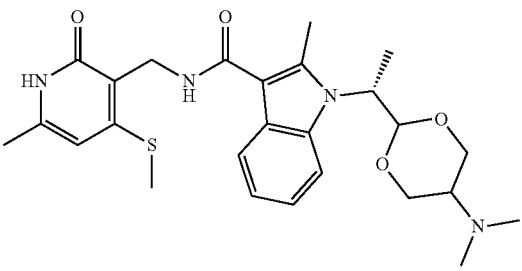 7 (isomer 2) | B | A |
| 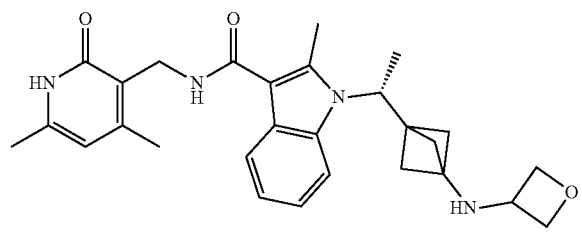 Comparator 11 | D | C |
| 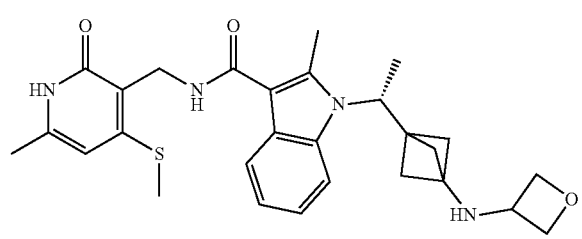 8 | B | A |
| 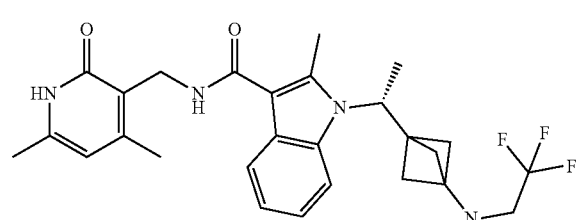 Comparator 12 | D | D |

TABLE 3-continued
| Example | Residence Time | EC$_{50}$ Cellular Activity |
|---|---|---|
| 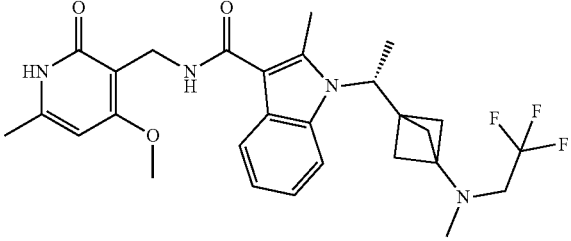 Comparator 13 | C | C |
| 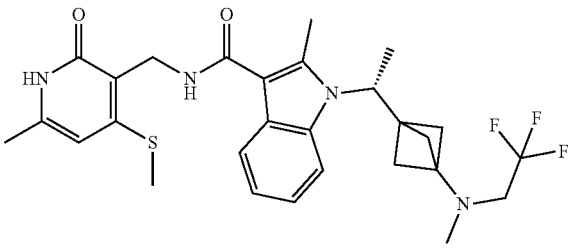 10 | B | B |
| 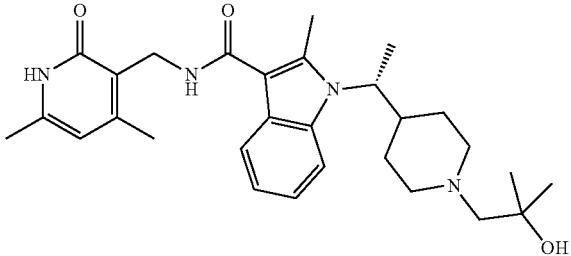 Comparator 14 | D | D |
| 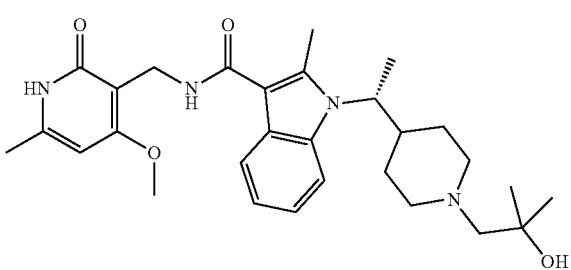 Comparator 15 | D | D |
| 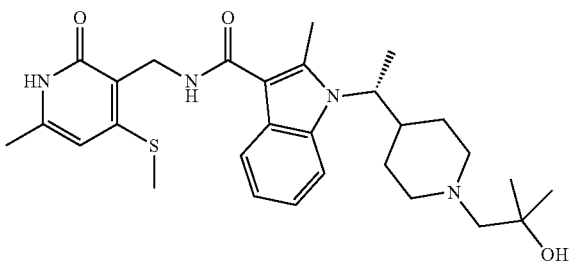 11 | B | C |

TABLE 3-continued

| Example | Residence Time | EC$_{50}$ Cellular Activity |
|---|---|---|
| Comparator 16 | D | C |
| Comparator 17 | C | B |
| 12 | B | A |
| Comparator 18 | D | C |
| Comparator 19 | D | C |

TABLE 3-continued

| Example | Residence Time | EC$_{50}$ Cellular Activity |
|---|---|---|
| Comparator 20 | C | C |
| 13 | C | A |
| 18 (isomer 1) | A | A |
| 18 (isomer 2) | ND | A |
| 19 (isomer 1) | B | A |
| 19 (isomer 2) | A | A |

TABLE 3-continued
| Example | Residence Time | EC$_{50}$ Cellular Activity |
|---|---|---|
| 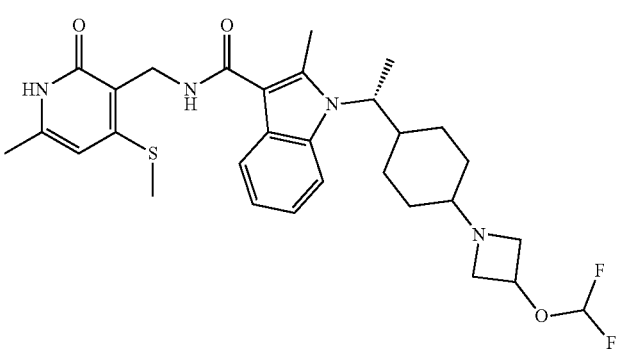 20 (isomer 1) | A | A |
| 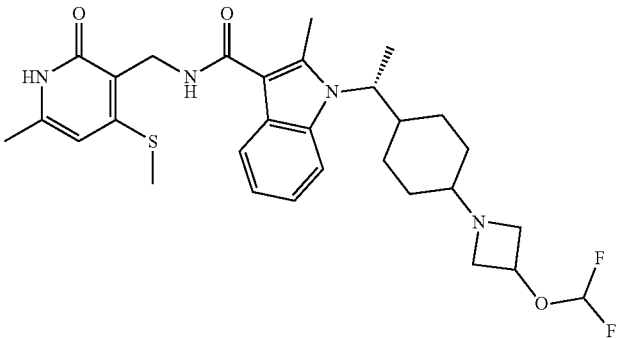 20 (isomer 2) | ND | B |
| 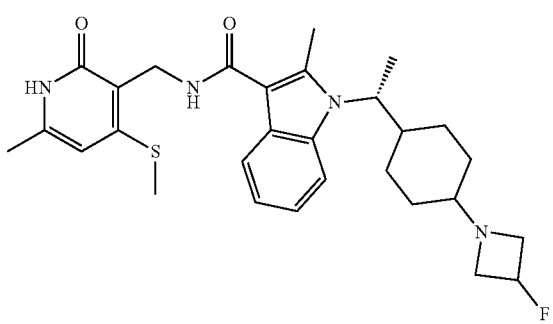 24 (isomer 1) | A | A |
| 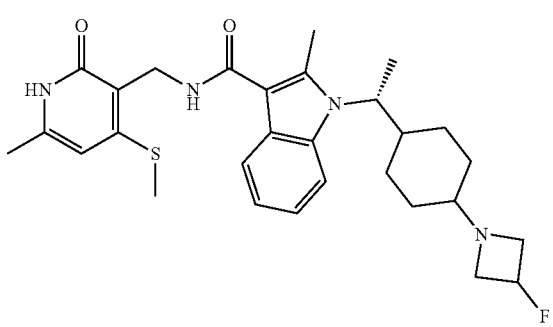 24 (isomer 2) | C | B |

TABLE 3-continued

| Example | Residence Time | EC$_{50}$ Cellular Activity |
|---|---|---|
| 26 | B | A |
| 27 (isomer 1) | B | A |
| 27 (isomer 2) | ND | ND |
| 76 (isomer 1) | B | B |

TABLE 3-continued
| Example | Residence Time | EC$_{50}$ Cellular Activity |
|---|---|---|
| 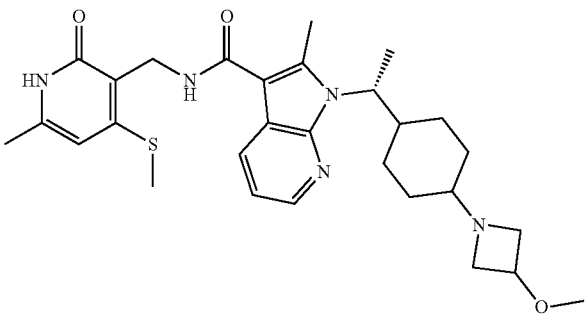 76 (isomer 2) | ND | D |
| 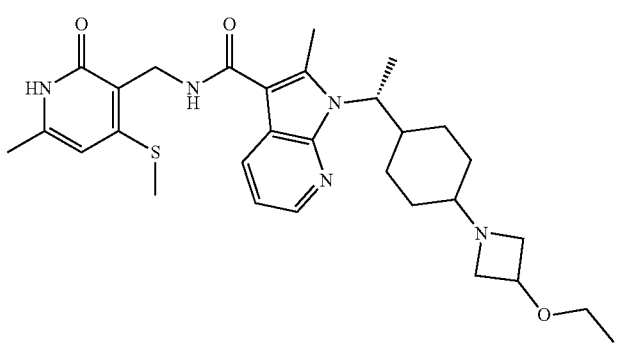 91 (isomer 1) | B | A |
| 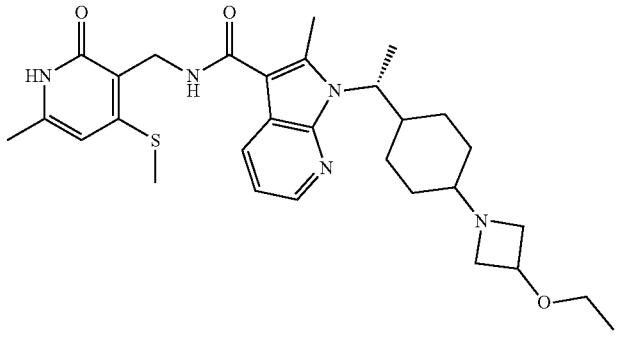 91 (isomer 2) | ND | C |
| 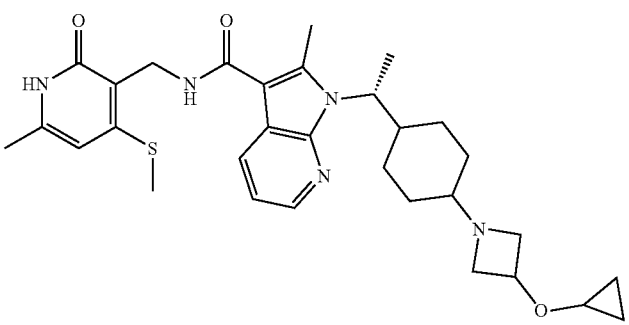 30 | B | A |

TABLE 3-continued
| Example | Residence Time | EC$_{50}$ Cellular Activity |
|---|---|---|
| 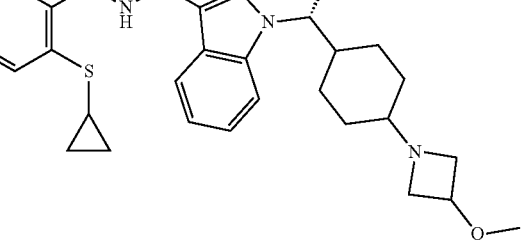 99 | B | B |
| 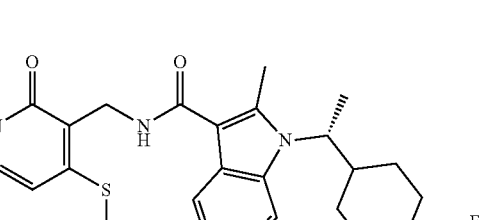 86 | D | C |
| 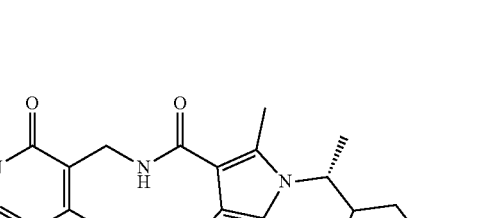 105 | D | C |
| 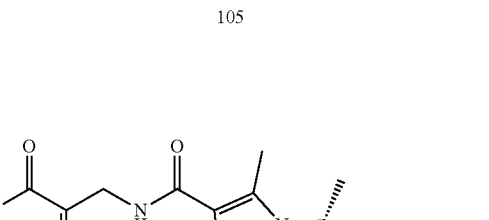 109 | C | C |

TABLE 3-continued

| Example | Residence Time | EC$_{50}$ Cellular Activity |
|---|---|---|
| 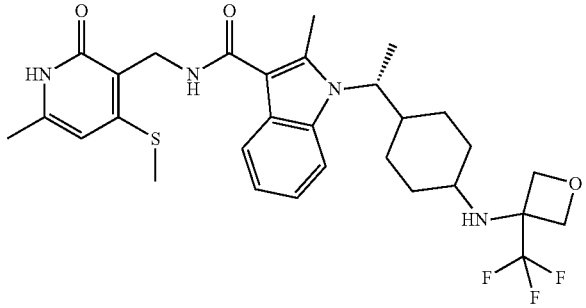 130 | B | A |
| 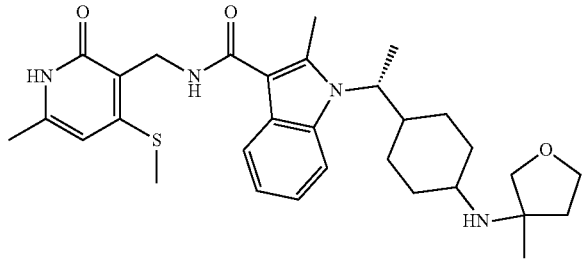 149 (isomer 1) | A | B |
| 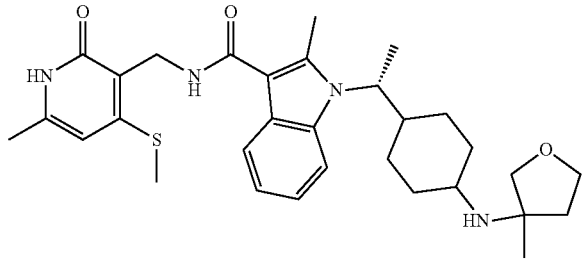 149 (isomer 2) | ND | C |

The inventions claimed is:

1. A compound having the Formula:

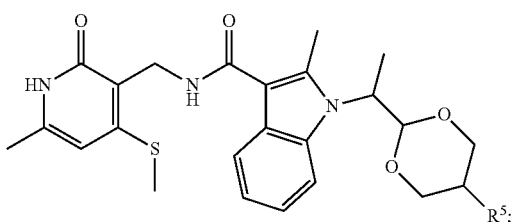

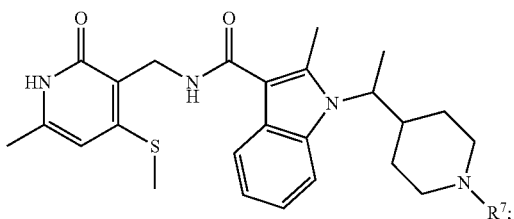

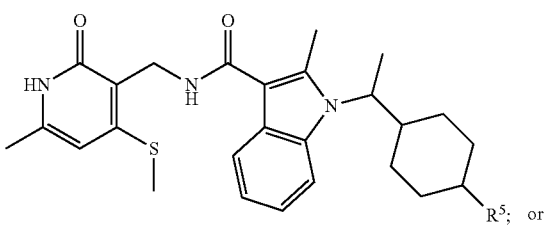

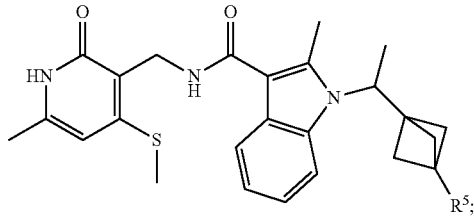

or a pharmaceutically acceptable salt thereof, wherein $R^5$ is hydroxyl, $(C_1-C_4)$alkoxy, or $NR^A R^B$;

$R^A$ is hydrogen, $(C_1-C_4)$alkyl, or halo$(C_1-C_4)$alkyl;

$R^B$ is $(C_1-C_4)$alkyl or monocyclic 4- to 6-membered heterocyclyl optionally substituted with 1 or 2 $(C_1-C_4)$alkyl; or $R^A$ and $R^B$ taken together with the nitrogen atom to which they are attached form a monocyclic 4- to 6-membered heterocyclyl optionally substituted with halo, $(C_1-C_4)$alkoxy or halo$(C_1-C_4)$alkoxy.

2. A compound having the Formula XXXIII:

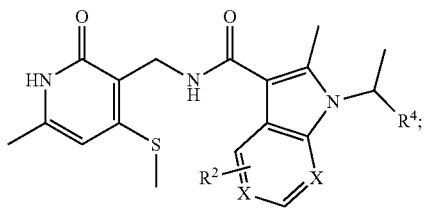

(XXXIII)

or a pharmaceutically acceptable salt thereof, wherein
$R^2$ is hydrogen or halo;
$R^4$ is cyclohexyl, piperidinyl or dioxanyl, each of which being optionally and independently substituted with 1 to 3 groups selected from $R^5$;
$R^5$ is selected from halo, $(C_3-C_6)$cycloalkyl, $OR^6$, —OC(O)$(C_1-C_4)$alkyl, —C(O)$(C_1-C_4)$alkylOH, —C(O)$(C_1-C_4)$alkylN$((C_1-C_4)$alkyl$)_2$, —SO$_2(C_1-C_4)$alkyl, 4-7 membered heterocyclyl, and NR$^A$R$^B$, wherein said cycloalkyl for $R^5$ is optionally substituted with —O$(C_1-C_4)$alkyl;
$R^A$ is hydrogen;
$R^B$ is $(C_3-C_5)$cycloalkyl or 4-7 membered heterocyclyl, wherein said heterocyclyl or cycloalkyl for $R^B$ is optionally substituted with 1 to 3 groups selected from $(C_1-C_4)$alkyl, halo$(C_1-C_4)$alkyl, and hydroxy$(C_1-C_4)$alkyl; or
$R^A$ and $R^B$ taken together with the nitrogen atom to which they are attached form a 3-7 membered heterocyclyl optionally substituted with 1 to 3 groups selected from halo, hydroxyl, cyano, $(C_1-C_4)$alkyl, hydroxy$(C_1-C_4)$alkyl, NMe$_2$, —SO$_2(C_1-C_4)$alkyl, 5-6 membered heteroaryl, and $(C_3-C_6)$cycloalkyl; and
$R^6$ is $(C_3-C_6)$cycloalkyl, 4-7 membered heterocyclyl, 5-6 membered heteroaryl, or —O$(C_1-C_4)$alkyl, wherein said 4-7 membered heterocyclyl and said 5-6 membered heteroaryl for $R^6$ are each optionally and independently substituted with 1 or 2 $(C_1-C_4)$alkyl groups.

3. The compound of claim 2, wherein
$R^5$ is selected from halo, $(C_3-C_6)$cycloalkyl, $OR^6$, —OC(O)$(C_1-C_4)$alkyl, —C(O)$(C_1-C_4)$alkylOH, —C(O)$(C_1-C_4)$alkylN$((C_1-C_4)$alkyl$)_2$, —SO$_2(C_1-C_4)$alkyl, 4-7 membered heterocyclyl, and NR$^A$R$^B$, wherein said cycloalkyl for $R^5$ is optionally substituted with —O$(C_1-C_4)$alkyl;
$R^A$ is hydrogen;
$R^B$ is $(C_3-C_5)$cycloalkyl or 4-7 membered heterocyclyl, wherein said heterocyclyl or cycloalkyl for $R^B$ are each optionally and independently substituted with 1 to 3 groups selected from $(C_1-C_4)$alkyl, halo$(C_1-C_4)$alkyl, and hydroxy$(C_1-C_4)$alkyl; or
$R^A$ and $R^B$ taken together with the nitrogen atom to which they are attached form a 3-7 membered heterocyclyl optionally substituted with 1 to 3 groups selected from halo, hydroxyl, cyano, $(C_1-C_4)$alkyl, NMe$_2$, hydroxy$(C_1-C_4)$alkyl, —SO$_2(C_1-C_4)$alkyl, 5-6 membered heteroaryl, and $(C_3-C_6)$cycloalkyl; and
$R^6$ is $(C_3-C_6)$cycloalkyl, 4-7 membered heterocyclyl, 5-6 membered heteroaryl, or —O$(C_1-C_4)$alkyl, wherein said 4-7 membered heterocyclyl and said 5-6 membered heteroaryl for $R^6$ are each optionally and independently substituted with 1 or 2 $(C_1-C_4)$alkyl groups.

4. The compound of claim 2, wherein
$R^5$ is selected from halo, $(C_3-C_6)$cycloalkyl, —OC(O)$(C_1-C_4)$alkyl, —C(O)$(C_1-C_4)$alkylOH, —C(O)$(C_1-C_4)$alkylN$((C_1-C_4)$alkyl$)_2$, —SO$_2(C_1-C_4)$alkyl, and NR$^A$R$^B$ wherein said cycloalkyl for $R^5$ is optionally substituted with —O$(C_1-C_4)$alkyl;
$R^B$ is $(C_3-C_5)$cycloalkyl or 4-7 membered heterocyclyl each optionally and independently substituted with 1 to 3 groups selected from $(C_1-C_4)$alkyl, halo$(C_1-C_4)$alkyl, and hydroxy$(C_1-C_4)$alkyl; or
$R^A$ and $R^B$ taken together with the nitrogen atom to which they are attached form a 3-7 membered heterocyclyl optionally substituted with 1 to 3 groups selected from halo, hydroxyl, cyano, $(C_1-C_4)$alkyl, NMe$_2$, —SO$_2(C_1-C_4)$alkyl, 5-6 membered heteroaryl, and $(C_3-C_6)$cycloalkyl; and
$R^6$ is 4-7 membered heterocyclyl or 5-6 membered heteroaryl, wherein said 4-7 membered heterocyclyl and said 5-6 membered heteroaryl for $R^6$ are each optionally and independently substituted with $(C_1-C_4)$alkyl.

5. A compound selected from:

(R)-2-methyl-N-((6-methyl-4-(methylthio)-2-oxo-1,2-dihydropyridin-3-yl)methyl)-1-(1-(4-((3-methyloxetan-3-yl)amino)cyclohexyl)ethyl)-1H-indole-3-carboxamide;
(R)-2-methyl-N-((6-methyl-4-(methylthio)-2-oxo-1,2-dihydropyridin-3-yl)methyl)-1-(1-(4-(oxetan-3-ylamino)cyclohexyl)ethyl)-1H-indole-3-carboxamide;
2-methyl-1-((1R)-1-(4-(methyl(3-methyloxetan-3-yl)amino)cyclohexylethyl)-N-((6-methyl-4-(methylthio)-2-oxo-1,2-dihydropyridin-3-yl)methyl)-1H-indole-3-carboxamide;
1-((1R)-1-(4-(3-methoxyazetidin-1-yl)cyclohexymethyl)-2-methyl-N-((6-methyl-4-(methylthio)-2-oxo-1,2-dihydropyridin-3-yl)methyl)-1H-indole-3-carboxamide;
1-((1R)-1-(5-(tert-butylamino)-1,3-dioxan-2-yl)ethyl)-2-methyl-N-((6-methyl-4-(methylthio)-2-oxo-1,2-dihydropyridin-3-yl)methyl)-1H-indole-3-carboxamide;
2-methyl-N-((6-methyl-4-(methylthio)-2-oxo-1,2-dihydropyridin-3-yl)methyl)-1-((1R)-1-(5-((3-methyloxetan-3-yl)amino)-1,3-dioxan-2-yl)ethyl)-1H-indole-3-carboxamide;
1-((1R)-1-(5-(dimethylamino)-1,3-dioxan-2-yl)ethyl)-2-methyl-N-((6-methyl-4-(methylthio)-2-oxo-1,2-dihydropyridin-3-yl)methyl)-1H-indole-3-carboxamide;
(R)-2-methyl-1-(1-(3-(methyl(oxetan-3-yl)amino)bicyclo[1.1.1]pentan-1-yl)ethyl)-N-((6-methyl-4-(methylthio)-2-oxo-1,2-dihydropyridin-3-yl)methyl)-1H-indole-3-carboxamide;
(R)-2-methyl-1-(1-(3-(methyl(2,2,2-trifluoroethyl)amino)bicyclo[1.1.1]pentan-1-yl)ethyl)-N-((6-methyl-4-(methylthio)-2-oxo-1,2-dihydropyridin-3-yl)methyl)-1H-indole-3-carboxamide;
(R)-1-(1-(1-(2-hydroxy-2-methylpropyl)piperidin-4-yl)ethyl)-2-methyl-N-((6-methyl-4-(methylthio)-2-oxo-1,2-dihydropyridin-3-yl)methyl)-1H-indole-3-carboxamide;
(R)-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide;
(R)-2-methyl-N-((6-methyl-4-(methylthio)-2-oxo-1,2-dihydropyridin-3-yl)methyl)-1-(1-(tetrahydro-2H-pyran-4-yl)ethyl)-1H-indole-3-carboxamide;

(S)-2-methyl-N-((6-methyl-4-(methylthio)-2-oxo-1,2-dihydropyridin-3-yl)methyl)-1-(1-(oxetan-3-yl)ethyl)-1H-indole-3-carboxamide;
(R)-1-(1-(5-(2,2-dimethylazetidin-1-yl)-1,3-dioxan-2-yl)ethyl)-2-methyl-N-((6-methyl-4-(methylthio)-2-oxo-1,2-dihydropyridin-3-yl)methyl)-1H-indole-3-carboxamide;
(R)-1-(1-(5-((2-methoxyethyl)(methyl)amino)-1,3-dioxan-2-yl)ethyl)-2-methyl-N-((6-methyl-4-(methylthio)-2-oxo-1,2-dihydropyridin-3-yl)methyl)-1H-indole-3-carboxamide;
(R)-2-methyl-N-((6-methyl-4-(methylthio)-2-oxo-1,2-dihydropyridin-3-yl)methyl)-1-(1-(5-(methylamino)-1,3-dioxan-2-yl)ethyl)-1H-indole-3-carboxamide;
1-((R)-1-((1r,4R)-4-methoxycyclohexyl)ethyl)-2-methyl-N-((6-methyl-4-(methylthio)-2-oxo-1,2-dihydrop yridin-3-yl)methyl)-1H-indole-3-carboxamide;
(R)-1-(1-(4-hydroxycyclohexyl)ethyl)-2-methyl-N-((6-methyl-4-(methylthio)-2-oxo-1,2-dihydropyridin-3-yl)methyl)-1H-indole-3-carboxamide;
(R)-1-(1-(4-(3-(difluoromethoxy)azetidin-1-yl)cyclohexyl)ethyl)-2-methyl-N-((6-methyl-4-(methylthio)-2-oxo-1,2-dihydropyridin-3-yl)methyl)-1H-indole-3-carboxamide;
(R)-1-(1-(4-(3-(trifluoromethoxy)azetidin-1-yl)cyclohexyl)ethyl)-2-methyl-N-((6-methyl-4-(methylthio)-2-oxo-1,2-dihydropyridin-3-yl)methyl)-1H-indole-3-carboxamide;
(R)-1-(1-(4-hydroxy-4-methylcyclohexyl)ethyl)-2-methyl-N-((6-methyl-4-(methylthio)-2-oxo-1,2-dihydropyridin-3-yl)methyl)-1H-indole-3-carboxamide;
(R)-1-(1-(4-(3,3-difluoroazetidin-1-yl)cyclohexyl)ethyl)-2-methyl-N-((6-methyl-4-(methylthio)-2-oxo-1,2-dihydropyridin-3-yl)methyl)-1H-indole-3-carboxamide;
(R)-1-(1-(4-(3-fluoroazetidin-1-yl)cyclohexyl)ethyl)-2-methyl-N-((6-methyl-4-(methylthio)-2-oxo-1,2-dihydropyridin-3-yl)methyl)-1H-indole-3-carboxamide;
(R)-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-pyrrolo[2,3-b]pyridine-3-carboxamide;
(R)-1-(1-(1-cyclopropylpiperidin-4-yl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
(R)-1-(1-(4-(3-(difluoromethoxy)azetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-(4-(3-cyclopropoxyazetidin-1-yl)cyclohexyl)ethyl)-5-fluoro-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-(4-(3-(difluoromethoxy)azetidin-1-yl)cyclohexyl)ethyl)-6-fluoro-2-methyl-N-((6-methyl-4-(methylthio)-2-oxo-1,2-dihydropyridin-3-yl)methyl)-1H-indole-3-carboxamide;
1-[(1R)-1-[4-[3-(cyclopropoxy)azetidin-1-yl]cyclohexyl]ethyl]-2-methyl-N-[(6-methyl-4-methylsulfanyl-2-oxo-1H-pyridin-3-yl)methyl]pyrrolo[2,3-b]pyridine-3-carboxamide;
2-methyl-N-((6-methyl-4-(methylthio)-2-oxo-1,2-dihydropyridin-3-yl)methyl)-1-((R)-1-(4-((3-(trifluoromethy)poxetan-3-yl)amino)cyclohexyl)ethyl)-1H-indole-3-carboxamide;
(R)-1-(1-hydroxypropan-2-yl)-2-methyl-N-((6-methyl-4-(methylthio)-2-oxo-1,2-dihydropyridin-3-yl)methyl)-1H-indole-3-carboxamide;
(R)-1-(1-methoxypropan-2-yl)-2-methyl-N-((6-methyl-4-(methylthio)-2-oxo-1,2-dihydropyridin-3-yl)methyl)-1H-indole-3-carboxamide;
(R)-1-(1-ethoxypropan-2-yl)-2-methyl-N-((6-methyl-4-(methylthio)-2-oxo-1,2-dihydropyridin-3-yl)methyl)-1H-indole-3-carboxamide;
(S)-2-methyl-N-((6-methyl-4-(methylthio)-2-oxo-1,2-dihydropyridin-3-yl)methyl)-1-(1-(2-methylpyrimidin-5-yl)ethyl)-1H-indole-3-carboxamide;
(R)-2-methyl-N-((6-methyl-4-(methylthio)-2-oxo-1,2-dihydropyridin-3-yl)methyl)-1-(1-(2-methylpyrimidin-5-yl)ethyl)-1H-indole-3-carboxamide;
1-((R)-1-(4-hydroxycyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-((3R,4R)-3-fluoropiperidin-4-yl)ethyl)-2-methyl-N-((6-methyl-4-(methylthio)-2-oxo-1,2-dihydropyridin-3-yl)methyl)-1H-indole-3-carboxamide;
1-((1R)-1-((3S)-3-fluoropiperidin-4-yl)ethyl)-2-methyl-N-((6-methyl-4-(methylthio)-2-oxo-1,2-dihydropyridin-3-yl)methyl)-1H-indole-3-carboxamide;
(R)-1-(1-(1-cyanopiperidin-4-yl)ethyl)-2-methyl-N-((6-methyl-4-(methylthio)-2-oxo-1,2-dihydropyridin-3-yl)methyl)-1H-indole-3-carboxamide;
1-((1R)-1-(4-hydroxycyclohexyl)ethyl)-2,6-dimethyl-N-((6-methyl-4-(methylthio)-2-oxo-1,2-dihydropyridin-3-yl)methyl)-1H-pyrrolo[2,3-b]pyridine-3-carboxamide;
7-((R)-1-(4-methoxycyclohexyl)ethyl)-6-methyl-N-((6-methyl-4-(methylthio)-2-oxo-1,2-dihydropyridin-3-yl)methyl)-7H-pyrrolo[2,3-d]pyrimidine-5-carboxamide;
1-((R)-1-((3R,4R)-3-fluoro-1-methylpiperidin-4-yl)ethyl)-2-methyl-N-((6-methyl-4-(methylthio)-2-oxo-1,2-dihydropyridin-3-yl)methyl)-1H-indole-3-carboxamide;
1-((1R)-1-((3S)-3-fluoro-1-methylpiperidin-4-yl)ethyl)-2-methyl-N-((6-methyl-4-(methylthio)-2-oxo-1,2-dihydropyridin-3-yl)methyl)-1H-indole-3-carboxamide;
6-fluoro-1-((R)-1-(4-hydroxycyclohexyl)ethyl)-2-methyl-N-((6-methyl-4-(methylthio)-2-oxo-1,2-dihydropyridin-3-yl)methyl)-1H-indole-3-carboxamide;
(R)-1-(1-(4,4-difluorocyclohexyl)ethyl)-2-methyl-N-((6-methyl-4-(methylthio)-2-oxo-1,2-dihydropyridin-3-yl)methyl)-1H-indole-3-carboxamide;
(R)-1-(1-(4-(dimethylamino)phenyl)ethyl)-2-methyl-N-((6-methyl-4-(methylthio)-2-oxo-1,2-dihydropyridin-3-yl)methyl)-1H-indole-3-carboxamide;
(S)-1-(1-(4-(dimethylamino)phenyl)ethyl)-2-methyl-N-((6-methyl-4-(methylthio)-2-oxo-1,2-dihydropyridin-3-yl)methyl)-1H-indole-3-carboxamide;
(R)-1-(1-(1-cyclopropylpiperidin-4-yl)ethyl)-2-methyl-N-((6-methyl-4-(methylthio)-2-oxo-1,2-dihydropyridin-3-yl)methyl)-1H-indole-3-carboxamide;
2-methyl-N-((6-methyl-4-(methylthio)-2-oxo-1,2-dihydropyridin-3-yl)methyl)-1-((R)-1-(3-(oxetan-3-ylamino)cyclobutyl)ethyl)-1H-indole-3-carboxamide;
(R)-7-(1-(1-cyclopropylpiperidin-4-yl)ethyl)-6-methyl-N-((6-methyl-4-(methylthio)-2-oxo-1,2-dihydropyridin-3-yl)methyl)-7H-pyrrolo[2,3-d]pyrimidine-5-carboxamide;
1-((R)-1-(4-(dimethylamino)cyclohexyl)ethyl)-2-methyl-N-((6-methyl-4-(methylthio)-2- oxo-1,2-dihydropyridin-3-yl)methyl)-1H-pyrrolo[2,3-b]pyridine-3-carboxamide;
(R)-1-(1-(1-(2-hydroxyethyl)piperidin-4-yl)ethyl)-2-methyl-N-((6-methyl-4-(methylthio)-2-oxo-1,2-dihydropyridin-3-yl))methyl)-1H-indole-3-carboxamide;
5-chloro-1-((R)-1-(4-hydroxycyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
(R)-2-methyl-N-((6-methyl-4-(methylthio)-2-oxo-1,2-dihydropyridin-3-yl)methyl)-1-(1-(1-(2,2,2-trifluoroethyl)azetidin-3-yl)ethyl)-1H-indole-3-carboxamide;
(S)-2-methyl-N-((6-methyl-4-(methylthio)-2-oxo-1,2-dihydropyridin-3-yl)methyl)-1-(1-(1-(2,2,2-trifluoroethyl)azetidin-3-yl)ethyl)-1H-indole-3-carboxamide;
1-((R)-1-((3S,4R)-1-cyclopropyl-3-fluoropiperidin-4-yl)ethyl)-2-methyl-N-((6-methyl-4-(methylthio)-2-oxo-1,2-dihydropyridin-3-yl)methyl)-1H-indole-3-carboxamide;
(R)-1-(1-(1-cyclopropylpiperidin-4-yl)ethyl)-6-fluoro-2-methyl-N-((6-methyl-4-(methylthio)-2-oxo-1,2-dihydropyridin-3-yl)methyl)-1H-indole-3-carboxamide;
(R)-1-(1-(1-cyclopropylpiperidin-4-yl)ethyl)-5-fluoro-2-methyl-N-((6-methyl-4-(methylthio)-2-oxo-1,2-dihydropyridin-3-yl)methyl)-1H-pyrrolo[2,3-b]pyridine-3-carboxamide;
(R)-1-(1-(1-(2,2-difluoroethyppiperidin-4-yl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-(4-(difluoromethoxy)cyclohexyl)ethyl)-2-methyl-N-((6-methyl-4-(methylthio)-2-oxo-1,2-dihydropyridin-3-yl)methyl)-1H-indole-3-carboxamide;
(R)-1-(1-(4-(tert-butylamino)cyclohexyl)ethyl)-2-methyl-N-((6-methyl-4-(methylthio)-2-oxo-1,2-dihydropyridin-3-yl)methyl)-1H-indole-3-carboxamide;
2-methyl-N-((6-methyl-4-(methylthio)-2-oxo-1,2-dihydropyridin-3-yl)methyl)-1-((R)-1-(4-(oxetan-3-ylamino)cyclohexyl)ethyl)-1H-pyrrolo[2,3-b]pyridine-3-carboxamide;
6-methyl-N-((6-methyl-4-(methylthio)-2-oxo-1,2-dihydropyridin-3-yl)methyl)-7-((R)-1-(4-(oxetan-3-ylamino)cyclohexyl)ethyl)-7H-pyrrolo[2,3-d]pyrimidine-5-carboxamide;
(R)-1-(1-(1-(3-fluorocyclobutyl)piperidin-4-yl)ethyl)-2-methyl-N-((6-methyl-4-(methylthio)-2-oxo-1,2-dihydropyridin-3-yl)methyl)-1H-indole-3-carboxamide;
1-((R)-1-(4-(3-fluoroazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
(R)-1-(1-(1-(3-fluorocyclobutyl)piperidin-4-yl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-(4-(2-methoxyethoxy)cyclohexyl)ethyl)-2-methyl-N-((6-methyl-4-(methylthio)-2-oxo-1,2-dihydropyridin-3-yl)methyl)-1H-indole-3-carboxamide;
7-((R)-1-(4-(3-fluoroazetidin-1-yl)cyclohexyl)ethyl)-6-methyl-N-((6-methyl-4-(methylthio)-2-oxo-1,2-dihydropyridin-3-yl)methyl)-7H-pyrrolo[2,3-d]pyrimidine-5-carboxamide;
(R)-5-chloro-1-(1-(1-cyclopropylpiperidin-4-yl)ethyl)-2-methyl-N-((6-methyl-4-(methylthio)-2-oxo-1,2-dihydrop yridin-3-yl)methyl)-1H-pyrrolo[2,3-b]pyridine-3-carboxamide;
1-((R)-1-((R)-1-cyclopropyl-3,3-difluoropiperidin-4-yl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-((S)-1-cyclopropyl-3,3-difluoropiperidin-4-yl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
2-methyl-1-((R)-1-((2S,4S)-1-methyl-2-(trifluoromethyl)piperidin-4-yl)ethyl)-N-((6-methyl-4-(methylthio)-2-oxo-1,2-dihydropyridin-3-yl)methyl)-1H-indole-3-carboxamide;
2-methyl-N-((6-methyl-4-(methylthio)-2-oxo-1,2-dihydropyridin-3-yl)methyl)-1-((R)-1-(4-(2-oxopyrrolidin-1-yl)cyclohexyl)ethyl)-1H-indole-3-carboxamide;
(R)-6-methyl-N-((6-methyl-4-(methylthio)-2-oxo-1,2-dihydropyridin-3-yl)methyl)-7-(1-(1-(2,2,2-trifluoroethyl)piperidin-4-yl)ethyl)-7H-pyrrolo[2,3-d]pyrimidine-5-carboxamide;
2-methyl-N-((6-methyl-4-(methylthio)-2-oxo-1,2-dihydropyridin-3-yl)methyl)-1-((R)-1-(4-(2-oxooxazolidin-3-yl)cyclohexyl)ethyl)-1H-indole-3-carboxamide;
2-methyl-N-((6-methyl-4-(methylthio)-2-oxo-1,2-dihydropyridin-3-yl)methyl)-1-((R)-1-(4-morpholinocyclohexyl)ethyl)-1H-indole-3-carboxamide;
1-((R)-1-(4-(3-methoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
7-((R)-1-(4-(3-methoxyazetidin-1-yl)cyclohexyl)ethyl)-6-methyl-N-((6-methyl-4-(methylthio)-2-oxo-1,2-dihydropyridin-3-yl)methyl)-7H-pyrrolo[2,3-d]pyrimidine-5-carboxamide;
1-((R)-1-(5-(3,3-dimethylazetidin-1-yl)-1,3-dioxan-2-yl)ethyl)-2-methyl-N-((6-methyl-4-(methylthio)-2-oxo-1,2-dihydropyridin-3-yl)methyl)-1H-indole-3-carboxamide;
1-((R)-1-(4-((R)-3-fluoropyrrolidin-1-yl)cyclohexyl)ethyl)-2-methyl-N-((6-methyl-4-(methylthio)-2-oxo-1,2-dihydropyridin-3-yl)methyl)-1H-indole-3-carboxamide;
1-((R)-1-(4-(3-fluoro-3-methylazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
(R)-1-(1-(1-(3,3-difluorocyclobutyl)piperidin-4-yl)ethyl)-2-methyl-N-((6-methyl-4-(methylthio)-2-oxo-1,2-dihydropyridin-3-yl)methyl)-1H-indole-3-carboxamide;
7-fluoro-1-((R)-1-(4-(3-fluoroazetidin-1-yl)cyclohexyl)ethyl)-2-methyl-N-((6-methyl-4-(methylthio)-2-oxo-1,2-dihydropyridin-3-yl)methyl)-1H-indole-3-carboxamide;
(R)-6-fluoro-1-(1-(4-(3-fluoroazetidin-1-yl)cyclohexyl)ethyl)-2-methyl-N-((6-methyl-4-(methylthio)-2-oxo-1,2-dihydropyridin-3-yl)methyl)-1H-indole-3-carboxamide;
5-fluoro-1-((R)-1-(4-(3-fluoroazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-(5-(3,3-difluoroazetidin-1-yl)-1,3-dioxan-2-yl)ethyl)-2-methyl-N-((6-methyl-4-

(methylthio)-2-oxo-1,2-dihydropyridin-3-yl)methyl)-1H-indole-3-carboxamide;
(R)-N-((4-(ethylthio)-6-methyl-2-oxo-1,2-dihydropyridin-3-yl)methyl)-2-methyl-1-(1-(1-(2,2,2-trifluoroethyppiperidin-4-yl)ethyl)-1H-indole-3-carboxamide;
(R)-2,4-dimethyl-N-((6-methyl-4-(methylthio)-2-oxo-1,2-dihydropyridin-3-yl)methyl)-1-(1-(1-(2,2,2-trifluoroethyl)piperidin-4- yl)ethyl)-1H-indole-3-carboxamide;
(R)-2-methyl-N-((6-methyl-4-(methylthio)-2-oxo-1,2-dihydropyridin-3-yl)methyl)-1-(1-(1-(3,3,3-trifluoropropyppiperidin-4-yl)ethyl)-1H-indole-3-carboxamide;
6-methyl-N-((6-methyl-4-(methylthio)-2-oxo-1,2-dihydropyridin-3-yl)methyl)-7-((R)-1-(4-((2,2,2-trifluoroethyl)amino)cyclohexyl)ethyl)-7H-pyrrolo[2,3-d]pyrimidine-5-carboxamide;
1-((R)-1-(4-(3-methoxy-3-methylazetidin-1-yl)cyclohexyl)ethyl)-2-methyl-N-((6-methyl-4-(methylthio)-2-oxo-1,2-dihydropyridin-3-yl)methyl)-1H-indole-3-carboxamide;
1-((R)-1-(4-(3-ethoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
(R)-6-fluoro-2-methyl-N-((6-methyl-4-(methylthio)-2-oxo-1,2-dihydropyridin-3-yl)methyl)-1-(1-(1-(2,2,2-trifluoroethyppiperidin-4-yl)ethyl)-1H-indole-3-carboxamide;
N-((4-((fluoromethyl)thio)-6-methyl-2-oxo-1,2-dihydropyridin-3-yl)methyl)-1-((R)-1-(4-(3-methoxyazetidin-1-yl)cyclohexyl)ethyl)-2-methyl-1H-indole-3-carboxamide;
5-fluoro-1-((R)-1-(4-(3-methoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-(4-(3,3-difluoropyrrolidin-1-yl)cyclohexyl)ethyl)-2-methyl-N-((6-methyl-4-(methylthio)-2-oxo-1,2-dihydropyridin-3-yl)methyl)-1H-indole-3-carboxamide;
1-((R)-1-(4-(3-(difluoromethyl)azetidin-1-yl)cyclohexyl)ethyl)-2-methyl-N-((6-methyl-4-(methylthio)-2-oxo-1,2-dihydrop yridin-3-yl)methyl)-1H-pyrrolo[2,3-b]pyridine-3-carboxamide;
(R)-4-cyano-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide;
5-chloro-1-((R)-1-(4-(3-fluoroazetidin-1-yl)cyclohexyl)ethyl)-2-methyl-N-((6-methyl-4-(methylthio)-2-oxo-1,2-dihydrop yridin-3-yl)methyl)-1H-pyrrolo[2,3-b]pyridine-3-carboxamide;
N-((4-(cyclopropylthio)-6-methyl-2-oxo-1,2-dihydropyridin-3-yl)methyl)-1-((R)-1-(4-(3-methoxyazetidin-1-yl)cyclohexyl)ethyl)-2-methyl-1H-indole-3-carboxamide;
1-((R)-1-(4-(3-cyclopropoxyazetidin-1-yl)cyclohexyl)ethyl)-2-methyl-N-((6-methyl-4-(methylthio)-2-oxo-1,2-dihydrop yridin-3-yl)methyl)-1H-indole-3-carboxamide;
(R)-4-methoxy-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide;
7-((R)-1-(4-(3-cyclopropoxyazetidin-1-yl)cyclohexyl)ethyl)-6-methyl-N-((6-methyl-4-(methylthio)-2-oxo-1,2-dihydrop yridin-3-yl)methyl)-7H-pyrrolo[2,3-d]pyrimidine-5-carboxamide;
(R)-4-chloro-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide;
1-((R)-1-(4-((3R,4R)-3-fluoro-4-methoxypyrrolidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
(R)-N-((4-((difluoromethyl)thio)-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide;
5-chloro-1-((R)-1-(4-(3-methoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
5-chloro-1-((R)-1-(4-((R)-3-fluoropyrrolidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
7-((R)-1-(4-(3-(difluoromethoxy)azetidin-1-yl)cyclohexyl)ethyl)-6-methyl-N-((6-methyl-4-(methylthio)-2-oxo-1,2-dihydropyridin-3-yl)methyl)-7H-pyrrolo[2,3-d]pyrimidine-5-carboxamide;
(R)-N-((4-(cyclobutylthio)-6-methyl-2-oxo-1,2-dihydropyridin-3-yl)methyl)-2-methyl-1-(1-(1-(2,2,2-trifluoroethyppiperidin-4-yl)ethyl)-1H-indole-3-carboxamide;
2-methyl-N-((6-methyl-4-(methylthio)-2-oxo-1,2-dihydropyridin-3-yl)methyl)-1-((R)-1-(4-(3-(trifluoromethyl)azetidin-1-yl)cyclohexyl)ethyl)-1H-pyrrolo[2,3-b]pyridine-3-carboxamide;
1-((1R)-1-(4-(3-cyclopropoxypyrrolidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-(4-(3-(tert-butoxy)azetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-(4-(3-cyclopropoxyazetidin-1-yl)cyclohexyl)ethyl)-7-fluoro-2-methyl-N-((6-methyl-4-(methylthio)-2-oxo-1,2-dihydropyridin-3-yl)methyl)-1H-indole-3-carboxamide;
(R)-4-(difluoromethyl)-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide;
1-((R)-1-(4-(3-(difluoromethoxy)azetidin-1-yl)cyclohexyl)ethyl)-2,5-dimethyl-N-((6-methyl-4-(methylthio)-2-oxo-1,2-dihydropyridin-3-yl)methyl)-1H-pyrrolo[2,3-b]pyridine-3-carboxamide;
1-((R)-1-(4-(3-(2,2-difluoroethoxy)azetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;

-continued 1-((S)-1-(4-(3-(difluoromethoxy)azetidin-1-yl)cyclohexyl)propyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-(4-(3-(difluoromethoxy)azetidin-1-yl)cyclohexyl)propyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-(4-((R)-3-(difluoromethoxy)pyrrolidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-(4-((S)-3-(difluoromethoxy)pyrrolidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-(4-(3-(difluoromethoxy)azetidin-1-yl)cyclohexyl)ethyl)-7-fluoro-2-methyl-N-((6-methyl-4-(methylthio)-2-oxo-1,2-dihydropyridin-3-yl)methyl)-1H-indole-3-carboxamide;
1-((R)-1-(4-(3-(difluoromethoxy)azetidin-1-yl)cyclohexyl)ethyl)-5-fluoro-2-methyl-N-((6-methyl-4-(methylthio)-2-oxo-1,2-dihydropyridin-3-yl)methyl)-1H-pyrrolo[2,3-b]pyridine-3-carboxamide;
6-methyl-N-((6-methyl-4-(methylthio)-2-oxo-1,2-dihydropyridin-3-yl)methyl)-7-((R)-1-(4-(3-(trifluoromethoxy)azetidin-1-yl)cyclohexyl)ethyl)-7H-pyrrolo[2,3-d]pyrimidine-5-carboxamide;
5-chloro-1-((R)-1-(4-(3-cyclopropoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-(4-(3-(difluoromethoxy)azetidin-1-yl)cyclohexyl)ethyl)-5-methoxy-2-methyl-N-((6-methyl-4-(methylthio)-2-oxo-1,2-dihydropyridin-3-yl)methyl)-1H-pyrrolo[2,3-b]pyridine-3-carboxamide;
5-chloro-1-((R)-1-(4-(3-cyclobutoxyazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
(R)-6-bromo-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide;
(R)-4-bromo-2-methyl-N-((6-methyl-4-(methylthio)-2-oxo-1,2-dihydropyridin-3-yl)methyl)-1-(1-(1-(2,2,2-trifluoroethyl)piperidin-4-yl)ethyl)-1H-indole-3-carboxamide;
1-((R)-1-(4-(3-(tert-butoxy)azetidin-1-yl)cyclohexyl)ethyl)-5-chloro-2-methyl-N-((6-methyl-4-(methylthio)-2-oxo-1,2-dihydropyridin-3-yl)methyl)-1H-pyrrolo[2,3-b]pyridine-3-carboxamide;
(R)-2-methyl-N-((6-methyl-4-(methylthio)-2-oxo-1,2-dihydropyridin-3-yl)methyl)-1-(1-(1-(1-methylcyclopropyl)piperidin-4-yl)ethyl)-1H-pyrrolo[2,3-b]pyridine-3-carboxamide;
1-((R)-1-(4-cyclopropoxycyclohexyl)ethyl)-2-methyl-N-((6-methyl-4-(methylthio)-2-oxo-1,2-dihydropyridin-3-yl)methyl)-1H-indole-3-carboxamide;
(R)-2-methyl-N-((6-methyl-4-(methylthio)-2-oxo-1,2-dihydropyridin-3-yl)methyl)-1-(1-(1-(oxetan-3-yl)piperidin-4-yl)ethyl)-1H-indole-3-carboxamide;
4-((R)-1-(2-methyl-3-(((6-methyl-4-(methylthio)-2-oxo-1,2-dihydropyridin-3-yl)methyl)carbamoyl)-1H-indol-1-yl)ethyl)cyclohexyl acetate;
(R)-1-(1-(1-(2-hydroxyacetyl)piperidin-4-yl)ethyl)-2-methyl-N-((6-methyl-4-(methylthio)-2-oxo-1,2-dihydropyridin-3-yl)methyl)-1H-indole-3-carboxamide;
(R)-1-(1-(4-(3-hydroxyazetidin-1-yl)cyclohexyl)ethyl)-2-methyl-N-((6-methyl-4-(methylthio)-2-oxo-1,2-dihydropyridin-3-yl)methyl)-1H-indole-3-carboxamide;
2-methyl-N-((6-methyl-4-(methylthio)-2-oxo-1,2-dihydropyridin-3-yl)methyl)-1-((R)-1-(4-(oxetan-3-yloxy)cyclohexyl)ethyl)-1H-indole-3-carboxamide;
1-((R)-1-(4-(3-cyanoazetidin-1-yl)cyclohexyl)ethyl)-2-methyl-N-((6-methyl-4-(methylthio)-2-oxo-1,2-dihydropyridin-3-yl)methyl)-1H-indole-3-carboxamide;
1-((R)-1-(4-(5-oxa-1-azaspiro[2.3]hexan-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
(R)-1-(1-(1-(3-methoxycyclobutyl)piperidin-4-yl)ethyl)-2-methyl-N-((6-methyl-4-(methylthio)-2-oxo-1,2-dihydropyridin-3-yl)methyl)-1H-indole-3-carboxamide;
(R)-1-(1-(1-(3-methoxycyclobutyl)piperidin-4-yl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
(R)-1-(1-(1-(dimethylglycyl)piperidin-4-yl)ethyl)-2-methyl-N-((6-methyl-4-(methylthio)-2-oxo-1,2-dihydropyridin-3-yl)methyl)-1H-indole-3-carboxamide;
4-((R)-1-(2-methyl-3-(((6-methyl-4-(methylthio)-2-oxo-1,2-dihydropyridin-3-yl)methyl)carbamoyl)-1H-indol-1-yl)ethyl)cyclohexyl butyrate;
4-((R)-1-(2-methyl-3-(((6-methyl-4-(methylthio)-2-oxo-1,2-dihydropyridin-3-yl)methyl)carbamoyl)-1H-indol-1-yl)ethyl)cyclohexyl isobutyrate;
2-methyl-N-((6-methyl-4-(methylthio)-2-oxo-1,2-dihydropyridin-3-yl)methyl)-1-((R)-1-(4-((1-methylazetidin-3-yl)oxy)cyclohexyl)ethyl)-1H-pyrrolo[2,3-b]pyridine-3-carboxamide;
(R)-1-(1-(1-(ethylsulfonyl)piperidin-4-yl)ethyl)-2-methyl-N-((6-methyl-4-(methylthio)-2-oxo-1,2-dihydropyridin-3-yl)methyl)-1H-indole-3-carboxamide;
2-methyl-1-((R)-1-(4-((1-methyl-1H-pyrazol-4-yl)oxy)cyclohexyl)ethyl)-N-((6-methyl-4-(methylthio)-2-oxo-1,2-dihydropyridin-3-yl)methyl)-1H-pyrrolo[2,3-b]pyridine-3-carboxamide;
1-((R)-1-(4-(3-(dimethylamino)azetidin-1-yl)cyclohexyl)ethyl)-2-methyl-N-((6-methyl-4-(methylthio)-2-oxo-1,2-dihydropyridin-3-yl)methyl)-1H-indole-3-carboxamide;
2-methyl-N-((6-methyl-4-(methylthio)-2-oxo-1,2-dihydropyridin-3-yl)methyl)-1-((1R)-1-(4-((3-methyltetrahydrofuran-3-yl)amino)cyclohexyl)ethyl)-1H-indole-3-carboxamide;

1-((R)-1-((2s,5S)-5-(6-oxa-1-azaspiro[3.3]heptan-1-yl)-1,3-dioxan-2-yl)ethyl)-2-methyl-N-((6-methyl-4-(methylthio)-2-oxo-1,2-dihydropyridin-3-yl)methyl)-1H-indole-3-carboxamide;
1-((S)-1-((2s,5R)-5-(6-oxa-1-azaspiro[3.3]heptan-1-yl)-1,3-dioxan-2-yl)ethyl)-2-methyl-N-((6-methyl-4-(methylthio)-2-oxo-1,2-dihydropyridin-3-yl)methyl)-1H-indole-3-carboxamide;
1-((R)-1-((3R,4R)-3-fluoro-1-(3-methoxycyclobutyl)piperidin-4-yl)ethyl)-2-methyl-N-((6-methyl-4-(methylthio)-2-oxo-1,2-dihydropyridin-3-yl)methyl)-1H-indole-3-carboxamide;
1-((R)-1-((3S,4R)-3-fluoro-1-(3-methoxycyclobutyl)piperidin-4-yl)ethyl)-2-methyl-N-((6-methyl-4-(methylthio)-2-oxo-1,2-dihydropyridin-3-yl)methyl)-1H-indole-3-carboxamide;
1-((R)-1-(4-(3-(fluoromethyl)oxetan-3-yl)amino)cyclohexyl)ethyl)-2-methyl-N-((6-methyl-4-(methylthio)-2-oxo-1,2-dihydropyridin-3-yl)methyl)-1H-indole-3-carboxamide;
1-((R)-1-(4-(3-(fluoromethyl)oxetan-3-yl)amino)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
7-((R)-1-(4-(3-(fluoromethyl)oxetan-3-yl)amino)cyclohexyl)ethyl)-6-methyl-N-((6-methyl-4-(methylthio)-2-oxo-1,2-dihydropyridin-3-yl)methyl)-7H-pyrrolo[2,3-d]pyrimidine-5-carboxamide;
1-((R)-1-(4-(3-cyclopropyl-3-fluoroazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
1-((R)-1-(4-(3-hydroxy-3-isopropylazetidin-1-yl)cyclohexyl)ethyl)-2-methyl-N-((6-methyl-4-(methylthio)-2-oxo-1,2-dihydropyridin-3-yl)methyl)-1H-pyrrolo[2,3-b]pyridine-3-carboxamide;
6-fluoro-1-((R)-1-(4-((3-(hydroxymethyl)oxetan-3-yl)amino)cyclohexyl)ethyl)-2-methyl-N-((6-methyl-4-(methylthio)-2-oxo-1,2-dihydropyridin-3-yl)methyl)-1H-indole-3-carboxamide;
1-((R)-1-(4-(3-(1H-1,2,3-triazol-1-yl)azetidin-1-yl)cyclohexyl)ethyl)-2-methyl-N-((6-methyl-4-(methylthio)-2-oxo-1,2-dihydropyridin-3-yl)methyl)-1H-indole-3-carboxamide;
2-methyl-N-((6-methyl-4-(methylthio)-2-oxo-1,2-dihydropyridin-3-yl)methyl)-1-((R)-1-(4-((1-(trifluoromethyl)cyclopropyl)amino)cyclohexyl)ethyl)-1H-pyrrolo[2,3-b]pyridine-3-carboxamide;
2-methyl-N-((6-methyl-4-(methylthio)-2-oxo-1,2-dihydropyridin-3-yl)methyl)-1-((R)-1-(4-(3-(methylsulfonyl)azetidin-1-yl)cyclohexyl)ethyl)-1H-indole-3-carboxamide;
2-methyl-N-((6-methyl-4-(methylthio)-2-oxo-1,2-dihydropyridin-3-yl)methyl)-1-((R)-1-(4-((3-(trifluoromethyl)oxetan-3-yl)amino)cyclohexyl)ethyl)-1H-pyrrolo[2,3-b]pyridine-3-carboxamide;
6-methyl-N-((6-methyl-4-(methylthio)-2-oxo-1,2-dihydropyridin-3-yl)methyl)-7-((R)-1-(4-((3-(trifluoromethyl)oxetan-3-yl)amino)cyclohexyl)ethyl)-7H-pyrrolo[2,3-d]pyrimidine-5-carboxamide;

or a pharmaceutically acceptable salt of any of the foregoing.

6. A pharmaceutical composition comprising the compound of claim 1, or a pharmaceutically acceptable salt thereof; and a pharmaceutically acceptable carrier.

7. A method for treating a cancer selected from breast cancer, prostate cancer, colon cancer, renal cell carcinoma, glioblastoma multiforme cancer, bladder cancer, melanoma, bronchial cancer, lymphoma, cholangiosarcoma, multiple myeloma, lung cancer, ovarian cancer, and liver cancer in a subject, comprising administering to the subject an effective amount of a compound of claim 1, or a pharmaceutically acceptable salt thereof.

8. A pharmaceutical composition comprising the compound of claim 2, or a pharmaceutically acceptable salt thereof; and a pharmaceutically acceptable carrier.

9. A pharmaceutical composition comprising the compound of claim 5, or a pharmaceutically acceptable salt thereof; and a pharmaceutically acceptable carrier.

10. A method for treating a cancer selected from breast cancer, prostate cancer, colon cancer, renal cell carcinoma, glioblastoma multiforme cancer, bladder cancer, melanoma, bronchial cancer, lymphoma, cholangiosarcoma, multiple myeloma, lung cancer, ovarian cancer, and liver cancer in a subject, comprising administering to the subject an effective amount of a compound of claim 2, or a pharmaceutically acceptable salt thereof.

11. A method for treating a cancer selected from breast cancer, prostate cancer, colon cancer, renal cell carcinoma, glioblastoma multiforme cancer, bladder cancer, melanoma, bronchial cancer, lymphoma, cholangiosarcoma, multiple myeloma, lung cancer, ovarian cancer, and liver cancer in a subject, comprising administering to the subject an effective amount of a compound of claim 5, or a pharmaceutically acceptable salt thereof.

* * * * *

UNITED STATES PATENT AND TRADEMARK OFFICE
CERTIFICATE OF CORRECTION

PATENT NO. : 11,459,315 B2
APPLICATION NO. : 16/762600
DATED : October 4, 2022
INVENTOR(S) : Jehrod B. Brenneman et al.

It is certified that error appears in the above-identified patent and that said Letters Patent is hereby corrected as shown below:

In the Claims

Column 252, Claim 1, Line 49, please add "$R^7$ is halo($C_1$-$C_4$)alkyl or –($C_1$-$C_4$)alkylOH;" after "$R^5$ is hydroxyl, ($C_1$-$C_4$)alkoxy, or $NR^A R^B$;" and before "$R^4$ is hydrogen, ($C_1$-$C_4$)alkyl, or halo($C_1$-$C_4$)alkyl;".

Column 253, Claim 2, Line 13, please add "each X is independently CH or N;" after "or a pharmaceutically acceptable salt thereof, wherein" and before "$R^2$ is hydrogen or halo;".

Column 253, Claim 2, Line 35, please replace "hydroxyl($C_1$-$C_4$)alkyl, $NMe_2$, -$SO_2$($C_1$-$C_4$)alkyl," with --hydroxyl($C_1$-$C_4$)alkyl, -N(Me)$_2$, -$SO_2$($C_1$-$C_4$)alkyl,--.

Column 254, Claim 3, Line 16, please replace "halo, hydroxyl, cyano, ($C_1$-$C_4$)alkyl, $NMe_2$, hydroxy" with --halo, hydroxyl, cyano, ($C_1$-$C_4$)alkyl, -N(Me)$_2$, hydroxy--.

Column 254, Claim 4, Lines 25-43, please replace "$R^5$ is selected from halo, ($C_3$-$C_6$)cycloalkyl, -OC(O)($C_1$-$C_4$)alkyl, -C(O)($C_1$-$C_4$)alkylOH, -C(O)($C_1$-$C_4$)alkylN(($C_1$-$C_4$)alkyl)$_2$, -$SO_2$($C_1$-$C_4$)alkyl, and $NR^A R^B$ wherein said cycloalkyl for $R^5$ is optionally substituted with -O($C_1$-$C_4$)alkyl;
$R^B$ is ($C_3$-$C_5$)cycloalkyl or 4-7 membered heterocyclyl each optionally and independently substituted with 1 to 3 groups selected from ($C_1$-$C_4$)alkyl, halo($C_1$-$C_4$)alkyl, and hydroxy($C_1$-$C_4$)alkyl; or
$R^A$ and $R^B$ taken together with the nitrogen atom to which they are attached form a 3-7 membered heterocyclyl optionally substituted with 1 to 3 groups selected from halo, hydroxyl, cyano, ($C_1$-$C_4$)alkyl, $NMe_2$, -$SO_2$($C_1$-$C_4$)alkyl, 5-6 membered heteroaryl, and ($C_3$-$C_6$)cycloalkyl; and
$R^6$ is 4-7 membered heterocyclyl or 5-6 membered heteroaryl, wherein said 4-7 membered heterocyclyl and said 5-6 membered heteroaryl for $R^6$ are each optionally and independently substituted with ($C_1$-$C_4$)alkyl." with
--$R^5$ is selected from halo, ($C_3$-$C_6$)cycloalkyl, -OC(O)($C_1$-$C_4$)alkyl, -C(O)($C_1$-$C_4$)alkylOH, -C(O)($C_1$-$C_4$)alkylN(($C_1$-$C_4$)alkyl)$_2$, -$SO_2$($C_1$-$C_4$)alkyl, and $NR^A R^B$ wherein said cycloalkyl for $R^5$ is optionally substituted with -O($C_1$-$C_4$)alkyl; and Signed and Sealed this
Twenty-first Day of February, 2023

*Katherine Kelly Vidal*
*Director of the United States Patent and Trademark Office*

$R^B$ is $(C_3-C_5)$cycloalkyl or 4-7 membered heterocyclyl each optionally and independently substituted with 1 to 3 groups selected from $(C_1-C_4)$alkyl, halo$(C_1-C_4)$alkyl, and hydroxy$(C_1-C_4)$alkyl; or $R^A$ and $R^B$ taken together with the nitrogen atom to which they are attached form a 3-7 membered heterocyclyl optionally substituted with 1 to 3 groups selected from halo, hydroxyl, cyano, $(C_1-C_4)$alkyl, $N(Me)_2$, $-SO_2(C_1-C_4)$alkyl, 5-6 membered heteroaryl, and $(C_3-C_6)$cycloalkyl.--.

SEQUENCE LISTING

```
<160> NUMBER OF SEQ ID NOS: 3

<210> SEQ ID NO 1
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: LysMe3

<400> SEQUENCE: 1

Arg Lys Gln Leu Ala Thr Lys Ala Ala Arg Xaa Ser Ala Pro Ala Thr
1               5                   10                  15

Gly Gly Val Lys Lys Pro
            20
```

```
<210> SEQ ID NO 2
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: LysMe1

<400> SEQUENCE: 2

Arg Lys Gln Leu Ala Thr Lys Ala Ala Arg Xaa Ser Ala Pro Ala Thr
1               5                   10                  15

Gly Gly Val Lys Lys Pro
            20

<210> SEQ ID NO 3
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Arg Lys Gln Leu Ala Thr Lys Ala Ala Arg Lys Ser Ala Pro Ala Thr
1               5                   10                  15

Gly Gly Val Lys Lys Pro
            20
```